US009908885B2

(12) United States Patent
Bennett et al.

(10) Patent No.: US 9,908,885 B2
(45) Date of Patent: Mar. 6, 2018

(54) BROMODOMAIN INHIBITORS

(71) Applicant: Celgene Quanticel Research, Inc., San Diego, CA (US)

(72) Inventors: Michael John Bennett, San Diego, CA (US); Juan Manuel Betancort, San Diego, CA (US); Amogh Boloor, San Diego, CA (US); Stephen W. Kaldor, San Diego, CA (US); Jeffrey Alan Stafford, San Diego, CA (US); James Marvin Veal, Apex, NC (US)

(73) Assignee: CELGENE QUANTICEL RESEARCH, INC., San Diego, CA (US)

( * ) Notice: Subject to any disclaimer, the term of this patent is extended or adjusted under 35 U.S.C. 154(b) by 0 days.

(21) Appl. No.: 15/130,503

(22) Filed: Apr. 15, 2016

(65) Prior Publication Data

US 2017/0050968 A1 Feb. 23, 2017

Related U.S. Application Data

(60) Provisional application No. 62/148,098, filed on Apr. 15, 2015.

(51) Int. Cl.
| | | |
|---|---|---|
| *C07D 417/04* | (2006.01) | |
| *C07D 473/34* | (2006.01) | |
| *C07D 405/04* | (2006.01) | |
| *C07D 401/04* | (2006.01) | |
| *C07D 413/04* | (2006.01) | |
| *C07D 471/04* | (2006.01) | |
| *C07D 491/04* | (2006.01) | |
| *C07D 401/14* | (2006.01) | |
| *C07D 413/14* | (2006.01) | |
| *C07D 471/06* | (2006.01) | |
| *C07D 498/04* | (2006.01) | |

(52) U.S. Cl.
CPC ......... *C07D 473/34* (2013.01); *C07D 401/04* (2013.01); *C07D 401/14* (2013.01); *C07D 405/04* (2013.01); *C07D 413/04* (2013.01); *C07D 413/14* (2013.01); *C07D 417/04* (2013.01); *C07D 471/04* (2013.01); *C07D 471/06* (2013.01); *C07D 491/04* (2013.01); *C07D 498/04* (2013.01)

(58) Field of Classification Search
CPC .................................................. C07D 491/04
USPC ...................................................... 514/230.5
See application file for complete search history.

(56) References Cited

U.S. PATENT DOCUMENTS

| | | | | |
|---|---|---|---|---|
| 9,034,900 B2 * | 5/2015 | Bennett | ................ | C07D 498/04 514/309 |
| 9,115,114 B2 * | 8/2015 | Bennett | ................ | C07D 498/04 |
| 9,598,372 B2 * | 3/2017 | Boloor | ................ | C07D 498/04 |
| 2007/0054892 A1 * | 3/2007 | Isaacs | ................ | C04B 35/632 514/210.21 |
| 2011/0263590 A1 | 10/2011 | Haydon et al. | | |
| 2015/0111885 A1 * | 4/2015 | Bennett | ................ | C07D 498/04 514/230.5 |
| 2015/0183784 A1 * | 7/2015 | Bennett | ................ | C07D 498/04 514/230.5 |
| 2015/0307493 A1 * | 10/2015 | Combs | ................ | C07D 471/04 514/230.5 |
| 2016/0115134 A1 * | 4/2016 | Bennett | ................ | C07D 498/04 544/105 |
| 2016/0184273 A1 * | 6/2016 | Liu | ................ | C07D 405/14 424/85.7 |
| 2016/0310423 A1 * | 10/2016 | Betancort | ................ | A61K 9/10 |

FOREIGN PATENT DOCUMENTS

| | | | |
|---|---|---|---|
| WO | WO 2012086735 | * | 6/2012 |
| WO | WO 2013130855 | * | 9/2013 |
| WO | WO 2016077378 | * | 5/2016 |

OTHER PUBLICATIONS

Boi; "The BET Bromodomain Inhibitor OTX015 Affects Pathogenetic Pathways in Preclinical B-cell Tumor Models and Synergizes with Targeted Drugs" Clin Cancer Res 2015, 21, 1628-1638.*
Fu; "Inhibition of BET bromodomains as a therapeutic strategy for cancer drug discovery" Oncotarget 2015, 6, 5501-5516.*
International Search Report and Written Opinion dated Oct. 31, 2016, in related International Application No. PCT/US2016/027874, filed Apr. 15, 2016.
Pubchem, Substance Record for SID 247797025, Create Date: Mar. 17, 2015 [retrieved on May 23, 2016]. Retrieved from the Internet: <https://pubchem.ncbi.nlm.nih.gov/substance/247797025>. Entire document.
Pubchem, Substantce for SID 129486299 Create Date: Dec. 4, 2011. [retrieved on May 23, 2016]. Retrieved from the internet: <https://pubchem.ncbi.nlm.nih.gov/substance/129486299>. Entire document.
Pubchem, Substance Record for SID 218129794 Create Date: Oct. 20, 2014. [retrieved on May 23, 2016]. Retrieved from the Internet: <https://pubchem.ncbi.nlm.nih.gov/substance/218129794>. Entire document.
Pubchem, Substance Record for SID 247995902 Create Date: Mar. 17, 2015. [retrieved on May 24, 2016]. Retrieved from the Internet: <https://pubchem.ncbi.nlm.nih.gov/substance/247995902>. Entire document.
International Preliminary Report on Patentability dated Oct. 26, 2017, issued in related International Patent Application No. PCT/US2016/027874, filed Apr. 15, 2016.

* cited by examiner

*Primary Examiner* — Daniel R Carcanague
(74) *Attorney, Agent, or Firm* — Wiley Rein LLP

(57) ABSTRACT

The present invention relates to substituted heterocyclic derivative compounds, compositions comprising said compounds, and the use of said compounds and compositions for epigenetic regulation by inhibition of bromodomain-mediated recognition of acetyl lysine regions of proteins, such as histones. Said compositions and methods are useful for the treatment of cancer and neoplastic disease.

24 Claims, No Drawings

BROMODOMAIN INHIBITORS

RELATED APPLICATION

This application claims priority benefit to U.S. Provisional Patent Application No. 62/148,098, filed 15 Apr. 2015, which is fully incorporated herein by reference for all purposes.

BACKGROUND

A need exists in the art for an effective treatment of cancer and neoplastic disease.

SUMMARY

Provided herein are substituted heterocyclic derivative compounds and pharmaceutical compositions comprising said compounds. The subject compounds and compositions are useful for epigenetic regulation by inhibition of bromodomain-mediated recognition of acetyl lysine regions of proteins, such as histones. Furthermore, the subject compounds and compositions are useful for the treatment of cancer, such as NUT midline carcinoma, prostate cancer, breast cancer, bladder cancer, lung cancer, melanoma, and the like. The substituted heterocyclic derivative compounds described herein are based upon pyridone and related heterocyclic structures. These pyridone and related heterocyclic structures are substituted at the 4-position with a fused bicyclic group such as an aryl, a heteroaryl and the like, and on the nitrogen atom of the isoquinolinone or related heterocyclic structure with a small alkyl group, such as a methyl group.

At least one embodiment provides a compound of Formula I, or a pharmaceutically acceptable salt thereof, Formula I represented by:

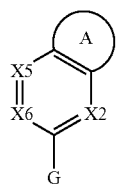

Formula I wherein
Ring A is an optionally substituted 5- or 6-membered heteroaryl ring containing at least one S or N atom, or an optionally substituted 5- or 6-membered heterocyclyl ring containing at least one S or N atom;
X2 is N or C—$R^{12}$, wherein $R^{12}$ is hydrogen, halogen, alkyl, or alkoxy;
X5 is N or C—$R^{15}$, wherein $R^{15}$ is hydrogen, halogen, —CN, alkyl or alkoxy;
X6 is N or C—$R^{16}$, wherein $R^{16}$ is hydrogen, halogen, or —W—X, wherein
W is a bond, —O—, —S—, or —NH—, and
X is alkyl, alkynyl, aryl, aralkyl, cycloalkyl, cycloalkylalkyl, cycloalkylalkynyl, heterocyclyl, heterocyclylalkyl, heteroaryl, or heteroarylalkyl; and G represented by:

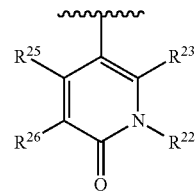

wherein,
$R^{22}$ is alkyl;
$R^{23}$ is hydrogen, halogen, or alkyl; or optionally, when $R^{23}$ is alkyl, $R^{22}$ and $R^{23}$ join to form a ring that is optionally substituted;
$R^{25}$ is hydrogen, halogen, alkyl, alkoxy, or alkenyl;
$R^{26}$ is hydrogen, halogen, alkyl, alkoxy, aminoalkyl, or alkenyl; or
optionally, when $R^{23}$ is hydrogen, $R^{25}$ is not hydrogen, and $R^{26}$ is neither hydrogen nor halogen, then $R^{25}$ and $R^{26}$ join to form an optionally substituted ring;
provided that the compound of Formula I is neither
4-(3,4-dihydro-2H-benzo[b][1,4]oxazin-6-yl)-2-methyl-isoquinolin-1(2H)-one,
2-methyl-4-(2-oxoindolin-6-yl)isoquinolin-1(2H)-one,
4-methyl-6-(2-methyl-1-oxo-1,2-dihydroisoquinolin-4-yl)-2H-benzo[b][1,4]oxazin-3(4H)-one,
nor
4-(1'-cyclobutyl-4H-spiro[benzo[d][1,3]dioxine-2,4'-piperidine]-6-yl)-2-methylisoquinolin-1(2H)-one.

At least one embodiment provides a compound of Formula II, or a pharmaceutically acceptable salt thereof, wherein Formula II is represented by

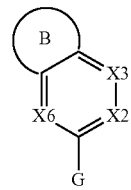

Formula II wherein
Ring B is an optionally substituted 5- or 6-membered heteroaryl ring containing at least one S or N atom, or an optionally substituted 5- or 6-membered heterocyclyl ring containing at least one S or N atom;
X2 is N or C—$R^{12}$, in which $R^{12}$ is hydrogen, halogen, alkyl, or alkoxy;
X3 is N or C—$R^{13}$, in which $R^{13}$ is —Y—Z, wherein
Y is selected from a bond, —$CH_2$—, or —CH($C_1$-$C_4$ alkyl)-,
Z is selected from —$SO_2R^b$, —N($R^a$)$SO_2R^b$, —$SO_2$N($R^a$)$_2$, —N($R^a$)$SO_2$N($R^a$)$_2$, —CON($R^a$)$_2$, —N($R^a$)$CO_2R^a$, —N($R^a$)CON($R^a$)$_2$, —N($R^a$)$COR^a$, —OC(O)N($R^a$)$_2$, —$OSO_2$N($R^a$)$_2$, or —N($R^a$)$SO_3R^b$, in which
each $R^a$ is independently hydrogen, alkyl, cycloalkyl, cycloalkylalkyl, aryl, aralkyl, heterocyclyl, heterocyclylalkyl, heteroaryl, or heteroarylalkyl, and
$R^b$ is alkyl, cycloalkyl, cycloalkylalkyl, aryl, aralkyl, heterocyclyl, heterocyclylalkyl, heteroaryl, or heteroarylalkyl;

X6 is N or C—R$^{16}$, in which R$^{16}$ is hydrogen, halogen, or —W—X, wherein
W is a bond, —O—, —S—, or —NH—, and
X is alkyl, alkynyl, aryl, aralkyl, cycloalkyl, cycloalkylalkyl, cycloalkylalkynyl, heterocyclyl, heterocyclylalkyl, heteroaryl, or heteroarylalkyl; and G is described by:

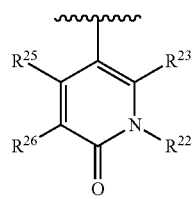

wherein
R$^{22}$ is alkyl;
R$^{23}$ is hydrogen, halogen, or alkyl; or optionally, when R$^{23}$ is alkyl, R$^{22}$ and R$^{23}$ join to form an optionally substituted ring;
R$^{25}$ is hydrogen, halogen, alkyl, alkoxy, or alkenyl; and
R$^{26}$ is hydrogen, halogen, alkyl, alkoxy, aminoalkyl, or alkenyl; or
optionally, when R$^{23}$ is hydrogen, R$^{25}$ is not hydrogen, and R$^{26}$ is neither hydrogen nor halogen, then R$^{25}$ and R$^{26}$ join to form an optionally substituted ring.

At least one embodiment provides a compound of Formula III, or a pharmaceutically acceptable salt thereof,

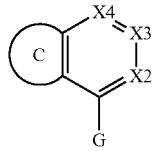

Formula III wherein
Ring C is an optionally substituted 5- or 6-membered heteroaryl ring containing at least one O, S or N atom;
X2 is N or C—R$^{12}$, in which R$^{12}$ is hydrogen, halogen, alkyl, or alkoxy;
X3 is N or C—R$^{13}$, in which R$^{13}$ is —Y—Z, wherein
Y is selected from a bond, —CH$_2$—, or —CH(C$_1$-C$_4$ alkyl)-, and
Z is selected from —SO$_2$R$^b$, —N(R$^a$)SO$_2$R$^b$, —SO$_2$N(R$^a$)$_2$, —N(R$^a$)SO$_2$N(R$^a$)$_2$, —CON(R$^a$)$_2$, —N(R$^a$)CO$_2$R$^a$, —N(R$^a$)CON(R$^a$)$_2$, —N(R$^a$)COR$^a$, —OC(O)N(R$^a$)$_2$, —OSO$_2$N(R$^a$)$_2$, or —N(R$^a$)SO$_3$R$^b$, in which
each R$^a$ is independently hydrogen, alkyl, cycloalkyl, cycloalkylalkyl, aryl, aralkyl, heterocyclyl, heterocyclylalkyl, heteroaryl, or heteroarylalkyl and
R$^b$ is alkyl, cycloalkyl, cycloalkylalkyl, aryl, aralkyl, heterocyclyl, heterocyclylalkyl, heteroaryl, or heteroarylalkyl;
X4 is N or C—R$^{14}$, in which R$^{14}$ is hydrogen, halogen, —CN, alkyl, cycloalkyl, or alkoxy; and G is described by:

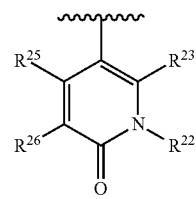

wherein
R$^{22}$ is alkyl;
R$^{23}$ is hydrogen, halogen, or alkyl; or optionally, when R$^{23}$ is alkyl, R$^{22}$ and R$^{23}$ join to form an optionally substituted ring;
R$^{25}$ is hydrogen, halogen, alkyl, alkoxy, or alkenyl;
R$^{26}$ is hydrogen, halogen, alkyl, alkoxy, aminoalkyl, or alkenyl; or
optionally, when both R$^{23}$ and R$^{25}$ are not hydrogen, and R$^{26}$ is neither hydrogen nor halogen, then R$^{25}$ and R$^{26}$ join to form an optionally substituted ring;
provided that the compound of Formula III is neither
4-(2-ethyl-5-(methylsulfonyl)benzofuran-7-yl)-2-methylisoquinolin-1(2H)-one
nor
4-(2-cyclopropyl-5-(methylsulfonyl)benzofuran-7-yl)-2-methylisoquinolin-1(2H)-one.

At least one embodiment provides a compound of Formula IV, or a pharmaceutically acceptable salt thereof, Formula IV represented by:

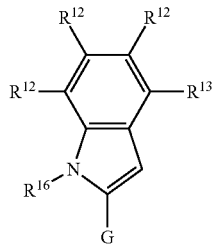

Formula IV wherein
each R$^{12}$ is independently hydrogen, halogen, alkyl, or alkoxy;
R$^{13}$ is —Y—Z, in which
Y is a bond, —CH$_2$—, or —CH(C$_1$-C$_4$ alkyl)-,
Z is —SO$_2$R$^b$, —N(R$^a$)SO$_2$R$^b$, —SO$_2$N(R$^a$)$_2$, —N(R$^a$)SO$_2$N(R$^a$)$_2$, —CON(R$^a$)$_2$, —N(R$^a$)CO$_2$R$^a$, —N(R$^a$)CON(R$^a$)$_2$, —N(R$^a$)COR$^a$, —OC(O)N(R$^a$)$_2$, —OSO$_2$N(R$^a$)$_2$, or —N(R$^a$)SO$_3$R$^b$, wherein
each R$^a$ is independently hydrogen, alkyl, cycloalkyl, cycloalkylalkyl, aryl, aralkyl, heterocyclyl, heterocyclylalkyl, heteroaryl, or heteroarylalkyl, and
R$^b$ is alkyl, cycloalkyl, cycloalkylalkyl, aryl, aralkyl, heterocyclyl, heterocyclylalkyl, heteroaryl, or heteroarylalkyl;
R$^{16}$ is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; and G is:

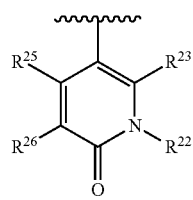

wherein
$R^{22}$ is alkyl;

$R^{23}$ is hydrogen, halogen, or alkyl; or optionally, when $R^{23}$ is alkyl, $R^{22}$ and $R^{23}$ join to form an optionally substituted ring;

$R^{25}$ is hydrogen, halogen, alkyl, alkoxy, or alkenyl;

$R^{26}$ is hydrogen, halogen, alkyl, alkoxy, aminoalkyl, or alkenyl; or optionally, when $R^{23}$ is hydrogen, $R^{25}$ is not hydrogen, and $R^{26}$ is neither hydrogen nor halogen, then $R^{25}$ and $R^{26}$ join to form an optionally substituted ring.

In one embodiment, the compound of Formula IV, or a pharmaceutically acceptable salt thereof, is a compound of Formula IVa:

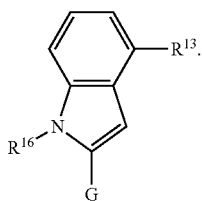

Formula IVa

In an embodiment of Formula IVa, $R^{13}$ is —Y—Z, in which Y is a bond or —CH$_2$—, and Z is —SO$_2$R$^b$, —N(R$^a$)SO$_2$R$^b$, or —SO$_2$N(R$^a$)$_2$, wherein each R$^a$ is independently hydrogen, alkyl, cycloalkyl, cycloalkylalkyl, aryl, aralkyl, heterocyclyl, heterocyclylalkyl, heteroaryl, or heteroarylalkyl, and R$^b$ is alkyl, cycloalkyl, cycloalkylalkyl, aryl, aralkyl, heterocyclyl, heterocyclylalkyl, heteroaryl, or heteroarylalkyl; $R^{16}$ is alkyl, alkynyl, aryl, aralkyl, cycloalkyl, cycloalkylalkyl, cycloalkylalkynyl, heterocyclyl, heterocyclylalkyl, heteroaryl, or heteroarylalkyl; and G is as described above.

In another embodiment of Formula IVa, $R^{13}$ is —Y—Z, wherein Y is a bond or —CH$_2$—, Z is —SO$_2$R$^b$ or —N(R$^a$)SO$_2$R$^b$, in which each R$^a$ is independently hydrogen or alkyl, and R$^b$ is alkyl; $R^{16}$ is alkyl or cycloalkylalkyl; and G is as described above.

At least one embodiment provides a compound of Formula Va:

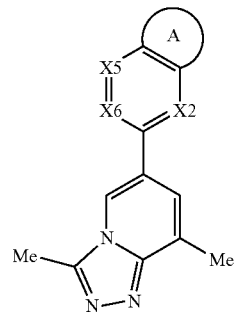

Formula Va or a pharmaceutically acceptable salt thereof, wherein
Ring A is an optionally substituted 5- or 6-membered heteroaryl ring containing at least one S or N atom, or an optionally substituted 5- or 6-membered heterocyclyl ring containing at least one S or N atom;

X2 is N or C—R$^{12}$, in which R$^{12}$ is hydrogen, halogen, alkyl, or alkoxy;

X5 is N or C—R$^{15}$, in which R$^{15}$ is hydrogen, halogen, —CN, alkyl or alkoxy; and X6 is N or C—R$^{16}$, in which R$^{16}$ is hydrogen, halogen, or —W—X, wherein
W is a bond, —O—, —S—, or —NH—, and
X is alkyl, alkynyl, aryl, aralkyl, cycloalkyl, cycloalkylalkyl, cycloalkylalkynyl, heterocyclyl, heterocyclylalkyl, heteroaryl, or heteroarylalkyl.

At least one embodiment provides a compound of Formula Vb:

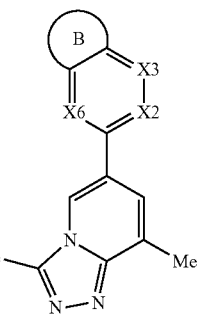

Formula Vb or a pharmaceutically acceptable salt thereof, wherein
Ring B is an optionally substituted 5- or 6-membered heteroaryl ring containing at least one S or N atom, or an optionally substituted 5- or 6-membered heterocyclyl ring containing at least one S or N atom;

X2 is N or C—R$^{12}$, in which R$^{12}$ is hydrogen, halogen, alkyl, or alkoxy;

X3 is N or C—R$^{13}$, in which R$^{13}$ is —Y—Z, wherein
Y is selected from a bond, —CH$_2$—, or —CH(C$_1$-C$_4$ alkyl)-, and
Z is selected from —SO$_2$R$^b$, —N(R$^a$)SO$_2$R$^b$, —SO$_2$N(R$^a$)$_2$, —N(R$^a$)SO$_2$N(R$^a$)$_2$, —CON(R$^a$)$_2$, —N(R$^a$)CO$_2$R$^a$, —N(R$^a$)CON(R$^a$)$_2$, —N(R$^a$)COR$^a$, —OC(O)N(R$^a$)$_2$, —OSO$_2$N(R$^a$)$_2$, or —N(R$^a$)SO$_3$R$^b$,
each R$^a$ is independently hydrogen, alkyl, cycloalkyl, cycloalkylalkyl, aryl, aralkyl, heterocyclyl, heterocyclylalkyl, heteroaryl, or heteroarylalkyl, and $R^b$ is alkyl, cycloalkyl, cycloalkylalkyl, aryl, aralkyl, heterocyclyl, heterocyclylalkyl, heteroaryl, or heteroarylalkyl; and X6 is N or C—$R^{16}$, in which $R^{16}$ is hydrogen, halogen, or —W—X, wherein
W is a bond, —O—, —S—, or —NH—, and
X is alkyl, alkynyl, aryl, aralkyl, cycloalkyl, cycloalkylalkyl, cycloalkylalkynyl, heterocyclyl, heterocyclylalkyl, heteroaryl, or heteroarylalkyl.

At least one embodiment provides a compound of Formula Vc, or a pharmaceutically acceptable salt thereof,

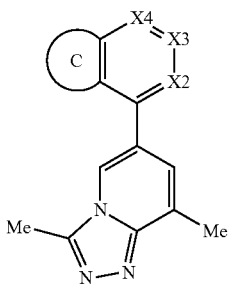

Formula Vc wherein
Ring C is an optionally substituted 5- or 6-membered heteroaryl ring containing at least one O, S or N atom;
X2 is N or C—$R^{12}$, in which $R^{12}$ is hydrogen, halogen, alkyl, or alkoxy;
X3 is N or C—$R^{13}$, in which $R^{13}$ is —Y—Z, wherein
Y is a bond, —CH$_2$—, or —CH(C$_1$-C$_4$ alkyl)-, and
Z is —SO$_2$R$^b$, —N(R$^a$)SO$_2$R$^b$, —SO$_2$N(R$^a$)$_2$, —N(R$^a$)SO$_2$N(R$^a$)$_2$, —CON(R$^a$)$_2$, —N(R$^a$)CO$_2$R$^a$, —N(R$^a$)CON(R$^a$)$_2$, —N(R$^a$)COR$^a$, —OC(O)N(R$^a$)$_2$, —OSO$_2$N(R$^a$)$_2$, or —N(R$^a$)SO$_3$R$^b$, wherein
each $R^a$ is independently hydrogen, alkyl, cycloalkyl, cycloalkylalkyl, aryl, aralkyl, heterocyclyl, heterocyclylalkyl, heteroaryl, or heteroarylalkyl, and
$R^b$ is alkyl, cycloalkyl, cycloalkylalkyl, aryl, aralkyl, heterocyclyl, heterocyclylalkyl, heteroaryl, or heteroarylalkyl; and
X4 is N or C—$R^{14}$, in which $R^{14}$ is hydrogen, halogen, —CN, alkyl, cycloalkyl, or alkoxy.

At least one embodiment provides a compound of Formula Vd, or a pharmaceutically acceptable salt thereof,

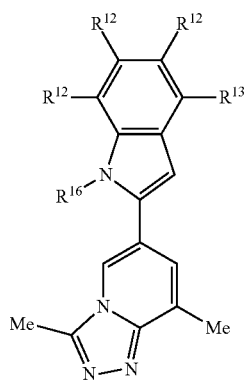

Formula Vd wherein
each $R^{12}$ is independently hydrogen, halogen, alkyl, or alkoxy;
$R^{13}$ is —Y—Z, in which
Y is a bond, —CH$_2$— or —CH(C$_1$-C$_4$ alkyl)-, and
Z is —SO$_2$R$^b$, —N(R$^a$)SO$_2$R$^b$, —SO$_2$N(R$^a$)$_2$, —N(R$^a$)SO$_2$N(R$^a$)$_2$, —CON(R$^a$)$_2$, —N(R$^a$)CO$_2$R$^a$, —N(R$^a$)CON(R$^a$)$_2$, —N(R$^a$)COR$^a$, —OC(O)N(R$^a$)$_2$, —OSO$_2$N(R$^a$)$_2$, or —N(R$^a$)SO$_3$R$^b$, wherein
each $R^a$ is independently hydrogen, alkyl, cycloalkyl, cycloalkylalkyl, aryl, aralkyl, heterocyclyl, heterocyclylalkyl, heteroaryl, or heteroarylalkyl, and
$R^b$ is alkyl, cycloalkyl, cycloalkylalkyl, aryl, aralkyl, heterocyclyl, heterocyclylalkyl, heteroaryl, or heteroarylalkyl; and
$R^{16}$ is from alkyl, alkynyl, aryl, aralkyl, cycloalkyl, cycloalkylalkyl, cycloalkylalkynyl, heterocyclyl, heterocyclylalkyl, heteroaryl, or heteroarylalkyl.

At least one embodiment provides a compound of Formula Ve:

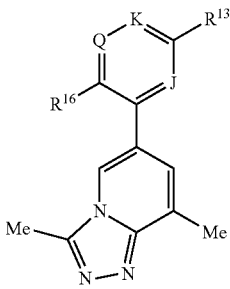

Formula Ve or a pharmaceutically acceptable salt thereof, wherein
J is N or C—$R^{12}$, in which $R^{12}$ is hydrogen, halogen, alkyl, or alkoxy;
$R^{13}$ is —Y—Z, in which
Y is a bond, —CH$_2$—, or —CH(C$_1$-C$_4$alkyl)-, and
Z is —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —COR$^{21}$, —OC(O)N(R$^{22}$)$_2$, —OSO$_2$N(R$^{22}$)$_2$, or —N(R$^{22}$)SO$_3$R$^{21}$, in which
each $R^{21}$ is independently alkyl, cycloalkyl, cycloalkylalkyl, aryl, aralkyl, heterocyclyl, heterocyclylalkyl, heteroaryl, or heteroarylalkyl, and wherein
each $R^{22}$ is independently hydrogen, alkyl, cycloalkyl, cycloalkylalkyl, aryl, aralkyl, heterocyclyl, heterocyclylalkyl, heteroaryl, or heteroarylalkyl;
K is N or C—$R^{14}$, in which $R^{14}$ is hydrogen, halogen, —CN, alkyl, cycloalkyl, or alkoxy;
Q is N or C—$R^{15}$, in which $R^{15}$ is hydrogen, halogen, —CN, alkyl, alkoxy, aryloxy, aralkyloxy, cycloalkylalkyloxy, heterocyclyloxy, heteroarylalkyloxy, or alkynyloxy; and
$R^{16}$ is hydrogen, halogen, —N(H)COX, or —W—X, wherein
W is a bond, —O—, —S—, or —NH—, and
X is alkyl, aryl, aralkyl, cycloalkyl, cycloalkylalkyl, alkynyl, cycloalkylalkynyl, heterocyclyl, heterocyclylalkyl, heteroaryl, or heteroarylalkyl.

At least one embodiment provides a compound of Formula VI, or a pharmaceutically acceptable salt thereof, in which Formula VI is

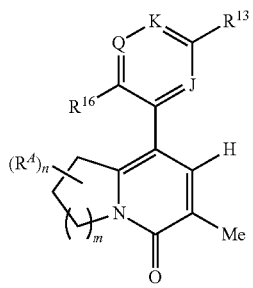

Formula VI wherein
n is 0 to 4;
m is 0 or 1;
$R^4$ is a halogen, C1-3 alkyl, or C1-3 alkoxy;
J is N or C—$R^{12}$, wherein $R^{12}$ is hydrogen, halogen, alkyl, or alkoxy;
$R^{13}$ is —Y—Z, in which
  Y is a bond, —$CH_2$—, or —CH($C_1$-$C_4$alkyl)-, and
  Z is —$SO_2R^{21}$, —N($R^{22}$)$SO_2R^{21}$, —$SO_2$N($R^{22}$)$_2$, —N($R^{22}$)$SO_2$N($R^{22}$)$_2$, —CON($R^{22}$)$_2$, —N($R^{22}$)$CO_2R^{21}$, —N($R^{22}$)CON($R^{22}$)$_2$, —N($R^{22}$)COR$^{21}$, —COR$^{21}$, —OC(O)N($R^{22}$)$_2$, —$OSO_2$N($R^{22}$)$_2$, or —N($R^{22}$)$SO_3R^{21}$, wherein
    each $R^{21}$ is independently alkyl, cycloalkyl, cycloalkylalkyl, aryl, aralkyl, heterocyclyl, heterocyclylalkyl, heteroaryl, or heteroarylalkyl, and
    each $R^{22}$ is independently hydrogen, alkyl, cycloalkyl, cycloalkylalkyl, aryl, aralkyl, heterocyclyl, heterocyclylalkyl, heteroaryl, or heteroarylalkyl.
K is N or C—$R^{14}$, wherein $R^{14}$ is hydrogen, halogen, —CN, alkyl, cycloalkyl, or alkoxy;
Q is N or C—$R^{15}$, wherein $R^{15}$ is hydrogen, halogen, —CN, alkyl, alkoxy, aryloxy, aralkyloxy, cycloalkylalkyloxy, heterocyclyloxy, heteroarylalkyloxy, or alkynyloxy; and
$R^{16}$ is hydrogen, halogen, —N(H)COX, or —W—X, wherein W is a bond, —O—, —S—, or —NH—, and X is selected from alkyl, aryl, aralkyl, cycloalkyl, cycloalkylalkyl, alkynyl, cycloalkylalkynyl, heterocyclyl, heterocyclylalkyl, heteroaryl, or heteroarylalkyl.

At least one embodiment provides a pharmaceutical composition comprising a compound of Formula I, or a pharmaceutically acceptable salt thereof. At least one embodiment provides a pharmaceutical composition comprising a compound of Formula II, or a pharmaceutically acceptable salt thereof. At least one embodiment provides a pharmaceutical composition comprising a compound of Formula III, or a pharmaceutically acceptable salt thereof. At least one embodiment provides a pharmaceutical composition comprising a compound of Formula IV, or a pharmaceutically acceptable salt thereof. At least one embodiment provides a pharmaceutical composition comprising a compound of Formula IVa, or a pharmaceutically acceptable salt thereof. At least one embodiment provides a pharmaceutical composition comprising a compound of Formula Va, or a pharmaceutically acceptable salt thereof. At least one embodiment provides a pharmaceutical composition comprising a compound of Formula Vb, or a pharmaceutically acceptable salt thereof. At least one embodiment provides a pharmaceutical composition comprising a compound of Formula Vc, or a pharmaceutically acceptable salt thereof. At least one embodiment provides a pharmaceutical composition comprising a compound of Formula Vd, or a pharmaceutically acceptable salt thereof. At least one embodiment provides a pharmaceutical composition comprising a compound of Formula Ve, or a pharmaceutically acceptable salt thereof. At least one embodiment provides a pharmaceutical composition comprising a compound of Formula VI, or a pharmaceutically acceptable salt thereof.

At least one embodiment provides a method of treating a cancer patient in need thereof, comprising administering to the patient a pharmaceutical composition comprising a compound of Formula I, or a pharmaceutically acceptable salt thereof. At least one embodiment provides a method of treating cancer in a patient in need thereof, comprising administering to the patient a pharmaceutical composition comprising a compound of Formula II, or a pharmaceutically acceptable salt thereof. At least one embodiment provides a method of treating a cancer patient in need thereof, comprising administering to the patient a pharmaceutical composition comprising a compound of Formula III, or a pharmaceutically acceptable salt thereof. At least one embodiment provides a method of treating a cancer patient in need thereof, comprising administering to the patient a pharmaceutical composition comprising a compound of Formula IV, or a pharmaceutically acceptable salt thereof. At least one embodiment provides a method of treating a cancer patient in need thereof, comprising administering to the patient a pharmaceutical composition comprising a compound of Formula IVa, or a pharmaceutically acceptable salt thereof. At least one embodiment provides a method of treating a cancer patient in need thereof, comprising administering to the patient a pharmaceutical composition comprising a compound of Formula Va, or a pharmaceutically acceptable salt thereof. At least one embodiment provides a method of treating a cancer patient in need thereof, comprising administering to the patient a pharmaceutical composition comprising a compound of Formula Vb, or a pharmaceutically acceptable salt thereof. At least one embodiment provides a method of treating a cancer patient in need thereof, comprising administering to the patient a pharmaceutical composition comprising a compound of Formula Vc, or a pharmaceutically acceptable salt thereof. At least one embodiment provides a method of treating a cancer patient in need thereof, comprising administering to the patient a pharmaceutical composition comprising a compound of Formula Vd, or a pharmaceutically acceptable salt thereof. At least one embodiment provides a method of treating a cancer patient in need thereof, comprising administering to the patient a pharmaceutical composition comprising a compound of Formula Ve, or a pharmaceutically acceptable salt thereof. At least one embodiment provides a method of treating a cancer patient in need thereof, comprising administering to the patient a pharmaceutical composition comprising a compound of Formula VI, or a pharmaceutically acceptable salt thereof.

DETAILED DESCRIPTION

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Other than in the operating examples, or where otherwise indicated, all numbers expressing quantities of ingredients or reaction conditions used herein should be understood as modified in all instances by the term "about."

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only, and is not intended to limit the scope of the present invention, which is defined solely by the claims. In order that the present disclosure can be more readily understood, certain terms are first defined. Additional definitions are set forth throughout the detailed description.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), or 1-pentyl (n-pentyl). The alkyl is attached to the rest of the molecule by a single bond. Unless specifically stated otherwise, an alkyl group is optionally substituted by at least one of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2), and —S(O)$_t$N(R$^a$)$_2$ (where t is 1 or 2), in which each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) in which each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O) N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises two to five carbon atoms (e.g., $C_2$-$C_5$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—R—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), in which each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—R—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl, where $R^c$ is an alkynylene chain as defined above. The carbocyclyl part of the carbocyclylalkynyl radical is optionally substituted as described above for a carbocyclyl group. In some embodiments the carbocyclyl group is a cycloalkyl group. The alkynylene chain part of the carbocyclylalkynyl radical is optionally substituted as defined above for an alkynylene chain.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to:

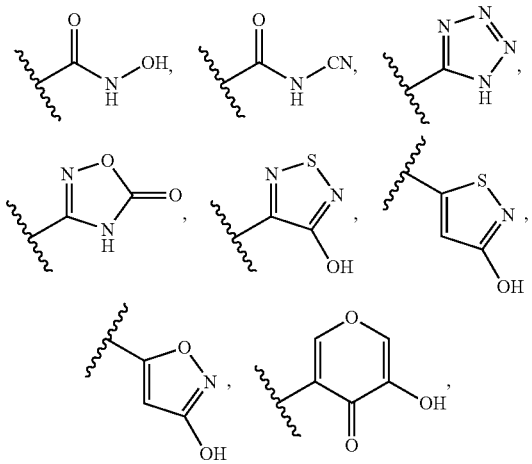

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s).

Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless specifically stated otherwise in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, $R^b$—$N(R^a)_2$, —$R^b$—C(O)$R^a$, —$R^b$—C(O)$OR^a$, —$R^b$—C(O)$N(R^a)_2$, —$R^b$—O—R—C(O)$N(R^a)_2$, —$R^b$—$N(R^a)$C(O)$OR^a$, —$R^b$—$N(R^a)$C(O)$R^a$, —$R^b$—$N(R^a)$S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t N(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen atom, and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, imidazolinyl, imidazolidinyl, pyrazolidinyl, 1-morpholinyl, 1-piperidinyl, 1-piperazinyl, and 1-pyrrolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpho-linyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—R-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s).

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]-thieno[2,3-d]pyrimidinyl, 5,6-dihydrobenzo[h]quinazolinyl, 5,6-dihydrobenzo[h]-cinnolinyl, 6,7-dihydro-5H-benzo[6,7]-cyclohepta[1,2-c]pyridazinyl, dibenzofuranyl, dibenzothiophenyl, furanyl, furanonyl, furo[3,2-c]pyridinyl, 5,6,7,8,9,10-hexahydro-cycloocta[d]pyrimidinyl, 5,6,7,8,9,10-hexa-hydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naph-thyridinonyl, oxadiazolyl, 2-oxoazepinyl, oxazolyl, oxiranyl, 5,6,6a,7,8,9,10,10a-octahydro-benzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]-pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein may contain one or more asymmetric centers and may thus give rise to enantiomers, diastereomers, and other stereoisomeric forms that may be defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans). Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

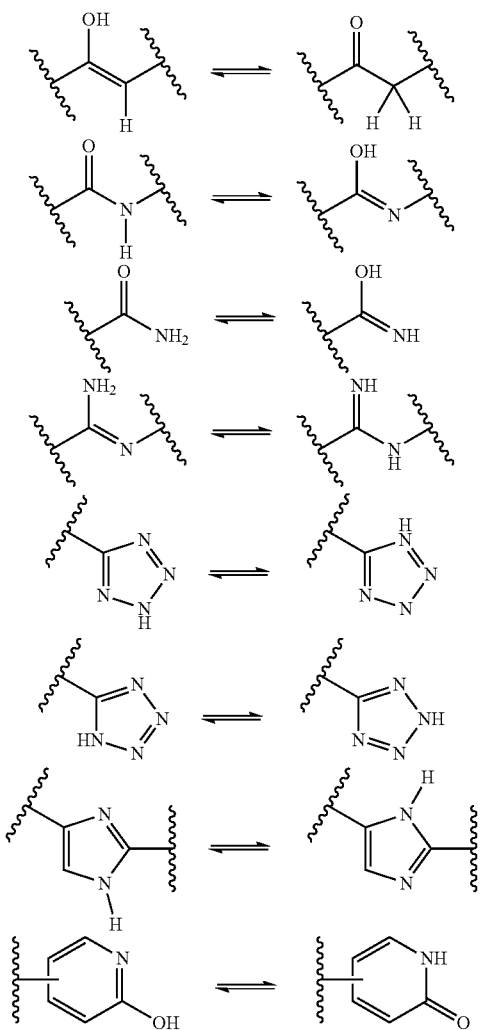

"Optional" or "optionally" means that a subsequently described event or circumstance may or may not occur and that the description includes instances when the event or circumstance occurs and instances in which it does not. For example, "optionally substituted aryl" and "aryl, optionally substituted" mean that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted heterocyclic derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and, aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates. See, e.g., Berge et al., *Pharmaceutical Salts*, 66 J. Pharm. Sci. 1 (1997). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methyl-glucamine, glucosamine, methylglucamine, theobromine, purines, piperazine, piperidine, N-ethylpiperidine, polyamine resins and the like. See Berge et al., 1997.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, "prodrug" refers to a precursor of a biologically active compound that is pharmaceutically acceptable. A prodrug may be inactive (or have partial or different activity) when administered to a subject, but is converted in vivo to the desired active compound, for example, by hydrolysis. A prodrug compound may offer advantages of solubility, tissue compatibility, or delayed release in a mammalian organism. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like. See, e.g., Bundgard, DESIGN OF PRODRUGS, at 7-9, 21-24 (Elsevier, Amsterdam, 1985); Higuchi et al., Pro-drugs as Novel Delivery Systems, 14 A.C.S. Symposium Series in BIOREVERSIBLE CARRIERS IN DRUG DESIGN (Roche, Ed.; Am. Pharm. Assoc. & Pergamon Press, 1987).

The compounds of the present disclosure may optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I), or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. All isotopic variations of the compounds of the present invention, whether radioactive or not, are encompassed within the scope of the present invention. Accordingly, unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure. In certain embodiments, the compounds disclosed herein have some or all of the $^1$H atoms replaced with $^2$H atoms. The methods of synthesis for deuterium-containing substituted heterocyclic derivative compounds are known in the art and include, by way of non-limiting example only, the following synthetic methods.

Deuterated starting materials are readily available and are subjected to the synthetic methods described herein to provide for the synthesis of deuterium-containing substituted heterocyclic derivative compounds. Large numbers of deuterium-containing reagents and building blocks are available commerically from chemical vendors, such as Aldrich Chemical Co. Deuterium-transfer reagents suitable for use in nucleophilic substitution reactions, such as iodomethane-d$_3$ (CD$_3$I), are readily available and may be employed to transfer a deuterium-substituted carbon atom under nucleophilic substitution reaction conditions to the reaction substrate. The use of CD$_3$I is illustrated, by way of example only, in the following reaction schemes:

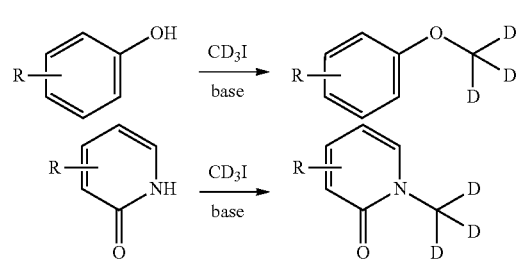

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the following reaction schemes:

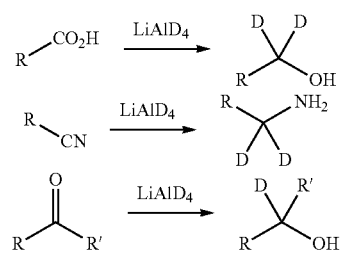

Deuterium gas and palladium catalyst are employed to reduce unsaturated carbon-carbon linkages and to perform a reductive substitution of aryl carbon-halogen bonds as illustrated, by way of example only, in the following reaction schemes:

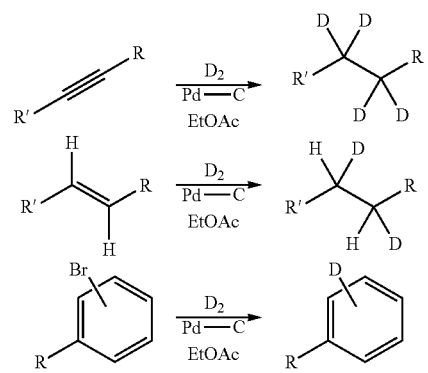

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

Substituted Heterocyclic Derivative Compounds

Substituted heterocyclic derivative compounds are described herein that are bromodomain inhibitors. These compounds, and compositions comprising these compounds, are useful for the treatment of cancer and neoplastic disease. The compounds described herein may, therefore, be useful for treating NUT midline carcinoma, prostate cancer, breast cancer, bladder cancer, lung cancer and/or melanoma and the like.

One embodiment provides a compound of Formula I, or a pharmaceutically acceptable salt thereof, Formula I having the structure:

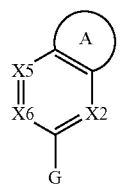

Formula I wherein

Ring A is an optionally substituted 5- or 6-membered heteroaryl ring containing at least one S or N atom, or an optionally substituted 5- or 6-membered heterocyclyl ring containing at least one S or N atom;

X2 is N or C—$R^{12}$, in which $R^{12}$ is hydrogen, halogen, alkyl, or alkoxy;

X5 is N or C—$R^{15}$, in which $R^{15}$ is hydrogen, halogen, —CN, alkyl or alkoxy;

X6 is N or C—$R^{16}$, in which $R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; and G is described by:

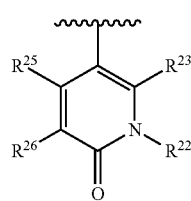

wherein, $R^{22}$ is alkyl;

$R^{23}$ is hydrogen, halogen, or alkyl; or optionally, when $R^{23}$ is alkyl, $R^{22}$ and $R^{23}$ join to form an optionally substituted ring;

$R^{25}$ is hydrogen, halogen, alkyl, alkoxy, or alkenyl;

$R^{26}$ is hydrogen, halogen, alkyl, alkoxy, aminoalkyl, or alkenyl; or optionally, when $R^{23}$ is hydrogen, $R^{25}$ is not hydrogen and $R^{26}$ is not hydrogen or halogen, $R^{25}$ and $R^{26}$ join to form an optionally substituted ring;

provided that the compound of Formula I is not 4-(3,4-dihydro-2H-benzo[b][1,4]oxazin-6-yl)-2-methylisoquinolin-1(2H)-one, 2-methyl-4-(2-oxoindolin-6-yl)isoquinolin-1(2H)-one, 4-methyl-6-(2-methyl-1-oxo-1,2-dihydroisoquinolin-4-yl)-2H-benzo[b][1,4]oxazin-3(4H)-one, nor 4-(1'-cyclobutyl-4H-spiro[benzo[d][1,3]dioxine-2,4'-piperidine]-6-yl)-2-methylisoquinolin-1(2H)-one.

Another embodiment provides the compound of Formula I, or a pharmaceutically acceptable salt thereof, wherein G is:

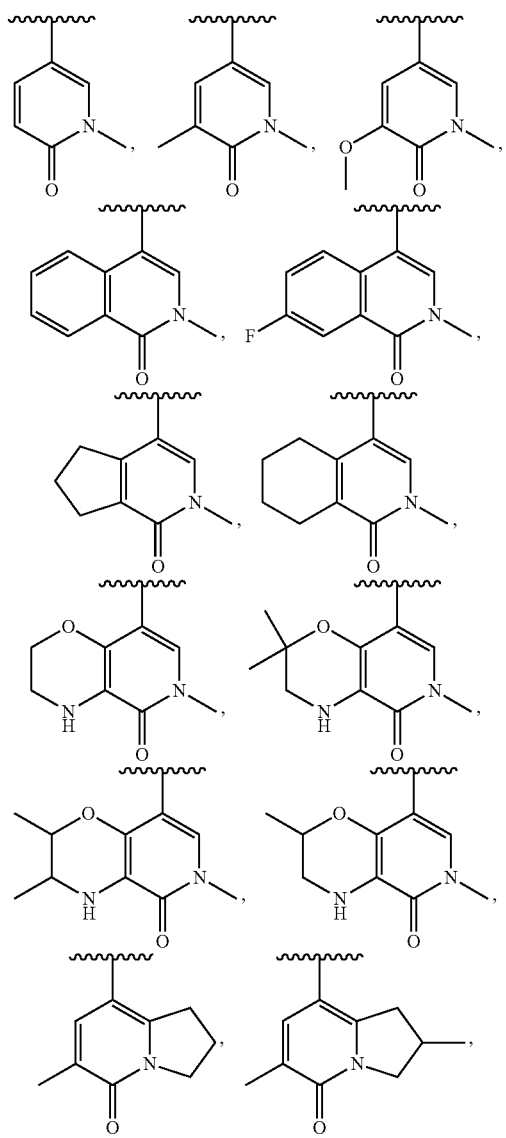

-continued

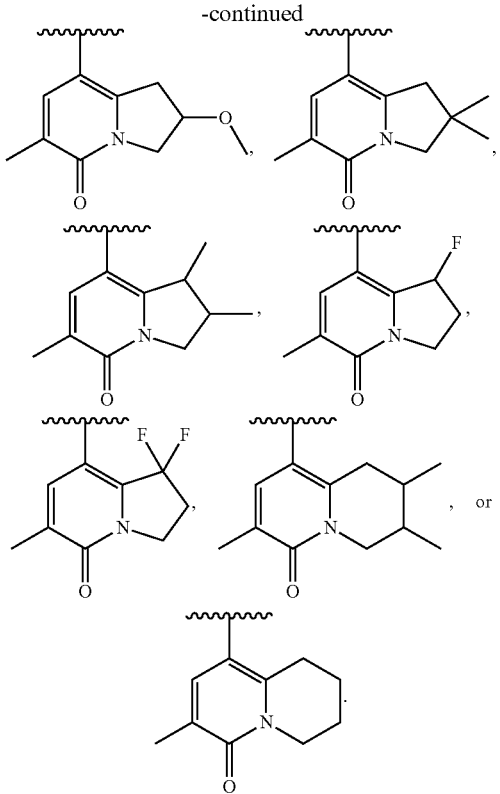

Another embodiment provides the compound of Formula I, or a pharmaceutically acceptable salt thereof, wherein G is:

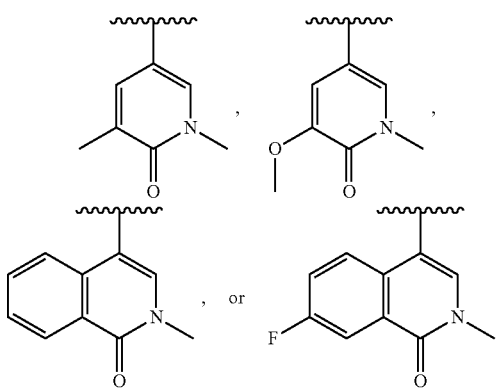

Another embodiment provides the compound of Formula I, or a pharmaceutically acceptable salt thereof, wherein G is:

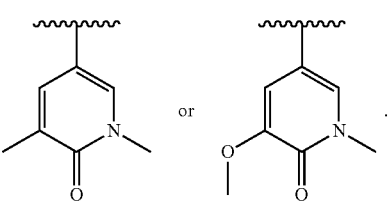

Another embodiment provides the compound of Formula I, or a pharmaceutically acceptable salt thereof, wherein G is:

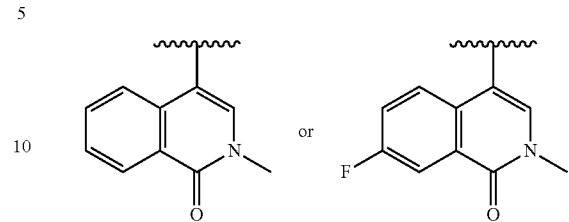

Another embodiment provides the compound of Formula I, or a pharmaceutically acceptable salt thereof, wherein ring A is an optionally substituted 5- or 6-membered heteroaryl ring containing at least one N atom. Another embodiment provides the compound of Formula I, or a pharmaceutically acceptable salt thereof, wherein ring A is an optionally substituted 5- or 6-membered heteroaryl ring containing at least one S atom. Another embodiment provides the compound of Formula I, or a pharmaceutically acceptable salt thereof, wherein ring A is an optionally substituted 5- or 6-membered heterocyclyl ring containing at least one N atom.

Another embodiment provides the compound of Formula I, or a pharmaceutically acceptable salt thereof, wherein ring A is an optionally substituted 5- or 6-membered heterocyclyl ring containing at least one S atom.

Another embodiment provides the compound of Formula I, or a pharmaceutically acceptable salt thereof, wherein X5 is C—$R^{15}$ and $R^{15}$ is as described above. Another embodiment provides the compound of Formula I, or a pharmaceutically acceptable salt thereof, wherein X6 is C—$R^{16}$ and $R^{16}$ is as described above. Another embodiment provides the compound of Formula I, or a pharmaceutically acceptable salt thereof, wherein X2 is C—$R^{12}$ and $R^{12}$ is as described above. Another embodiment provides the compound of Formula I, or a pharmaceutically acceptable salt thereof, wherein X5 is N. Another embodiment provides the compound of Formula I, or a pharmaceutically acceptable salt thereof, wherein X6 is N. Another embodiment provides the compound of Formula I, or a pharmaceutically acceptable salt thereof, wherein X2 is N. Another embodiment provides the compound of Formula I, or a pharmaceutically acceptable salt thereof, wherein X2 is C—$R^{12}$, X5 is C—$R^{15}$, and X6 is C—$R^{16}$, wherein $R^{12}$, $R^{15}$, and $R^{16}$ are as described above.

Another embodiment provides the compound of Formula I, or a pharmaceutically acceptable salt thereof, wherein ring A is:

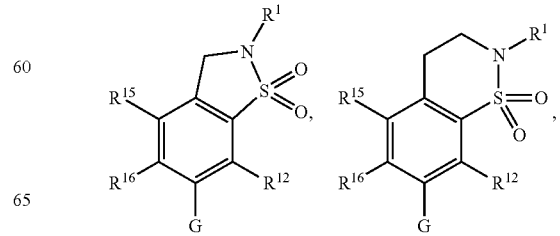

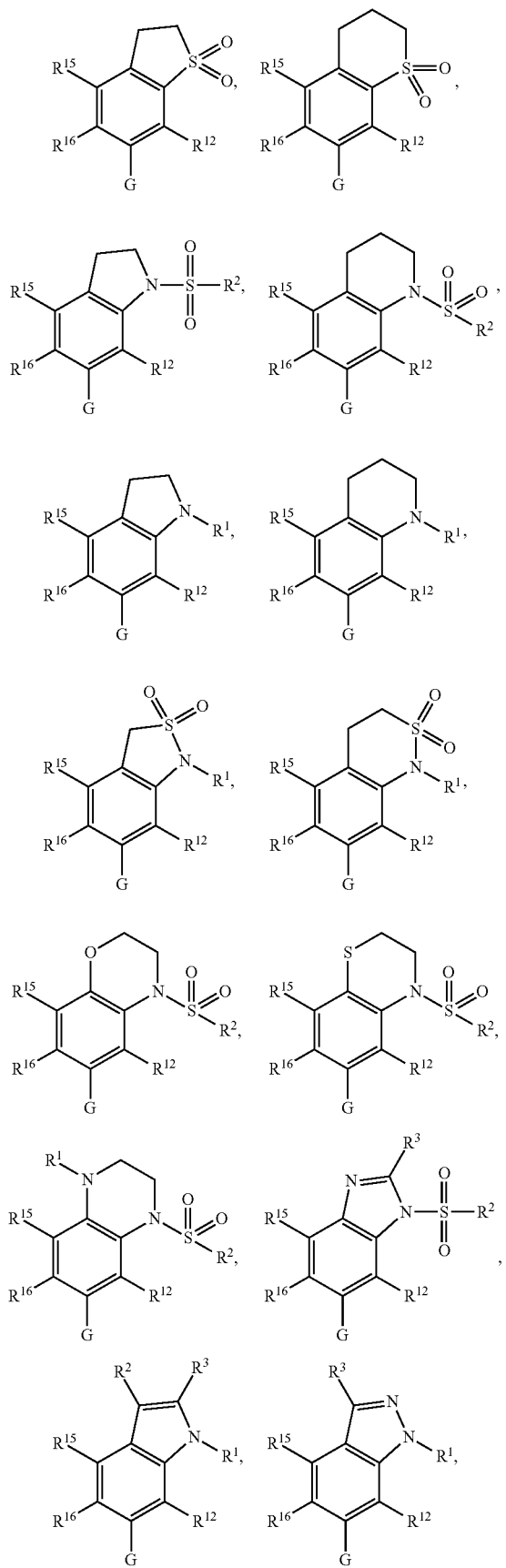

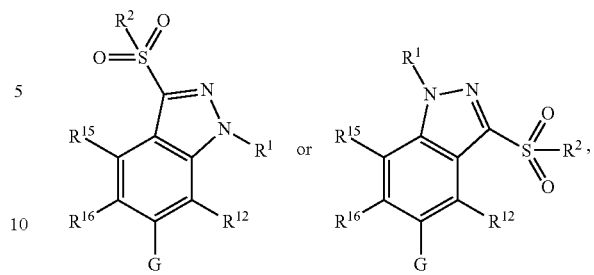

wherein
R¹ is hydrogen, alkyl, alkylsulfonyl, alkylsulfinyl, cycloalkyl, cycloalkylalkyl, aryl, aralkyl, heterocyclyl, heterocyclylalkyl, heteroaryl, or heteroarylalkyl;

R² is alkyl, cycloalkyl, cycloalkylalkyl, aryl, aralkyl, heterocyclyl, heterocyclylalkyl, heteroaryl, or heteroarylalkyl;

each R³ is independently hydrogen, halogen, alkyl, alkoxy, alkoxyalkyl, cycloalkyl, cycloalkylalkyl, aryl, aralkyl, heterocyclyl, heterocyclylalkyl, heteroaryl, or heteroarylalkyl; and R¹², R¹⁵, and R¹⁶ are as described above.

Another embodiment provides the compound of Formula I, or a pharmaceutically acceptable salt thereof, wherein ring A, optionally, excludes:

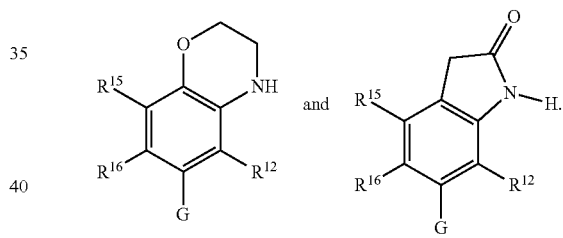

Another embodiment provides the compound of Formula I, or a pharmaceutically acceptable salt thereof, wherein ring A is:

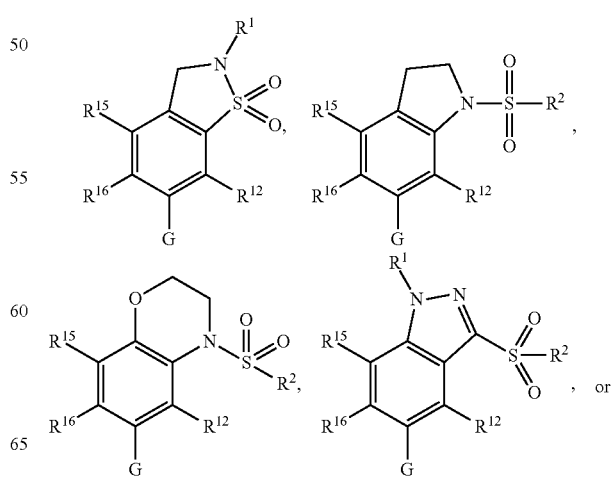

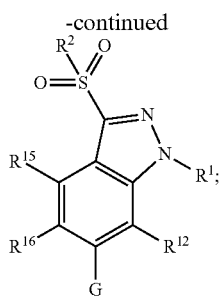

and wherein $R^1$, $R^2$, $R^{12}$, $R^{15}$, and $R^{16}$ are as described above.

Another embodiment provides the compound of Formula I, or a pharmaceutically acceptable salt thereof, wherein ring A is:

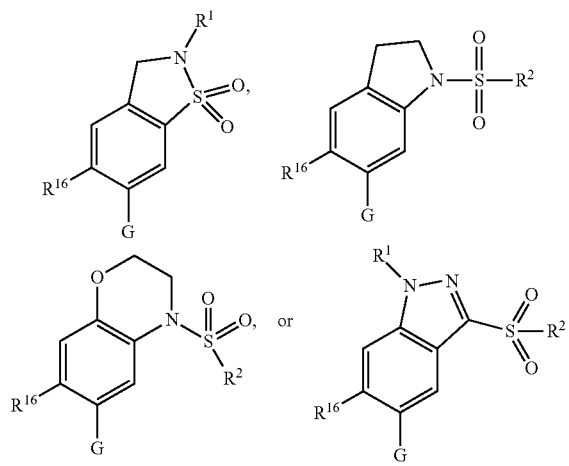

wherein $R^1$, $R^2$, and $R^{16}$ are as described above.

Another embodiment provides the compound of Formula I, or a pharmaceutically acceptable salt thereof, wherein $R^{16}$ is hydrogen or —W—X, wherein W is a —O—, —S—, or —NH—, and X is alkyl, alkynyl, aryl, aralkyl, cycloalkyl, cycloalkylalkyl, cycloalkyl-alkynyl, heterocyclyl, heterocyclylalkyl, heteroaryl, or heteroarylalkyl; $R^1$ is hydrogen, alkyl, alkylsulfonyl, alkylsulfinyl, cycloalkyl, cycloalkylalkyl, aryl, aralkyl, heterocyclyl, heterocyclylalkyl, heteroaryl, or heteroarylalkyl; and $R^2$ alkyl, cycloalkyl, cycloalkylalkyl, aryl, aralkyl, heterocyclyl, heterocyclylalkyl, heteroaryl, or heteroarylalkyl.

Another embodiment provides the compound of Formula I, or a pharmaceutically acceptable salt thereof, wherein $R^{16}$ is —W—X, wherein W is —O— and X is alkyl aryl, cycloalkyl, or cycloalkylalkyl; $R^1$ is hydrogen or alkyl; and $R^2$ is alkyl.

Another embodiment provides the compound of Formula I, or a pharmaceutically acceptable salt thereof, wherein $R^{16}$ is:

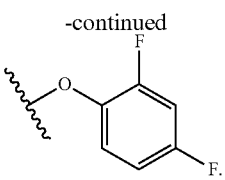

Another embodiment provides the compound of Formula I, or a pharmaceutically acceptable salt thereof, wherein $R^{16}$ is:

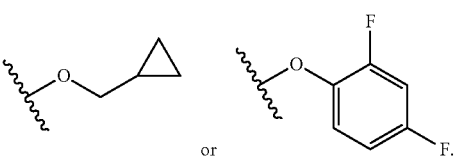 [SMILES: *OCC1CC1 ; *Oc1ccc(F)cc1F ; "or"]

At least one embodiment provides a compound of Formula II, or a pharmaceutically acceptable salt thereof, Formula II represented by

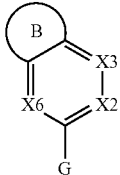

Formula II wherein

Ring B is an optionally substituted 5- or 6-membered heteroaryl ring containing at least one S or N atom, or an optionally substituted 5- or 6-membered heterocyclyl ring containing at least one S or N atom;

X2 is N or C—$R^{12}$, in which $R^{12}$ is hydrogen, halogen, alkyl, or alkoxy;

X3 is N or C—$R^{13}$, in which $R^{13}$ is —Y—Z, in which Y is a bond, —CH$_2$—, or —CH(C$_1$-C$_4$ alkyl)-, and Z is —SO$_2$R$^b$, —N(R$^a$)SO$_2$R$^b$, —SO$_2$N(R$^a$)$_2$, —N(R$^a$)SO$_2$N(R$^a$)$_2$, —CON(R$^a$)$_2$, —N(R$^a$)CO$_2$R$^a$, —N(R$^a$)CON(R$^a$)$_2$, —N(R$^a$)COR$^a$, —OC(O)N(R$^a$)$_2$, —OSO$_2$N(R$^a$)$_2$, or —N(R$^a$)SO$_3$R$^b$, and wherein each R$^a$ is independently hydrogen, alkyl, cycloalkyl, cycloalkylalkyl, aryl, aralkyl, heterocyclyl, heterocyclylalkyl, heteroaryl, or heteroarylalkyl, and R$^b$ is alkyl, cycloalkyl, cycloalkylalkyl, aryl, aralkyl, heterocyclyl, heterocyclylalkyl, heteroaryl, or heteroarylalkyl;

X6 is N or C—$R^{16}$, in which $R^{16}$ is hydrogen, halogen, or —W—X, wherein W is a bond, —O—, —S—, or —NH—, and X is alkyl, alkynyl, aryl, aralkyl, cycloalkyl, cycloalkylalkyl, cycloalkylalkynyl, heterocyclyl, heterocyclylalkyl, heteroaryl, or heteroarylalkyl; and G is:

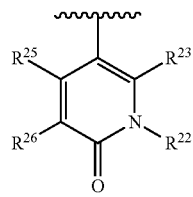

wherein
$R^{22}$ is alkyl;
$R^{23}$ is hydrogen, halogen, or alkyl; or optionally, when $R^{23}$ is alkyl, $R^{22}$ and $R^{23}$ join to form an optionally substituted ring;
$R^{25}$ is hydrogen, halogen, alkyl, alkoxy, or alkenyl; and
$R^{26}$ is hydrogen, halogen, alkyl, alkoxy, aminoalkyl, or alkenyl, or,
optionally, when $R^{23}$ is hydrogen, $R^{25}$ is not hydrogen (i.e., $R^{25}$ is halogen, alkyl, alkoxy, or alkenyl), and $R^{26}$ is not hydrogen or halogen (i.e., $R^{26}$ is alkyl, alkoxy, aminoalkyl, or alkenyl), then $R^{25}$ and $R^{26}$ join to form an optionally substituted ring.

Another embodiment provides the compound of Formula II, or a pharmaceutically acceptable salt thereof, wherein G is:

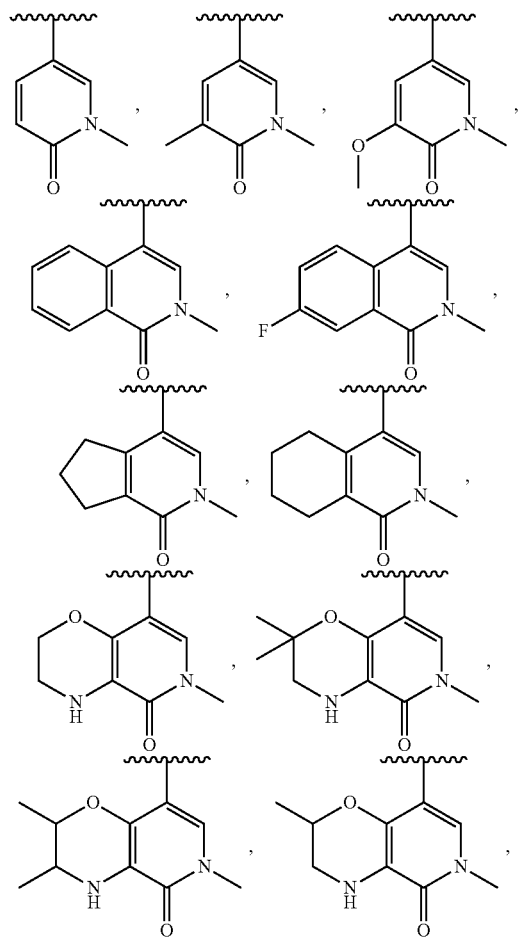

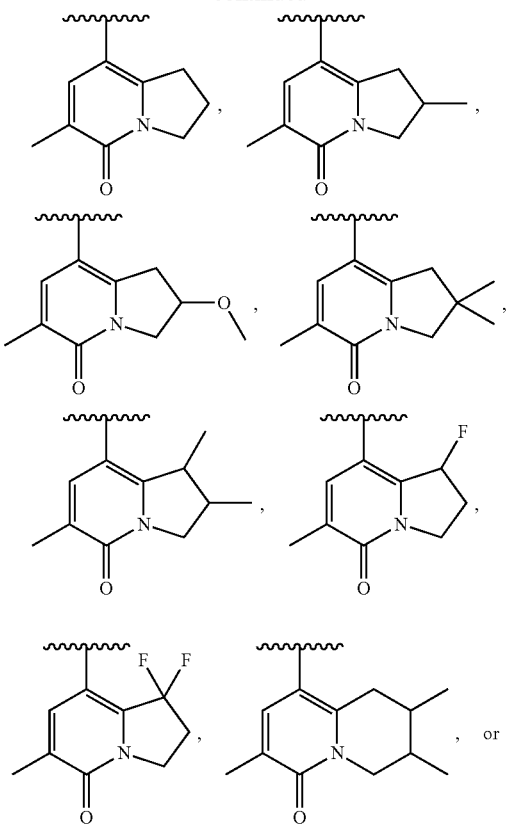

Another embodiment provides the compound of Formula II, or a pharmaceutically acceptable salt thereof, wherein G is:

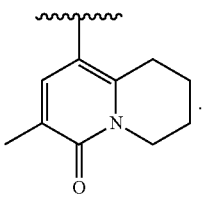

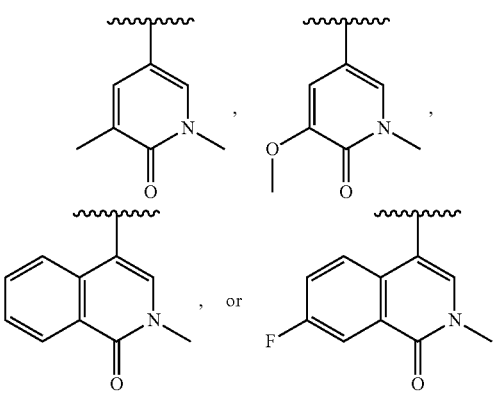

Another embodiment provides the compound of Formula II, or a pharmaceutically acceptable salt thereof, wherein G is:

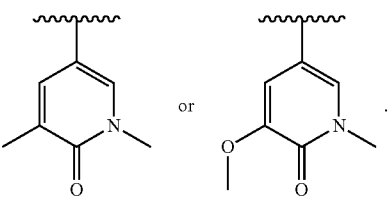
Another embodiment provides the compound of Formula II, or a pharmaceutically acceptable salt thereof, wherein G is:
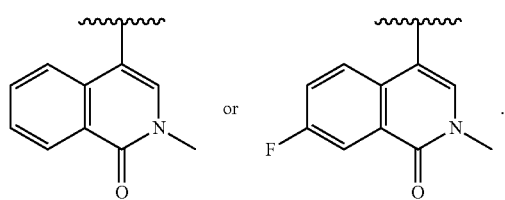 [SMILES: *c1cn(C)c(=O)c2ccccc12 ; *c1cn(C)c(=O)c2cc(F)ccc12]
Another embodiment provides the compound of Formula II, or a pharmaceutically acceptable salt thereof, wherein ring B is:
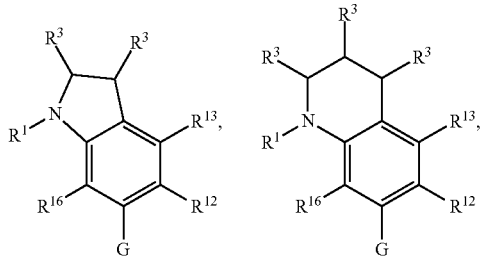
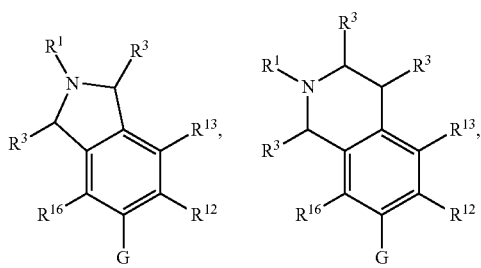
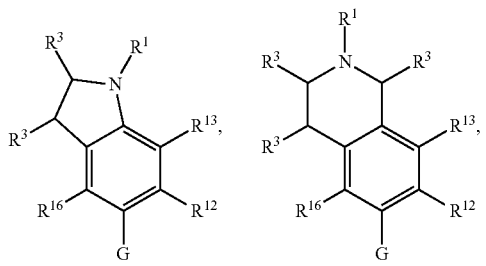
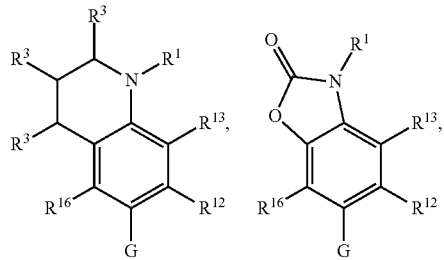
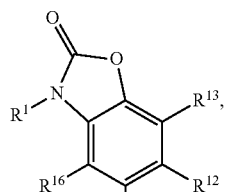
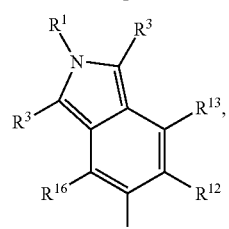
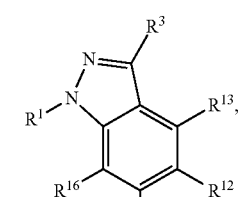
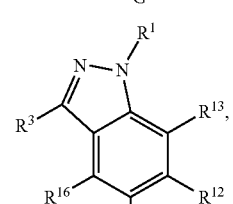
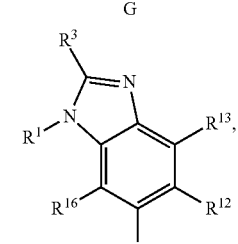
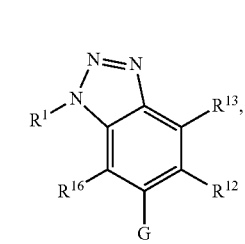

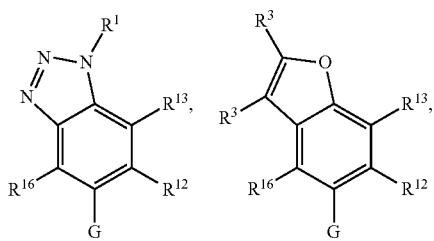

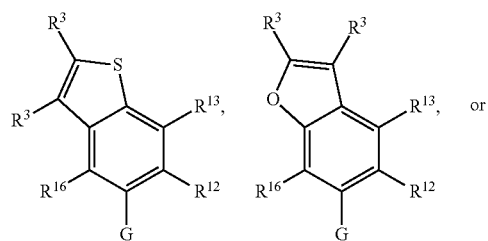

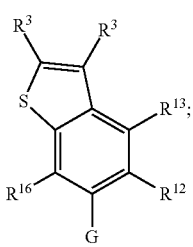

wherein R¹ is hydrogen, alkyl, cycloalkyl, cycloalkylalkyl, aryl, aralkyl, heterocyclyl, heterocyclylalkyl, heteroaryl, or heteroarylalkyl; each R³ is independently hydrogen, halogen, alkyl, alkylsulfonyl, alkylsulfinyl, alkoxy, alkoxyalkyl, cycloalkyl, cycloalkylalkyl, aryl, aralkyl, heterocyclyl, heterocyclylalkyl, heteroaryl, or heteroarylalkyl; and wherein $R^{12}$, $R^{13}$, and $R^{16}$ are as described above.

Another embodiment provides the compound of Formula II, or a pharmaceutically acceptable salt thereof, wherein ring B is:

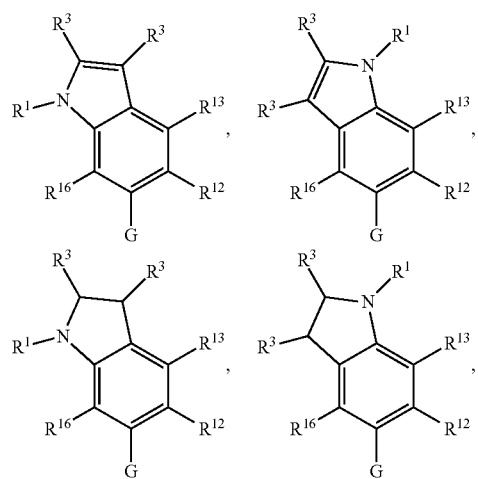

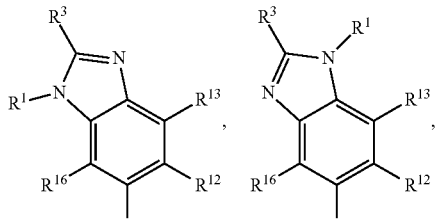

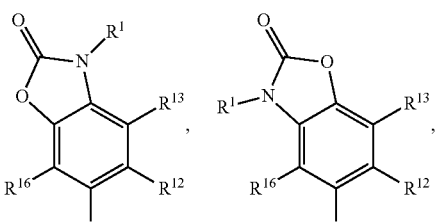

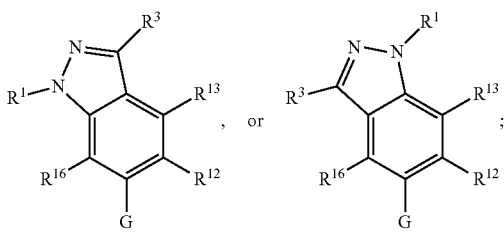

in which $R^1$, $R^3$, $R^{12}$, $R^{13}$, and $R^{16}$ are as described above.

Another embodiment provides the compound of Formula II, or a pharmaceutically acceptable salt thereof, wherein ring B is illustrated by a formula:

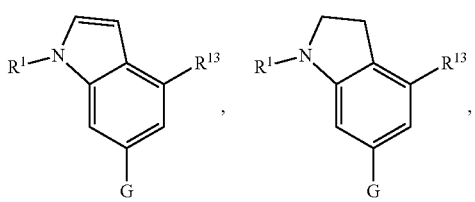

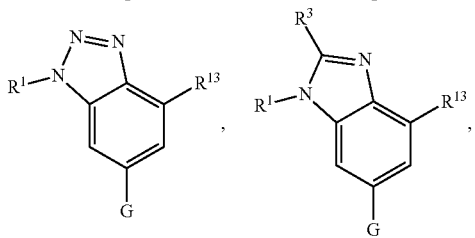

-continued

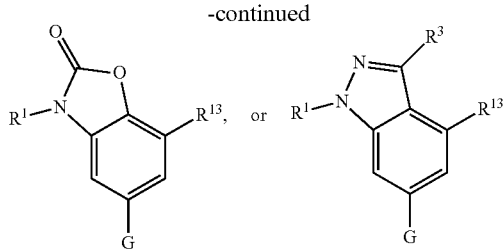

wherein R¹, R³, and R¹³ are as described above.

Another embodiment provides the compound of Formula II, or a pharmaceutically acceptable salt thereof, wherein ring B is an optionally substituted 5- or 6-membered heteroaryl ring containing at least one S or N atom. Another embodiment provides the compound of Formula II, or a pharmaceutically acceptable salt thereof, wherein ring B is an optionally substituted 5- or 6-membered heterocyclyl ring containing at least one S or N atom.

Another embodiment provides the compound of Formula II, or a pharmaceutically acceptable salt thereof, wherein ring B is an optionally substituted 5- or 6-membered heterocyclyl ring containing at least one N atom. Another embodiment provides the compound of Formula II, or a pharmaceutically acceptable salt thereof, wherein ring B is an optionally substituted 5- or 6-membered heteroaryl ring containing at least one N atom.

Another embodiment provides the compound of Formula II, or a pharmaceutically acceptable salt thereof, wherein ring B is an optionally substituted 5- or 6-membered heterocyclyl ring containing at least one S atom. Another embodiment provides the compound of Formula II, or a pharmaceutically acceptable salt thereof, wherein ring B is an optionally substituted 5- or 6-membered heteroaryl ring containing at least one S atom.

Another embodiment provides the compound of Formula II, or a pharmaceutically acceptable salt thereof, wherein X2 is N. Another embodiment provides the compound of Formula II, or a pharmaceutically acceptable salt thereof, wherein X3 is N. Another embodiment provides the compound of Formula II, or a pharmaceutically acceptable salt thereof, wherein X6 is N. Another embodiment provides the compound of Formula II, or a pharmaceutically acceptable salt thereof, wherein X2 is C—R¹² and R¹² is as described above. Another embodiment provides the compound of Formula II, or a pharmaceutically acceptable salt thereof, wherein X3 is C—R¹³ and R¹³ is as described above. Another embodiment provides the compound of Formula II, or a pharmaceutically acceptable salt thereof, wherein X6 is C—R¹⁶ and R¹⁶ is as described above. Another embodiment provides the compound of Formula II, or a pharmaceutically acceptable salt thereof, wherein X2 is C—R¹², X3 is C—R¹³, and X6 is C—R¹⁶, wherein R¹², R¹³, and R¹⁶ are as described above.

Another embodiment provides the compound of Formula II, or a pharmaceutically acceptable salt thereof, wherein R¹³ is —Y—Z, in which Y is a bond or —CH₂—, and Z is —SO₂R^b—N(R^a)SO₂R^b, or —SO₂N(R^a)₂, each R^a is independently hydrogen, alkyl, cycloalkyl, cycloalkylalkyl, aryl, aralkyl, heterocyclyl, heterocyclylalkyl, heteroaryl, or heteroarylalkyl, and R^b is alkyl, cycloalkyl, cycloalkylalkyl, aryl, aralkyl, heterocyclyl, heterocyclylalkyl, heteroaryl, or heteroarylalkyl; wherein R¹ is hydrogen, alkyl, cycloalkyl, cycloalkylalkyl, aryl, aralkyl, heterocyclyl, heterocyclylalkyl, heteroaryl, or heteroarylalkyl; and wherein R³ is hydrogen, halogen, alkyl, alkylsulfonyl, alkylsulfinyl, alkoxy, alkoxyalkyl, cycloalkyl, cycloalkylalkyl, aryl, aralkyl, heterocyclyl, heterocyclylalkyl, heteroaryl, or heteroarylalkyl.

Another embodiment provides the compound of Formula II, or a pharmaceutically acceptable salt thereof, wherein R¹³ is —Y—Z in which Y is a bond or —CH₂—, Z is —SO₂R^b or —N(R^a)SO₂R^b, each R^a is independently hydrogen or alkyl, and R^b is alkyl; wherein R¹ is alkyl, cycloalkylalkyl, or aralkyl; and wherein R³ is hydrogen, halogen, alkyl, or alkoxy.

Another embodiment provides the compound of Formula II, or a pharmaceutically acceptable salt thereof, wherein R¹⁶ is —W—X, wherein W is —O—, and X is alkyl aryl, cycloalkyl, or cycloalkylalkyl; wherein R¹ is hydrogen or alkyl; and wherein R² is alkyl.

Another embodiment provides the compound of Formula II, or a pharmaceutically acceptable salt thereof, wherein R¹⁶ is:

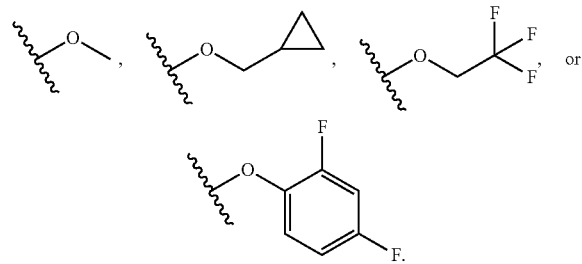

Another embodiment provides the compound of Formula II, or a pharmaceutically acceptable salt thereof, wherein R¹⁶ is:

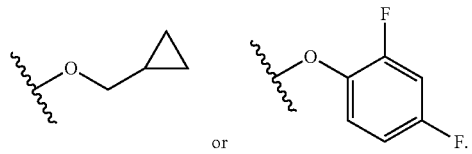 [SMILES: *OCC1CC1 ; *Oc1ccc(F)cc1F ; "or"]

At least one embodiment provides a compound of Formula III, or a pharmaceutically acceptable salt thereof, Formula III represented by:

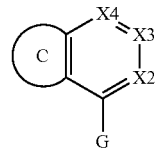

Formula III wherein

Ring C is an optionally substituted 5- or 6-membered heteroaryl ring containing at least one O, S or N atom;

X2 is N or C—R¹², wherein R¹² is hydrogen, halogen, alkyl, or alkoxy;

X3 is N or C—R¹³, wherein R¹³ is —Y—Z, in which Y is selected from a bond, —CH₂—, or —CH(C₁-C₄ alkyl)- and Z is selected from —SO₂R^b, —N(R^a) SO₂R^b, —SO₂N(R^a)₂, —N(R^a)SO₂N(R^a)₂, —CON (R^a)₂, —N(R^a)CO₂R^a, —N(R^a)CON(R^a)₂, —N(R^a)

COR$^a$, —OC(O)N(R$^a$)$_2$, —OSO$_2$N(R$^a$)$_2$, or —N(R$^a$)SO$_3$R$^b$, and wherein each R$^a$ is independently selected from hydrogen, alkyl, cycloalkyl, cycloalkylalkyl, aryl, aralkyl, heterocyclyl, heterocyclylalkyl, heteroaryl, or heteroarylalkyl, and R$^b$ is selected from alkyl, cycloalkyl, cycloalkylalkyl, aryl, aralkyl, heterocyclyl, heterocyclylalkyl, heteroaryl, or heteroarylalkyl;

X4 is N or C—R$^{14}$, wherein R$^{14}$ is hydrogen, halogen, —CN, alkyl, cycloalkyl, or alkoxy; and G is:

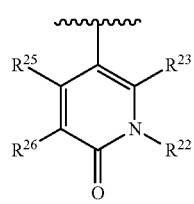

wherein,

R$^{22}$ is alkyl;

R$^{23}$ is hydrogen, halogen, or alkyl; or optionally, when R$^{23}$ is alkyl, R$^{22}$ and R$^{23}$ join to form an optionally substituted ring;

R$^{25}$ is hydrogen, halogen, alkyl, alkoxy, or alkenyl;

R$^{26}$ is hydrogen, halogen, alkyl, alkoxy, aminoalkyl, or alkenyl; or optionally, when R$^{23}$ is hydrogen, R$^{25}$ is not hydrogen and R$^{26}$ is not hydrogen or halogen, then R$^{25}$ and R$^{26}$ form an optionally substituted ring;

provided that the compound of Formula III is neither 4-(2-ethyl-5-(methyl-sulfonyl) benzofuran-7-yl)-2-methylisoquinolin-1(2H)-one, nor 4-(2-cyclopropyl-5-(methyl-sulfonyl)benzofuran-7-yl)-2-methylisoquinolin-1(2H)-one.

Another embodiment provides the compound of Formula III, or a pharmaceutically acceptable salt thereof, wherein G is:

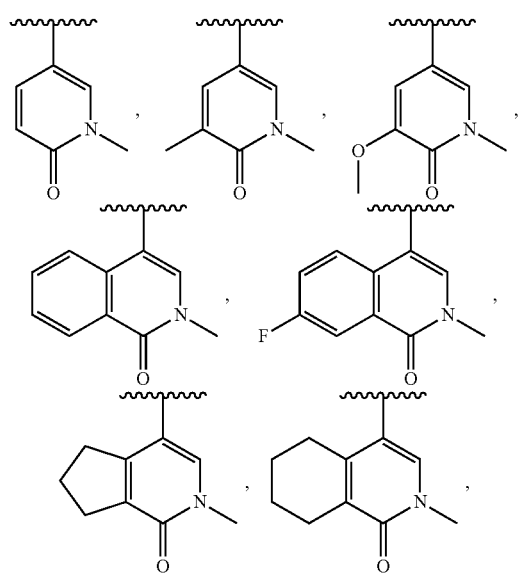

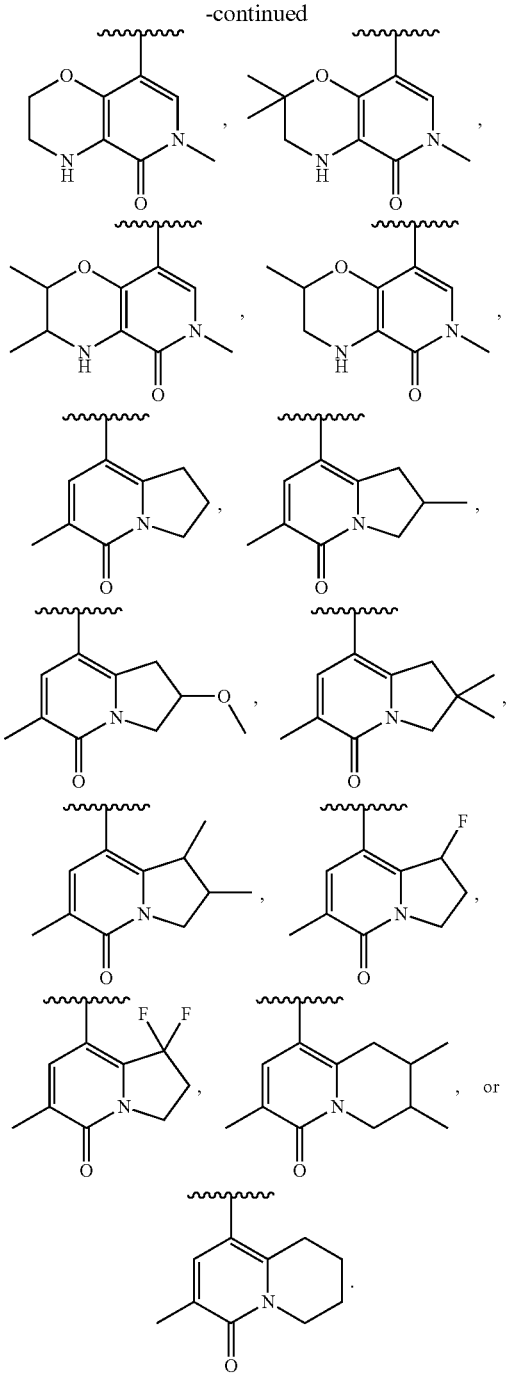

Another embodiment provides the compound of Formula III, or a pharmaceutically acceptable salt thereof, wherein G is:

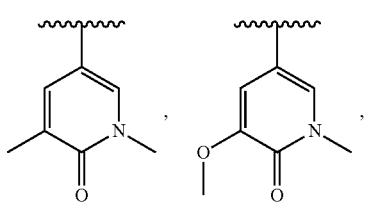

-continued

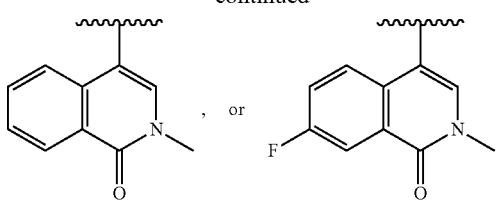

Another embodiment provides the compound of Formula III, or a pharmaceutically acceptable salt thereof, wherein G is:

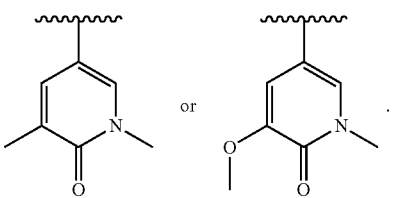

Another embodiment provides the compound of Formula III, or a pharmaceutically acceptable salt thereof, wherein G is:

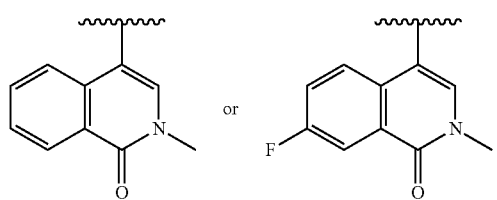

Another embodiment provides the compound of Formula III, or a pharmaceutically acceptable salt thereof, wherein ring C is:

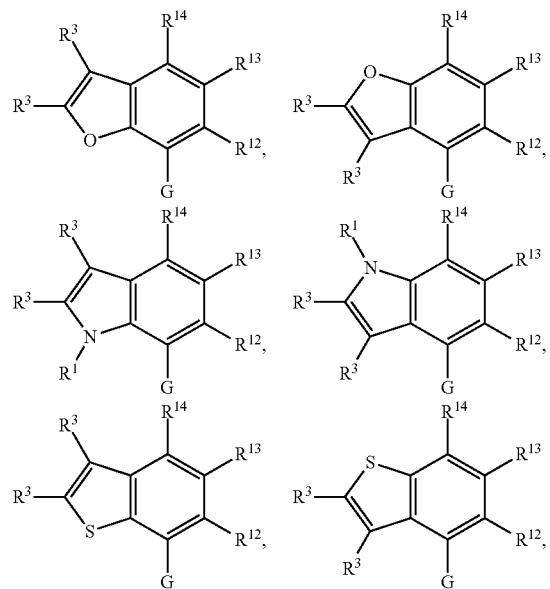

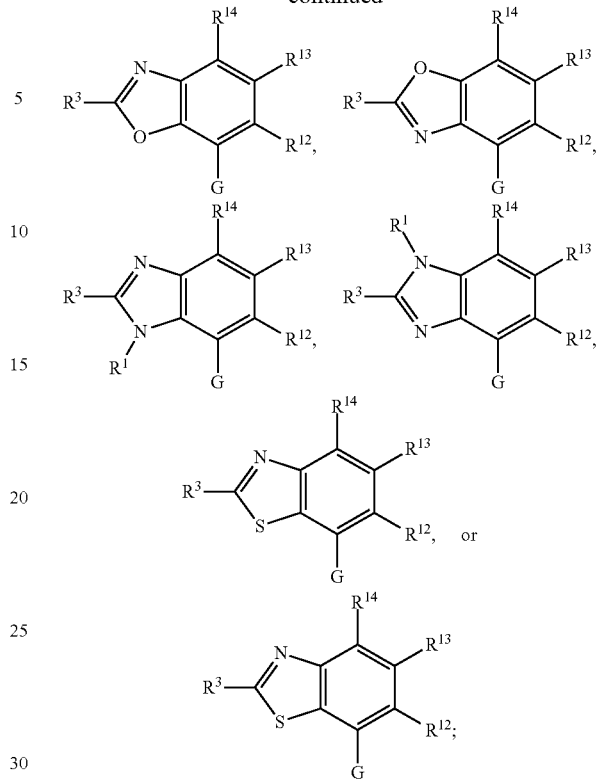

wherein $R^1$ is hydrogen, alkyl, cycloalkyl, cycloalkylalkyl, aryl, aralkyl, heterocyclyl, heterocyclylalkyl, heteroaryl, or heteroarylalkyl; and $R^3$ is hydrogen, halogen, alkyl, alkylsulfonyl, alkylsulfinyl, alkoxy, alkoxyalkyl, cycloalkyl, cycloalkylalkyl, aryl, aralkyl, heterocyclyl, heterocyclylalkyl, heteroaryl, or heteroarylalkyl; and $R^{12}$, $R^{13}$, and $R^{14}$ are as described above.

Another embodiment provides the compound of Formula III, or a pharmaceutically acceptable salt thereof, wherein ring C is:

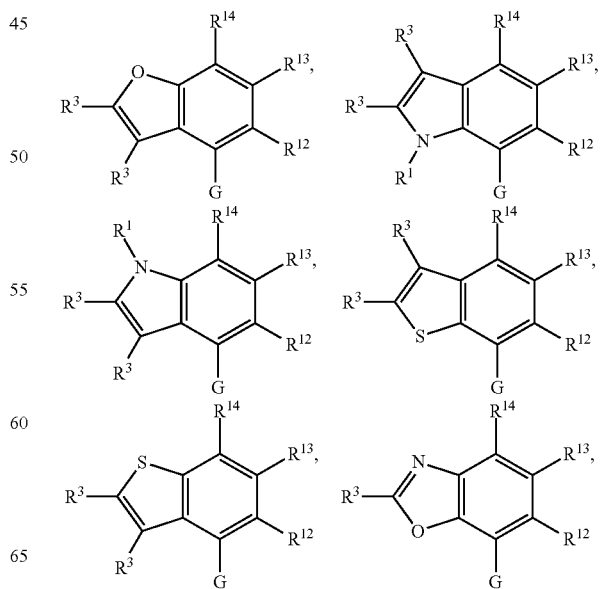

-continued

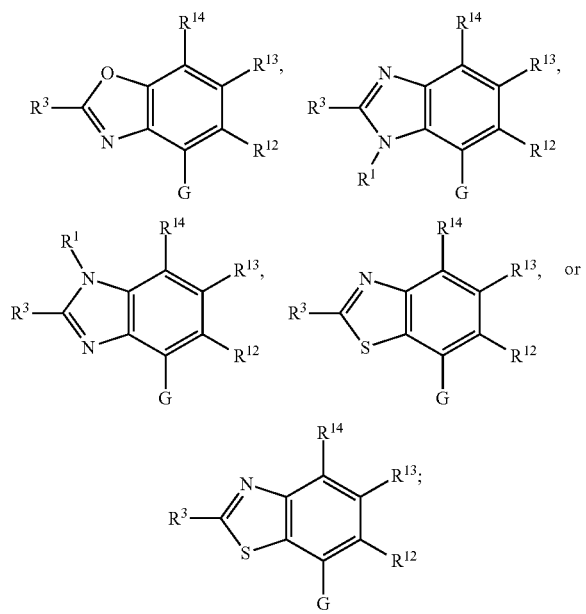

wherein $R^1$ is hydrogen, alkyl, cycloalkyl, cycloalkylalkyl, aryl, aralkyl, heterocyclyl, heterocyclylalkyl, heteroaryl, or heteroarylalkyl; and $R^3$ is hydrogen, halogen, alkyl, alkylsulfonyl, alkylsulfinyl, alkoxy, alkoxyalkyl, cycloalkyl, cycloalkylalkyl, aryl, aralkyl, heterocyclyl, heterocyclylalkyl, heteroaryl, or heteroarylalkyl; and wherein $R^{12}$, $R^{13}$, and $R^{14}$ are as described above.

Another embodiment provides the compound of Formula III, or a pharmaceutically acceptable salt thereof, wherein ring C is:

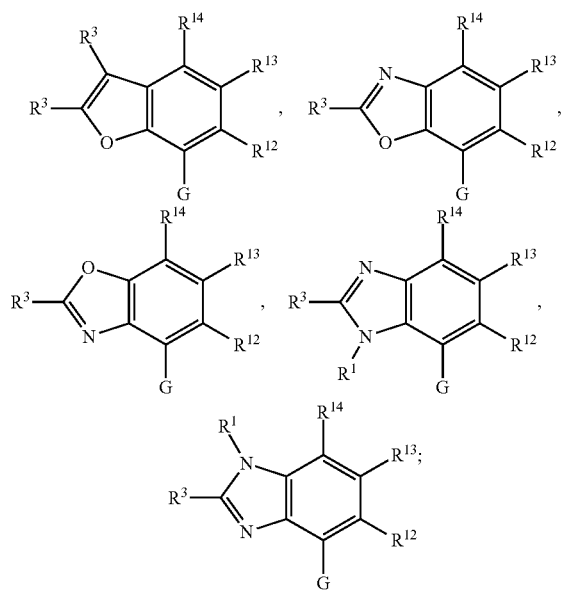

wherein $R^1$, $R^3$, $R^{12}$, $R^{13}$, and $R^{14}$ are as described above.

Another embodiment provides the compound of Formula III, or a pharmaceutically acceptable salt thereof, wherein ring C is:

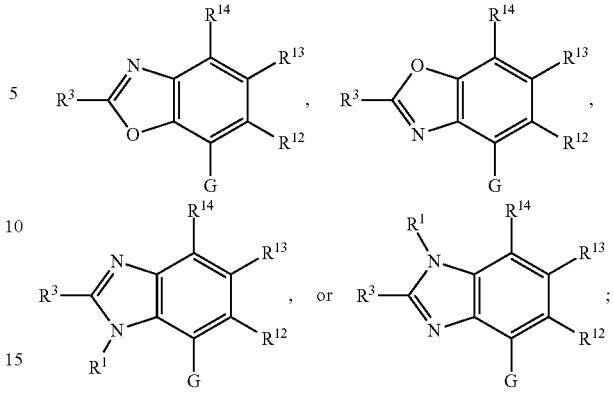

wherein $R^1$, $R^3$, $R^{12}$, $R^{13}$, and $R^{14}$ are as described above.

Another embodiment provides the compound of Formula III, or a pharmaceutically acceptable salt thereof, wherein ring C is:

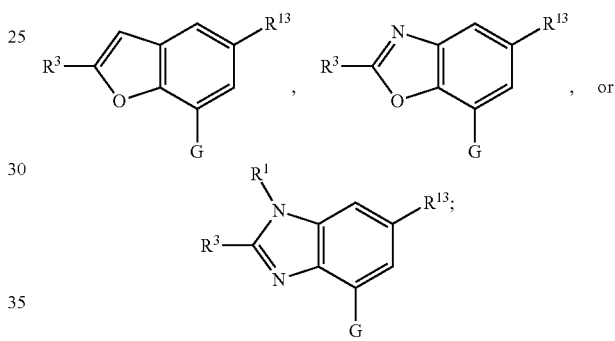

wherein $R^1$, $R^3$, and $R^{13}$ are as described above.

Another embodiment provides the compound of Formula III, or a pharmaceutically acceptable salt thereof, wherein ring C is:

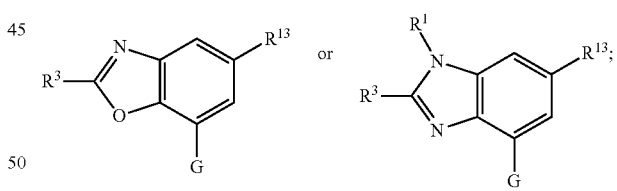

wherein $R^1$, $R^3$, and $R^{13}$ are as described above.

Another embodiment provides the compound of Formula III, or a pharmaceutically acceptable salt thereof, wherein ring C is:

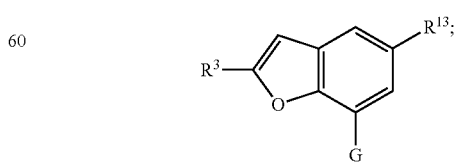

wherein $R^1$ and $R^{13}$ are as described above.

An alternative embodiment provides the compound of Formula III, or a pharmaceutically acceptable salt thereof, wherein, optionally, ring C is not:

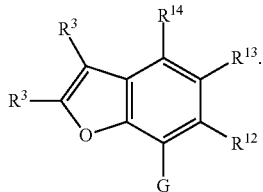

Another embodiment provides the compound of Formula III, or a pharmaceutically acceptable salt thereof, wherein $R^{13}$ is —Y—Z, in which Y is a bond, or —CH$_2$— and Z is selected from —SO$_2$R$^b$, —N(R$^a$)SO$_2$R$^b$, or —SO$_2$N(R$^a$)$_2$, and in which each R$^a$ is independently hydrogen, alkyl, cycloalkyl, cycloalkylalkyl, aryl, aralkyl, heterocyclyl, heterocyclylalkyl, heteroaryl, or heteroarylalkyl, and R$^b$ is alkyl, cycloalkyl, cycloalkylalkyl, aryl, aralkyl, heterocyclyl, heterocyclylalkyl, heteroaryl, or heteroarylalkyl; $R^1$ is hydrogen, alkyl, cycloalkyl, cycloalkylalkyl, aryl, aralkyl, heterocyclyl, heterocyclylalkyl, heteroaryl, or heteroarylalkyl; and $R^3$ is hydrogen, halogen, alkyl, alkylsulfonyl, alkylsulfinyl, alkoxy, alkoxyalkyl, cycloalkyl, cycloalkylalkyl, aryl, aralkyl, heterocylyl, heterocyclylalkyl, heteroaryl, or heteroarylalkyl; and wherein each remaining substituent is otherwise as described above.

Another embodiment provides the compound of Formula III, or a pharmaceutically acceptable salt thereof, wherein $R^{13}$ is —Y—Z in which Y is a bond, or —CH$_2$— and Z is selected from —SO$_2$R$^b$, or —N(R$^a$)SO$_2$R$^b$, in which each R$^a$ is independently hydrogen or alkyl, R$^b$ is alkyl, $R^1$ is alkyl, and $R^3$ is alkyl, cycloalkyl, or aryl.

Another embodiment provides the compound of Formula III, or a pharmaceutically acceptable salt thereof, wherein ring C is an optionally substituted 5- or 6-membered heteroaryl ring containing at least one O atom. Another embodiment provides the compound of Formula III, or a pharmaceutically acceptable salt thereof, wherein ring C is an optionally substituted 5- or 6-membered heteroaryl ring containing at least one S atom. Another embodiment provides the compound of Formula III, or a pharmaceutically acceptable salt thereof, wherein ring C is an optionally substituted 5- or 6-membered heteroaryl ring containing at least one N atom.

Another embodiment provides the compound of Formula III, or a pharmaceutically acceptable salt thereof, wherein X2 is N. Another embodiment provides the compound of Formula III, or a pharmaceutically acceptable salt thereof, wherein X3 is N. Another embodiment provides the compound of Formula III, or a pharmaceutically acceptable salt thereof, wherein X4 is N.

Another embodiment provides the compound of Formula III, or a pharmaceutically acceptable salt thereof, wherein X2 is C—R$^{12}$, wherein R$^{12}$ is as described above. Another embodiment provides the compound of Formula III, or a pharmaceutically acceptable salt thereof, wherein X3 is C—R$^{13}$, wherein R$^{13}$ is as described above. Another embodiment provides the compound of Formula III, or a pharmaceutically acceptable salt thereof, wherein X4 is C—R$^{14}$ wherein R$^{14}$ is as described above. Another embodiment provides the compound of Formula III, or a pharmaceutically acceptable salt thereof, wherein X2 is C—R$^{12}$, X3 is C—R$^{13}$, and X4 is C—R$^{14}$ wherein R$^{12}$, R$^{13}$, and R$^{14}$ are as described above.

One embodiment provides a compound of Formula IV, or a pharmaceutically acceptable salt thereof, Formula IV represented by:

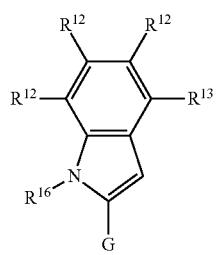

Formula IV wherein each $R^{12}$ is independently hydrogen, halogen, alkyl, or alkoxy;

$R^{13}$ is —Y—Z, in which Y is selected from a bond, —CH$_2$—, or —CH(C$_1$-C$_4$ alkyl)- and Z is selected from —SO$_2$R$^b$, —N(R$^a$)SO$_2$R$^b$, —SO$_2$N(R$^a$)$_2$, —N(R$^a$)SO$_2$N(R$^a$)$_2$, —CON(R$^a$)$_2$, —N(R$^a$)CO$_2$R$^a$, —N(R$^a$)CON(R$^a$)$_2$, —N(R$^a$)COR$^a$, —OC(O)N(R$^a$)$_2$, —OSO$_2$N(R$^a$)$_2$, or —N(R$^a$)SO$_3$R$^b$, wherein each R$^a$ is independently hydrogen, alkyl, cycloalkyl, cycloalkylalkyl, aryl, aralkyl, heterocyclyl, heterocyclylalkyl, heteroaryl, or heteroarylalkyl, and R$^b$ is alkyl, cycloalkyl, cycloalkylalkyl, aryl, aralkyl, heterocyclyl, heterocyclylalkyl, heteroaryl, or heteroarylalkyl;

$R^{16}$ is alkyl, alkynyl, aryl, aralkyl, cycloalkyl, cycloalkylalkyl, cycloalkylalkynyl, heterocyclyl, heterocyclylalkyl, heteroaryl, or heteroarylalkyl; and G is:

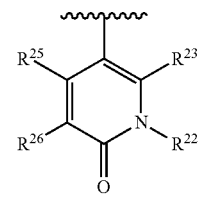

wherein, $R^{22}$ is alkyl;

$R^{23}$ is hydrogen, halogen, or alkyl; or, optionally, when $R^{23}$ is alkyl, $R^{22}$ and $R^{23}$ join to form an optionally substituted ring;

$R^{25}$ is hydrogen, halogen, alkyl, alkoxy, or alkenyl;

$R^{26}$ is hydrogen, halogen, alkyl, alkoxy, aminoalkyl, or alkenyl; or optionally, when $R^{23}$ is hydrogen, $R^{25}$ is not hydrogen, and $R^{26}$ is neither hydrogen nor halogen, then $R^{25}$ and $R^{26}$ join to form an optionally substituted ring.

Another embodiment provides the compound of Formula IV, or a pharmaceutically acceptable salt thereof, wherein G is:

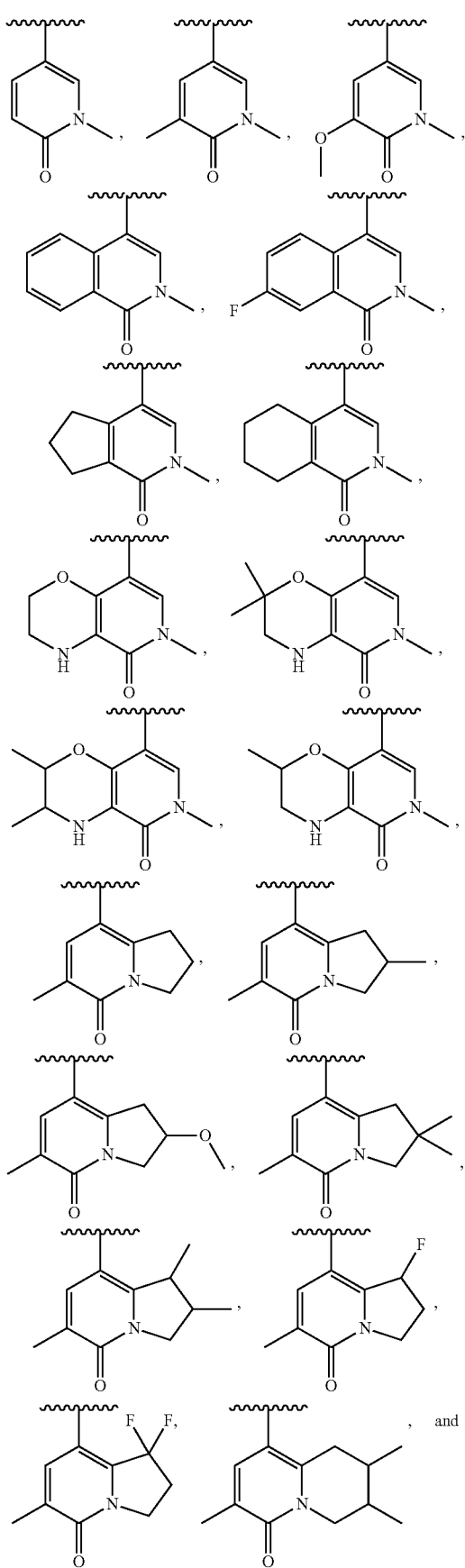

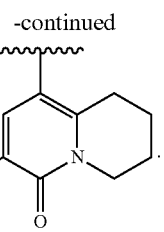

Another embodiment provides the compound of Formula IV, or a pharmaceutically acceptable salt thereof, wherein G is:

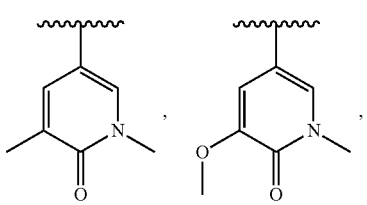

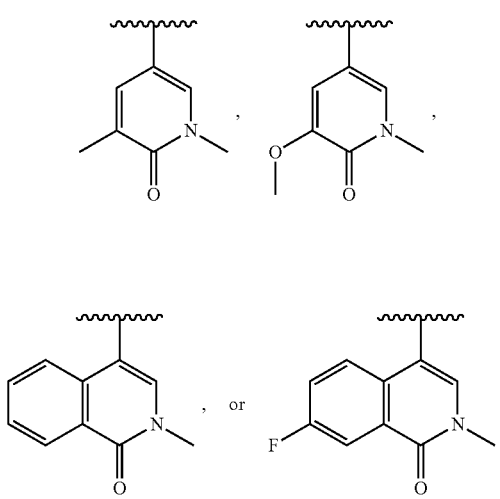

Another embodiment provides the compound of Formula IV, or a pharmaceutically acceptable salt thereof, wherein G is:

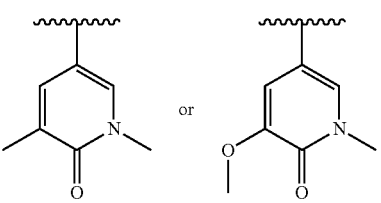

Another embodiment provides the compound of Formula IV, or a pharmaceutically acceptable salt thereof, wherein G is:

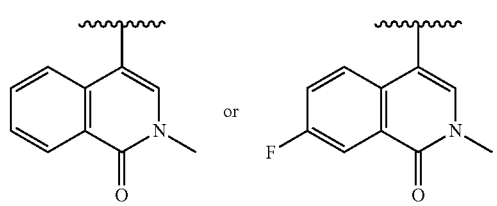

Another embodiment provides the compound of Formula IV that is Formula IVa, or a pharmaceutically acceptable salt thereof, wherein $R^{13}$, $R^{14}$, and G are as described above:

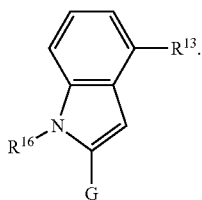

Formula IVa

Another embodiment provides the compound of Formula IVa, or a pharmaceutically acceptable salt thereof, wherein $R^{13}$ is —Y—Z, in which Y is a bond or —CH$_2$—, and Z is —SO$_2$R$^b$—N(R$^a$)SO$_2$R$^b$, or —SO$_2$N(R$^a$)$_2$, in which each R$^a$ is independently hydrogen, alkyl, cycloalkyl, cycloalkylalkyl, aryl, aralkyl, heterocyclyl, heterocyclylalkyl, heteroaryl, or heteroarylalkyl, and R$^b$ is alkyl, cycloalkyl, cycloalkylalkyl, aryl, aralkyl, heterocyclyl, heterocyclylalkyl, heteroaryl, or heteroarylalkyl; and R$^{16}$ is alkyl, alkynyl, aryl, aralkyl, cycloalkyl, cycloalkylalkyl, cycloalkylalkynyl, heterocyclyl, heterocyclylalkyl, heteroaryl, or heteroarylalkyl.

Another embodiment provides the compound of Formula IVa, or a pharmaceutically acceptable salt thereof, wherein $R^{13}$ is —Y—Z, in which Y is a bond or —CH$_2$—, Z is —SO$_2$R$^b$ or —N(R$^a$)SO$_2$R$^b$, in which each R$^a$ is independently hydrogen or alkyl, and R$^b$ is alkyl; and wherein R$^{16}$ is selected from alkyl or cycloalkylalkyl.

At least one embodiment provides a compound of Formula Va, or a pharmaceutically acceptable salt thereof, having the structure:

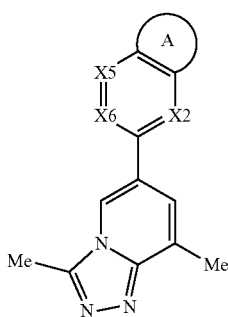

Formula Va wherein
Ring A is an optionally substituted 5- or 6-membered heteroaryl ring containing at least one S or N atom, or an optionally substituted 5- or 6-membered heterocyclyl ring containing at least one S or N atom;
X2 is N or C—R$^{12}$, in which R$^{12}$ is hydrogen, halogen, alkyl, or alkoxy;
X5 is N or C—R$^{15}$, in which R$^{15}$ is hydrogen, halogen, —CN, alkyl or alkoxy; and
X6 is N or C—R$^{16}$, in which R$^{16}$ is hydrogen, halogen, or —W—X, wherein W is a bond, —O—, —S—, or —NH—, and X is alkyl, alkynyl, aryl, aralkyl, cycloalkyl, cycloalkylalkyl, cycloalkylalkynyl, heterocyclyl, heterocyclylalkyl, heteroaryl, or heteroarylalkyl.

One embodiment provides a compound of Formula Vb, or a pharmaceutically acceptable salt thereof, Formula Vb represented by:

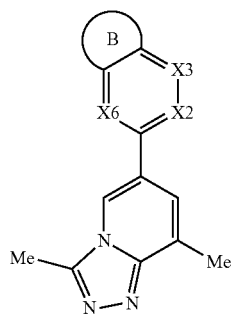

Formula Vb wherein
Ring B is an optionally substituted 5- or 6-membered heteroaryl ring containing at least one S or N atom, or an optionally substituted 5- or 6-membered heterocyclyl ring containing at least one S or N atom;
X2 is N or C—R$^{12}$, in which R$^{12}$ is hydrogen, halogen, alkyl, or alkoxy;
X3 is N or C—R$^{13}$, in which R$^{13}$ is —Y—Z, wherein Y is selected from a bond, —CH$_2$—, or —CH(C$_1$-C$_4$ alkyl)-, and Z is selected from —SO$_2$R$^b$, —N(R$^a$)SO$_2$R$^b$, —SO$_2$N(R$^a$)$_2$, —N(R$^a$)SO$_2$N(R$^a$)$_2$, —CON(R$^a$)$_2$, —N(R$^a$)CO$_2$R$^a$, —N(R$^a$)CON(R$^a$)$_2$, —N(R$^a$)COR$^a$, —OC(O)N(R$^a$)$_2$, —OSO$_2$N(R$^a$)$_2$, or —N(R$^a$)SO$_3$R$^b$, each R$^a$ is independently hydrogen, alkyl, cycloalkyl, cycloalkylalkyl, aryl, aralkyl, heterocyclyl, heterocyclylalkyl, heteroaryl, or heteroarylalkyl, and R$^b$ is alkyl, cycloalkyl, cycloalkylalkyl, aryl, aralkyl, heterocyclyl, heterocyclylalkyl, heteroaryl, or heteroarylalkyl; and
X6 is N or C—R$^{16}$, in which R$^{16}$ is hydrogen, halogen, or —W—X, wherein W is a bond, —O—, —S—, or —NH—, and X is alkyl, alkynyl, aryl, aralkyl, cycloalkyl, cycloalkylalkyl, cycloalkylalkynyl, heterocyclyl, heterocyclylalkyl, heteroaryl, or heteroarylalkyl.

At least one embodiment provides a compound of Formula Vc, or a pharmaceutically acceptable salt thereof:

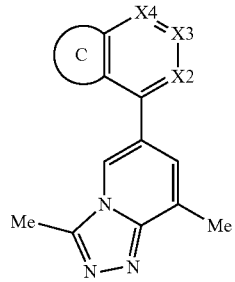

Formula Vc wherein
Ring C is an optionally substituted 5- or 6-membered heteroaryl ring containing at least one O, S or N atom;
X2 is N or C—R$^{12}$, in which R$^{12}$ is hydrogen, halogen, alkyl, or alkoxy;
X3 is N or C—R$^{13}$, in which R$^{13}$ is —Y—Z, in which Y is a bond, —CH$_2$—, or —CH(C$_1$-C$_4$ alkyl)-, and Z is selected from —SO$_2$R$^b$, —N(R$^a$)SO$_2$R$^b$, —SO$_2$N(R$^a$)$_2$, —N(R$^a$)SO$_2$N(R$^a$)$_2$, —CON(R$^a$)$_2$, —N(R$^a$)CO$_2$R$^a$, —N(R$^a$)CON(R$^a$)$_2$, —N(R$^a$)COR$^a$, —OC(O)

N(R$^a$)$_2$, —OSO$_2$N(R$^a$)$_2$, or —N(R$^a$)SO$_3$R$^b$, wherein each R$^a$ is independently hydrogen, alkyl, cycloalkyl, cycloalkylalkyl, aryl, aralkyl, heterocyclyl, heterocyclylalkyl, heteroaryl, or heteroarylalkyl, and R$^b$ is alkyl, cycloalkyl, cycloalkylalkyl, aryl, aralkyl, heterocyclyl, heterocyclylalkyl, heteroaryl, or heteroarylalkyl; and X4 is N or C—R$^{14}$, in which R$^{14}$ is hydrogen, halogen, —CN, alkyl, cycloalkyl, or alkoxy.

At least on embodiment provides a compound of Formula Vd, or a pharmaceutically acceptable salt thereof,

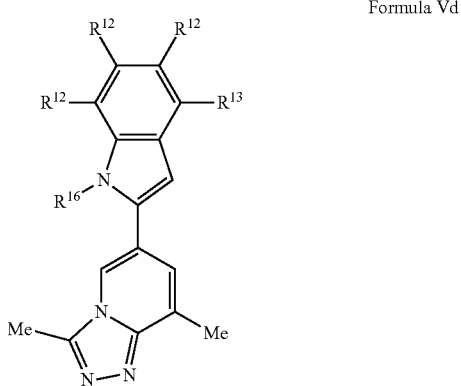

Formula Vd wherein each R$^{12}$ is independently hydrogen, halogen, alkyl, or alkoxy;

R$^{13}$ is —Y—Z, in which Y is a bond, —CH$_2$—, or —CH(C$_1$-C$_4$ alkyl)-, and Z is selected from —SO$_2$R$^b$, —N(R$^a$)SO$_2$R$^b$, —SO$_2$N(R$^a$)$_2$, —N(R$^a$)SO$_2$N(R$^a$)$_2$, —CON(R$^a$)$_2$, —N(R$^a$)CO$_2$R$^a$, —N(R$^a$)CON(R$^a$)$_2$, —N(R$^a$)COR$^a$, —OC(O)N(R$^a$)$_2$, —OSO$_2$N(R$^a$)$_2$, or —N(R$^a$)SO$_3$R$^b$, wherein each R$^a$ is independently hydrogen, alkyl, cycloalkyl, cycloalkylalkyl, aryl, aralkyl, heterocyclyl, heterocyclylalkyl, heteroaryl, or heteroarylalkyl, and R$^b$ is alkyl, cycloalkyl, cycloalkylalkyl, aryl, aralkyl, heterocyclyl, heterocyclylalkyl, heteroaryl, or heteroarylalkyl; and R$^{16}$ is alkyl, alkynyl, aryl, aralkyl, cycloalkyl, cycloalkylalkyl, cycloalkylalkynyl, heterocyclyl, heterocyclylalkyl, heteroaryl, or heteroarylalkyl.

At least one embodiment provides a compound of Formula Ve, or a pharmaceutically acceptable salt thereof:

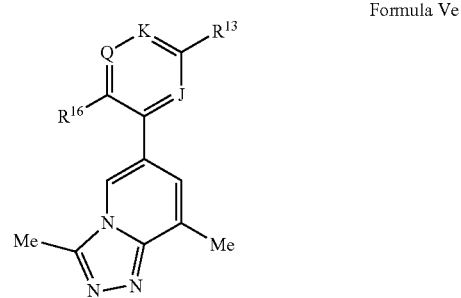

Formula Ve wherein

J is N or C—R$^{12}$, in which R$^{12}$ is hydrogen, halogen, alkyl, or alkoxy;

R$^{13}$ is —Y—Z, in which Y is a bond, —CH$_2$—, or —CH(C$_1$-C$_4$alkyl)-, and Z is —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —COR$^{21}$, —OC(O)N(R$^{22}$)$_2$, —OSO$_2$N(R$^{22}$)$_2$, or —N(R$^{22}$)SO$_3$R$^{21}$, in which each R$^{21}$ is independently alkyl, cycloalkyl, cycloalkylalkyl, aryl, aralkyl, heterocyclyl, heterocyclylalkyl, heteroaryl, or heteroarylalkyl, and wherein each R$^{22}$ is independently hydrogen, alkyl, cycloalkyl, cycloalkylalkyl, aryl, aralkyl, heterocyclyl, heterocyclylalkyl, heteroaryl, or heteroarylalkyl;

K is N or C—R$^{14}$, in which R$^{14}$ is hydrogen, halogen, —CN, alkyl, cycloalkyl, or alkoxy;

Q is N or C—R$^{15}$, in which R$^{15}$ is hydrogen, halogen, —CN, alkyl, alkoxy, aryloxy, aralkyloxy, cycloalkylalkyloxy, heterocyclyloxy, heteroarylalkyloxy, or alkynyloxy; and R$^{16}$ is hydrogen, halogen, —N(H)COX, or —W—X, wherein W is a bond, —O—, —S—, or —NH—, and X is alkyl, aryl, aralkyl, cycloalkyl, cycloalkylalkyl, alkynyl, cycloalkylalkynyl, heterocyclyl, heterocyclylalkyl, heteroaryl, or heteroarylalkyl.

At least one embodiment provides a compound of Formula VI, or a pharmaceutically acceptable salt thereof, in which Formula VI is:

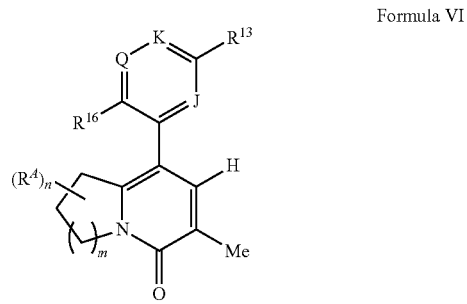

Formula VI wherein n is 0 to 4; m is 0 or 1;

R$^A$ is a halogen, C1-3 alkyl, or C1-3 alkoxy;

J is N or C—R$^{12}$, wherein R$^{12}$ is hydrogen, halogen, alkyl, or alkoxy;

R$^{13}$ is —Y—Z, in which Y is a bond, —CH$_2$—, or —CH(C$_1$-C$_4$alkyl)-, and Z is —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —COR$^{21}$, —OC(O)N(R$^{22}$)$_2$, —OSO$_2$N(R$^{22}$)$_2$, or —N(R$^{22}$)SO$_3$R$^{21}$, wherein each R$^{21}$ is independently alkyl, cycloalkyl, cycloalkylalkyl, aryl, aralkyl, heterocyclyl, heterocyclylalkyl, heteroaryl, or heteroarylalkyl, and each R$^{22}$ is independently hydrogen, alkyl, cycloalkyl, cycloalkylalkyl, aryl, aralkyl, heterocyclyl, heterocyclylalkyl, heteroaryl, or heteroarylalkyl.

K is N or C—R$^{14}$, wherein R$^{14}$ is hydrogen, halogen, —CN, alkyl, cycloalkyl, or alkoxy;

Q is N or C—R$^{15}$, wherein R$^{15}$ is hydrogen, halogen, —CN, alkyl, alkoxy, aryloxy, aralkyloxy, cycloalkylalkyloxy, heterocyclyloxy, heteroarylalkyloxy, or alkynyloxy; and R$^{16}$ is hydrogen, halogen, —N(H)COX, or —W—X, wherein W is a bond, —O—, —S—, or —NH—, and X is alkyl, aryl, aralkyl, cycloalkyl, cycloalkylalkyl, alkynyl, cycloalkylalkynyl, heterocyclyl, heterocyclylalkyl, heteroaryl, or heteroarylalkyl.

In some embodiments, the substituted heterocyclic derivative compound disclosed herein has the structure and chemical name provided in Table 1, in which "Ex. No." refers to the Example describing the synthesis of the compound.

TABLE 1

| Ex. No | Structure | Name |
|---|---|---|
| 1 | 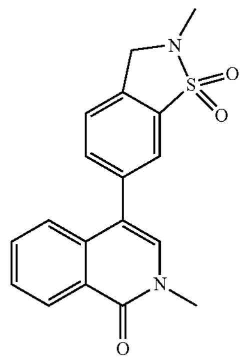 [SMILES: CN1Cc2ccc(-c3cn(C)c(=O)c4ccccc34)cc2S1(=O)=O] | 2-methyl-4-(2-methyl-1,1-dioxo-3H-1,2-benzothiazol-6-yl)isoquinolin-1-one |
| 2 | 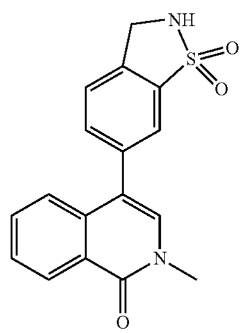 [SMILES: Cn1cc(-c2ccc3c(c2)S(=O)(=O)NC3)c2ccccc2c1=O] | 4-(1,1-dioxo-2,3-dihydro-1,2-benzothiazol-6-yl)-2-methylisoquinolin-1-one |
| 3 | 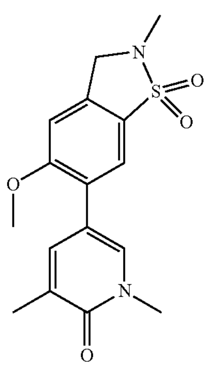 [SMILES: COc1cc2c(cc1-c1cc(C)c(=O)n(C)c1)S(=O)(=O)N(C)C2] | 5-(5-methoxy-2-methyl-1,1-dioxo-3H-1,2-benzothiazol-6-yl)-1,3-dimethylpyridin-2-one |
| 4 | 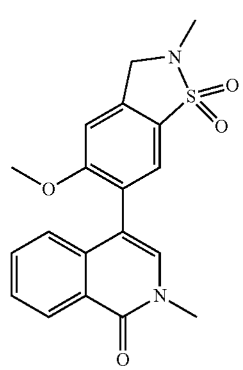 [SMILES: COc1cc2c(cc1-c1cn(C)c(=O)c3ccccc13)S(=O)(=O)N(C)C2] | 4-(5-methoxy-2-methyl-1,1-dioxo-3H-1,2-benzothiazol-6-yl)-2-methylisoquinolin-1-one |

TABLE 1-continued

| Ex. No | Structure | Name |
|---|---|---|
| 5 | 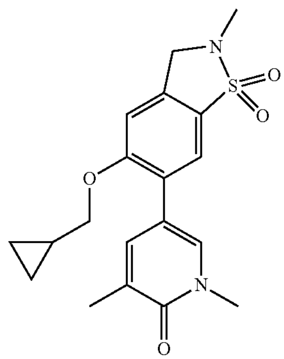 [SMILES: Cc1cc(-c2cc3c(cc2OCC2CC2)CN(C)S3(=O)=O)cn(C)c1=O] | 5-[5-(cyclopropylmethoxy)-2-methyl-1,1-dioxo-3H-1,2-benzothiazol-6-yl]-1,3-dimethylpyridin-2-one |
| 6 | 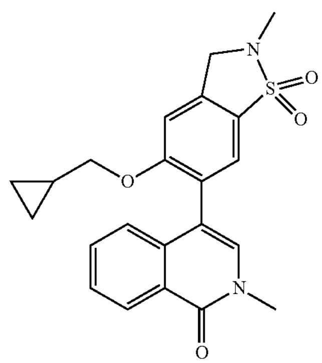 [SMILES: CN1Cc2cc(OCC3CC3)c(-c3cn(C)c(=O)c4ccccc34)cc2S1(=O)=O] | 4-[5-(cyclopropylmethoxy)-2-methyl-1,1-dioxo-3H-1,2-benzothiazol-6-yl]-2-methylisoquinolin-1-one |
| 7 | 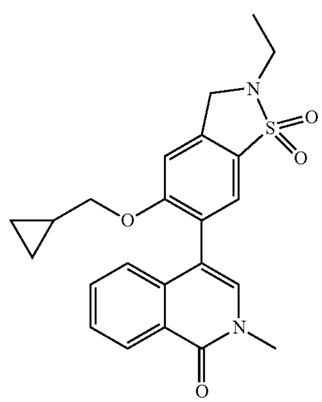 [SMILES: CCN1Cc2cc(OCC3CC3)c(-c3cn(C)c(=O)c4ccccc34)cc2S1(=O)=O] | 4-[5-(cyclopropylmethoxy)-2-ethyl-1,1-dioxo-3H-1,2-benzothiazol-6-yl]-2-methylisoquinolin-1-one |
| 8 | 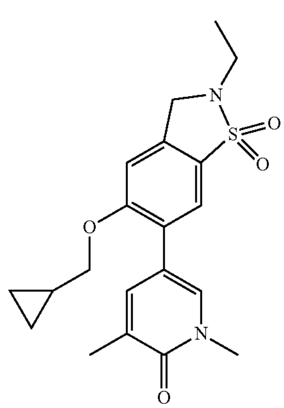 [SMILES: CCN1Cc2cc(OCC3CC3)c(-c3cc(C)c(=O)n(C)c3)cc2S1(=O)=O] | 5-[5-(cyclopropylmethoxy)-2-ethyl-1,1-dioxo-3H-1,2-benzothiazol-6-yl]-1,3-dimethylpyridin-2-one |

TABLE 1-continued

| Ex. No | Structure | Name |
|---|---|---|
| 9 | 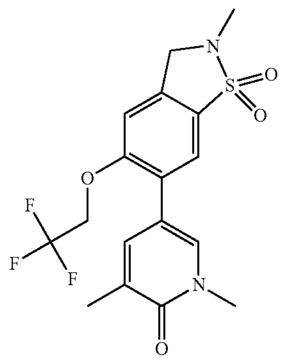 [SMILES: Cc1cc(-c2cc3c(cc2OCC(F)(F)F)CN(C)S3(=O)=O)cn(C)c1=O] | 1,3-dimethyl-5-[2-methyl-1,1-dioxo-5-(2,2,2-trifluoroethoxy)-3H-1,2-benzothiazol-6-yl]pyridin-2-one |
| 10 | 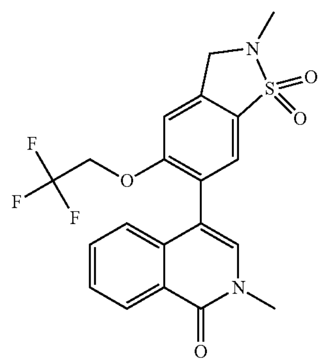 [SMILES: CN1Cc2cc(OCC(F)(F)F)c(-c3cn(C)c(=O)c4ccccc34)cc2S1(=O)=O] | 2-methyl-4-[2-methyl-1,1-dioxo-5-(2,2,2-trifluoroethoxy)-3H-1,2-benzothiazol-6-yl]isoquinolin-1-one |
| 11 | 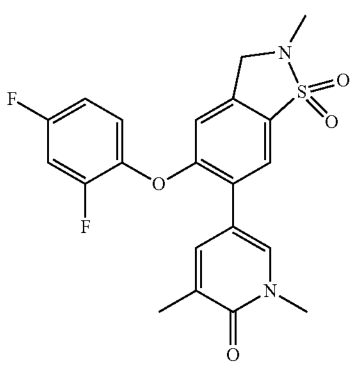 [SMILES: Cc1cc(-c2cc3c(cc2Oc2ccc(F)cc2F)CN(C)S3(=O)=O)cn(C)c1=O] | 5-[5-(2,4-difluorophenoxy)-2-methyl-1,1-dioxo-3H-1,2-benzothiazol-6-yl]-1,3-dimethylpyridin-2-one |
| 12 | 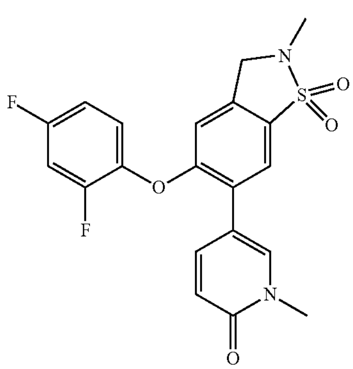 [SMILES: CN1Cc2cc(Oc3ccc(F)cc3F)c(-c3ccc(=O)n(C)c3)cc2S1(=O)=O] | 5-[5-(2,4-difluorophenoxy)-2-methyl-1,1-dioxo-3H-1,2-benzothiazol-6-yl]-1-methylpyridin-2-one |

TABLE 1-continued

| Ex. No | Structure | Name |
|---|---|---|
| 13 | 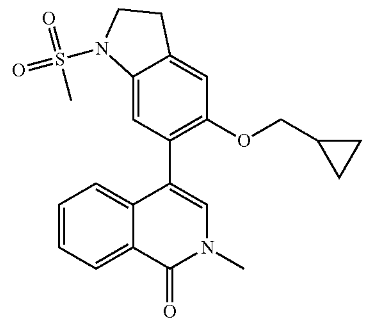 [SMILES: Cn1cc(-c2cc3c(cc2OCC2CC2)CCN3S(C)(=O)=O)c2ccccc2c1=O] | 4-[5-(cyclopropylmethoxy)-1-methylsulfonyl-2,3-dihydroindol-6-yl]-2-methylisoquinolin-1-one |
| 14 | 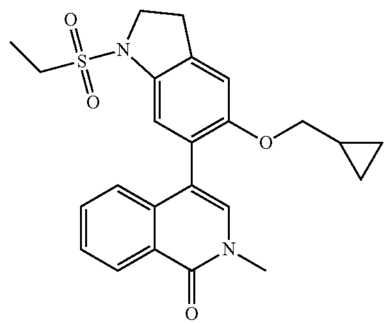 [SMILES: CCS(=O)(=O)N1CCc2cc(OCC3CC3)c(-c3cn(C)c(=O)c4ccccc34)cc21] | 4-[5-(cyclopropylmethoxy)-1-ethylsulfonyl-2,3-dihydroindol-6-yl]-2-methylisoquinolin-1-one |
| 15 | 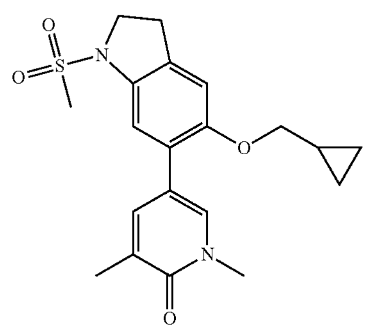 [SMILES: Cc1cc(-c2cc3c(cc2OCC2CC2)CCN3S(C)(=O)=O)cn(C)c1=O] | 5-[5-(cyclopropylmethoxy)-1-methylsulfonyl-2,3-dihydroindol-6-yl]-1,3-dimethylpyridin-2-one |
| 16 | 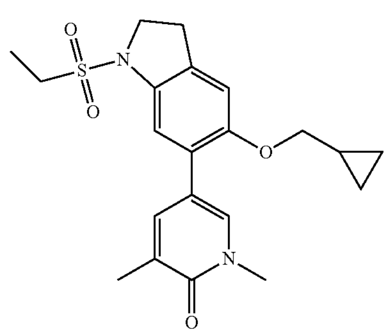 [SMILES: CCS(=O)(=O)N1CCc2cc(OCC3CC3)c(-c3cc(C)c(=O)n(C)c3)cc21] | 5-[5-(cyclopropylmethoxy)-1-ethylsulfonyl-2,3-dihydroindol-6-yl]-1,3-dimethylpyridin-2-one |

TABLE 1-continued

| Ex. No | Structure | Name |
|---|---|---|
| 17 | 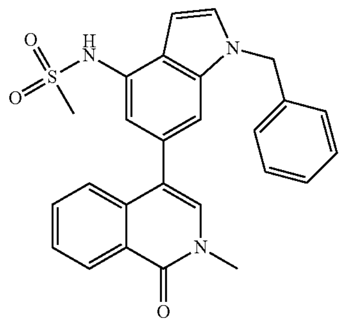 [SMILES: Cn1cc(-c2cc(NS(C)(=O)=O)c3ccn(Cc4ccccc4)c3c2)c2ccccc2c1=O] | N-[1-benzyl-6-(2-methyl-1-oxoisoquinolin-4-yl)indol-4-yl]methanesulfonamide |
| 18 | 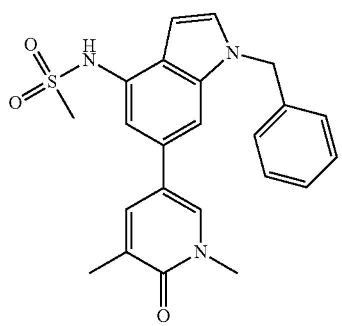 [SMILES: Cc1cc(-c2cc(NS(C)(=O)=O)c3ccn(Cc4ccccc4)c3c2)cn(C)c1=O] | N-[1-benzyl-6-(1,5-dimethyl-6-oxopyridin-3-yl)indol-4-yl]methanesulfonamide |
| 19 | 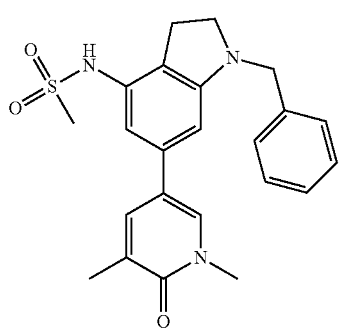 [SMILES: Cc1cc(-c2cc(NS(C)(=O)=O)c3c(c2)N(Cc2ccccc2)CC3)cn(C)c1=O] | N-[1-benzyl-6-(1,5-dimethyl-6-oxopyridin-3-yl)-2,3-dihydroindol-4-yl]methanesulfonamide |
| 20 | 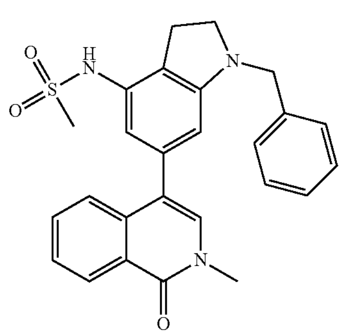 [SMILES: Cn1cc(-c2cc(NS(C)(=O)=O)c3c(c2)N(Cc2ccccc2)CC3)c2ccccc2c1=O] | N-[1-benzyl-6-(2-methyl-1-oxoisoquinolin-4-yl)-2,3-dihydroindol-4-yl]methanesulfonamide |

TABLE 1-continued

| Ex. No | Structure | Name |
|---|---|---|
| 21 | 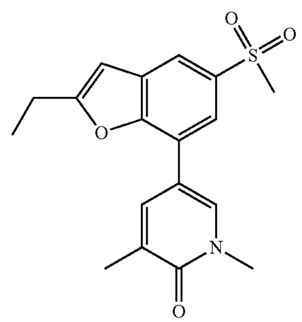 [SMILES: CCc1cc2cc(S(C)(=O)=O)cc(-c3cc(C)c(=O)n(C)c3)c2o1] | 5-(2-ethyl-5-methylsulfonyl-1-benzofuran-7-yl)-1,3-dimethylpyridin-2-one |
| 22 | 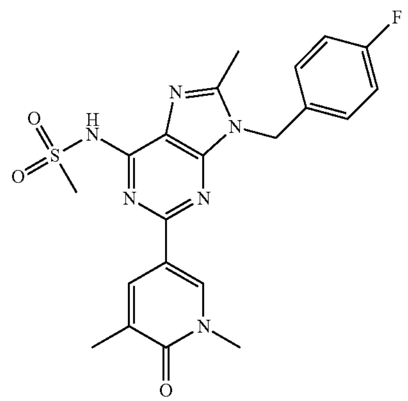 [SMILES: Cc1cc(-c2nc(NS(C)(=O)=O)c3nc(C)n(Cc4ccc(F)cc4)c3n2)cn(C)c1=O] | N-[2-(1,5-dimethyl-6-oxopyridin-3-yl)-9-[(4-fluorophenyl)methyl]-8-methylpurin-6-yl]methanesulfonamide |
| 23 | 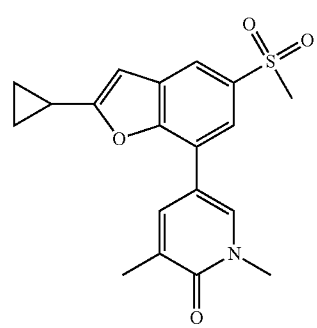 [SMILES: Cc1cc(-c2cc(S(C)(=O)=O)cc3cc(C4CC4)oc23)cn(C)c1=O] | 5-(2-cyclopropyl-5-methylsulfonyl-1-benzofuran-7-yl)-1,3-dimethylpyridin-2-one |
| 24 | 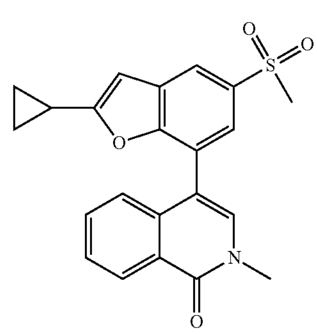 [SMILES: Cn1cc(-c2cc(S(C)(=O)=O)cc3cc(C4CC4)oc23)c2ccccc2c1=O] | 4-(2-cyclopropyl-5-methylsulfonyl-1-benzofuran-7-yl)-2-methylisoquinolin-1-one |

TABLE 1-continued

| Ex. No | Structure | Name |
|---|---|---|
| 25 | 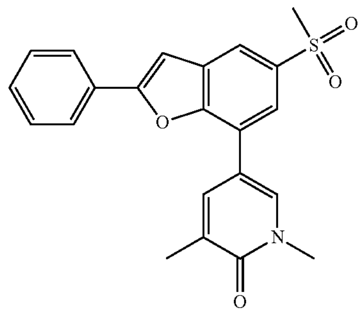 [SMILES: Cc1cc(-c2cc(S(C)(=O)=O)cc3cc(-c4ccccc4)oc23)cn(C)c1=O] | 1,3-dimethyl-5-(5-methylsulfonyl-2-phenyl-1-benzofuran-7-yl)pyridin-2-one |
| 26 | 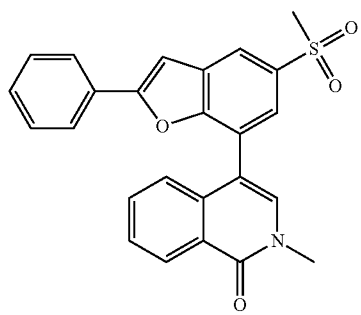 [SMILES: Cn1cc(-c2cc(S(C)(=O)=O)cc3cc(-c4ccccc4)oc23)c2ccccc2c1=O] | 2-methyl-4-(5-methylsulfonyl-2-phenyl-1-benzofuran-7-yl)isoquinolin-1-one |
| 27 | 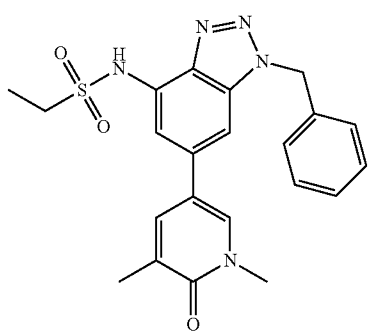 [SMILES: CCS(=O)(=O)Nc1cc(-c2cc(C)c(=O)n(C)c2)cc2c1nnn2Cc1ccccc1] | N-[1-benzyl-6-(1,5-dimethyl-6-oxopyridin-3-yl)benzotriazol-4-yl]ethanesulfonamide |
| 28 | 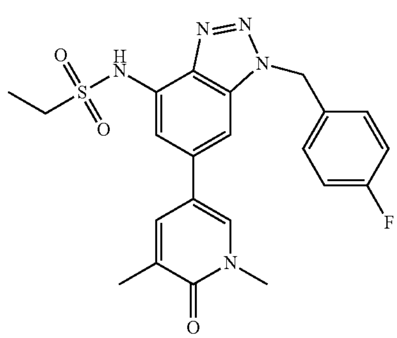 [SMILES: CCS(=O)(=O)Nc1cc(-c2cc(C)c(=O)n(C)c2)cc2c1nnn2Cc1ccc(F)cc1] | N-[6-(1,5-dimethyl-6-oxopyridin-3-yl)-1-[(4-fluorophenyl)methyl]benzotriazol-4-yl]ethanesulfonamide |

TABLE 1-continued

| Ex. No | Structure | Name |
|---|---|---|
| 29 | 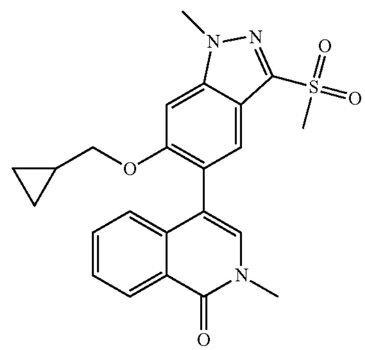 [SMILES: Cn1cc(-c2cc3c(S(C)(=O)=O)nn(C)c3cc2OCC2CC2)c2ccccc2c1=O] | 4-[6-(cyclopropylmethoxy)-1-methyl-3-methylsulfonylindazol-5-yl]-2-methylisoquinolin-1-one |
| 30 | 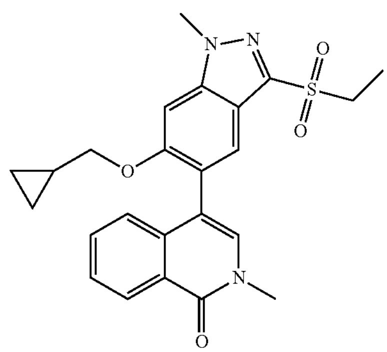 [SMILES: CCS(=O)(=O)c1nn(C)c2cc(OCC3CC3)c(-c3cn(C)c(=O)c4ccccc34)cc12] | 4-[6-(cyclopropylmethoxy)-3-ethylsulfonyl-1-methylindazol-5-yl]-2-methylisoquinolin-1-one |
| 31 | 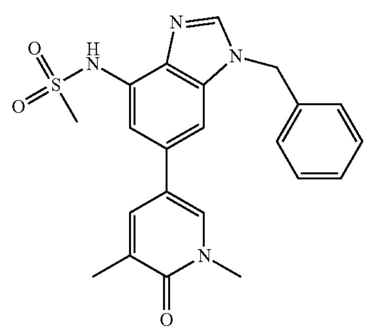 [SMILES: Cc1cc(-c2cc(NS(C)(=O)=O)c3ncn(Cc4ccccc4)c3c2)cn(C)c1=O] | N-[1-benzyl-6-(1,5-dimethyl-6-oxopyridin-3-yl)benzoimidazol-4-yl]methanesulfonamide |
| 32 | 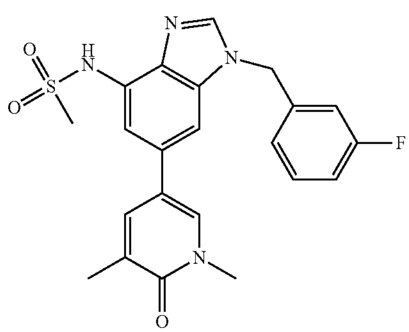 [SMILES: Cc1cc(-c2cc(NS(C)(=O)=O)c3ncn(Cc4cccc(F)c4)c3c2)cn(C)c1=O] | N-[6-(1,5-dimethyl-6-oxopyridin-3-yl)-1-[(3-fluorophenyl)methyl]benzimidazol-4-yl]methanesulfonamide |

TABLE 1-continued

| Ex. No | Structure | Name |
|---|---|---|
| 33 | 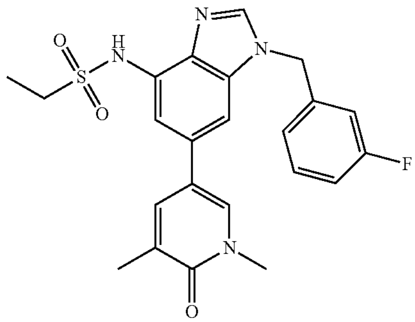 [SMILES: CCS(=O)(=O)Nc1cc(-c2cc(C)c(=O)n(C)c2)cc2c1ncn2Cc1cccc(F)c1] | N-[6-(1,5-dimethyl-6-oxopyridin-3-yl)-1-[(3-fluorophenyl)methyl]benzimidazol-4-yl]ethanesulfonamide |
| 34 | 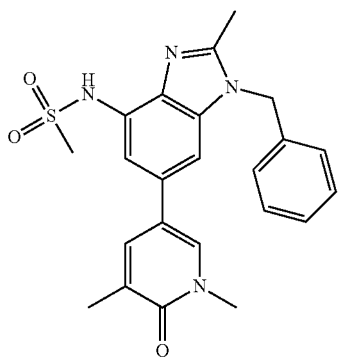 [SMILES: Cc1cc(-c2cc(NS(C)(=O)=O)c3nc(C)n(Cc4ccccc4)c3c2)cn(C)c1=O] | N-[1-benzyl-6-(1,5-dimethyl-6-oxopyridin-3-yl)-2-methylbenzimidazol-4-yl]methanesulfonamide |
| 35 | 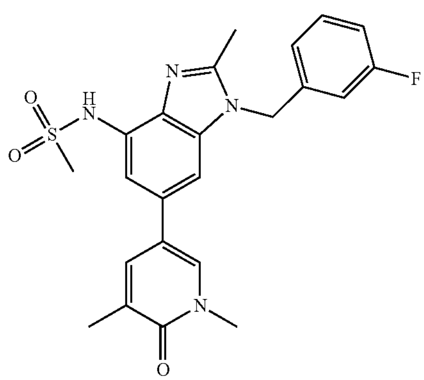 [SMILES: Cc1cc(-c2cc(NS(C)(=O)=O)c3nc(C)n(Cc4cccc(F)c4)c3c2)cn(C)c1=O] | N-[6-(1,5-dimethyl-6-oxopyridin-3-yl)-1-[(3-fluorophenyl)methyl]-2-methylbenzimidazol-4-yl]methanesulfonamide |
| 36 | 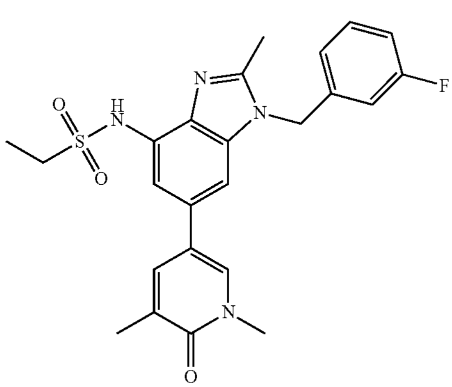 [SMILES: CCS(=O)(=O)Nc1cc(-c2cc(C)c(=O)n(C)c2)cc2c1nc(C)n2Cc1cccc(F)c1] | N-[6-(1,5-dimethyl-6-oxopyridin-3-yl)-1-[(3-fluorophenyl)methyl]-2-methylbenzimidazol-4-yl]ethanesulfonamide |

TABLE 1-continued

| Ex. No | Structure | Name |
|---|---|---|
| 37 | 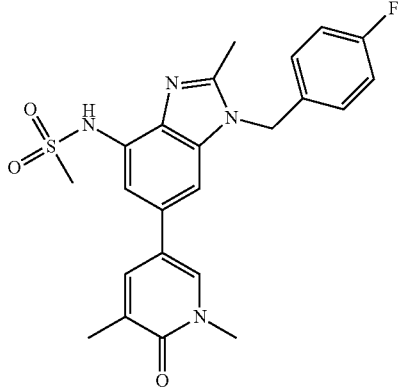 [SMILES: Cc1cc(-c2cc(NS(C)(=O)=O)c3nc(C)n(Cc4ccc(F)cc4)c3c2)cn(C)c1=O] | N-[6-(1,5-dimethyl-6-oxopyridin-3-yl)-1-[(4-fluorophenyl)methyl]-2-methylbenzimidazol-4-yl]methanesulfonamide |
| 38 | 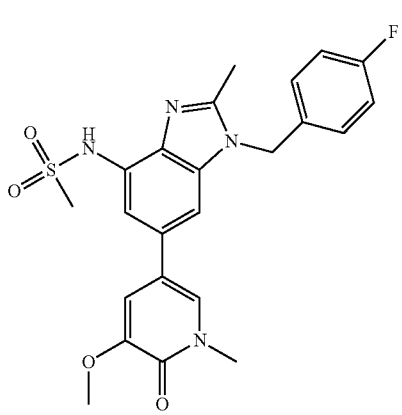 [SMILES: COc1cc(-c2cc(NS(C)(=O)=O)c3nc(C)n(Cc4ccc(F)cc4)c3c2)cn(C)c1=O] | N-[1-[(4-fluorophenyl)methyl]-6-(5-methoxy-1-methyl-6-oxopyridin-3-yl)-2-methylbenzimidazol-4-yl]methanesulfonamide |
| 39 | 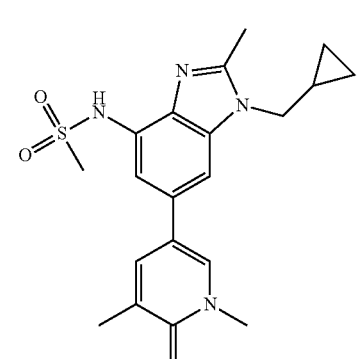 | N-[1-(cyclopropylmethyl)-6-(1,5-dimethyl-6-oxopyridin-3-yl)-2-methylbenzimidazol-4-yl]methanesulfonamide |
| 40 | 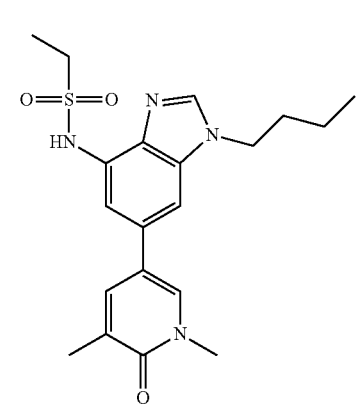 [SMILES: CCCCn1cnc2c(NS(=O)(=O)CC)cc(-c3cc(C)c(=O)n(C)c3)cc21] | N-[1-butyl-6-(1,5-dimethyl-6-oxopyridin-3-yl)benzimidazol-4-yl]ethanesulfonamide |

TABLE 1-continued

| Ex. No | Structure | Name |
|---|---|---|
| 41 | 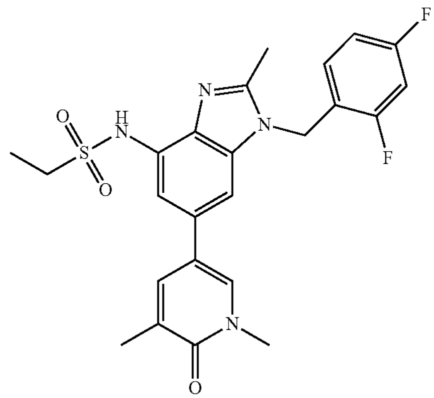 [SMILES: CCS(=O)(=O)Nc1cc(-c2cc(C)c(=O)n(C)c2)cc2c1nc(C)n2Cc1ccc(F)cc1F] | N-[1-[(2,4-difluorophenyl)methyl]-6-(1,5-dimethyl-6-oxopyridin-3-yl)benzimidazol-4-yl]ethanesulfonamide |
| 42 | 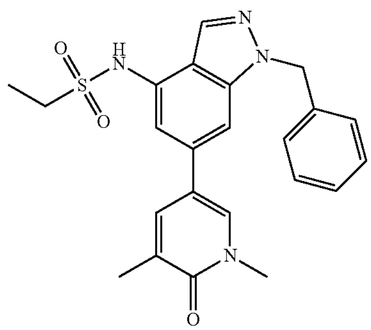 [SMILES: CCS(=O)(=O)Nc1cc(-c2cc(C)c(=O)n(C)c2)cc2c1cnn2Cc1ccccc1] | N-[1-benzyl-6-(1,5-dimethyl-6-oxopyridin-3-yl)indazol-4-yl]ethanesulfonamide |
| 43 | 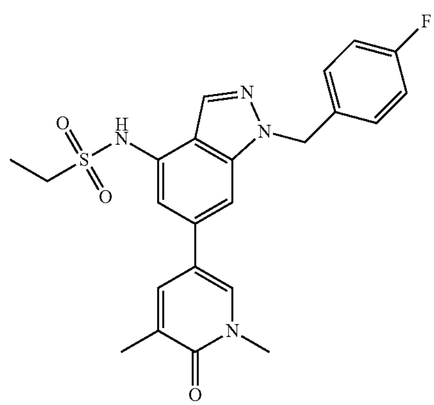 [SMILES: CCS(=O)(=O)Nc1cc(-c2cc(C)c(=O)n(C)c2)cc2c1cnn2Cc1ccc(F)cc1] | N-[6-(1,5-dimethyl-6-oxopyridin-3-yl)-1-[(4-fluorophenyl)methyl]indazol-4-yl]ethanesulfonamide |
| 44 | 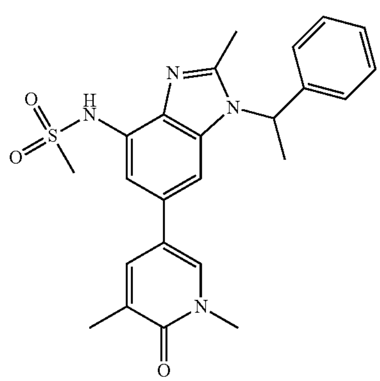 [SMILES: Cc1cc(-c2cc(NS(C)(=O)=O)c3nc(C)n(C(C)c4ccccc4)c3c2)cn(C)c1=O] | N-[6-(1,5-dimethyl-6-oxopyridin-3-yl)-2-methyl-1-(1-phenylethyl)benzimidazol-4-yl]methanesulfonamide |

TABLE 1-continued

| Ex. No | Structure | Name |
|---|---|---|
| 45 | 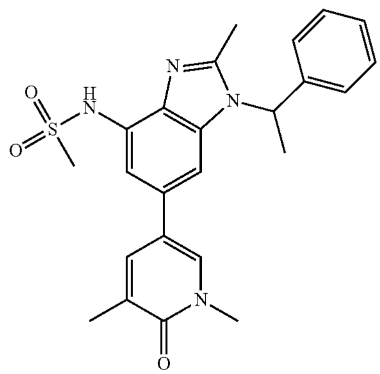 [SMILES: Cc1cc(-c2cc(NS(C)(=O)=O)c3nc(C)n(C(C)c4ccccc4)c3c2)cn(C)c1=O] | N-[6-(1,5-dimethyl-6-oxopyridin-3-yl)-2-methyl-1-(1-phenylethyl)benzimidazol-4-yl]methanesulfonamide |
| 46 | 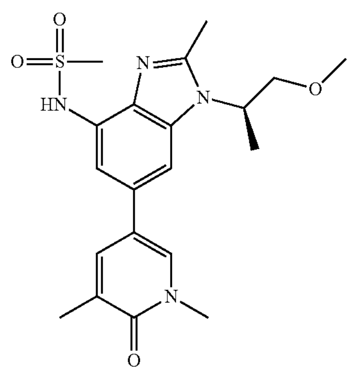 [SMILES: COC[C@@H](C)n1c(C)nc2c(NS(C)(=O)=O)cc(-c3cc(C)c(=O)n(C)c3)cc21] | N-[6-(1,5-dimethyl-6-oxopyridin-3-yl)-1-[(2R)-1-methoxypropan-2-yl]-2-methylbenzimidazol-4-yl]methanesulfonamide |
| 47 | 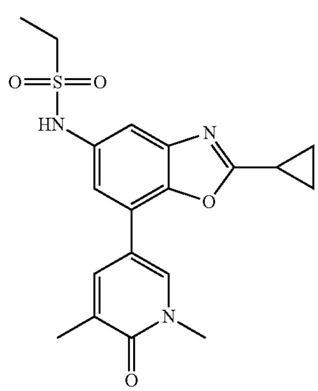 [SMILES: CCS(=O)(=O)Nc1cc(-c2cc(C)c(=O)n(C)c2)c2oc(C3CC3)nc2c1] | N-[2-cyclopropyl-7-(1,5-dimethyl-6-oxopyridin-3-yl)-1,3-benzoxazol-5-yl]ethanesulfonamide |
| 48 | 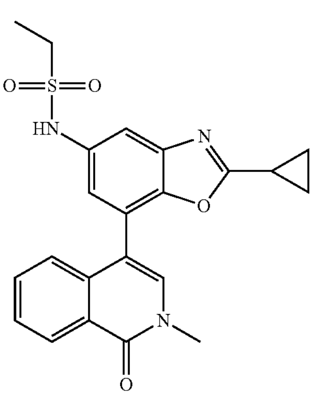 [SMILES: CCS(=O)(=O)Nc1cc(-c2cn(C)c(=O)c3ccccc23)c2oc(C3CC3)nc2c1] | N-[2-cyclopropyl-7-(2-methyl-1-oxoisoquinolin-4-yl)-1,3-benzoxazol-5-yl]ethanesulfonamide |

TABLE 1-continued

| Ex. No | Structure | Name |
|---|---|---|
| 49 | 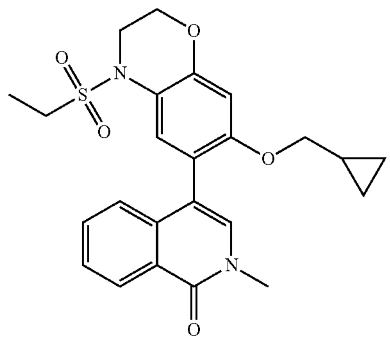 [SMILES: CCS(=O)(=O)N1CCOc2cc(OCC3CC3)c(-c3cn(C)c(=O)c4ccccc34)cc21] | 4-[7-(cyclopropylmethoxy)-4-ethylsulfonyl-2,3-dihydro-1,4-benzoxazin-6-yl]-2-methylisoquinolin-1-one |
| 50 | 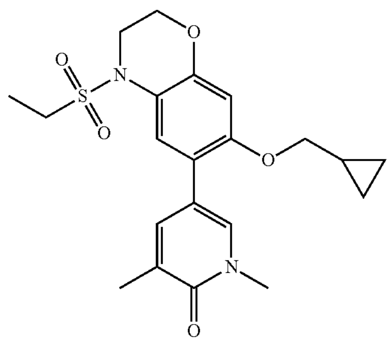 [SMILES: CCS(=O)(=O)N1CCOc2cc(OCC3CC3)c(-c3cc(C)c(=O)n(C)c3)cc21] | 5-[7-(cyclopropylmethoxy)-4-ethylsulfonyl-2,3-dihydro-1,4-benzoxazin-6-yl]-1,3-dimethylpyridin-2-one |
| 51 | 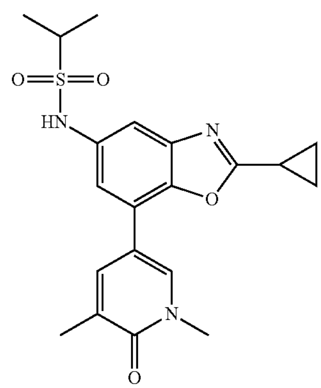 [SMILES: Cc1cc(-c2cc(NS(=O)(=O)C(C)C)cc3nc(C4CC4)oc23)cn(C)c1=O] | N-[2-cyclopropyl-7-(1,5-dimethyl-6-oxopyridin-3-yl)-1,3-benzoxazol-5-yl]propane-2-sulfonamide |
| 52 | 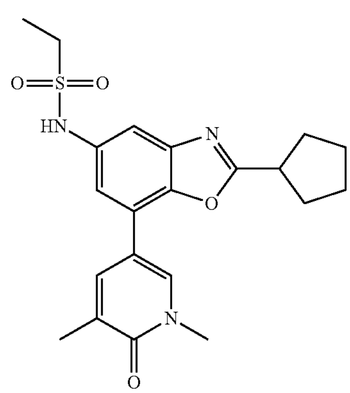 [SMILES: CCS(=O)(=O)Nc1cc(-c2cc(C)c(=O)n(C)c2)c2oc(C3CCCC3)nc2c1] | N-[2-cyclopentyl-7-(1,5-dimethyl-6-oxopyridin-3-yl)-1,3-benzoxazol-5-yl]ethanesulfonamide |

TABLE 1-continued

| Ex. No | Structure | Name |
|---|---|---|
| 53 | 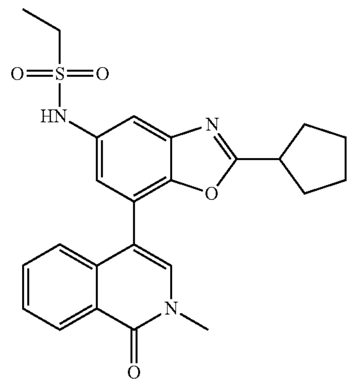 [SMILES: CCS(=O)(=O)Nc1cc(-c2cn(C)c(=O)c3ccccc23)c2oc(C3CCCC3)nc2c1] | N-[2-cyclopentyl-7-(2-methyl-1-oxoisoquinolin-4-yl)-1,3-benzoxazol-5-yl]ethanesulfonamide |
| 54 | 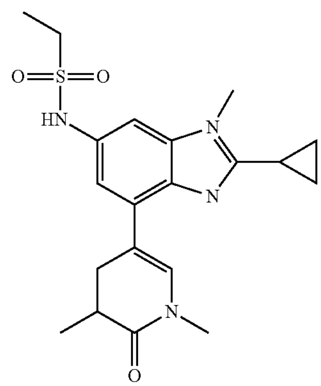 | N-[2-cyclopropyl-7-(1,5-dimethyl-6-oxopyridin-3-yl)-3-methylbenzimidazol-5-yl]ethanesulfonamide |
| 55 | 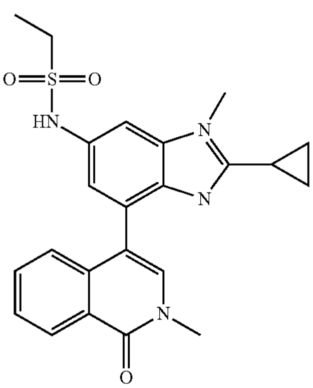 | N-[2-cyclopropyl-3-methyl-7-(2-methyl-1-oxoisoquinolin-4-yl)benzimidazol-5-yl]ethanesulfonamide |
| 56 | 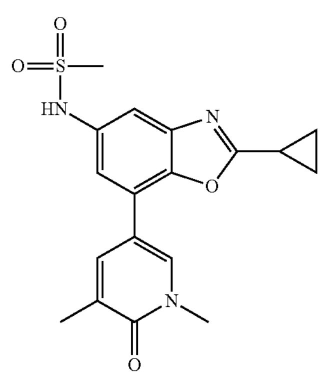 [SMILES: Cc1cc(-c2cc(NS(C)(=O)=O)cc3nc(C4CC4)oc23)cn(C)c1=O] | 5-[2-cyclopropyl-5-(methylsulfonylmethyl)-1,3-benzoxazol-7-yl]-1,3-dimethylpyridin-2-one |

TABLE 1-continued

| Ex. No | Structure | Name |
|---|---|---|
| 57 | 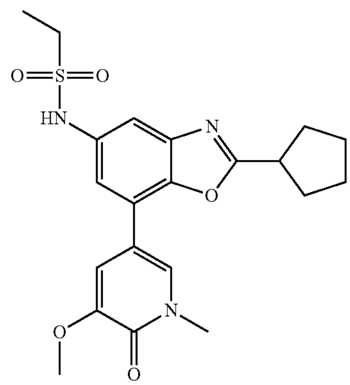 [SMILES: CCS(=O)(=O)Nc1cc(-c2cc(OC)c(=O)n(C)c2)c2oc(C3CCCC3)nc2c1] | N-[2-cyclopentyl-7-(5-methoxy-1-methyl-6-oxopyridin-3-yl)-1,3-benzoxazol-5-yl]ethanesulfonamide |
| 58 | 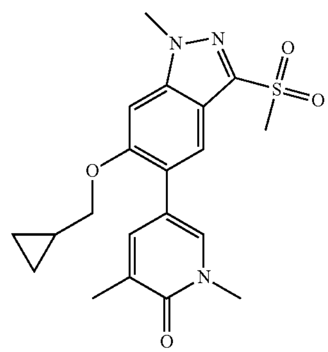 [SMILES: Cc1cc(-c2cc3c(S(C)(=O)=O)nn(C)c3cc2OCC2CC2)cn(C)c1=O] | 5-[6-(cyclopropylmethoxy)-1-methyl-3-methylsulfonylindazol-5-yl]-1,3-dimethylpyridin-2-one |
| 59 | 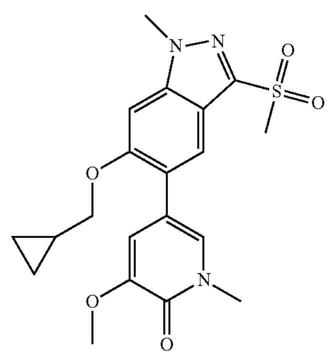 [SMILES: COc1cc(-c2cc3c(S(C)(=O)=O)nn(C)c3cc2OCC2CC2)cn(C)c1=O] | 5-[6-(cyclopropylmethoxy)-1-methyl-3-methylsulfonylindazol-5-yl]-3-methoxy-1-methylpyridin-2-one |
| 60 | 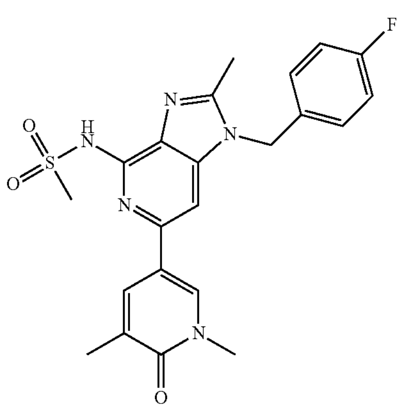 [SMILES: Cc1cc(-c2cc3c(nc(C)n3Cc3ccc(F)cc3)c(NS(C)(=O)=O)n2)cn(C)c1=O] | N-[6-(1,5-dimethyl-6-oxopyridin-3-yl)-1-[(4-fluorophenyl)methyl]-2-methylimidazo[4,5-c]pyridin-4-yl]methanesulfonamide |

TABLE 1-continued

| Ex. No | Structure | Name |
|---|---|---|
| 61 | 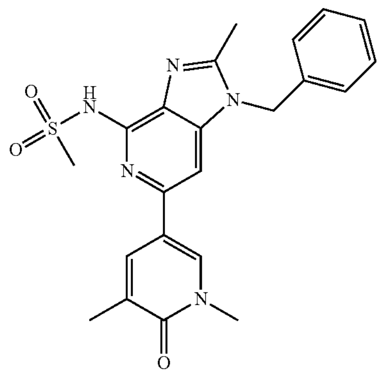 [SMILES: Cc1cc(-c2cc3c(nc(C)n3Cc3ccccc3)c(NS(C)(=O)=O)n2)cn(C)c1=O] | N-[1-benzyl-6-(1,5-dimethyl-6-oxopyridin-3-yl)-2-methylimidazo[4,5-c]pyridin-4-yl]methanesulfonamide |
| 62 | 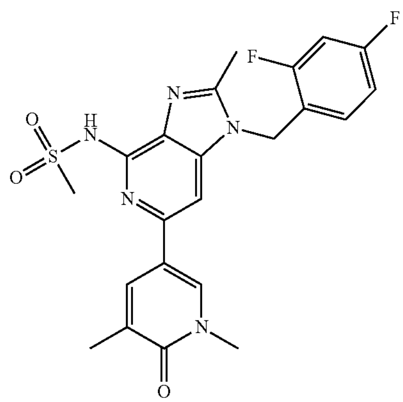 [SMILES: Cc1cc(-c2cc3c(nc(C)n3Cc3ccc(F)cc3F)c(NS(C)(=O)=O)n2)cn(C)c1=O] | N-[1-(2,4-difluorophenyl)methyl]-6-(1,5-dimethyl-6-oxopyridin-3-yl)-2-methylimidazo[4,5-c]pyridin-4-yl]methanesulfonamide |
| 63 | 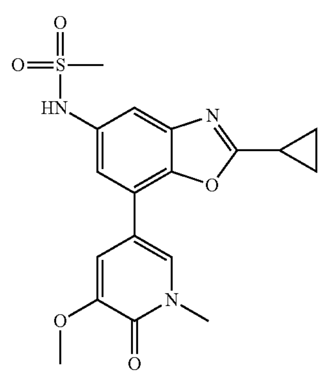 [SMILES: COc1cc(-c2cc(NS(C)(=O)=O)cc3nc(C4CC4)oc23)cn(C)c1=O] | 5-[2-cyclopropyl-5-(methylsulfonylmethyl)-1,3-benzoxazol-7-yl]-3-methoxy-1-methylpyridin-2-one |
| 64 | 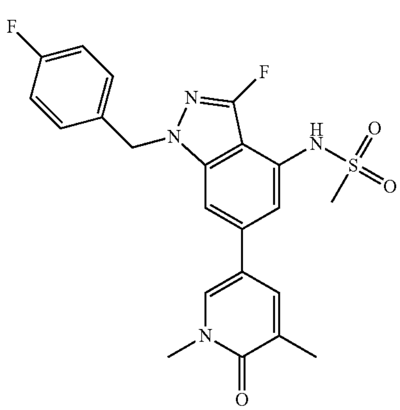 [SMILES: Cc1cc(-c2cc(NS(C)(=O)=O)c3c(F)nn(Cc4ccc(F)cc4)c3c2)cn(C)c1=O] | N-[6-(1,5-dimethyl-6-oxopyridin-3-yl)-3-fluoro-1-[(4-fluorophenyl)methyl]indazol-4-yl]methanesulfonamide |

TABLE 1-continued

| Ex. No | Structure | Name |
| --- | --- | --- |
| 65 | 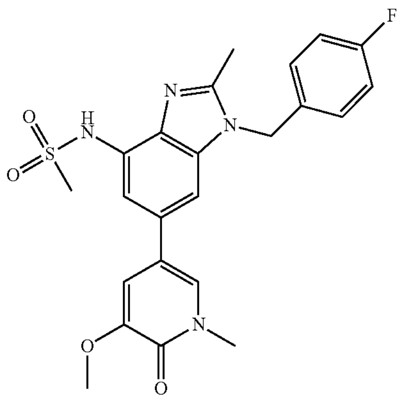 [SMILES: COc1cc(-c2cc(NS(C)(=O)=O)c3nc(C)n(Cc4ccc(F)cc4)c3c2)cn(C)c1=O] | N-[3-fluoro-1-[(4-fluorophenyl)methyl]-6-(5-methoxy-1-methyl-6-oxopyridin-3-yl)indazol-4-yl]methanesulfonamide |
| 66 | 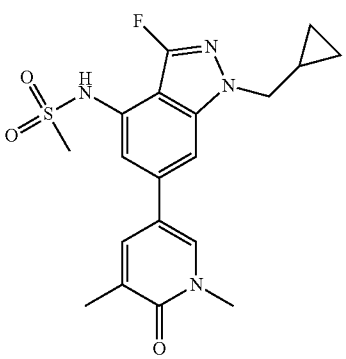 [SMILES: Cc1cc(-c2cc(NS(C)(=O)=O)c3c(F)nn(CC4CC4)c3c2)cn(C)c1=O] | N-[1-(cyclopropylmethyl)-6-(1,5-dimethyl-6-oxopyridin-3-yl)-3-fluoroindazol-4-yl]methanesulfonamide |
| 67 | 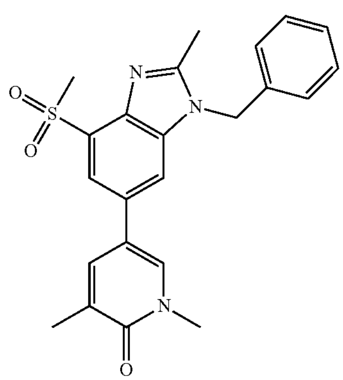 [SMILES: Cc1cc(-c2cc(S(C)(=O)=O)c3nc(C)n(Cc4ccccc4)c3c2)cn(C)c1=O] | 5-(3-benzyl-2-methyl-7-methylsulfonylbenzimidazol-5-yl)-1,3-dimethylpyridin-2-one |
| 68 | 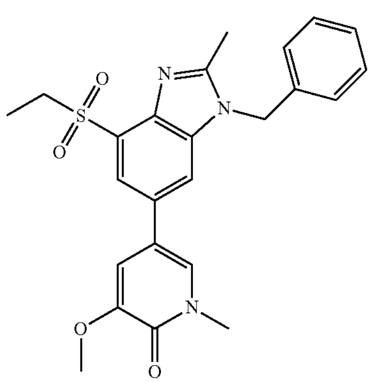 [SMILES: CCS(=O)(=O)c1cc(-c2cc(OC)c(=O)n(C)c2)cc2c1nc(C)n2Cc1ccccc1] | 5-(3-benzyl-7-ethylsulfonyl-2-methylbenzimidazol-5-yl)-3-methoxy-1-methylpyridin-2-one |

TABLE 1-continued

| Ex. No | Structure | Name |
|---|---|---|
| 69 | 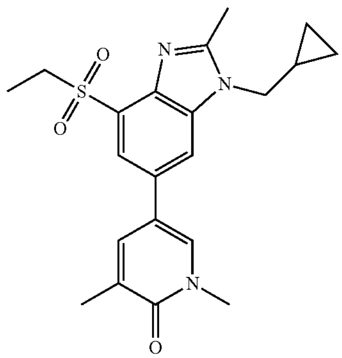 [SMILES: CCS(=O)(=O)c1cc(-c2cc(C)c(=O)n(C)c2)cc2c1nc(C)n2CC1CC1] | 5-[3-(cyclopropylmethyl)-7-ethylsulfonyl-2-methylbenzamidazol-5-yl]-1,3-dimethylpyridin-2-one |
| 70 | 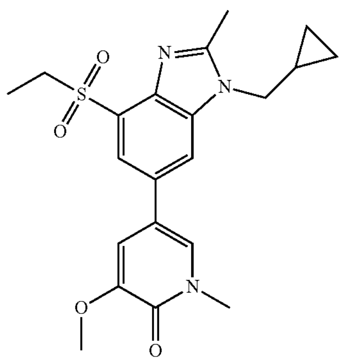 [SMILES: CCS(=O)(=O)c1cc(-c2cc(OC)c(=O)n(C)c2)cc2c1nc(C)n2CC1CC1] | 5-[3-(cyclopropylmethyl)-7-ethylsulfonyl-2-methylbenzimidazol-5-yl]-3-methoxy-1-methylpyridin-2-one |
| 71 | 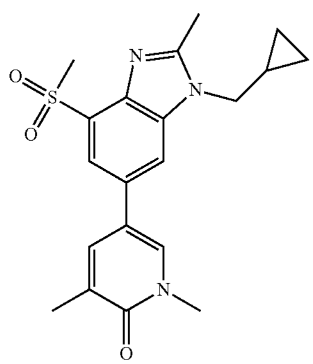 [SMILES: Cc1cc(-c2cc(S(C)(=O)=O)c3nc(C)n(CC4CC4)c3c2)cn(C)c1=O] | 5-[3-(cyclopropylmethyl)-2-methyl-7-methylsulfonylbenzimidazol-5-yl]-1,3-dimethylpyridin-2-one |
| 72 | 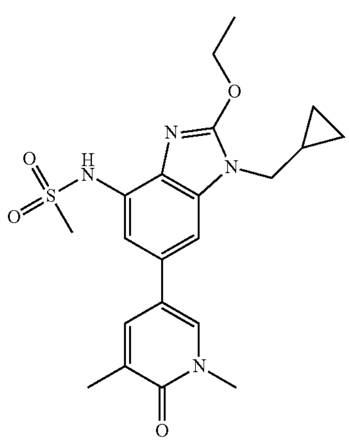 [SMILES: CCOc1nc2c(NS(C)(=O)=O)cc(-c3cc(C)c(=O)n(C)c3)cc2n1CC1CC1] | N-[1-(cyclopropylmethyl)-6-(1,5-dimethyl-6-oxopyridin-3-yl)-2-ethoxybenzimidazol-4-yl]methanesulfonamide |

TABLE 1-continued

| Ex. No | Structure | Name |
|---|---|---|
| 73 | 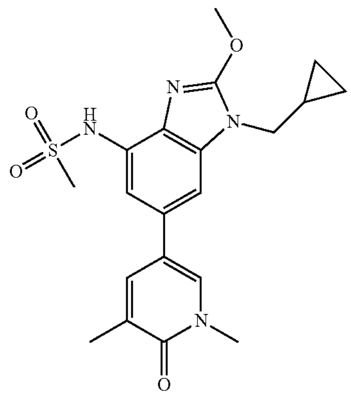 [SMILES: COc1nc2c(NS(C)(=O)=O)cc(-c3cc(C)c(=O)n(C)c3)cc2n1CC1CC1] | N-[1-(cyclopropylmethyl)-6-(1,5-dimethyl-6-oxopyridin-3-yl)-2-methoxybenzimidazol-4-yl]methanesulfonamide |
| 74 | 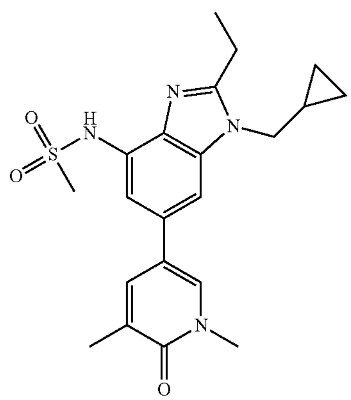 [SMILES: CCc1nc2c(NS(C)(=O)=O)cc(-c3cc(C)c(=O)n(C)c3)cc2n1CC1CC1] | N-[1-(cyclopropylmethyl)-6-(1,5-dimethyl-6-oxopyridin-3-yl)-2-ethylbenzimidazol-4-yl]methanesulfonamide |
| 75 | 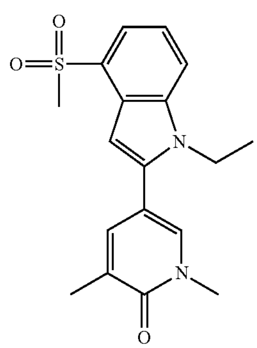 [SMILES: CCn1c(-c2cc(C)c(=O)n(C)c2)cc2c(S(C)(=O)=O)cccc21] | 5-(1-ethyl-4-methylsulfonylindol-2-yl)-1,3-dimethylpyridin-2-one |
| 76 | 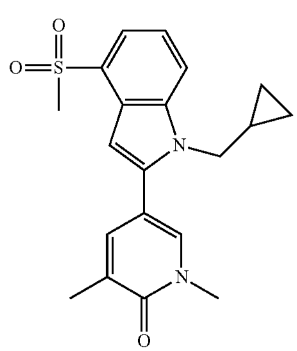 [SMILES: Cc1cc(-c2cc3c(S(C)(=O)=O)cccc3n2CC2CC2)cn(C)c1=O] | 5-[1-(cyclopropylmethyl)-4-methylsulfonylindol-2-yl]-1,3-dimethylpyridin-2-one |

TABLE 1-continued

| Ex. No | Structure | Name |
|---|---|---|
| 77 | 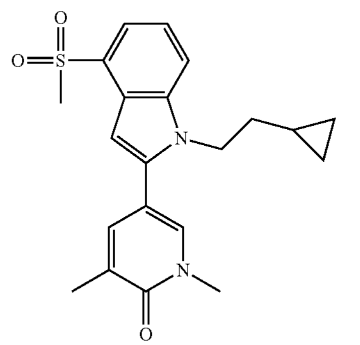 [SMILES: Cc1cc(-c2cc3c(S(C)(=O)=O)cccc3n2CCC2CC2)cn(C)c1=O] | 5-[1-(2-cyclopropylethyl)-4-methylsulfonylindol-2-yl]-1,3-dimethylpyridin-2-one |
| 78 | 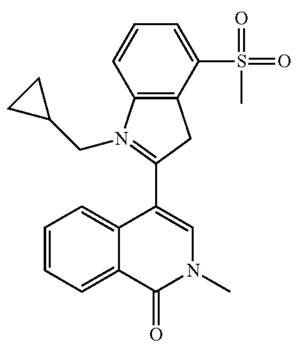 | 4-[1-(cyclopropylmethyl)-4-methylsulfonylindol-2-yl]-2-methylisoquinolin-1-one |
| 79 | 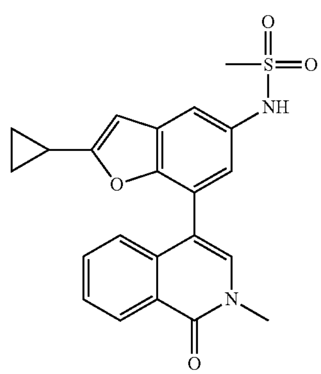 [SMILES: Cn1cc(-c2cc(NS(C)(=O)=O)cc3cc(C4CC4)oc23)c2ccccc2c1=O] | N-[2-cyclopropyl-7-(2-methyl-1-oxoisoquinolin-4-yl)-1-benzofuran-5-yl]methanesulfonamide |
| 80 | 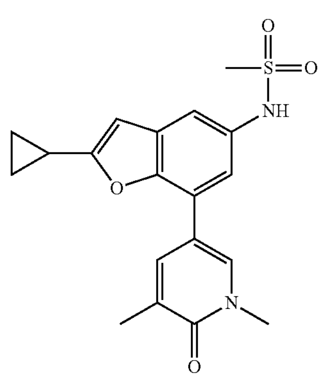 [SMILES: Cc1cc(-c2cc(NS(C)(=O)=O)cc3cc(C4CC4)oc23)cn(C)c1=O] | N-[2-cyclopropyl-7-(1,5-dimethyl-6-oxopyridin-3-yl)-1-benzofuran-5-yl]methanesulfonamide |

TABLE 1-continued

| Ex. No | Structure | Name |
|---|---|---|
| 81 | 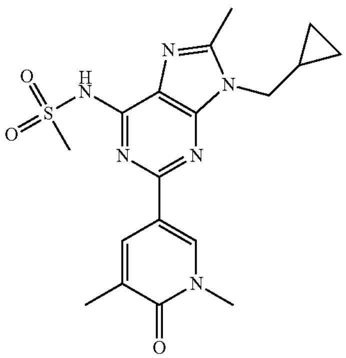 [SMILES: Cc1cc(-c2nc(NS(C)(=O)=O)c3nc(C)n(CC4CC4)c3n2)cn(C)c1=O] | N-[9-(cyclopropylmethyl)-2-(1,5-dimethyl-6-oxopyridin-3-yl)-8-methylpurin-6-yl]methanesulfonamide |
| 82 | 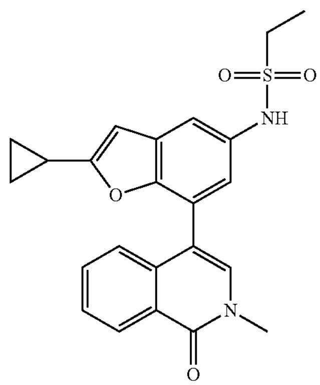 [SMILES: CCS(=O)(=O)Nc1cc(-c2cn(C)c(=O)c3ccccc23)c2oc(C3CC3)cc2c1] | N-[2-cyclopropyl-7-(2-methyl-1-oxoisoquinolin-4-yl)-1-benzofuran-5-yl]ethanesulfonamide |
| 83 | 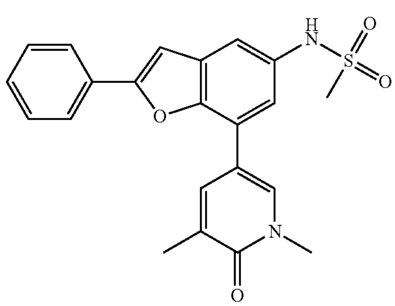 [SMILES: Cc1cc(-c2cc(NS(C)(=O)=O)cc3cc(-c4ccccc4)oc23)cn(C)c1=O] | N-[7-(1,5-dimethyl-6-oxopyridin-3-yl)-2-phenyl-1-benzofuran-5-yl]methanesulfonamide |
| 84 | 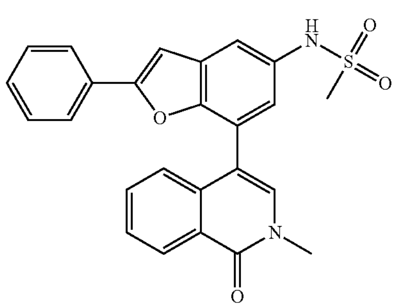 [SMILES: Cn1cc(-c2cc(NS(C)(=O)=O)cc3cc(-c4ccccc4)oc23)c2ccccc2c1=O] | N-[7-(2-methyl-1-oxoisoquinolin-4-yl)-2-phenyl-1-benzofuran-5-yl]methanesulfonamide |

| Ex. No | Structure | Name |
|---|---|---|
| 85 | 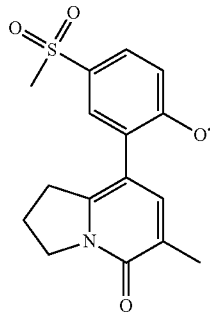 | 8-[2-(cyclopropylmethoxy)-5-methylsulfonylphenyl]-6-methyl-2,3-dihydro-1H-indolizin-5-one |
| 86 | 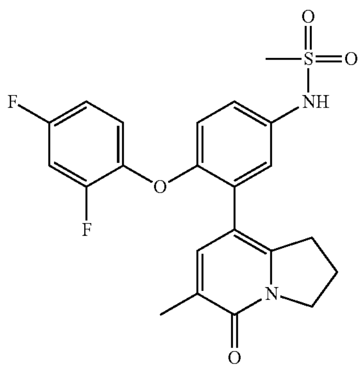 [SMILES: Cc1cc(-c2cc(NS(C)(=O)=O)ccc2Oc2ccc(F)cc2F)c2n(c1=O)CCC2] | N-[4-(2,4-difluorophenoxy)-3-(6-methyl-5-oxo-2,3-dihydro-1H-indolizin-8-yl)phenyl]methanesulfonamide |
| 87 | 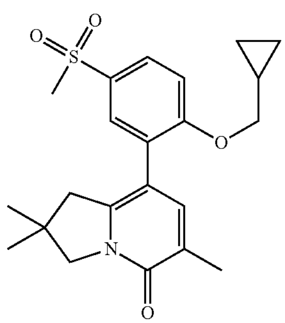 [SMILES: Cc1cc(-c2cc(S(C)(=O)=O)ccc2OCC2CC2)c2n(c1=O)CC(C)(C)C2] | 8-[2-(cyclopropylmethoxy)-5-methylsulfonylphenyl]-2,2,6-trimethyl-1,3-dihydroindolizin-5-one |
| 88 | 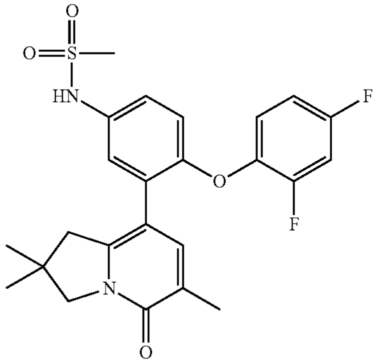 [SMILES: Cc1cc(-c2cc(NS(C)(=O)=O)ccc2Oc2ccc(F)cc2F)c2n(c1=O)CC(C)(C)C2] | N-[4-(2,4-difluorophenoxy)-3-(2,2,6-trimethyl-5-oxo-1,3-dihydroindolizin-8-yl)phenyl]methanesulfonamide |

TABLE 1-continued

| Ex. No | Structure | Name |
|---|---|---|
| 89 | 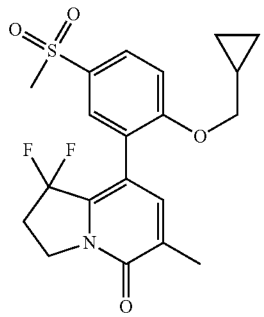 [SMILES: Cc1cc(-c2cc(S(C)(=O)=O)ccc2OCC2CC2)c2n(c1=O)CCC2(F)F] | 8-[2-(cyclopropylmethoxy)-5-methylsulfonylphenyl]-1,1-difluoro-6-methyl-2,3-dihydroindolizin-5-one |
| 90 | 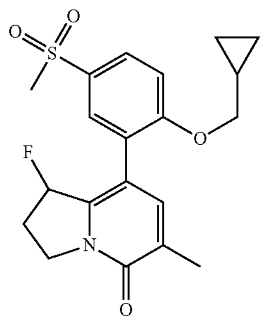 [SMILES: Cc1cc(-c2cc(S(C)(=O)=O)ccc2OCC2CC2)c2n(c1=O)CCC2F] | 8-[2-(cyclopropylmethoxy)-5-methylsulfonylphenyl]-1-fluoro-6-methyl-2,3-dihydro-1H-indolizin-5-one |
| 91 | 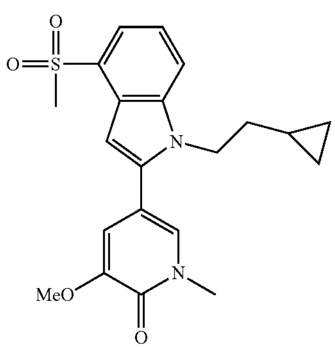 [SMILES: COc1cc(-c2cc3c(S(C)(=O)=O)cccc3n2CCC2CC2)cn(C)c1=O] | 5-[1-(2-cyclopropylethyl)-4-methylsulfonylindol-2-yl]-3-methoxy-1-methylpyridin-2-one |
| 92 | 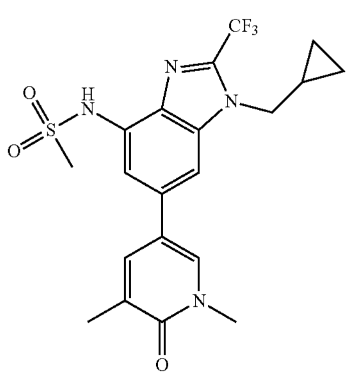 [SMILES: Cc1cc(-c2cc(NS(C)(=O)=O)c3nc(C(F)(F)F)n(CC4CC4)c3c2)cn(C)c1=O] | N-[1-(cyclopropylmethyl)-6-(1,5-dimethyl-6-oxopyridin-3-yl)-2-(trifluoromethyl)benzimidazol-4-yl]methanesulfonamide |

TABLE 1-continued

| Ex. No | Structure | Name |
|---|---|---|
| 93 | 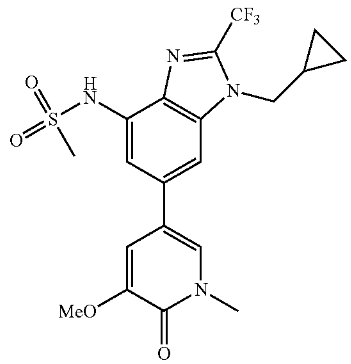 [SMILES: COc1cc(-c2cc(NS(C)(=O)=O)c3nc(C(F)(F)F)n(CC4CC4)c3c2)cn(C)c1=O] | N-[1-(cyclopropylmethyl)-6-(5-methoxy-1-methyl-6-oxopyridin-3-yl)-2-(trifluoromethyl)benzimidazol-4-yl]methanesulfonamide |
| 94 | 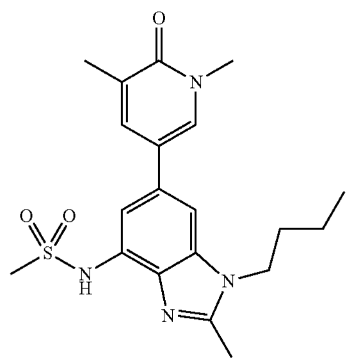 [SMILES: CCCCn1c(C)nc2c(NS(C)(=O)=O)cc(-c3cc(C)c(=O)n(C)c3)cc21] | N-[1-butyl-6-(1,5-dimethyl-6-oxopyridin-3-yl)-2-methylbenzimidazol-4-yl]methanesulfonamide |
| 95 | 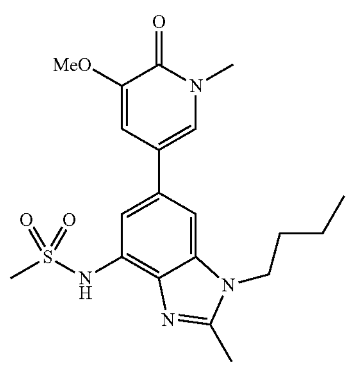 [SMILES: CCCCn1c(C)nc2c(NS(C)(=O)=O)cc(-c3cc(OC)c(=O)n(C)c3)cc21] | N-[1-butyl-6-(5-methoxy-1-methyl-6-oxopyridin-3-yl)-2-methylbenzimidazol-4-yl]methanesulfonamide |
| 96 | 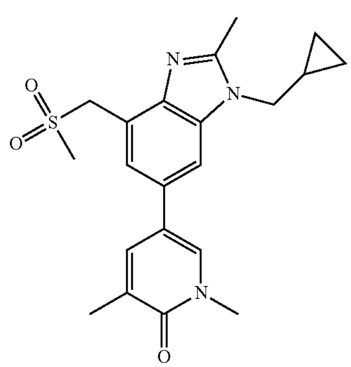 [SMILES: Cc1cc(-c2cc(CS(C)(=O)=O)c3nc(C)n(CC4CC4)c3c2)cn(C)c1=O] | 5-[3-(cyclopropylmethyl)-2-methyl-7-(methylsulfonylmethyl)benzimidazol-5-yl]-1,3-dimethylpyridin-2-one |

| Ex. No | Structure | Name |
|---|---|---|
| 97 | 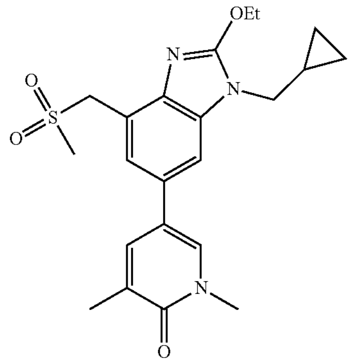 [SMILES: CCOc1nc2c(CS(C)(=O)=O)cc(-c3cc(C)c(=O)n(C)c3)cc2n1CC1CC1] | 5-[3-(cyclopropylmethyl)-2-ethoxy-7-(methylsulfonylmethyl)benzimidazol-5-yl]-1,3-dimethylpyridin-2-one |
| 98 | 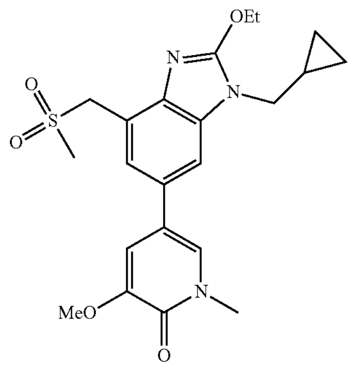 [SMILES: CCOc1nc2c(CS(C)(=O)=O)cc(-c3cc(OC)c(=O)n(C)c3)cc2n1CC1CC1] | 5-[3-(cyclopropylmethyl)-2-ethoxy-7-(methylsulfonylmethyl)benzimidazol-5-yl]-3-methoxy-1-methylpyridin-2-one |
| 99 | 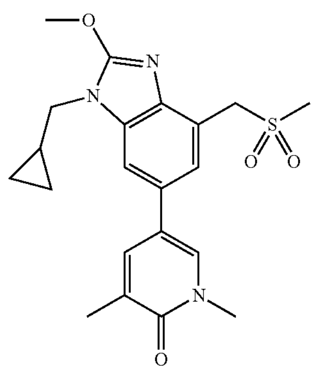 [SMILES: COc1nc2c(CS(C)(=O)=O)cc(-c3cc(C)c(=O)n(C)c3)cc2n1CC1CC1] | 5-[3-(cyclopropylmethyl)-2-methoxy-7-(methylsulfonylmethyl)benzimidazol-5-yl]-1,3-dimethylpyridin-2-one |
| 100 | 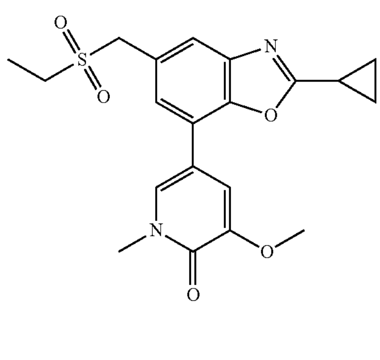 [SMILES: CCS(=O)(=O)Cc1cc(-c2cc(OC)c(=O)n(C)c2)c2oc(C3CC3)nc2c1] | 5-[2-cyclopropyl-5-(ethylsulfonylmethyl)-1,3-benzoxazol-7-yl]-3-methoxy-1-methylpyridin-2-one |

TABLE 1-continued

| Ex. No | Structure | Name |
|---|---|---|
| 101 | 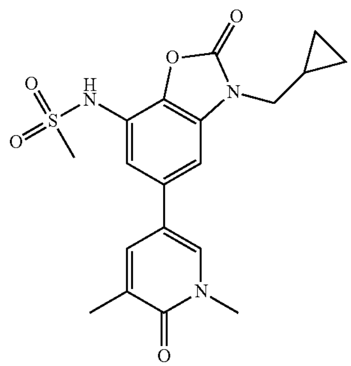 [SMILES: Cc1cc(-c2cc(NS(C)(=O)=O)c3oc(=O)n(CC4CC4)c3c2)cn(C)c1=O] | N-[3-(cyclopropylmethyl)-5-(1,5-dimethyl-6-oxopyridin-3-yl)-2-oxo-1,3-benzoxazol-7-yl]methanesulfonamide |
| 102 | 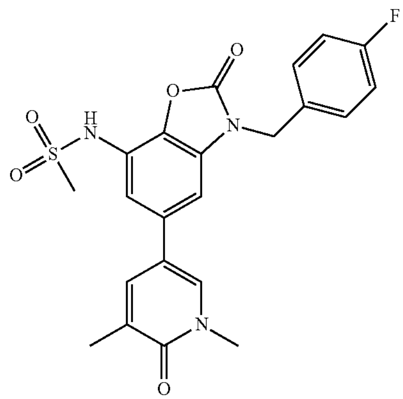 [SMILES: Cc1cc(-c2cc(NS(C)(=O)=O)c3oc(=O)n(Cc4ccc(F)cc4)c3c2)cn(C)c1=O] | N-[5-(1,5-dimethyl-6-oxopyridin-3-yl)-3-[(4-fluorophenyl)methyl]-2-oxo-1,3-benzoxazol-7-yl]methanesulfonamide |
| 103 | 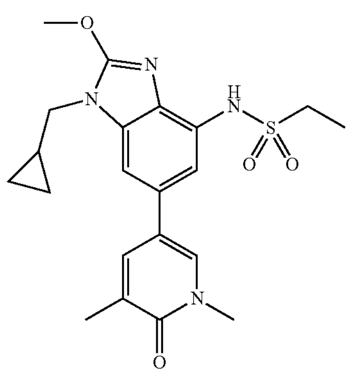 [SMILES: CCS(=O)(=O)Nc1cc(-c2cc(C)c(=O)n(C)c2)cc2c1nc(OC)n2CC1CC1] | N-[1-(cyclopropylmethyl)-6-(1,5-dimethyl-6-oxopyridin-3-yl)-2-methoxybenzimidazol-4-yl]ethanesulfonamide |
| 104 | 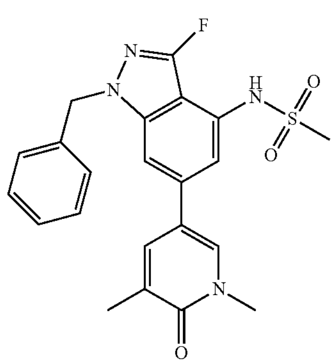 [SMILES: Cc1cc(-c2cc(NS(C)(=O)=O)c3c(F)nn(Cc4ccccc4)c3c2)cn(C)c1=O] | N-[1-benzyl-6-(1,5-dimethyl-6-oxopyridin-3-yl)-3-fluoroindazol-4-yl]methanesulfonamide |

TABLE 1-continued

| Ex. No | Structure | Name |
|---|---|---|
| 105 | 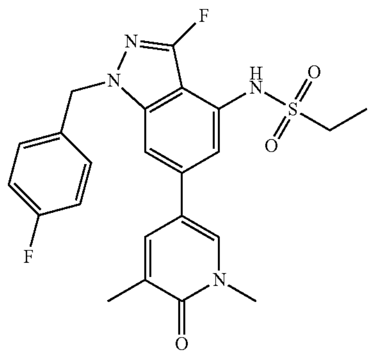 [SMILES: CCS(=O)(=O)Nc1cc(-c2cc(C)c(=O)n(C)c2)cc2c1c(F)nn2Cc1ccc(F)cc1] | N-[6-(1,5-dimethyl-6-oxopyridin-3-yl)-3-fluoro-1-[(4-fluorophenyl)methyl]indazol-4-yl]ethanesulfonamide |
| 106 | 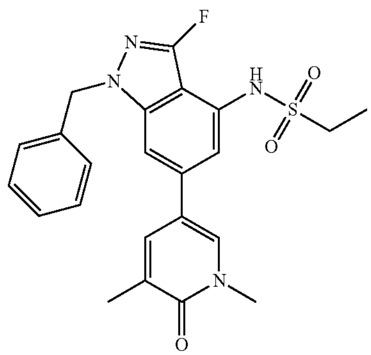 [SMILES: CCS(=O)(=O)Nc1cc(-c2cc(C)c(=O)n(C)c2)cc2c1c(F)nn2Cc1ccccc1] | N-[1-benzyl-6-(1,5-dimethyl-6-oxopyridin-3-yl)-3-fluoroindazol-4-yl]ethanesulfonamide |

In some embodiments, the substituted heterocyclic derivative compound disclosed herein has the structure provided in Table 2.

TABLE 2

TABLE 2-continued
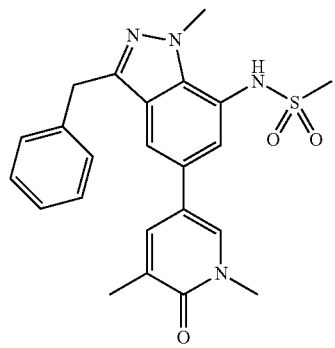 [SMILES: Cc1cc(-c2cc(NS(C)(=O)=O)c3c(c2)c(Cc2ccccc2)nn3C)cn(C)c1=O]
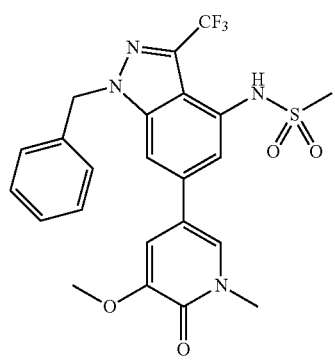 [SMILES: COc1cc(-c2cc(NS(C)(=O)=O)c3c(C(F)(F)F)nn(Cc4ccccc4)c3c2)cn(C)c1=O]
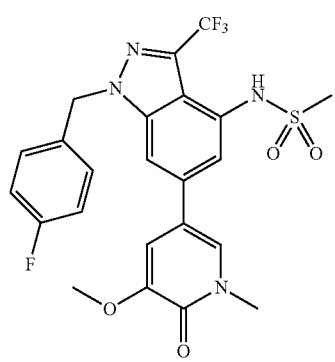 [SMILES: COc1cc(-c2cc(NS(C)(=O)=O)c3c(C(F)(F)F)nn(Cc4ccc(F)cc4)c3c2)cn(C)c1=O]
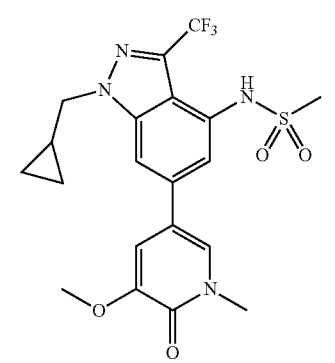 [SMILES: COc1cc(-c2cc(NS(C)(=O)=O)c3c(C(F)(F)F)nn(CC4CC4)c3c2)cn(C)c1=O]
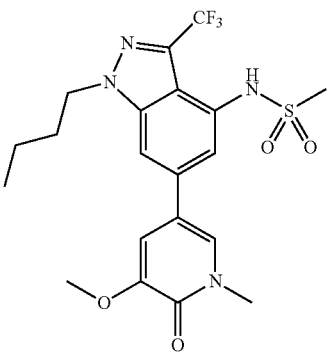 [SMILES: CCCCn1nc(C(F)(F)F)c2c(NS(C)(=O)=O)cc(-c3cc(OC)c(=O)n(C)c3)cc21]
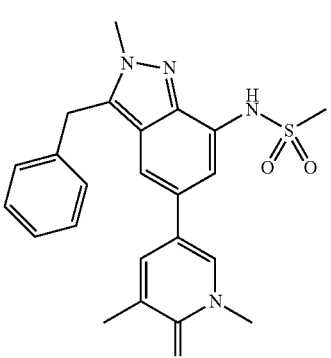
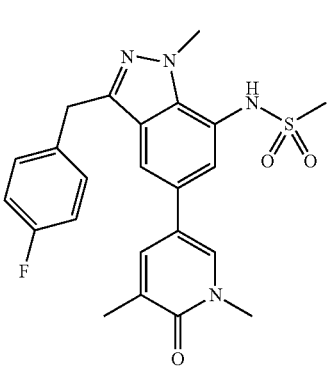 [SMILES: Cc1cc(-c2cc(NS(C)(=O)=O)c3c(c2)c(Cc2ccc(F)cc2)nn3C)cn(C)c1=O]
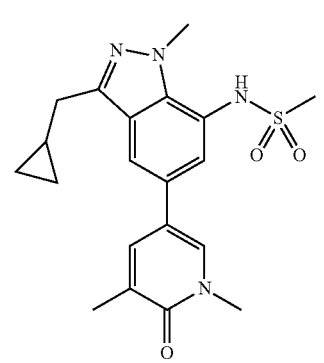 [SMILES: Cc1cc(-c2cc(NS(C)(=O)=O)c3c(c2)c(CC2CC2)nn3C)cn(C)c1=O]

TABLE 2-continued
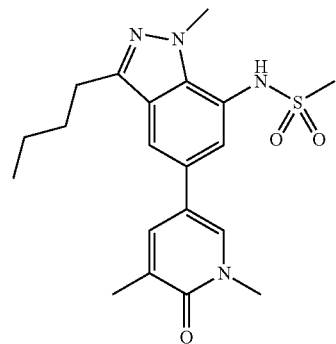 [SMILES: CCCCc1nn(C)c2c(NS(C)(=O)=O)cc(-c3cc(C)c(=O)n(C)c3)cc12]
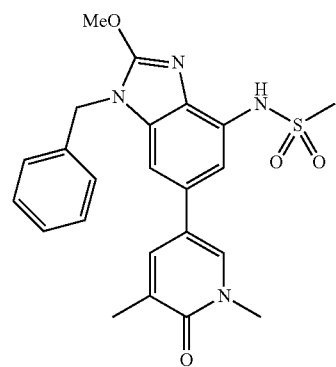 [SMILES: COc1nc2c(NS(C)(=O)=O)cc(-c3cc(C)c(=O)n(C)c3)cc2n1Cc1ccccc1]
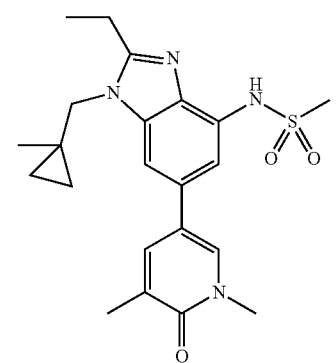
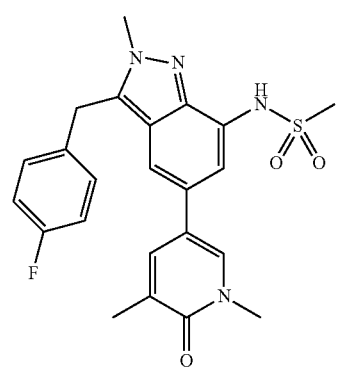 [SMILES: Cc1cc(-c2cc(NS(C)(=O)=O)c3nn(C)c(Cc4ccc(F)cc4)c3c2)cn(C)c1=O]
TABLE 2-continued
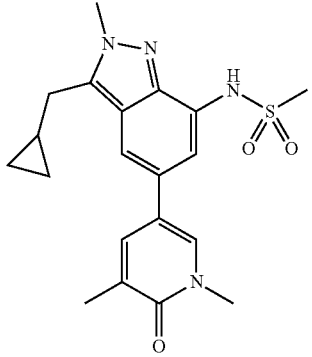 [SMILES: Cc1cc(-c2cc(NS(C)(=O)=O)c3nn(C)c(CC4CC4)c3c2)cn(C)c1=O]
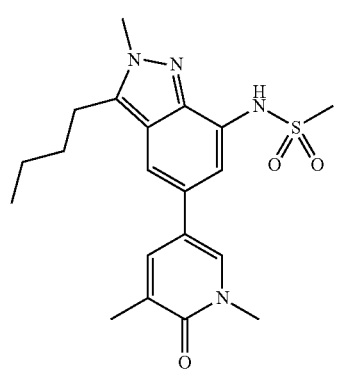 [SMILES: CCCCc1c2cc(-c3cc(C)c(=O)n(C)c3)cc(NS(C)(=O)=O)c2nn1C]
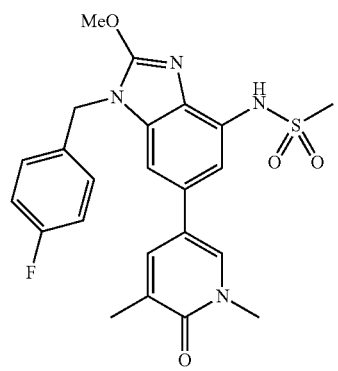 [SMILES: COc1nc2c(NS(C)(=O)=O)cc(-c3cc(C)c(=O)n(C)c3)cc2n1Cc1ccc(F)cc1]
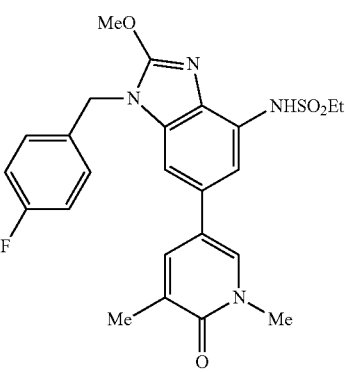

TABLE 2-continued
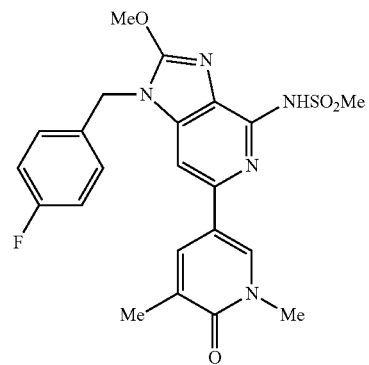
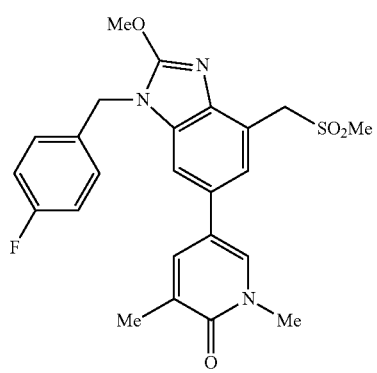
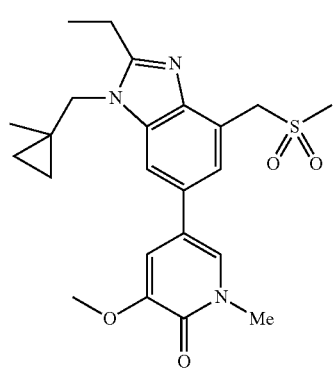
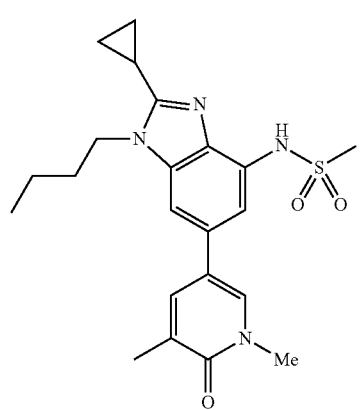 [SMILES: CCCCn1c(C2CC2)nc2c(NS(C)(=O)=O)cc(-c3cc(C)c(=O)n(C)c3)cc21]
TABLE 2-continued
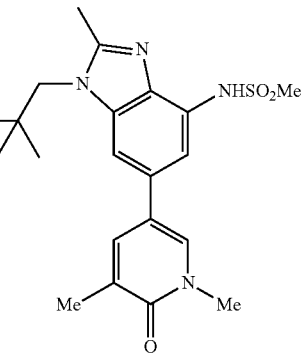
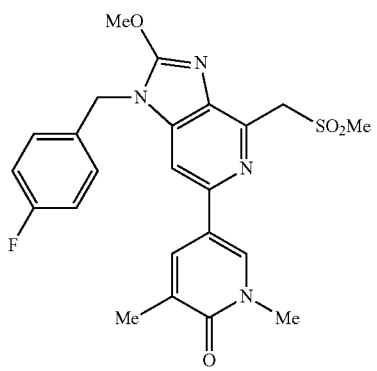 [SMILES: COc1nc2c(CS(C)(=O)=O)nc(-c3cc(C)c(=O)n(C)c3)cc2n1Cc1ccc(F)cc1]
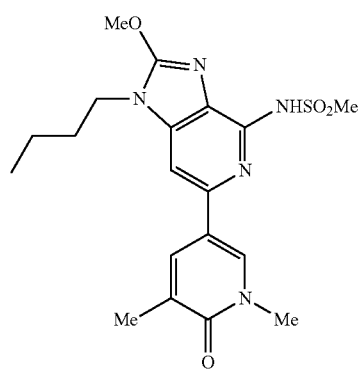
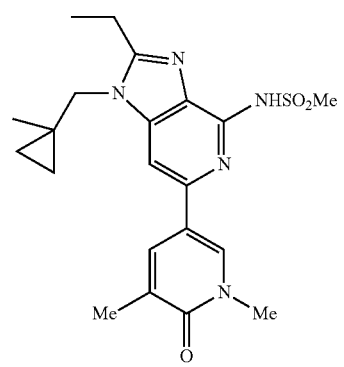

TABLE 2-continued
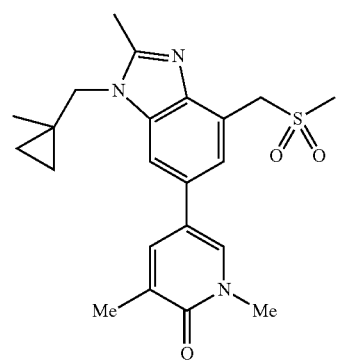
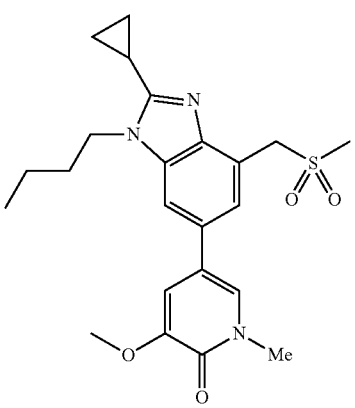 [SMILES: CCCCn1c(C2CC2)nc2c(CS(C)(=O)=O)cc(-c3cc(OC)c(=O)n(C)c3)cc21]
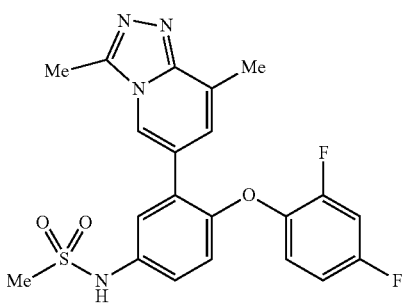 [SMILES: Cc1cc(-c2cc(NS(C)(=O)=O)ccc2Oc2ccc(F)cc2F)cn2c(C)nnc12]
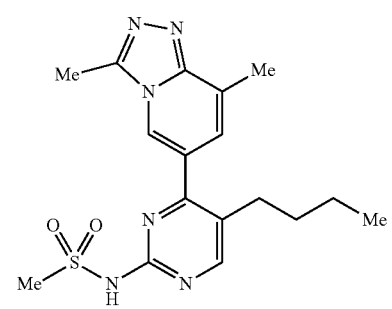 [SMILES: CCCCc1cnc(NS(C)(=O)=O)nc1-c1cc(C)c2nnc(C)n2c1]
TABLE 2-continued
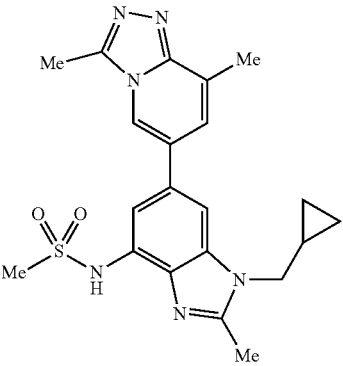 [SMILES: Cc1cc(-c2cc(NS(C)(=O)=O)c3nc(C)n(CC4CC4)c3c2)cn2c(C)nnc12]
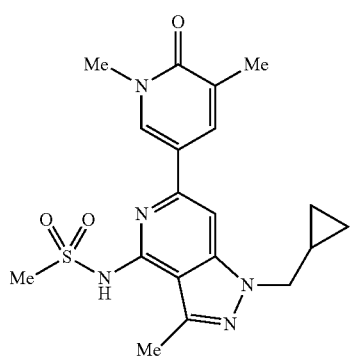 [SMILES: Cc1cc(-c2cc3c(c(C)nn3CC3CC3)c(NS(C)(=O)=O)n2)cn(C)c1=O]
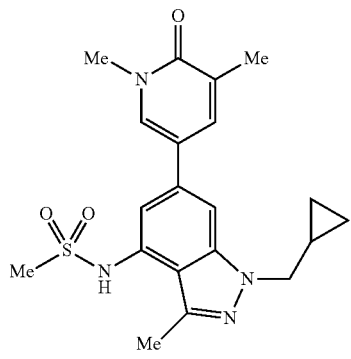 [SMILES: Cc1cc(-c2cc(NS(C)(=O)=O)c3c(C)nn(CC4CC4)c3c2)cn(C)c1=O]
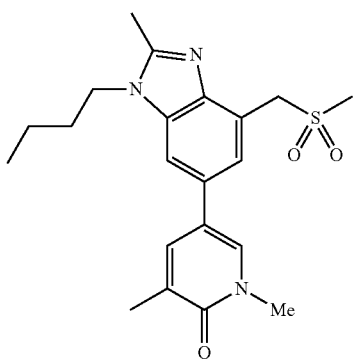 [SMILES: CCCCn1c(C)nc2c(CS(C)(=O)=O)cc(-c3cc(C)c(=O)n(C)c3)cc21]

TABLE 2-continued
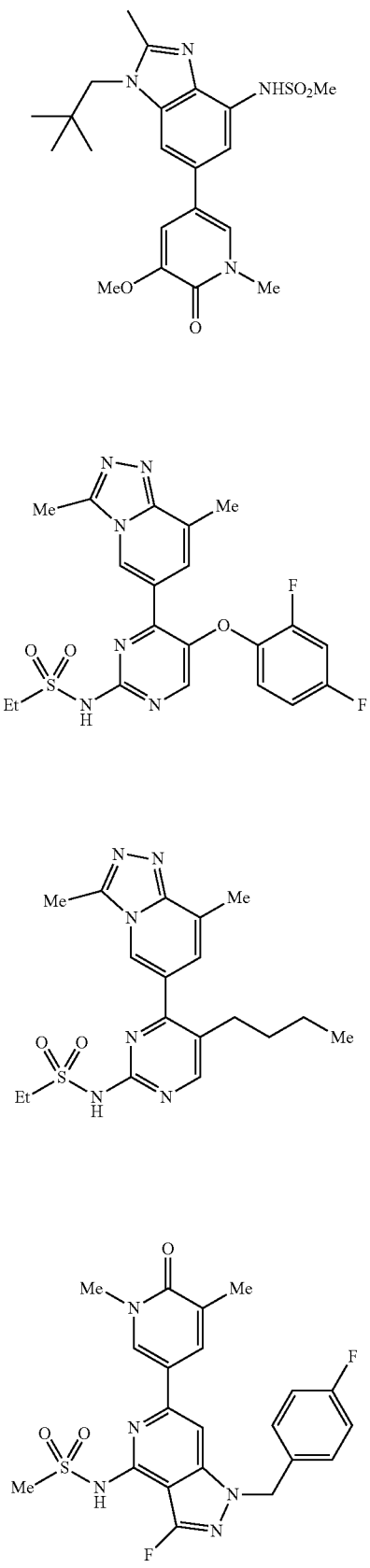
TABLE 2-continued
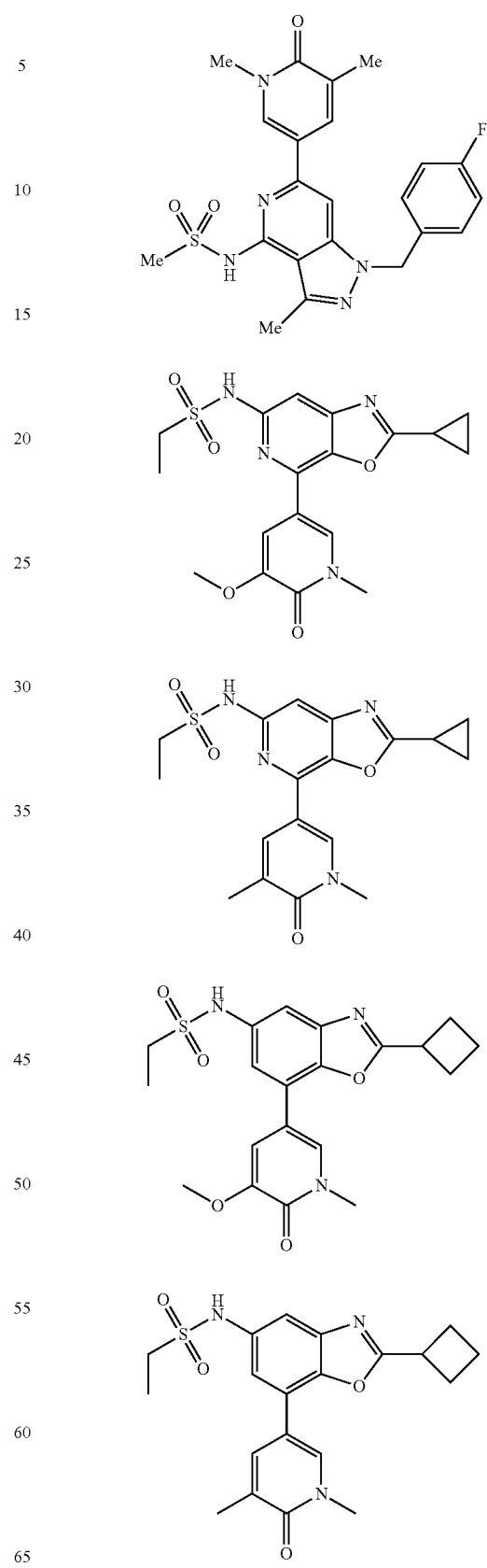

TABLE 2-continued
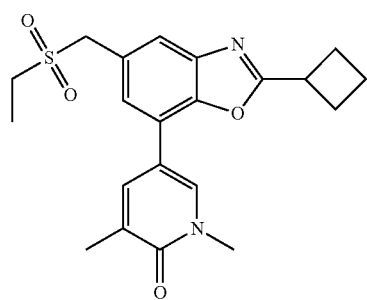 [SMILES: CCS(=O)(=O)Cc1cc(-c2cc(C)c(=O)n(C)c2)c2oc(C3CCC3)nc2c1]
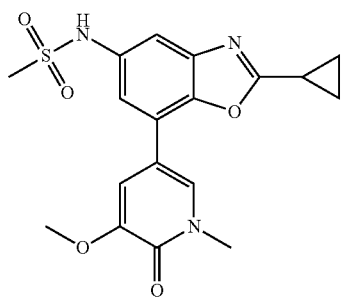 [SMILES: COc1cc(-c2cc(NS(C)(=O)=O)cc3nc(C4CC4)oc23)cn(C)c1=O]
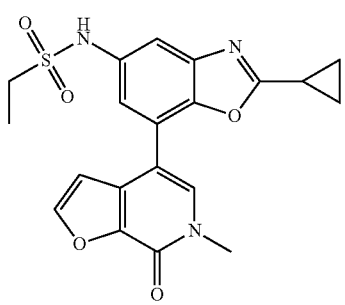 [SMILES: CCS(=O)(=O)Nc1cc(-c2cn(C)c(=O)c3occc23)c2oc(C3CC3)nc2c1]
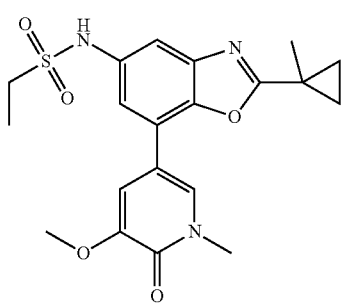 [SMILES: CCS(=O)(=O)Nc1cc(-c2cc(OC)c(=O)n(C)c2)c2oc(C3(C)CC3)nc2c1]
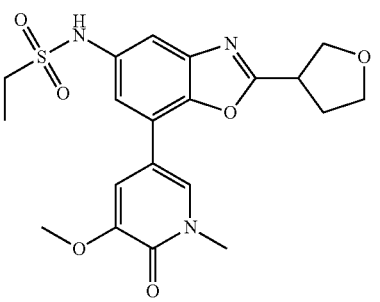 [SMILES: CCS(=O)(=O)Nc1cc(-c2cc(OC)c(=O)n(C)c2)c2oc(C3CCOC3)nc2c1]
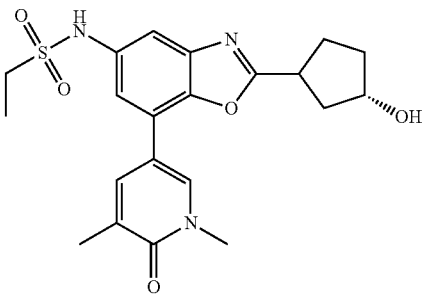 [SMILES: CCS(=O)(=O)Nc1cc(-c2cc(C)c(=O)n(C)c2)c2oc(C3CC[C@H](O)C3)nc2c1]

TABLE 2-continued
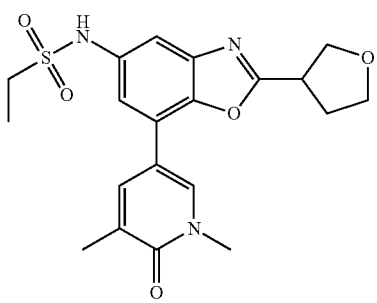 [SMILES: CCS(=O)(=O)Nc1cc(-c2cc(C)c(=O)n(C)c2)c2oc(C3CCOC3)nc2c1]
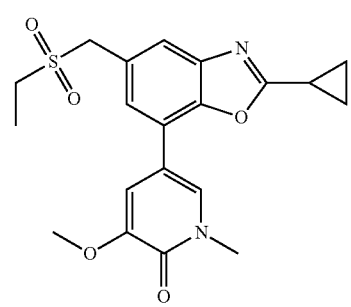 [SMILES: CCS(=O)(=O)Cc1cc(-c2cc(OC)c(=O)n(C)c2)c2oc(C3CC3)nc2c1]
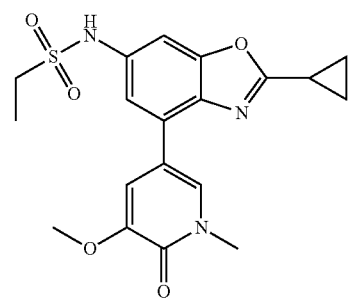 [SMILES: CCS(=O)(=O)Nc1cc(-c2cc(OC)c(=O)n(C)c2)c2nc(C3CC3)oc2c1]
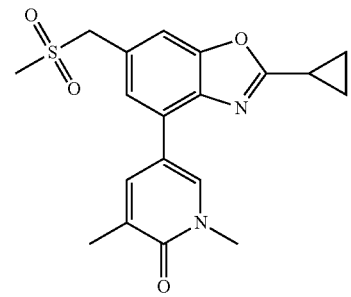 [SMILES: Cc1cc(-c2cc(CS(C)(=O)=O)cc3oc(C4CC4)nc23)cn(C)c1=O]
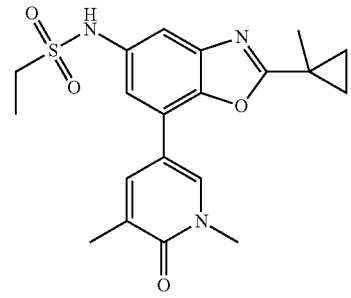 [SMILES: CCS(=O)(=O)Nc1cc(-c2cc(C)c(=O)n(C)c2)c2oc(C3(C)CC3)nc2c1]
TABLE 2-continued
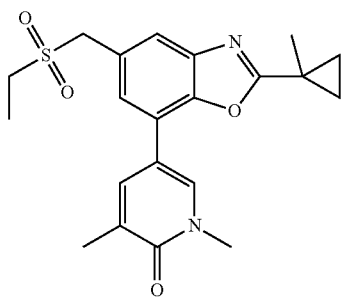 [SMILES: CCS(=O)(=O)Cc1cc(-c2cc(C)c(=O)n(C)c2)c2oc(C3(C)CC3)nc2c1]
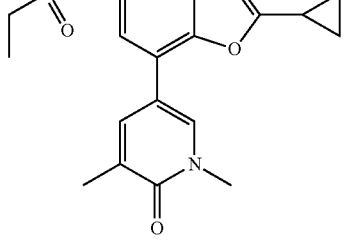
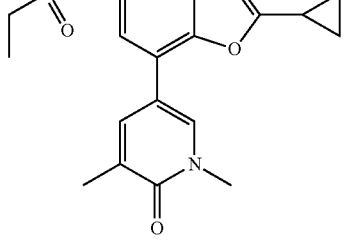
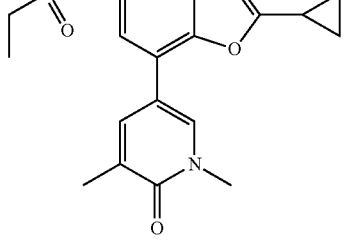
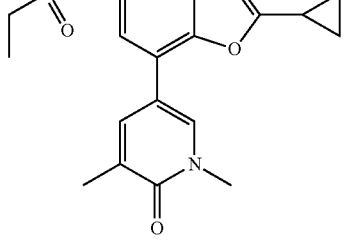

TABLE 2-continued
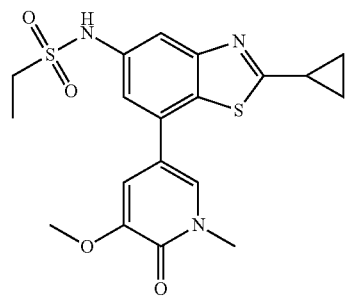 [SMILES: CCS(=O)(=O)Nc1cc(-c2cc(OC)c(=O)n(C)c2)c2sc(C3CC3)nc2c1]
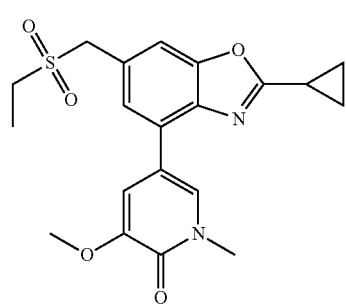 [SMILES: CCS(=O)(=O)Cc1cc(-c2cc(OC)c(=O)n(C)c2)c2nc(C3CC3)oc2c1]
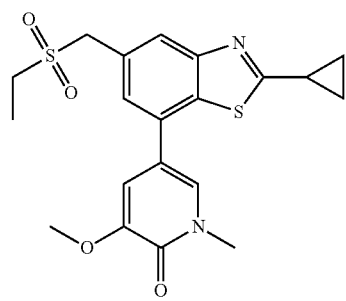 [SMILES: CCS(=O)(=O)Cc1cc(-c2cc(OC)c(=O)n(C)c2)c2sc(C3CC3)nc2c1]
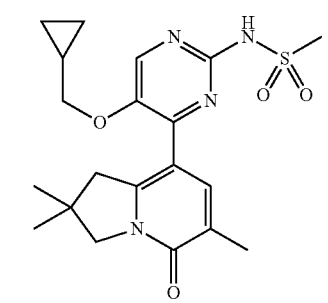
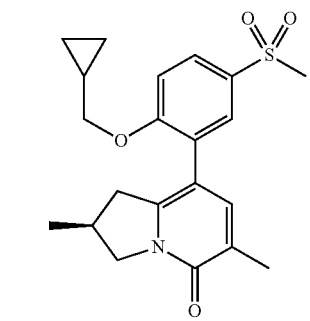
TABLE 2-continued
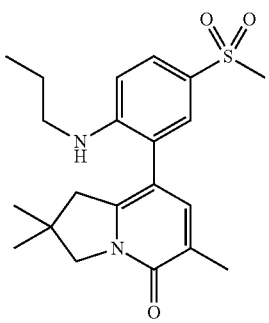 [SMILES: CCCNc1ccc(S(C)(=O)=O)cc1-c1cc(C)c(=O)n2c1CC(C)(C)C2]
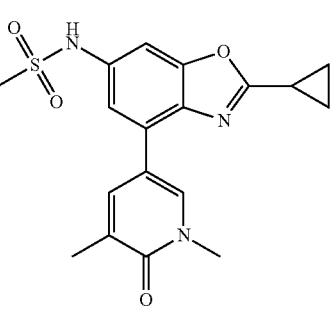
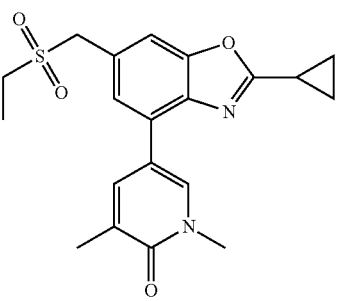 [SMILES: CCS(=O)(=O)Cc1cc(-c2cc(C)c(=O)n(C)c2)c2nc(C3CC3)oc2c1]
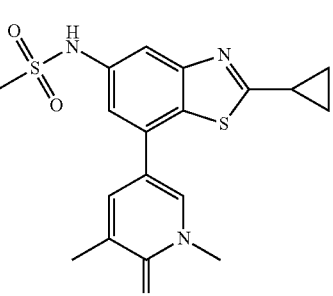
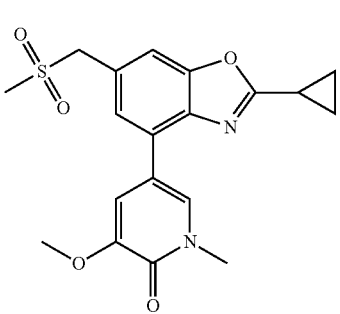 [SMILES: COc1cc(-c2cc(CS(C)(=O)=O)cc3oc(C4CC4)nc23)cn(C)c1=O]

TABLE 2-continued
125
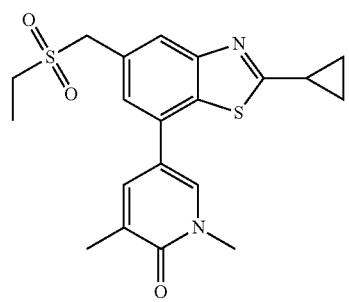
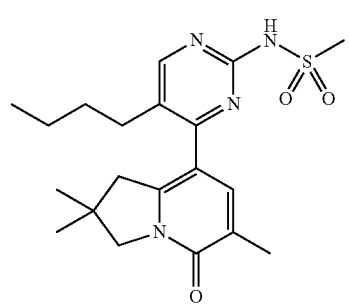 [SMILES: CCCCc1cnc(NS(C)(=O)=O)nc1-c1cc(C)c(=O)n2c1CC(C)(C)C2]
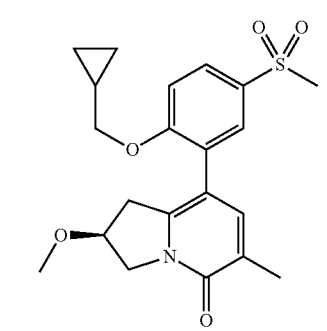
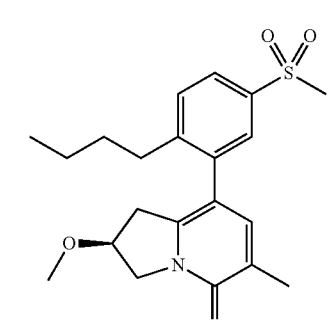
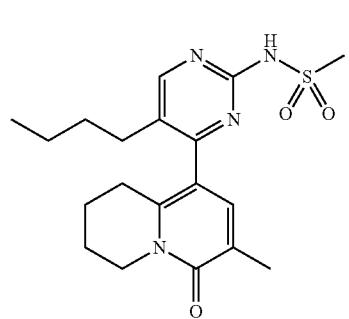 [SMILES: CCCCc1cnc(NS(C)(=O)=O)nc1-c1cc(C)c(=O)n2c1CCCC2]
TABLE 2-continued
126
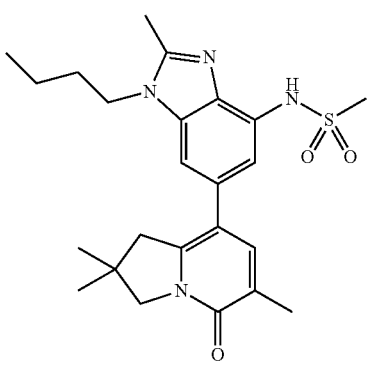 [SMILES: CCCCn1c(C)nc2c(NS(C)(=O)=O)cc(-c3cc(C)c(=O)n4c3CC(C)(C)C4)cc21]
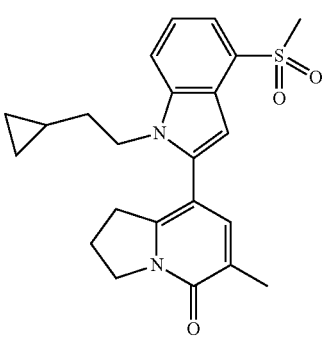 [SMILES: Cc1cc(-c2cc3c(S(C)(=O)=O)cccc3n2CCC2CC2)c2n(c1=O)CCC2]
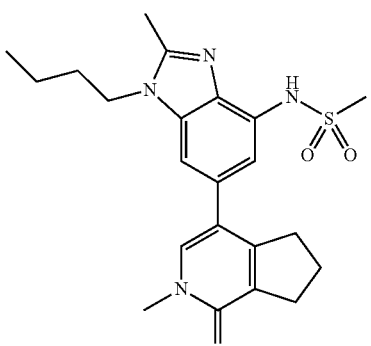
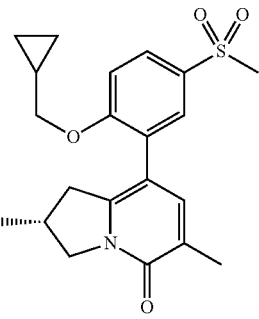

TABLE 2-continued
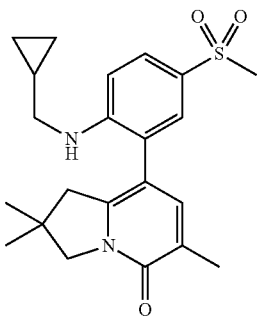
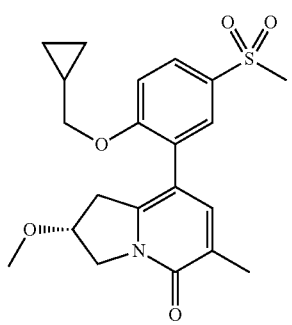
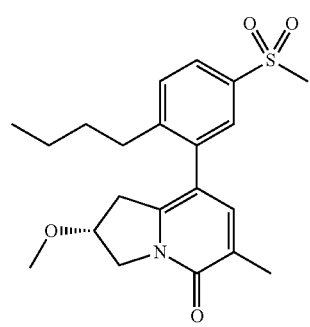 [SMILES: CCCCc1ccc(S(C)(=O)=O)cc1-c1cc(C)c(=O)n2c1C[C@@H](OC)C2]
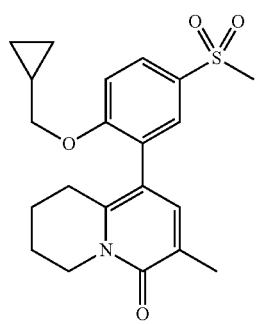 [SMILES: Cc1cc(-c2cc(S(C)(=O)=O)ccc2OCC2CC2)c2n(c1=O)CCCC2]
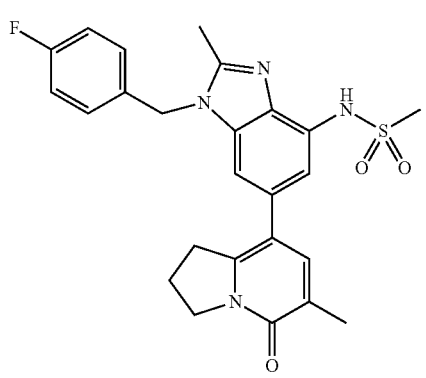 [SMILES: Cc1cc(-c2cc(NS(C)(=O)=O)c3nc(C)n(Cc4ccc(F)cc4)c3c2)c2n(c1=O)CCC2]
TABLE 2-continued
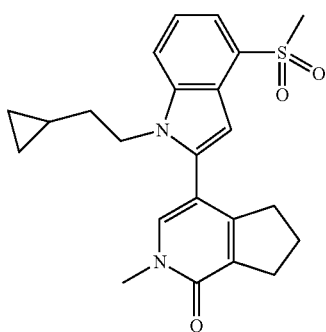 [SMILES: Cn1cc(-c2cc3c(S(C)(=O)=O)cccc3n2CCC2CC2)c2c(c1=O)CCC2]
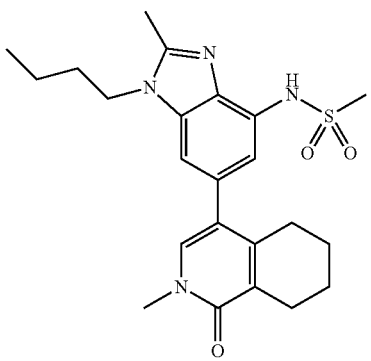 [SMILES: CCCCn1c(C)nc2c(NS(C)(=O)=O)cc(-c3cn(C)c(=O)c4c3CCCC4)cc21]
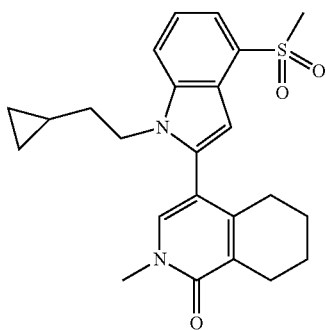 [SMILES: Cn1cc(-c2cc3c(S(C)(=O)=O)cccc3n2CCC2CC2)c2c(c1=O)CCCC2]
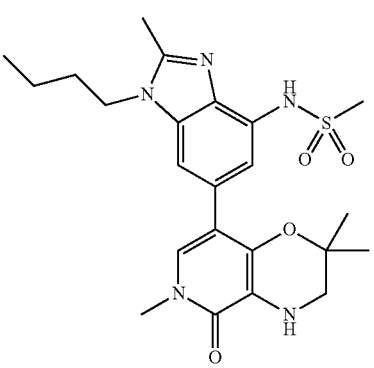 [SMILES: CCCCn1c(C)nc2c(NS(C)(=O)=O)cc(-c3cn(C)c(=O)c4c3OC(C)(C)CN4)cc21]

TABLE 2-continued
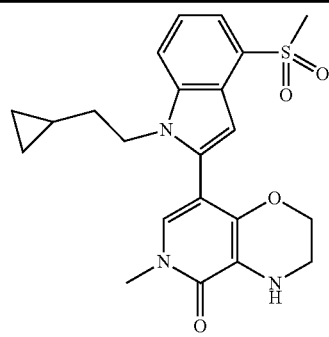
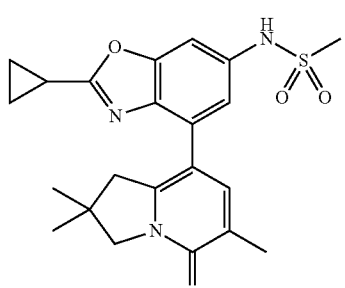
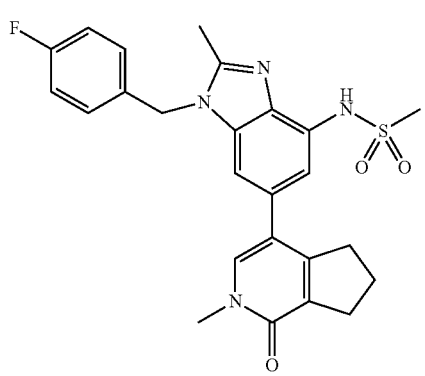 [SMILES: Cc1nc2c(NS(C)(=O)=O)cc(-c3cn(C)c(=O)c4c3CCC4)cc2n1Cc1ccc(F)cc1]
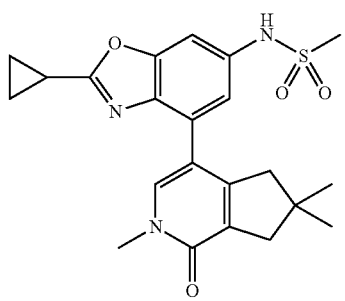 [SMILES: Cn1cc(-c2cc(NS(C)(=O)=O)cc3oc(C4CC4)nc23)c2c(c1=O)CC(C)(C)C2]
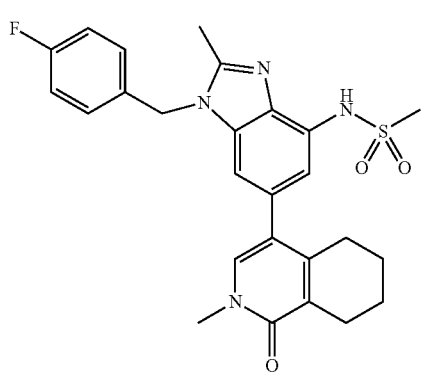 [SMILES: Cc1nc2c(NS(C)(=O)=O)cc(-c3cn(C)c(=O)c4c3CCCC4)cc2n1Cc1ccc(F)cc1]
TABLE 2-continued
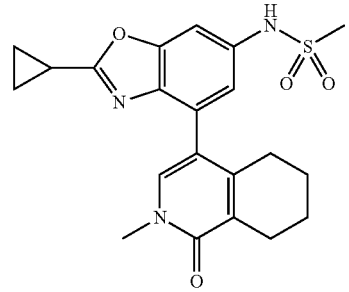 [SMILES: Cn1cc(-c2cc(NS(C)(=O)=O)cc3oc(C4CC4)nc23)c2c(c1=O)CCCC2]
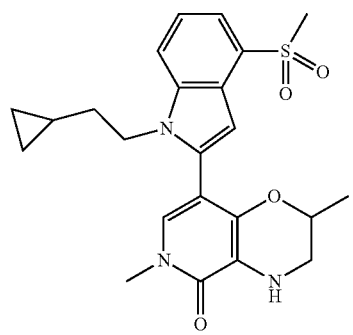 [SMILES: CC1CNc2c(c(-c3cc4c(S(C)(=O)=O)cccc4n3CCC3CC3)cn(C)c2=O)O1]
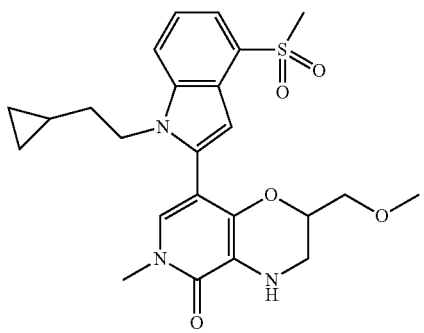 [SMILES: COCC1CNc2c(c(-c3cc4c(S(C)(=O)=O)cccc4n3CCC3CC3)cn(C)c2=O)O1]
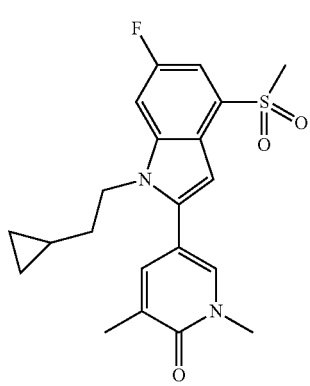 [SMILES: Cc1cc(-c2cc3c(S(C)(=O)=O)cc(F)cc3n2CCC2CC2)cn(C)c1=O]

TABLE 2-continued
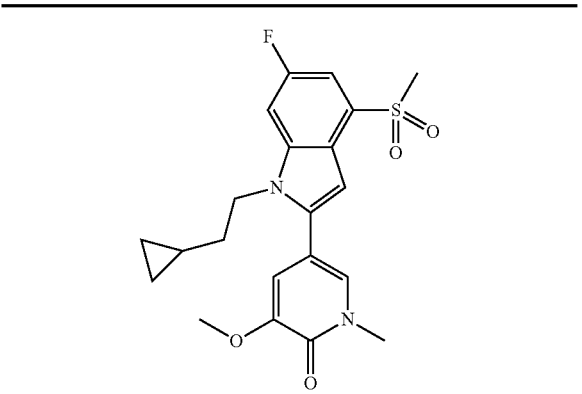
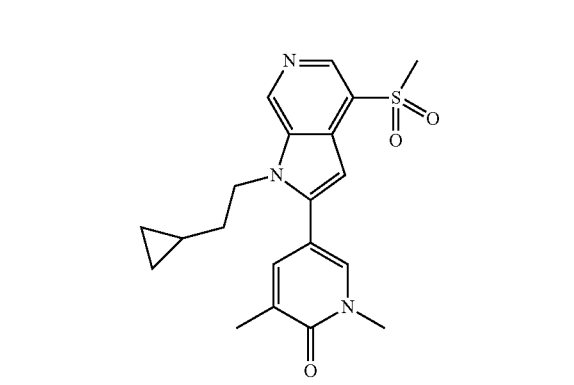 [SMILES: Cc1cc(-c2cc3c(S(C)(=O)=O)cncc3n2CCC2CC2)cn(C)c1=O]
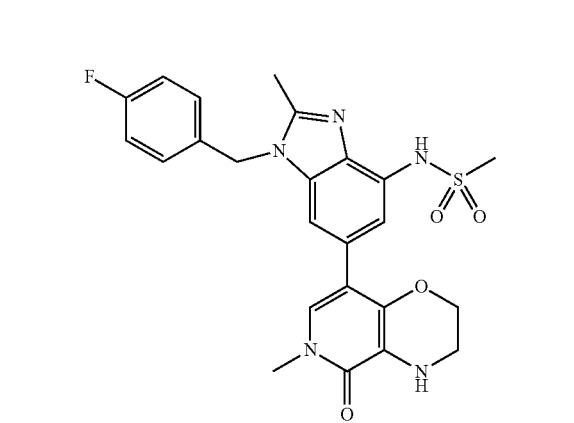 [SMILES: Cc1nc2c(NS(C)(=O)=O)cc(-c3cn(C)c(=O)c4c3OCCN4)cc2n1Cc1ccc(F)cc1]
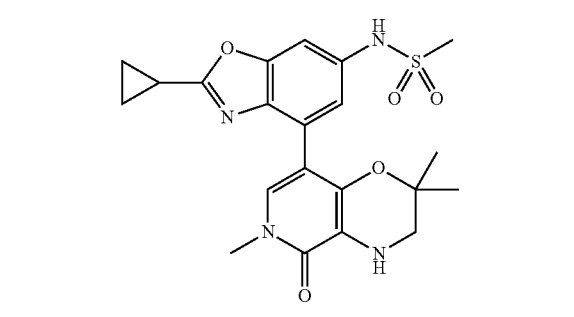 [SMILES: Cn1cc(-c2cc(NS(C)(=O)=O)cc3oc(C4CC4)nc23)c2c(c1=O)NCC(C)(C)O2]
TABLE 2-continued
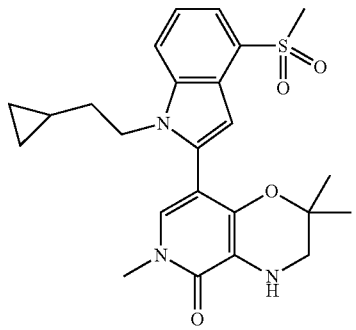 [SMILES: Cn1cc(-c2cc3c(S(C)(=O)=O)cccc3n2CCC2CC2)c2c(c1=O)NCC(C)(C)O2]
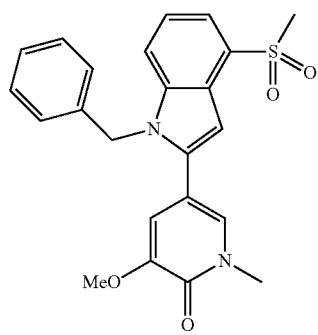
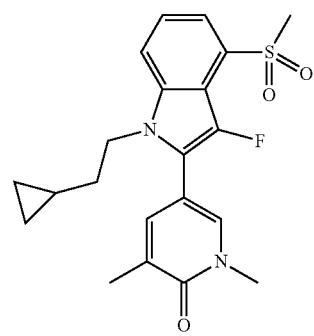 [SMILES: Cc1cc(-c2c(F)c3c(S(C)(=O)=O)cccc3n2CCC2CC2)cn(C)c1=O]
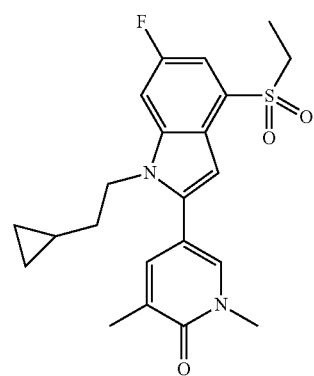 [SMILES: CCS(=O)(=O)c1cc(F)cc2c1cc(-c1cc(C)c(=O)n(C)c1)n2CCC1CC1]

TABLE 2-continued
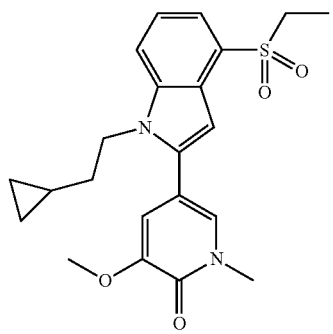 [SMILES: CCS(=O)(=O)c1cccc2c1cc(-c1cc(OC)c(=O)n(C)c1)n2CCC1CC1]
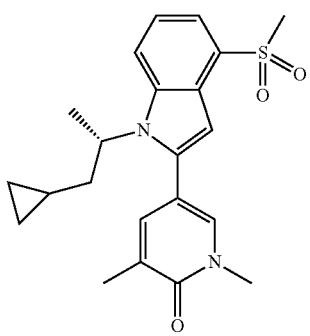 [SMILES: Cc1cc(-c2cc3c(S(C)(=O)=O)cccc3n2[C@@H](C)CC2CC2)cn(C)c1=O]
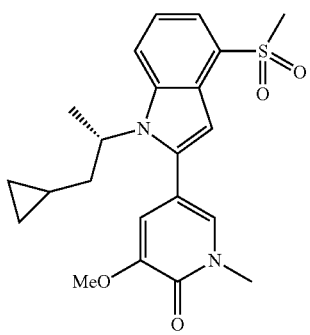 [SMILES: COc1cc(-c2cc3c(S(C)(=O)=O)cccc3n2[C@@H](C)CC2CC2)cn(C)c1=O]
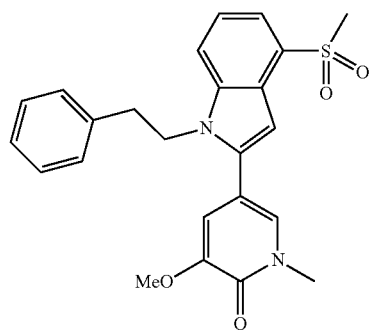 [SMILES: COc1cc(-c2cc3c(S(C)(=O)=O)cccc3n2CCc2ccccc2)cn(C)c1=O]
TABLE 2-continued
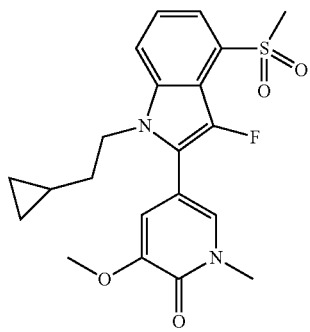 [SMILES: COc1cc(-c2c(F)c3c(S(C)(=O)=O)cccc3n2CCC2CC2)cn(C)c1=O]
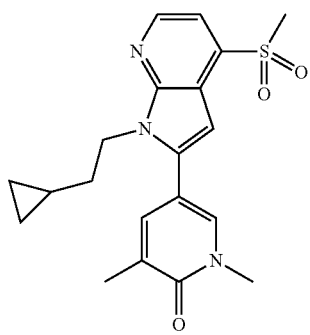 [SMILES: Cc1cc(-c2cc3c(S(C)(=O)=O)ccnc3n2CCC2CC2)cn(C)c1=O]
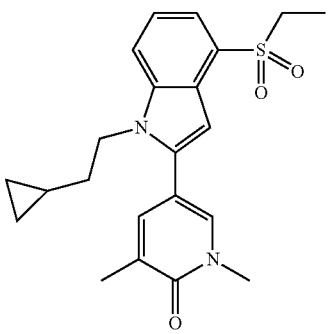 [SMILES: CCS(=O)(=O)c1cccc2c1cc(-c1cc(C)c(=O)n(C)c1)n2CCC1CC1]
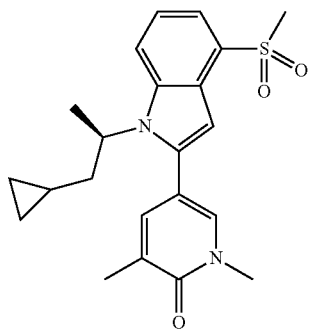 [SMILES: Cc1cc(-c2cc3c(S(C)(=O)=O)cccc3n2[C@H](C)CC2CC2)cn(C)c1=O]

TABLE 2-continued
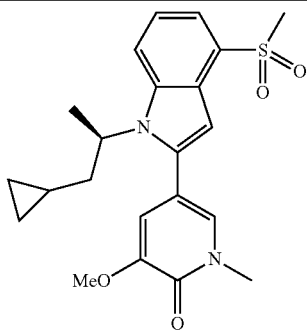
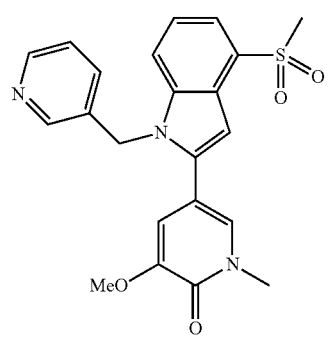 [SMILES: COc1cc(-c2cc3c(S(C)(=O)=O)cccc3n2Cc2cccnc2)cn(C)c1=O]
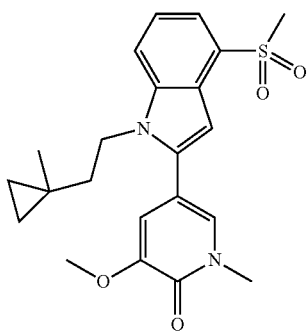 [SMILES: COc1cc(-c2cc3c(S(C)(=O)=O)cccc3n2CCC2(C)CC2)cn(C)c1=O]
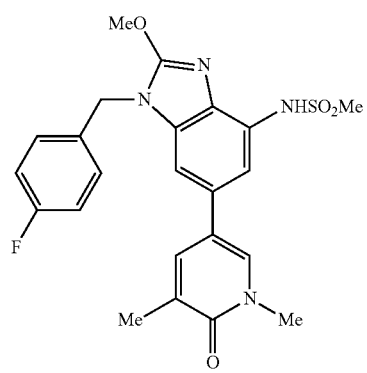
TABLE 2-continued
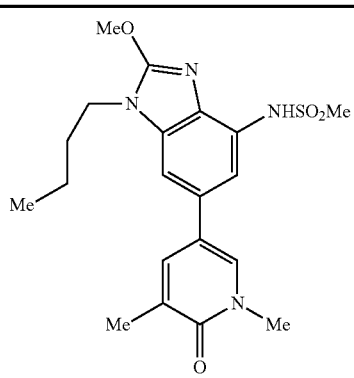
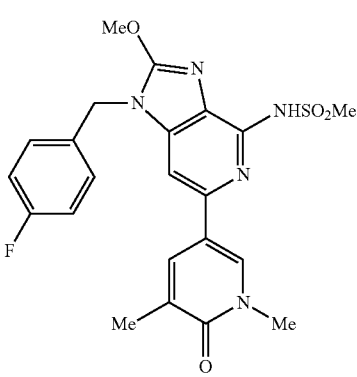
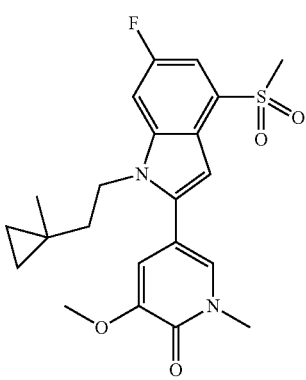 [SMILES: COc1cc(-c2cc3c(S(C)(=O)=O)cc(F)cc3n2CCC2(C)CC2)cn(C)c1=O]
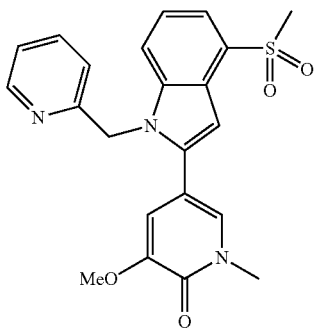 [SMILES: COc1cc(-c2cc3c(S(C)(=O)=O)cccc3n2Cc2ccccn2)cn(C)c1=O]

TABLE 2-continued
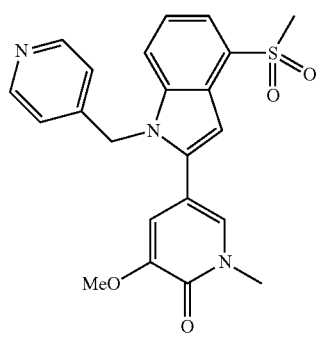 [SMILES: COc1cc(-c2cc3c(S(C)(=O)=O)cccc3n2Cc2ccncc2)cn(C)c1=O]
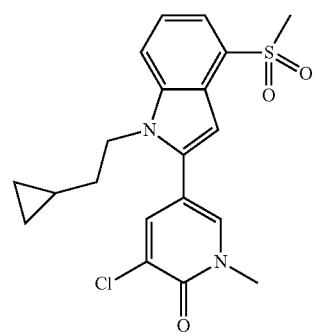 [SMILES: Cn1cc(-c2cc3c(S(C)(=O)=O)cccc3n2CCC2CC2)cc(Cl)c1=O]
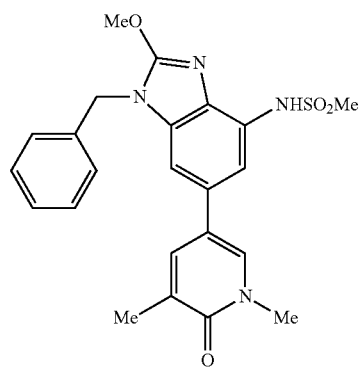
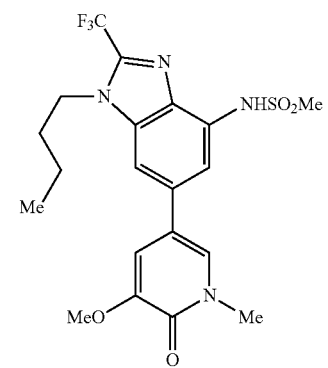
TABLE 2-continued
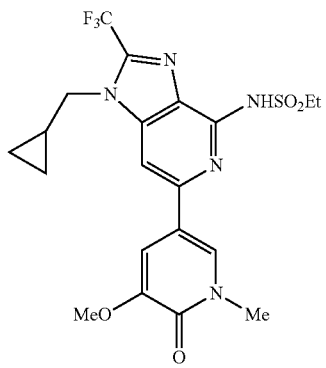
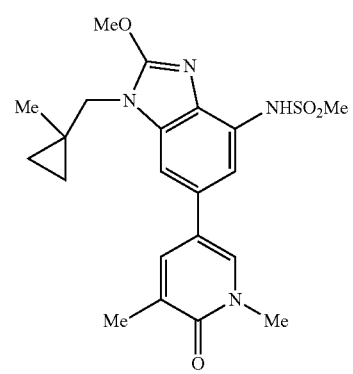
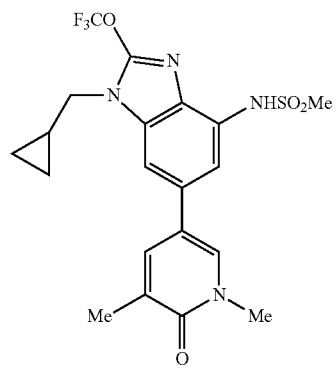
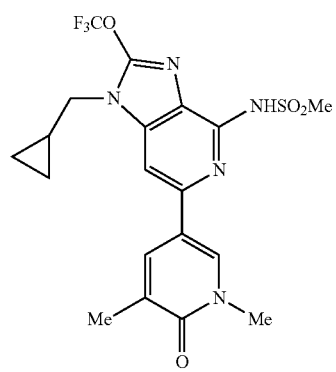

TABLE 2-continued
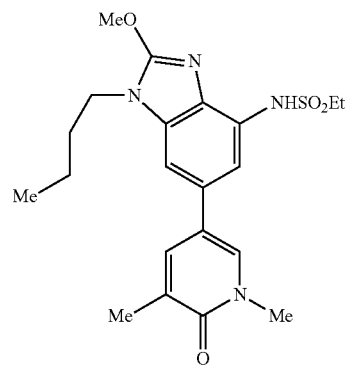
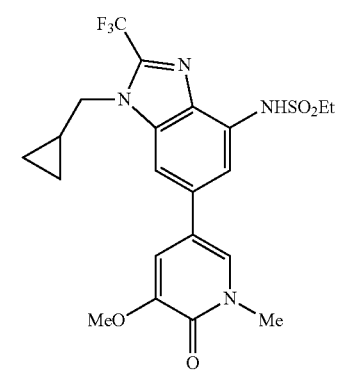
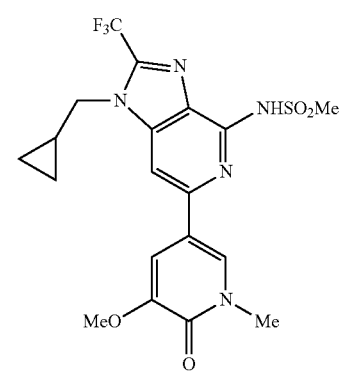
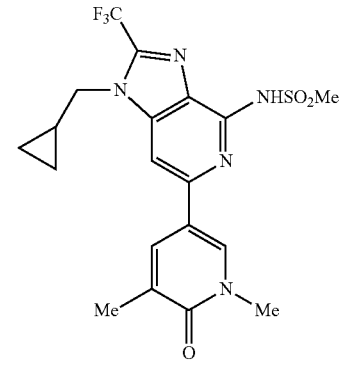
TABLE 2-continued
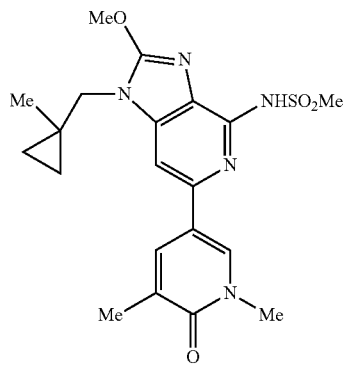
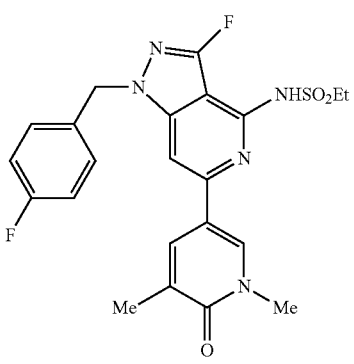
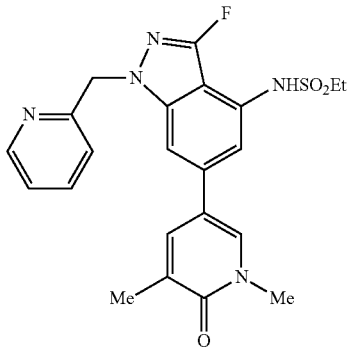
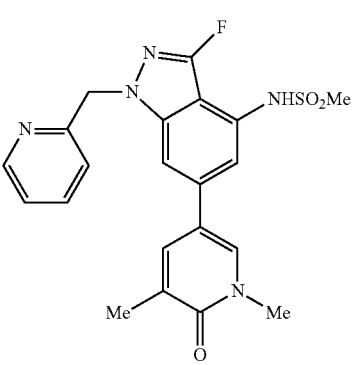

TABLE 2-continued

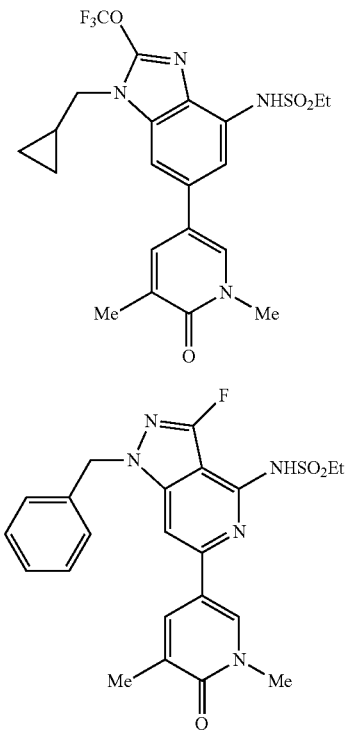

Preparation of the Substituted Heterocyclic Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including, for example, Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatises detail the synthesis of reactants useful in the preparation of compounds described herein, or provide references to articles that describe the preparation. See, e.g., SYNTHETIC ORGANIC CHEM. (John Wiley & Sons, Inc., NY); Sandler et al., ORGANIC FUNCTIONAL GROUP PREPARATIONS (2nd Ed., Acad. Press, N Y, 1983); House, MODERN SYNTHETIC REACTIONS (2nd Ed., W.A. Benjamin, Inc., Menlo Park, Calif., 1972); Gilchrist, HETEROCYCLIC CHEM. (2nd Ed., John Wiley & Sons, N Y, 1992); March, ADV. ORGANIC CHEM.: REACTIONS, MECH. & STRUCTURE (4th Ed., Wiley-Intersci., NY, 1992). Additional suitable reference books and treatises detail the synthesis of reactants useful in the preparation of compounds described herein, or provide references to articles that describe such preparations. See, e.g., Fuhrhop & Penzlin, ORGANIC SYNTHESIS: CONCEPTS, METHODS, STARTING MATERIALS: SECOND, REVISED & ENLARGED ED. (John Wiley & Sons ISBN: 3-527-29074-5, 1994); Hoffman, ORGANIC CHEM., AN INTERMEDIATE TEXT (Oxford Univ. Press, ISBN 0-19-509618-5, 1996); Larock, COMPREHENSIVE ORGANIC TRANSFORMATIONS: GUIDE TO FUNCTIONAL GROUP PREPARATIONS (2nd Ed., Wiley-VCH, ISBN: 0-471-19031-4, 1999); Otera (Ed.), MODERN CARBONYL CHEM. (Wiley-VCH, ISBN: 3-527-29871-1, 2000); Patai, PATAI'S 1992 GUIDE TO THE CHEM. OF FUNCTIONAL GROUPS (Intersci. ISBN: 0-471-93022-9, 1992); Solomons, ORGANIC CHEM. (7th Ed., John Wiley & Sons, ISBN: 0-471-19095-0, 2000); Stowell, INTERMEDIATE ORGANIC CHEM. (2nd Ed. Wiley-Intersci., ISBN: 0-471-57456-2, 1993); INDUS. ORGANIC CHEM.: STARTING MATS. & INTERMEDIATES: AN ULLMANN'S ENCYCLO. (John Wiley & Sons, ISBN: 3-527-29645-X, 1999), in 8 vols.; ORGANIC REACTIONS (John Wiley & Sons, 1942-2000), in over 55 volumes; CHEM. OF FUNCTIONAL GROUPS (John Wiley & Sons), in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted heterocyclic derivative compounds described herein is Stahl & Wermuth, HANDBOOK OF PHARMACEUTICAL SALTS (Verlag Helvetica Chimica Acta, Zurich, 2002).

General methods for the synthesis of substituted heterocyclic derivatives are provided in, but not limited to, the following references: WO 2009/158396; WO 2005/63768; WO 2006/112666; Briet et. al., 58 Tetrahedron 5761 (2002); WO 2008/77550; WO 2008/77551; WO 2008/77556; WO 2007/12421; WO 2007/12422; US 2007/99911; WO 2008/77550; Havera et al., 42 J. Med. Chem. 3860 (1999); WO 2004/29051; and US 2009/0054434. Additional examples of the synthesis of substituted heterocyclic derivatives are found in the following references: WO 2012/171337; WO 2011/044157; WO 2009/097567; WO 2005/030791; EP 203216; Becknell et al., 21 Bioorg. & Med. Chem. Letters 7076 (2011); Svechkarev et al., 770 Вісник Харківського національного університету імені В.Н.Каразіна 201 (2007); Coskun et al., 35 Synth. Commc'ns 2435 (2005); Alvarez et al., 15 Sci. Synth. 839 (2005); Kihara et al., 53 Heterocycles 359 (2000); Couture et al., 7 J. Chem. Soc'y 789 (1999); Kihara et al., 48 Heterocycles 2473 (1998); Couture et al., 52 Tetrahedron 4433 (1996); Couturre et al., 37 Tetrahedron Letters 3697 (1996); Natsugari et al., 38 J. Med. Chem. 3106 (1995); Moehrle et al., 321 Archiv der Pharm. 759 (1988); Gore et al., 3 J. Chem. Soc'y 481 (1999); Narasimhan et al., 3 J. Chem. Soc'y, Chem. Commc'ns 191 (1987); Henry et al., 40 J. Org. Chem. 1760 (1975); Berti, 90 Gazzetta Chimica Italiana 559 (1960); Berti et al., 49 Annali di Chimica 2110, 1253 (Rome, Italy, 1959); WO 2012/000595;

Couture et al., 52 Tetrahedron 4433 (1996); WO 2010/069504; WO 2010/069504; WO 2006/030032; WO 2005/095384; US 2005/0222159; WO 2013/064984; Mishra et al., 2013 Eur. J. Org. Chem. 693 (2013); Vachhani et al., 69 Tetrahedron 359 (2013); Xie et al., 45 Eur. J. Med. Chem. 210 (2010); Mukaiyama et al., 15 Bioorg. & Med. Chem. 868 (2007); JP 2005/089352; Wang et al., 9 Molecules 574 (2004); WO 2000/023487; US 2006/0287341; CN 103183675; Hares et al., 32 Egyptian J. Pharm. Sci. 303 (1991); DE 2356005; DE 2133898; DE 2133998; DE 2011970; U.S. Pat. No. 3,816,422; Staehle et al., 8 Justus Liebigs Annalen der Chem. 1275 (1973).

In some embodiments, the substituted heterocyclic derivative compounds disclosed herein are prepared by the general synthetic routes described below in Schemes 1-9. These schemes are intended to exemplary to one of skill in the art and are not limiting. Additional methods for the synthesis of the substituted heterocyclic derivative compounds disclosed herein are readily available to one of skill in the art.

A method for preparing compounds of Formulas I-IV is provided in Scheme 1:

Further palladium-catalyzed cross coupling reaction of compound (1-5) with a suitable halide provides the isoquinolinone (1-6).

A method for preparing compounds of Formulas I-IV is provided in Scheme 2:

Scheme 2

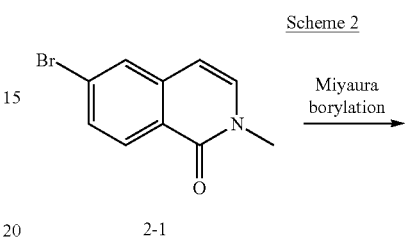

2-1

Scheme 1

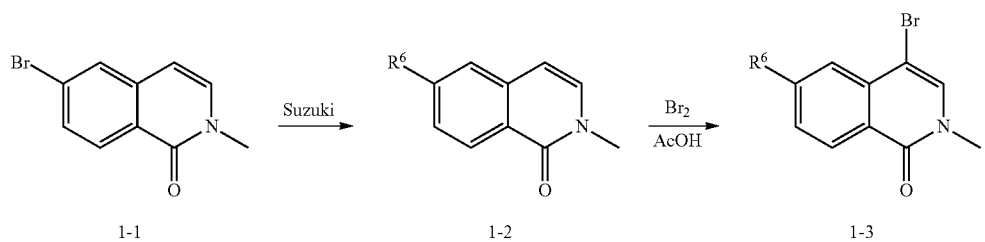

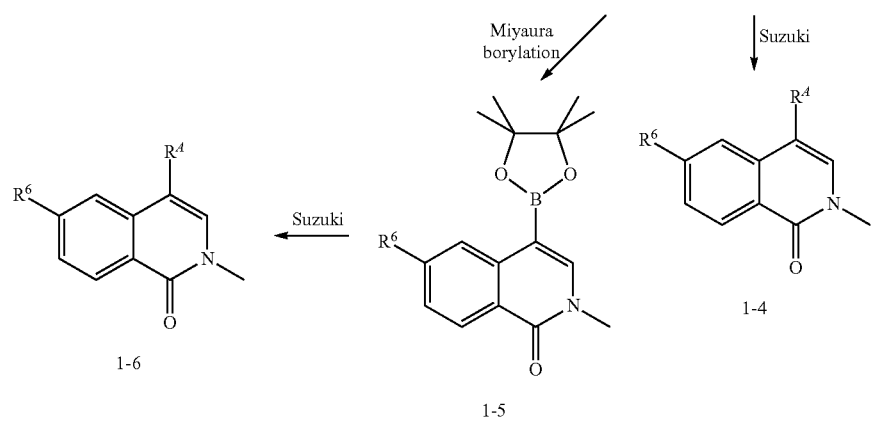

According to Scheme 1, the compound 6-bromo-2-methylisoquinolin-1(2H)-one (1-1) is subjected to a palladium-catalyzed cross coupling reaction to provide isoquinolinone (1-2). Bromination under acidic conditions provides compound (1-3). Further palladium-catalyzed cross coupling reaction with a boronic acid, or ester, provides the isoquinolinone (1-4). Alternatively, palladium-catalyzed cross coupling of compound (1-3) with 4,4,5,5-tetramethyl-2-(tetramethyl-1,3,2-dioxaborolan-2-yl)-1,3,2-dioxaborolane under the conditions described by Miyaura (Ishiyama et al., 60 J. Org. Chem. 7508 (1995) provides the boron ester (1-5).

-continued

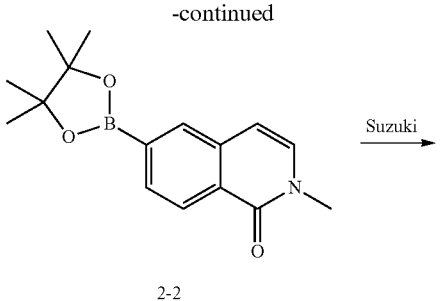

2-2

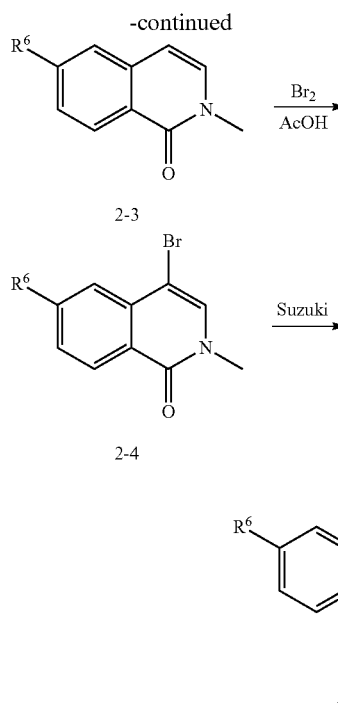

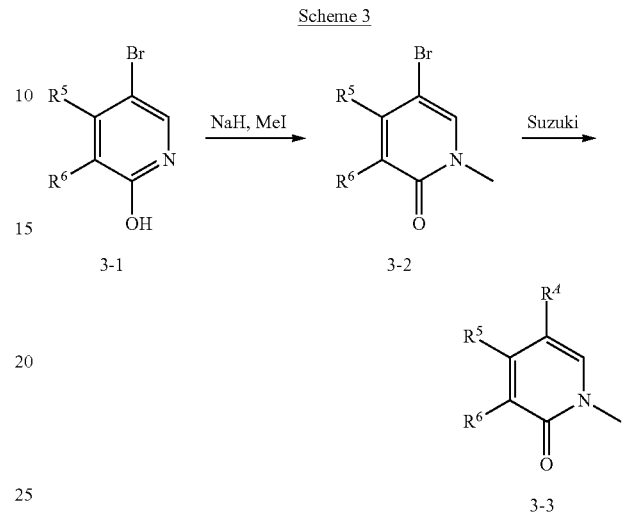

Further palladium-catalyzed cross coupling reaction with a boronic acid, or ester, provides the isoquinolinone (2-5).

A method for preparing compounds of Formulas I-IV is provided in Scheme 3:

As provided in Scheme 2, the compound 6-bromo-2-methylisoquinolin-1(2H)-one (2-1) is subjected to a palladium-catalyzed cross coupling reaction with 4,4,5,5-tetramethyl-2-(tetramethyl-1,3,2-dioxaborolan-2-yl)-1,3,2-dioxaborolane to provide boron ester (2-2). Further palladium-catalyzed cross coupling reaction of compound (2-2) with a suitable halide provides compound (2-3). Bromination under acidic conditions provides compound (2-4).

According to the method provided in Scheme 3, the compound 5-bromo-pyridin-2-ol derivative (3-1) is subjected to alkylation with methyl iodide under basic conditions to provide the related 5-bromo-1-methylpyridin-2(1H)-one derivative (3-2). Further palladium-catalyzed cross coupling reaction of compound (3-2) with a suitable halide provides compound (3-3).

A method for preparing compounds of Formulas I-IV is further provided in Scheme 4:

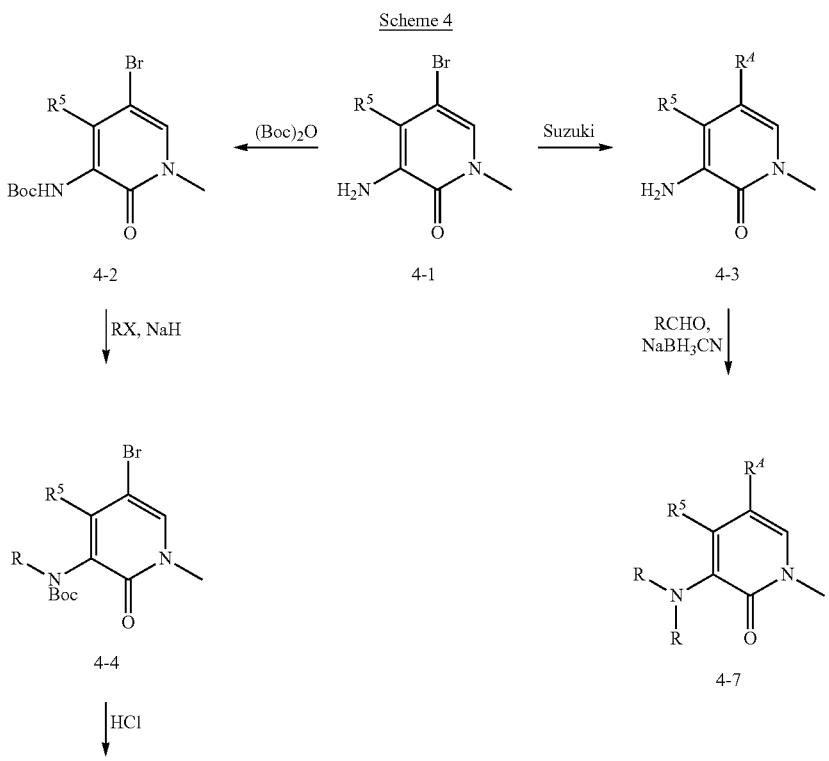

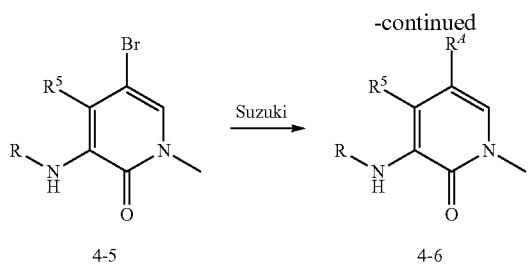

According to the method for preparing compounds of Formulas I-IV as provided in Scheme 4, the compound 3-amino-5-bromo-1-methylpyridin-2(1H)-one derivative (4-1) is used as a starting material for several routes. In one route, compound (4-1) is directly subjected to a palladium-catalyzed cross coupling reaction to provide pyridone (4-3). The amino group of compound (4-3) is subjected to a reductive amination with an aldehyde and a reducing agent, such as sodium cyanoborohydride, to provide the substituted amino derivative compound (4-7). A second route involving selective alkylation of the amino group of compound (4-1) begins with protection of the amino group as the BOC carbamate. Alkylation of the carbamate under basic conditions followed by removal of the BOC carbamate under acidic conditions provides the secondary amine compound (4-5). Treatment of (4-5) with a suitable halide under palladium-catalyzed cross coupling conditions affords compound (4-6).

Further, a method for preparing benzimidazole compounds of Formula II is provided in Scheme 5:

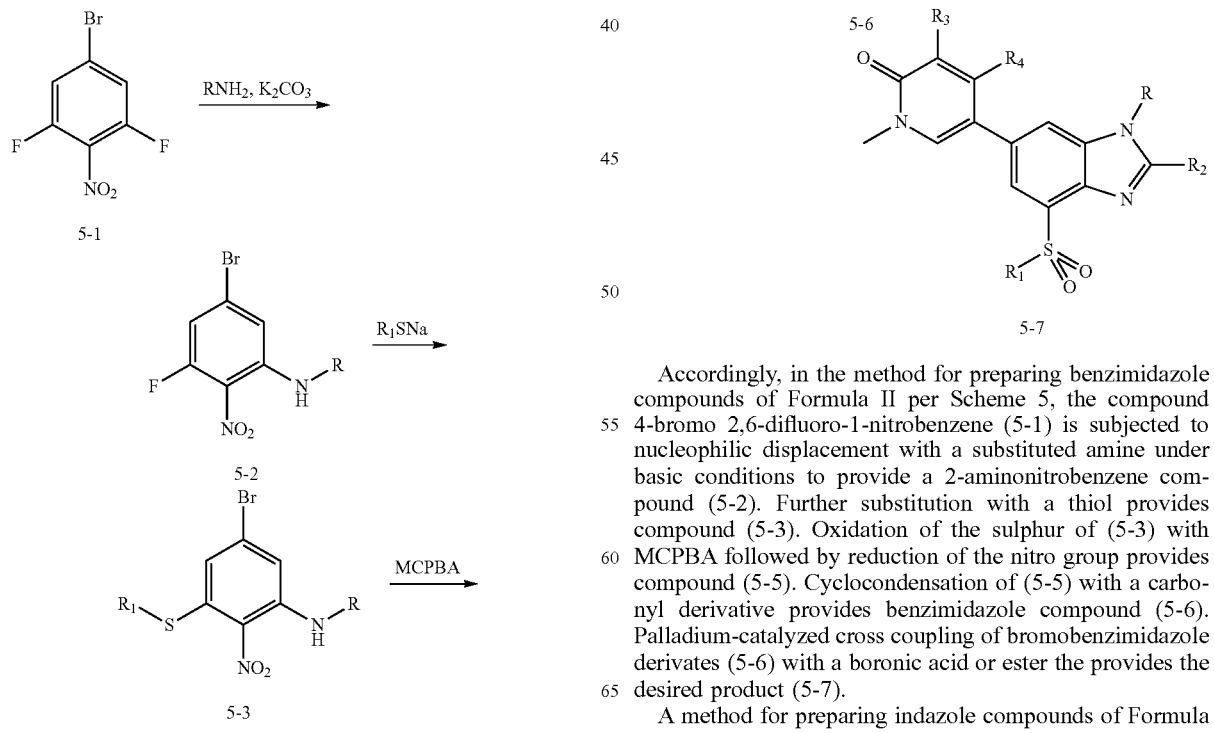

Accordingly, in the method for preparing benzimidazole compounds of Formula II per Scheme 5, the compound 4-bromo 2,6-difluoro-1-nitrobenzene (5-1) is subjected to nucleophilic displacement with a substituted amine under basic conditions to provide a 2-aminonitrobenzene compound (5-2). Further substitution with a thiol provides compound (5-3). Oxidation of the sulphur of (5-3) with MCPBA followed by reduction of the nitro group provides compound (5-5). Cyclocondensation of (5-5) with a carbonyl derivative provides benzimidazole compound (5-6). Palladium-catalyzed cross coupling of bromobenzimidazole derivates (5-6) with a boronic acid or ester the provides the desired product (5-7).

A method for preparing indazole compounds of Formula II is provided in Scheme 6:

Scheme 6

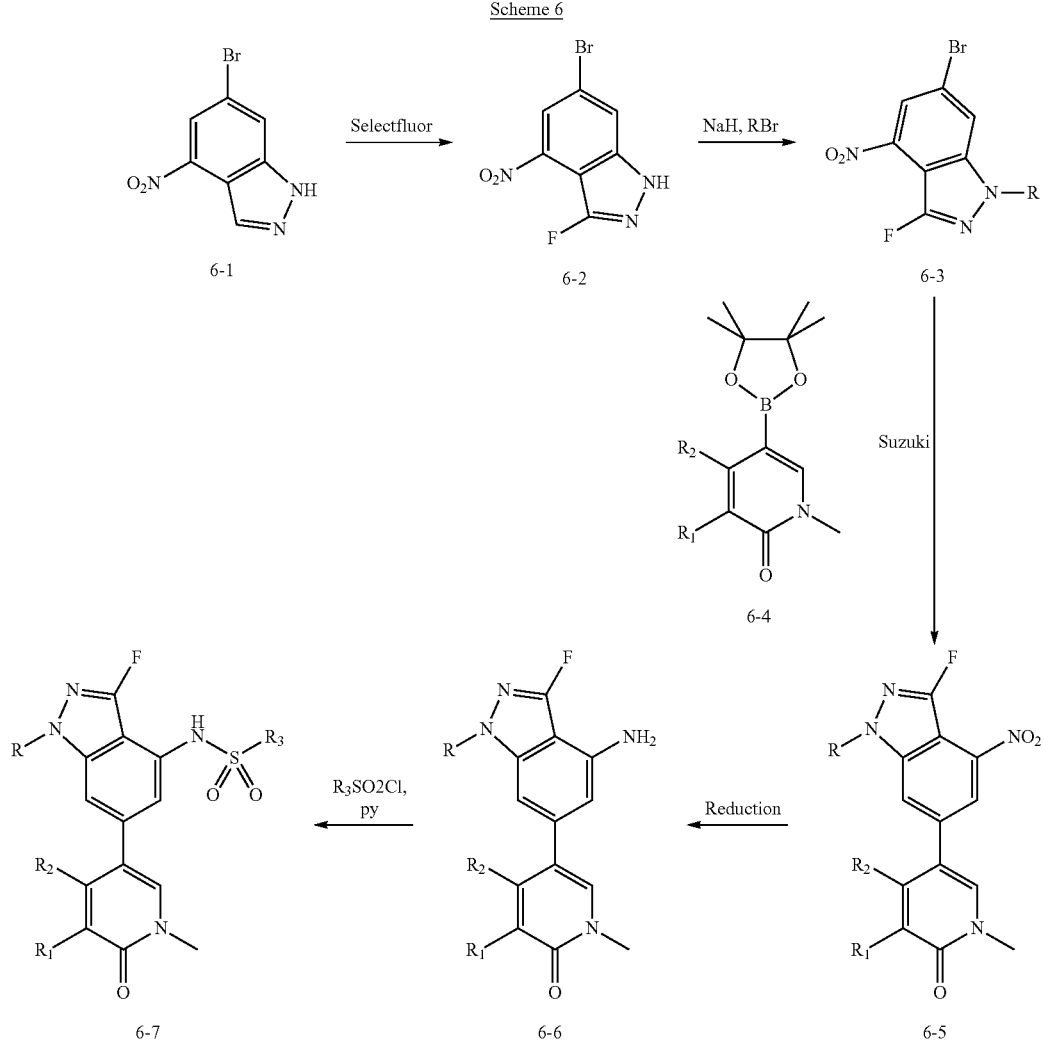

As per Scheme 6, Bromoindazole derivative (6-1) is subjected to fluorination to provide compound (6-2). Alkylation on nitrogen provides the substituted indazole (6-3). Palladium-catalyzed cross coupling of (6-3) with a boronic acid or ester provides the desired product (6-5). Reduction of the nitro group provides aniline (6-6) which is then reacted with sulfonyl chloride to afford sulfonamide (6-7).

A method for preparing benzimidazole compounds of Formula II is provided in Scheme 7:

Scheme 7

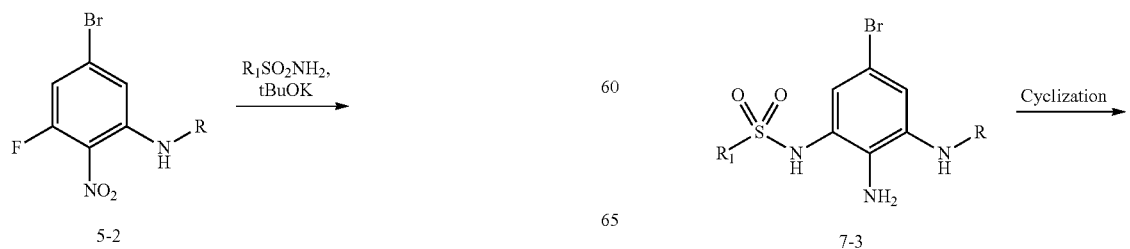

-continued

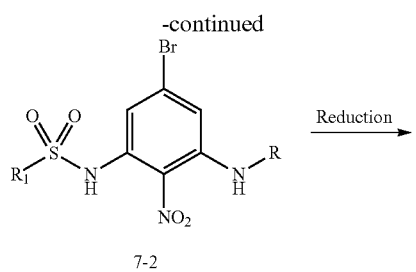

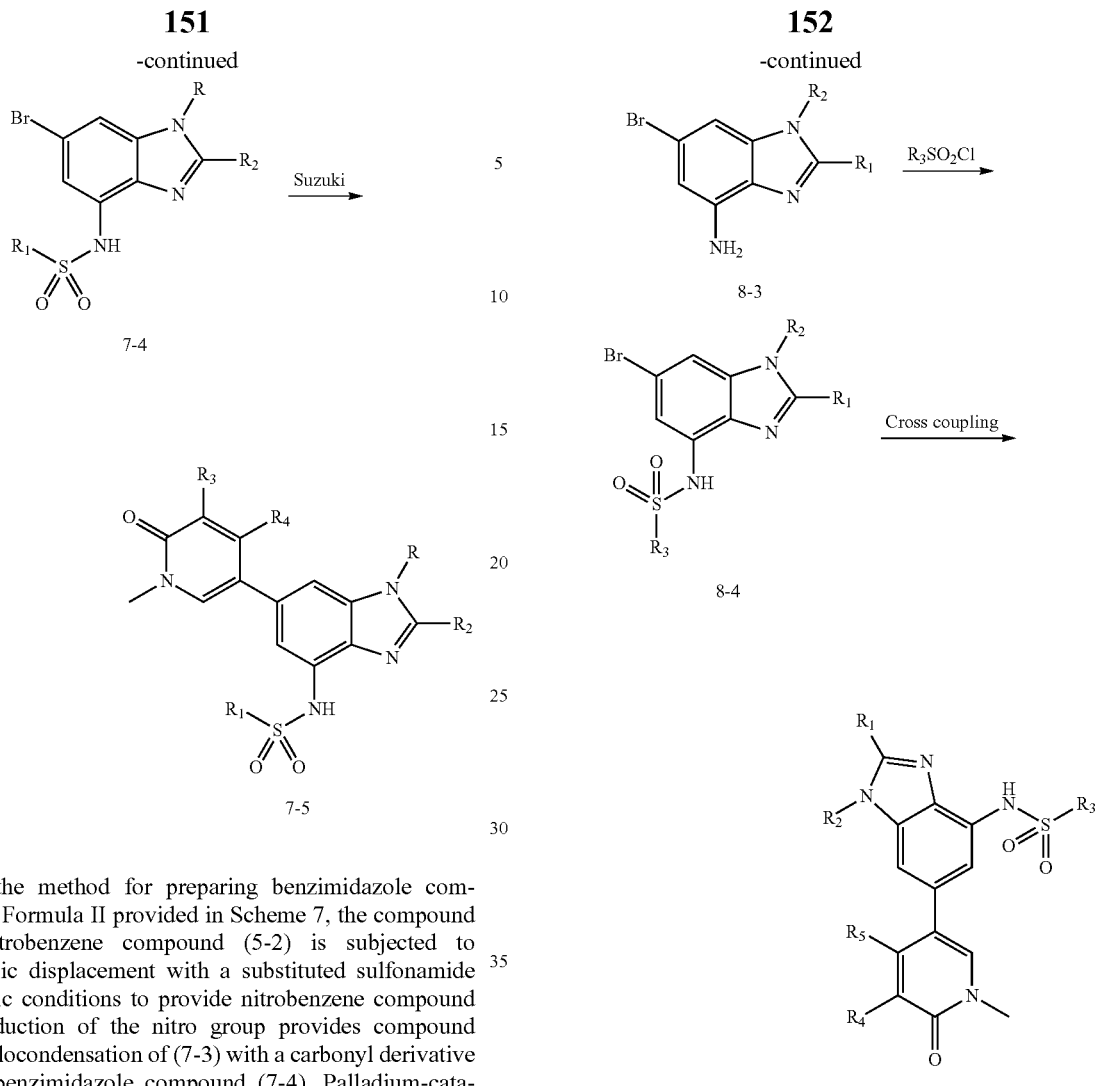

7-4

7-5

Using the method for preparing benzimidazole compounds of Formula II provided in Scheme 7, the compound 2-aminonitrobenzene compound (5-2) is subjected to nucleophilic displacement with a substituted sulfonamide under basic conditions to provide nitrobenzene compound (7-2). Reduction of the nitro group provides compound (7-3). Cyclocondensation of (7-3) with a carbonyl derivative provides benzimidazole compound (7-4). Palladium-catalyzed cross coupling of bromobenzimidazole derivates (7-4) with a boronic acid or ester provides the desired product (7-5).

A method for preparing benzimidazole compounds of Formula II is provided in Scheme 8:

Scheme 8

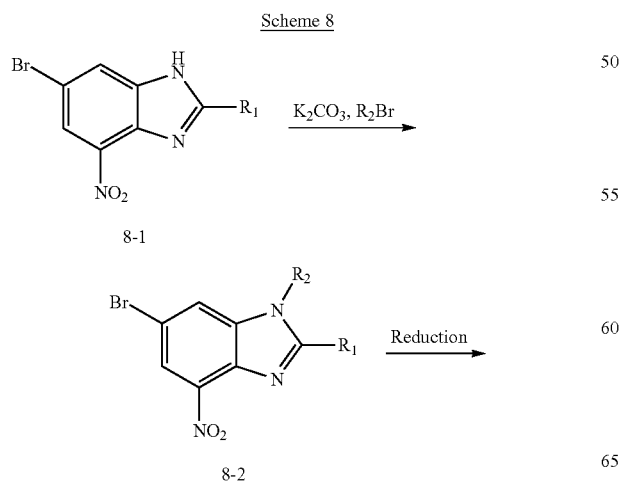

8-1

8-2

8-3

8-4

8-5

In accord with Scheme 8, bromonitrobenzimidazole compound (8-1) is alkylated on nitrogen under basic conditions to provide nitro compound (8-2). Reduction of the nitro group provides compound (8-3). Reaction of (8-3) with a sulphonyl chloride derivative under basic conditions provides benzimidazole compound (8-4). Palladium-catalyzed cross coupling of bromobenzimidazole derivate (8-4) with a boronic acid or ester provides the desired product (8-5).

An alternative method for preparing benzimidazole compounds of Formula II is provided in Scheme 9:

Scheme 9

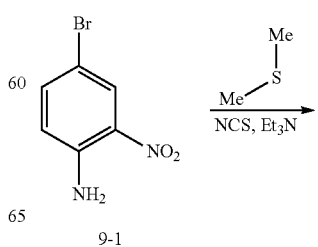

9-1

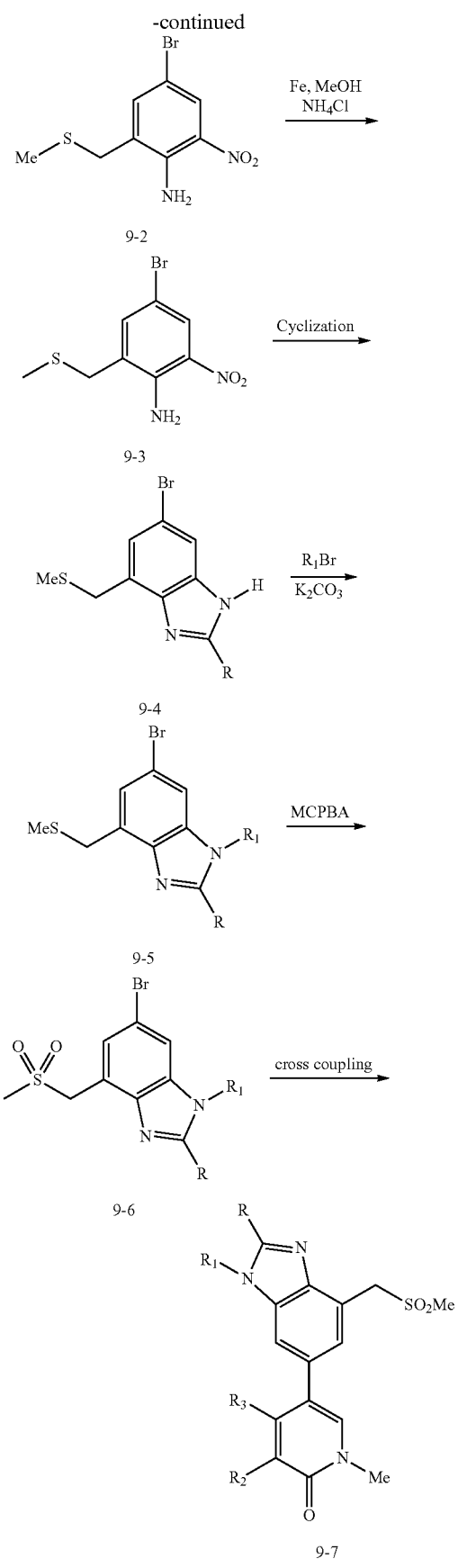

As outlined of Scheme 9, the compound 2-bromo-6-aminonitrobenzene (9-1) is alkylated to afford thiomethyl derivative (9-2). Reduction of the nitro group provides compound (9-3). Cyclocondensation of (9-3) with a carbonyl derivative provides benzimidazole compound (9-4). Compound (9-4) is alkylated on nitrogen under basic conditions to provide sulfide (9-5) which is oxidized with MCPBA to sulfone (9-6). Palladium-catalyzed cross coupling of bromobenzimidazole derivate (9-6) with a boronic acid or ester provides the desired product (9-7).

In each of the above reaction procedures or schemes, the various substituents may be selected from among the various substituents otherwise taught herein.

Pharmaceutical Compositions

In certain embodiments, a substituted heterocyclic derivative compound as described herein is administered as a pure chemical or salt thereof. In other embodiments, the substituted heterocyclic derivative compound described herein is prepared in a pharmaceutical composition in which the substituted heterocyclic derivative compound is combined with at least one pharmaceutically acceptable or pharmaceutically suitable excipient (also referred to herein as a pharmaceutically suitable (or acceptable) carrier, physiologically suitable (or acceptable) excipient, or physiologically suitable (or acceptable) carrier), selected on the basis of a chosen route of administration and standard pharmaceutical practices, as are well known. See, e.g., REMINGTON: SCI. & PRACTICE PHARM. (Gennaro, 21$^{st}$ Ed., Mack Pub. Co., Easton, Pa., 2005).

Accordingly, provided herein are pharmaceutical compositions that comprise at least one substituted heterocyclic derivative compound, or a stereoisomer, pharmaceutically acceptable salt, hydrate, solvate, or N-oxide thereof, together with at least one pharmaceutically acceptable excipient. The excipient (or carrier) is acceptable or suitable if the excipient is compatible with the other active agents or excipients of the composition, not deleterious to the recipient (i.e., the subject) of the composition, and prepared under good laboratory practices as required for the particular dosage form.

One embodiment provides a pharmaceutical composition comprising a compound of Formula I, or a pharmaceutically acceptable salt thereof. One embodiment provides a pharmaceutical composition comprising a compound of Formula II, or a pharmaceutically acceptable salt thereof. One embodiment provides a pharmaceutical composition comprising a compound of Formula III, or a pharmaceutically acceptable salt thereof. One embodiment provides a pharmaceutical composition comprising a compound of Formula IV, or a pharmaceutically acceptable salt thereof. One embodiment provides a pharmaceutical composition comprising a compound of Formulas Va-Ve, or a pharmaceutically acceptable salt thereof. One embodiment provides a pharmaceutical composition comprising a compound of Formula VI, or a pharmaceutically acceptable salt thereof. Another embodiment provides a pharmaceutical composition comprising 4-(2-ethyl-5-(methylsulfonyl)benzofuran-7-yl)-2-methylisoquinolin-1(2H)-one, or a pharmaceutically acceptable salt thereof, from; or 4-(2-cyclopropyl-5-(methylsulfonyl)benzofuran-7-yl)-2-methylisoquinolin-1 (2H)-one, or a pharmaceutically acceptable salt thereof.

In certain embodiments, the substituted heterocyclic derivative compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. See, e.g., REMINGTON, 2005.

The dose of the composition comprising at least one substituted heterocyclic derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome), such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses typically range from about 1.0 mg to about 1000 mg, one to four times, or more, per day.

Bromodomain Inhibition

Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which modify histones at various sites.

Epigenetics is the study of heritable changes in gene expression caused by mechanisms other than the underlying DNA sequence. Molecular mechanisms that play a role in epigenetic regulation include DNA methylation and chromatin/histone modifications.

The genomes of eukaryotic organisms are highly organized within the nucleus of the cell. Tremendous compaction is required to package the 3 billion nucleotides of the human genome into the nucleus of a cell, where the chromosomes exist in a complex of nucleic acids and proteins called chromatin. Histones are the chief protein components of chromatin. There are a total of six classes of histones (H1, H2A, H2B, H3, H4, and H5) organized into two classes: core histones (H2A, H2B, H3, and H4) and linker histones (H1 and H5). The basic unit of chromatin is a nucleosome, which comprises about 147 base pairs of DNA wrapped around a core histone octamer which includes two copies each of the core histones: H2A, H2B, H3, and H4. These nucleosome units are then further organized and condensed by the aggregation and folding of nucleosomes to form the highly condensed chromatin structure. A range of different states of condensation are possible, and the tightness of chromatin structure varies during the cell cycle, being most compact during the process of cell division.

Accordingly, chromatin structure plays a critical role in regulating gene transcription, which cannot occur efficiently in highly condensed chromatin. Chromatin structure is controlled by a series of post translational modifications to histone proteins, notably to histones H3 and H4, and most commonly within the "histone tails" which extend beyond the core nucleosome structure. These post translational modifications include acetylation, methylation, phosphorylation, ribosylation sumoylation, ubiquitination, citrullination, deimination, and biotinylation. In addition to the histone tails, the cores of histones H2A and H3 can be modified. Given the function of histones in chromatin, histone modifications are integral to diverse biological processes such as gene expression, DNA replication, DNA repair, and chromosome condensation.

Histone Acetylation and Bromodomains

Histone acetylation is generally associated with the activation of gene transcription, as the modification is known to loosen the interaction of the DNA and the histone octamer by changing the electrostatic state. In addition to this physical change, specific proteins are known to bind to acetylated lysine residues within histones in order to function according to the epigenetic code. Bromodomains are small (~110 amino acids) distinct domains within proteins that commonly, but not exclusively, bind to acetylated lysine residues in the context of histones. Approximately fifty proteins are known to contain bromodomains, and they have a range of functions within the cell.

The BET family of bromodomain containing proteins comprises four proteins (BRD2, BRD3, BRD4, and BRD-t) which contain tandem bromodomains capable of binding to two acetylated lysine residues that are positioned in close proximity, increasing the specificity of the interaction. Bromodomain-containing proteins that recognize acetylated lysines on histones (such as BET proteins and non-BET proteins) have been implicated in proliferative disease. For example, homozygous BRD4 knockout mice are compromised in their ability to maintain an inner cell mass and die shortly after embryo implantation, and heterozygote BRD4 knockouts display pre- and postnatal growth defects associated with reduced proliferation rates. BRD4 regulates genes expressed during M/G1, including growth-associated genes, and remains bound to chromatin throughout the cell cycle. Dey, et al., 20 Mol. Biol. Cell 4899 (2009). BRD4 also associates physically with Mediator and P-TEFb (a heterodimer of Cyclin-dependent kinase 9 [CDK9], cyclin K, cyclin T, or cyclin T2a or T2b) to facilitate transcriptional elongation. Yang et al., 24 Oncogene 1653 (2005); Yang et al., 19 Mol. Cell 535 (2005). CDK9 is linked to c-Myc-dependent transcription, and is thus a validated target in chronic lymphocytic leukemia (CLL). Phelps et al., 113 Blood 2637 (2009); Rahl et al., 141 Cell 432 (2010).

Moreover, BRD4 is translocated to the nuclear protein in testis (NUT protein) in patients with lethal midline carcinoma, an aggressive form of human squamous carcinoma. French et al., 159 Am. J. Pathol. 1987 (2001). In vitro analysis with RNAi supports a causal role for BRD4 in a recurrent chromosomal translocation, t(15; 19)(q13; p13.1), which defines a lethal midline carcinoma. French et al., 63 Cancer Res. 304 (2003). Also, inhibition of the BRD4 bromodomains has been found to result in growth arrest/differentiation of BRD4-NUT cell lines in vitro and in vivo. Filippakopoulos et al., *Selective Inhibition of BET Bromodomains*, 468 Nature 1067 (2010).

Bromodomain-containing proteins (such as BET proteins) have also been implicated in inflammatory diseases. BET proteins (e.g., BRD2, BRD3, BRD4, and BRDT) regulate assembly of histone acetylation-dependent chromatin complexes that control inflammatory gene expression. Hargreaves et al., 138 Cell 129 (2009); LeRoy et al., 30 Molec. Cell 51 (2008); Jang et al., 19 Molec. Cell 523 (2005); Yang et al., 19 Molec. Cell 535 (2005). Key inflammatory genes (secondary response genes) are down-regulated upon bromodomain inhibition of the BET subfamily, and non-responsive genes (primary response genes) are poised for transcription. BET bromodomain inhibition protects against LPS-induced endotoxic shock and bacteria-induced sepsis in vivo. Nicodeme et al., *Suppression of Inflammation by a Synthetic Histone Mimic*, 468 Nature 1119 (2010).

Bromodomain-containing proteins (such as BET proteins) have also been found to play a role in viral infection. For example, BRD4 is implicated in the primary and persistent phases of human papilloma virus (HPV) infection of basal epithelia, in which BRD4 binding maintains the viral genome as an extra-chromosomal episome. In some strains of HPV, BRD4 binding to the HPV transcriptional activator protein, E2 (early protein 2), tethers the viral genome to infected-cell chromosomes. BRD4-E2 binding is crucial for both transactivating E2 and repressing transcription of two HPV oncoproteins (early protein 6 [E6] and early protein 7 [E7]). Disruption of BRD4 or the BRD4-E2 interaction blocks E2-dependent gene activation. BRD4 also functions to tether other classes of viral genomes (e.g., Herpes virus, Epstein-Barr virus) to the chromatin of infected cells. Kurg, in DNA REPLICATION—CURRENT ADVANCES 613 (Seligmann, ed., InTech, Rijeka, Croatia, 2011).

Bromodomain-containing proteins has also been found to bind to acetylated lysine residues on proteins other than histones. For example, the bromodomain of CREB binding protein transcriptional coactivator (CBP) allows for recognition of p53 with acetylated Lys382. The interaction between the bromodomain and acetyl-p53 follows DNA damage and promotes p53-induced transcriptional activation of the CDK inhibitor p21 and cell cycle arrest.

Another novel bromodomain-containing protein is BAZ2B, whose biological function, is believed to function similarly to ACF1, the *Drosophila* BAZ2B ortholog. ACF complexes play roles in establishing regular nucleosome spacing during chromatin assembly and influencing different remodeling outcomes at target loci.

One embodiment provides a method of regulating gene transcription in a cell comprising contacting a bromodomain-containing protein with a compound of Formula I.

One embodiment provides a method of inhibiting bromodomain-mediated recognition of an acetyl lysine region of a protein comprising contacting the bromodomain with a compound of Formula I.

One embodiment provides a method of regulating gene transcription in a cell comprising contacting a bromodomain containing protein with a compound of Formula II.

One embodiment provides a method of inhibiting bromodomain-mediated recognition of an acetyl lysine region of a protein comprising contacting the bromodomain with a compound of Formula II.

One embodiment provides a method of regulating gene transcription in a cell comprising contacting a bromodomain containing protein with a compound of Formula III.

One embodiment provides a method of inhibiting bromodomain-mediated recognition of an acetyl lysine region of a protein comprising contacting the bromodomain with a compound of Formula III.

One embodiment provides a method of regulating gene transcription in a cell comprising contacting a bromodomain containing protein with a compound of Formula IV.

One embodiment provides a method of inhibiting bromodomain-mediated recognition of an acetyl lysine region of a protein comprising contacting the bromodomain with a compound of Formula IV.

One embodiment provides a method of regulating gene transcription in a cell comprising contacting a bromodomain containing protein with a compound of Formula Va-Formula Ve.

One embodiment provides a method of inhibiting bromodomain-mediated recognition of an acetyl lysine region of a protein comprising contacting the bromodomain with a compound of Formula Va-Formula Ve.

One embodiment provides a method of regulating gene transcription in a cell comprising contacting a bromodomain containing protein with a compound of Formula VI.

One embodiment provides a method of inhibiting bromodomain-mediated recognition of an acetyl lysine region of a protein comprising contacting the bromodomain with a compound of Formula VI.

One embodiment provides a method of regulating gene transcription in a cell comprising contacting a bromodomain containing protein with 4-(2-ethyl-5-(methylsulfonyl)benzofuran-7-yl)-2-methylisoquinolin-1(2H)-one or 4-(2-cyclopropyl-5-(methylsulfonyl)benzofuran-7-yl)-2-methylisoquinolin-1(2H)-one.

One embodiment provides a method of inhibiting bromodomain-mediated recognition of an acetyl lysine region of a protein comprising contacting the bromodomain with 4-(2-ethyl-5-(methylsulfonyl)benzofuran-7-yl)-2-methylisoquinolin-1(2H)-one or 4-(2-cyclopropyl-5-(methylsulfonyl)benzofuran-7-yl)-2-methylisoquinolin-1(2H)-one.

Methods of Treatment

Compounds and compositions described herein are generally useful for the inhibition of activity of one or more proteins involved in epigenetic regulation. Thus, at least one embodiment provides a method of modulating epigenetic regulation mediated by one or more proteins containing acetyl-lysine recognition motifs, also known as bromodomains (e.g., BET proteins, such as BRD2, BRD3, BRD4, or BRDT, and non-BET proteins, such as CBP, ATAD2A, GCN5L, BAZ2B, FALZ, TAF1, or BRPF1) or a mutant thereof, by contacting the bromodomain with a substituted heterocyclic derivative compound described herein. Another embodiment provides a method of modulating epigenetic regulation by administering a substituted heterocyclic derivative compound described herein, or administering a pharmaceutical composition comprising such substituted heterocyclic derivative compound.

In some embodiments, the substituted heterocyclic derivative compounds described herein are capable of inhibiting the activity of a bromodomain-containing protein, such as a BET protein (BRD2, BRD3, BRD4, or BRDT), non-BET proteins (such as CBP, ATAD2A, GCN5L, BAZ2B, FALZ, TAF1, or BRPF1) or a mutant thereof, in a biological sample, in a manner useful for a variety of purposes as are known to one of skill in the art. Examples of such purposes include, but are not limited to, blood transfusion, organ-transplantation, biological specimen storage, and biological assays.

Some embodiments provide a method of inhibiting the activity of a bromodomain-containing protein, such as a BET protein (BRD2, BRD3, BRD4, or BRDT), non-BET proteins (such as CBP, ATAD2A, GCN5L, BAZ2B, FALZ, TAF1, or BRPF1) or a mutant thereof, in a patient in need of treatment, comprising administering to the patient a substituted heterocyclic derivative compound as described herein, or a pharmaceutical composition comprising the compound.

Some embodiments provide a method of inhibiting the activity of a bromodomain-containing protein, such as a BET protein (BRD2, BRD3, BRD4, or BRDT), non-BET proteins (such as CBP, ATAD2A, GCN5L, BAZ2B, FALZ, TAF1, or BRPF1), or mutants thereof, in a biological sample, comprising the step of contacting the biological sample with a substituted heterocyclic derivative compound described herein. In some embodiments, the bromodomain-containing protein is a BET protein. In some embodiments, the BET protein is BRD4.

Some embodiments provide a method of inhibiting the activity of a bromodomain-containing protein, such as a BET protein (BRD2, BRD3, BRD4, or BRDT), non-BET proteins (such as CBP, ATAD2A, GCN5L, BAZ2B, FALZ, TAF1, or BRPF1), or a mutant thereof, in a patient in need of treatment, comprising the step of administering to said patient a substituted heterocyclic derivative compound (or pharmaceutical composition comprising the compound) described herein. In some embodiments, the bromodomain-containing protein is a BET protein. In some embodiments, the BET protein is BRD4.

Diseases and conditions treatable according to the methods of these embodiments include cancer, neoplastic disease or other proliferative disorders, or viral infections. Thus, one aspect is a method of treating a subject having cancer, a neoplastic disease, or other proliferative disorder; the method comprising administration of a substituted heterocyclic derivative compound as described herein to the subject. In one embodiment, a human patient is treated with a pharmaceutical composition comprising a substituted heterocyclic derivative compound described herein, wherein the compound is present in an amount sufficient to measurably inhibit bromodomain-containing protein activity (such as BRD2, BRD3, BRD4, or BRDT activity) in the patient. The amount may be referred to as an effective amount.

The embodiments further provide a method of treating a subject, such as a human, suffering from cancer, a neoplastic disease, or other proliferative disorder. The method comprises administering to a subject in need of such treatment a therapeutically effective amount of at least one substituted heterocyclic derivative compound described herein, which functions by inhibiting a bromodomain and, in general, by modulating gene expression, to modulate various cellular effects, in particular inducting or repressing gene expression, arresting cell proliferation, inducing cell differentiation, or inducing apoptosis.

The embodiments further provide a therapeutic method of modulating protein methylation, gene expression, cell proliferation, cell differentiation, or apoptosis in vivo in conditions, illnesses, disorders, infections, or diseases disclosed herein, in particular cancer, inflammatory disease, or viral disease, comprising administering to a subject in need of such therapy a pharmacologically active or therapeutically effective amount of at least one substituted heterocyclic derivative compound described herein, which may be administered in a pharmaceutical composition.

The embodiments further provide a method of regulating endogenous or heterologous promoter activity by contacting a cell with a substituted heterocyclic derivative compound described herein. The embodiments further provide a method of regulating endogenous or heterologous promoter activity by contacting chromatin with a substituted heterocyclic derivative compound described herein. The embodiments further provide a method of regulating endogenous or heterologous promoter activity by contacting a viral episome with a substituted heterocyclic derivative compound described herein.

The embodiments further relate to a method for treating or ameliorating cancer, neoplastic disease, or another proliferative disorder by administration of an effective amount of a pharmaceutical composition comprising a substituted heterocyclic derivative compound a described herein, to a mammal, in particular a human, in need of such treatment. In some aspects, the disease to be treated by the methods of the present embodiments is cancer.

In certain embodiments, the cancer is NUT midline carcinoma, prostate cancer, breast cancer, bladder cancer, lung cancer, melanoma, or glioblastoma.

One embodiment provides a method of treating cancer in a patient in need thereof, comprising administering to the patient a pharmaceutical composition comprising a compound of Formula I, or a pharmaceutically acceptable salt thereof.

One embodiment provides a method of treating cancer in a patient in need thereof, comprising administering to the patient a pharmaceutical composition comprising a compound of Formula II, or a pharmaceutically acceptable salt thereof.

One embodiment provides a method of treating cancer in a patient in need thereof, comprising administering to the patient a pharmaceutical composition comprising a compound of Formula III, or a pharmaceutically acceptable salt thereof.

One embodiment provides a method of treating cancer in a patient in need thereof, comprising administering to the patient a pharmaceutical composition comprising a compound of Formula IV, or a pharmaceutically acceptable salt thereof.

One embodiment provides a method of treating cancer in a patient in need thereof, comprising administering to the patient a pharmaceutical composition comprising at least one compound selected from Formula Va to Formula Ve, or a pharmaceutically acceptable salt thereof.

One embodiment provides a method of treating cancer in a patient in need thereof, comprising administering to the patient a pharmaceutical composition comprising a compound of Formula VI, or a pharmaceutically acceptable salt thereof.

One embodiment provides a method of treating a cancer patient in need thereof, comprising administering to the patient a pharmaceutical composition comprising compound, or a pharmaceutically acceptable salt thereof, selected from 4-(2-ethyl-5-(methylsulfonyl)benzofuran-7-yl)-2-methylisoquinolin-1(2H)-one, or 4-(2-cyclopropyl-5-(methylsulfonyl)benzofuran-7-yl)-2-methylisoquinolin-1(2H)-one.

Other embodiments and uses will be apparent to one of ordinary skill in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants (J) are reported in Hertz. For $^1$H NMR spectra, the solvent peak was used as the reference peak.

Example 1

2-methyl-4-(2-methyl-1,1-dioxo-3H-1,2-benzothiazol-6-yl)isoquinolin-1-one

Step 1: 6-bromo-2-methyl-3H-1,2-benzothiazole 1,1-dioxide

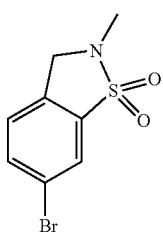

To a solution of 6-bromo-2,3-dihydro-1,2-benzothiazole 1,1-dioxide (100 mg, 0.4 mmol) in DMF (3 ml) at room temperature (RT) was added NaH (18 mg, 0.45 mmol). The mixture was stirred for 10 min and methyl iodide (30 µL, 0.5 mmol) was then added dropwise. The reaction was stirred overnight. The contents were poured over a precooled saturated ammonium chloride solution (10 mL). The mixture was extracted with EtOAc (3×7 mL). The combined organic layers were dried over Na$_2$SO$_4$, filtered and concentrated under reduced pressure. The residue was purified by silica gel column chromatography (20%-100% EtOAc/Hexane) to provide the title compound (89 mg, 84%). LCMS: 261.9 [M+H]$^+$.

Step 2: 2-methyl-4-(2-methyl-1,1-dioxo-3H-1,2-benzothiazol-6-yl)isoquinolin-1-one

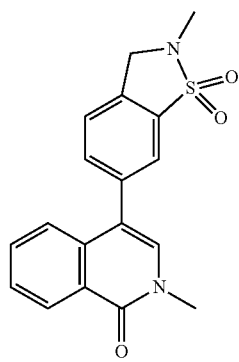 [SMILES: CN1Cc2ccc(-c3cn(C)c(=O)c4ccccc34)cc2S1(=O)=O]

A mixture of 2-methyl-4-(4,4,5,5-tetramethyl-1,2-dioxaborolan-2-yl)isoquinolin-1-one (25 mg, 0.09 mmol), 6-bromo-2-methyl-3H-1,2-benzothiazole 1,1-dioxide (23 mg, 0.09 mmol), K$_3$PO$_4$ (45 mg, 0.22 mmol) and Pd(dppf)Cl$_2$ (7 mg, 0.01 mmol) in dioxane (1 mL) and H$_2$O (0.1 mL) was degassed with N$_2$ for 10 min and then stirred at 70° C. for 2 hr. The reaction mixture was diluted with EtOAc (5 mL), dried over Na$_2$SO$_4$, filtered and concentrated under reduced pressure. The residue was purified by normal phase silica gel column chromatography to give the title compound (22 mg, 73%). $^1$H NMR (DMSO-d6, 400 MHz): δ 8.35 (d, J=8.0 Hz, 1H), 7.92 (s, 1H), 7.80 (dd, J$_1$=7.9 Hz, J$_2$=1.3 Hz, 1H), 7.72 (m, 2H), 7.64 (s, 1H), 7.58 (m, 1H), 7.43 (d, J=8.1 Hz, 1H), 4.49 (s, 2H), 3.58 (s, 3H), 2.86 (s, 3H). LCMS: 341.0 [M+H]$^+$.

Example 2

4-(1,1-dioxo-2,3-dihydro-1,2-benzothiazol-6-yl)-2-methylisoquinolin-1-one

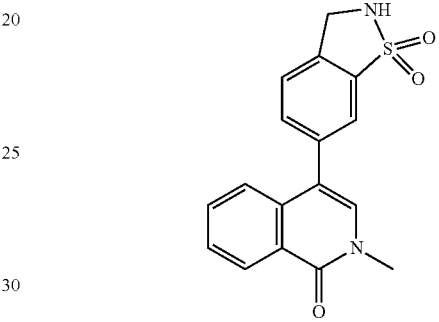

The title compound was prepared in a manner similar to Example 1, by substituting 6-bromo-2,3-dihydro-1,2-benzothiazole 1,1-dioxide for 6-bromo-2-methyl-3H-1,2-benzothiazole 1,1-dioxide in step 2. $^1$H NMR (DMSO-d6, 400 MHz): δ 8.35 (d, J=7.4 Hz, 1H), 7.91 (m, 1H), 7.85 (m, 1H), 7.72 (m, 3H), 7.62 (s, 1H), 7.58 (m, 1H), 7.43 (d, J=8.4 Hz, 1H), 4.49 (m, 2H), 3.58 (s, 3H). LCMS: 327.05 [M+H]$^+$.

Example 3

5-(5-methoxy-2-methyl-1,1-dioxo-3H-1,2-benzothiazol-6-yl)-1,3-dimethylpyridin-2-one Step 1: 5-bromo-4-fluoro-2-methylbenzenesulfonyl chloride

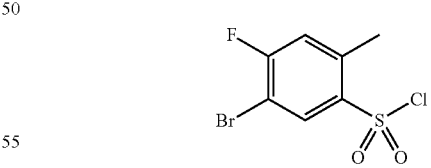

1-bromo-2-fluoro-4-methylbenzene (5 g, 26.45 mmol) was added dropwise to ClSO$_3$H (15.5 g, 133.62 mmol) at 0° C. over 15 min. The mixture was stirred at 0° C. for 45 min. The mixture was poured into ice-water (30 mL) at 0° C. and extracted with EA (20 mL×3). The combined organic layers were dried, filtered and concentrated to give the title compound (6.2 g, 81%) as a gray solid which was used in the next step without further purification. $^1$H NMR (DMSO-d6, 400 MHz): δ 7.90 (d, J=7.6 Hz, 1H), 7.18 (d, J=10.0 Hz, 1H), 2.47 (s, 3H).

Step 2:
5-bromo-4-fluoro-2-methylbenzenesulfonamide

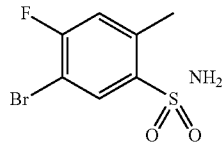

To a saturated solution of NH$_3$ in THF (60 mL) was added a solution of the title compound from step 1 (6.2 g, 21.56 mmol) in THF (20 mL) dropwise at 0° C. The reaction was stirred at 0° C. for 1 hr. The mixture was poured into ice-water (60 mL) and extracted with EA (30 mL×3). The organic layer was dried, filtered and concentrated to give the title compound (5.5 g, 95%) as an off-white solid which was used directly without further purification. $^1$H NMR (DMSO-d6, 400 MHz): δ 8.05 (d, J=7.2 Hz, 1H), 7.59 (s, 2H), 7.47 (d, J=9.6 Hz, 1H), 2.55 (s, 3H).

Step 3:
5-bromo-2-(bromomethyl)-4-fluorobenzenesulfonamide

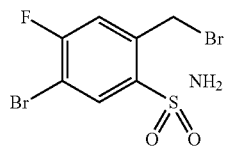

A mixture of the title compound from step 2 (11 g, 41.03 mmol), BPO (1.36 g, 5.59 mmol) and NBS (14.6 g, 82.06 mmol) in CCl$_4$ (200 mL) was stirred at 80° C. for 12 hr under N$_2$. The mixture was concentrated and the residue was purified by column chromatography on silica gel (PE:EA=5:1) to give the title compound (3.1 g, 22%) as a light yellow solid. $^1$H NMR (CDCl$_3$, 400 MHz): δ 8.27 (d, J=6.8 Hz, 1H), 7.32 (d, J=8.8 Hz, 1H), 4.81 (s, 2H).

Step 4:
6-bromo-5-fluoro-2,3-dihydro-1,2-benzothiazole 1,1-dioxide

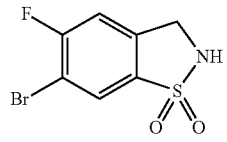

A mixture of the title compound from step 3 (3.1 g, 8.93 mmol) and NaHCO$_3$ (2.25 g, 26.80 mmol) in CH$_3$CN (300 mL) was stirred at 80° C. for 12 hr. H$_2$O (100 mL) was added and the mixture was extracted with EA (50 mL×2). The organic layer was dried, filtered and concentrated. The residue was purified by column chromatography on silica gel (PE:EA=5:1) to give the title compound (1.8 g, 76%) as a light yellow solid. $^1$H NMR (CDCl$_3$, 400 MHz): δ 7.97 (d, J=6.0 Hz, 1H), 7.14 (d, J=7.6 Hz, 1H), 4.44 (s, 2H).

Step 5:
6-bromo-5-fluoro-2-methyl-3H-1,2-benzothiazole 1,1-dioxide

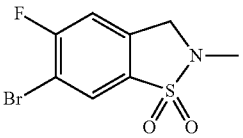

To a mixture of the title compound from step 4 (300 mg, 1.13 mmol) and MeI (240 mg, 1.69 mmol) in CH$_3$CN (3 mL) was added K$_2$CO$_3$ (311 mg, 2.25 mmol). The mixture was stirred at 20° C. for 12 hr. The mixture was then poured over water (10 mL) and extracted with EA (10 mL×2). The organic layer was dried and concentrated to give the title compound (300 mg, 96%) as a solid which was used directly without further purification. LCMS: 279.9 [M+H]$^+$.

Step 6:
6-bromo-5-methoxy-2-methyl-3H-1,2-benzothiazole 1,1-dioxide

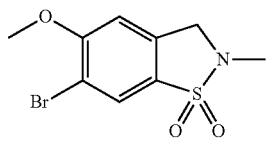

A mixture of the title compound from step 5 (300 mg, 1.07 mmol) and CH$_3$ONa (168 mg, 3.12 mmol) in MeOH (6 mL) was stirred at 60° C. for 8 hr. The mixture was concentrated and the residue was purified by column chromatography on silica gel (PE:EA=2:1) to give the title compound (140 mg, 46%) as a white solid. $^1$H NMR (CDCl$_3$, 400 MHz): δ 7.97 (s, 1H), 6.82 (s, 1H), 4.27 (s, 2H), 3.97 (s, 3H), 2.94 (s, 3H). LCMS: 291.9 [M+H]$^+$.

Step 7: 5-(5-methoxy-2-methyl-1,1-dioxo-3H-1,2-benzothiazol-6-yl)-1,3-dimethylpyridin-2-one

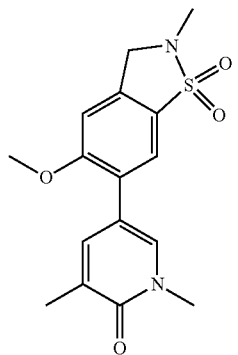 [SMILES: COc1cc2c(cc1-c1cc(C)c(=O)n(C)c1)S(=O)(=O)N(C)C2]

A mixture of the title compound of step 6 (40 mg, 0.137 mmol), 1,3-dimethyl-5-(4,4,5,5-tetramethyl-1,3,2-dioxaborolan-2-yl)pyridin-2-one (41 mg, 0.164 mmol), Pd(dppf)Cl$_2$ (10 mg, 0.014 mmol) and K$_3$PO$_4$ (73 mg, 0.343 mmol)

in dioxane/H₂O (4/0.4 mL) was stirred at 80° C. for 12 hr under N₂. The mixture was concentrated and the residue was purified by column chromatography on silica gel (PE:EA=2:1) to give a yellow solid which was further purified by prep-HPLC to afford the title compound (20.2 mg, 44%). ¹H NMR (CDCl₃, 400 MHz): δ 7.64 (s, 1H), 7.40-7.38 (m, 2H), 6.87 (s, 1H), 4.34 (s, 2H), 3.92 (s, 3H), 3.61 (s, 3H), 2.96 (s, 3H), 2.21 (s, 3H). LCMS: 335.1 [M+H]⁺.

Example 4

4-(5-methoxy-2-methyl-1,1-dioxo-3H-1,2-benzothiazol-6-yl)-2-methylisoquinolin-1-one

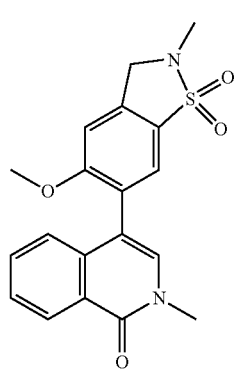 [SMILES: COc1cc2c(cc1-c1cn(C)c(=O)c3ccccc13)S(=O)(=O)N(C)C2]

The title compound was prepared in a manner similar to Example 3 by substituting 2-methyl-4-(4,4,5,5-tetramethyl-1,3,2-dioxaborolan-2-yl)isoquinolin-1-one for 1,3-dimethyl-5-(4,4,5,5-tetramethyl-1,3,2-dioxaborolan-2-yl)pyridin-2-one in step 7. ¹H NMR (CDCl₃, 400 MHz): δ 8.52-8.50 (m, 1H), 7.71 (s, 1H), 7.56-7.51 (m, 2H), 7.07 (d, J=6.8 Hz, 1H), 7.05 (s, 1H), 6.94 (s, 1H), 4.41 (s, 2H), 3.80 (s, 3H), 3.66 (s, 3H), 2.99 (s, 3H). LCMS: 371.1 [M+H]⁺.

Example 5

5-[5-(cyclopropylmethoxy)-2-methyl-1,1-dioxo-3H-1,2-benzothiazol-6-yl]-1,3-dimethylpyridin-2-one Step 1: 6-bromo-5-(cyclopropylmethoxy)-2-methyl-3H-1,2-benzothiazole 1,1-dioxide

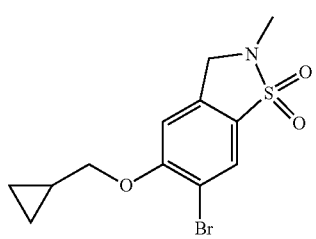 [SMILES: CN1Cc2cc(OCC3CC3)c(Br)cc2S1(=O)=O]

To a solution of cyclopropylmethanol (159 mg, 2.21 mmol) in THF (4 mL) was added NaH (66 mg, 1.66 mmol, 60% in mineral oil) under N₂ at 0° C. The mixture was stirred at 0° C. for 30 min and then a solution of the title compound from Example 3, step 5 (300 mg, 1.07 mmol) in THF (2 mL), was added. The reaction was stirred at 60° C. for 5 hr. The mixture was quenched with H₂O (5 mL) and extracted with EtOAc (5 mL×2). The combined organic layers were dried, filtered and concentrated. The residue was purified by column chromatography on silica gel (PE:EA=4:1) to give the title compound (160 mg, 45%). 1H NMR (CDCl3, 400 MHz): δ 7.97 (s, 1H), 7.77 (s, 1H), 4.24 (s, 2H), 3.95 (d, J=6.4 Hz, 2H), 2.93 (s, 3H), 1.37-1.32 (m, 1H), 0.72-0.68 (m, 2H), 0.45-0.08 (m, 2H). LCMS: 332.0 [M+H]⁺.

Step 2: 5-[5-(cyclopropylmethoxy)-2-methyl-1,1-dioxo-3H-1,2-benzothiazol-6-yl]-1,3-dimethylpyridin-2-one

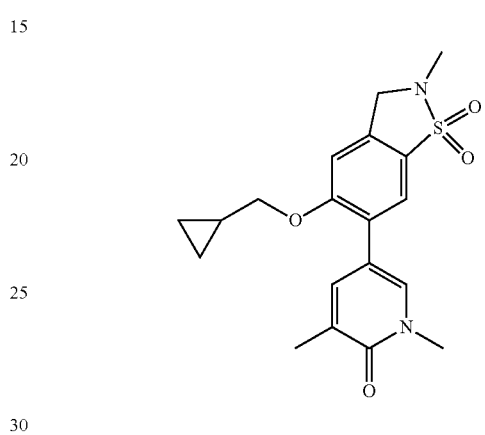

The title compound was prepared in a manner similar to Example 1, step 2, by substituting 6-bromo-5-(cyclopropylmethoxy)-2-methyl-3H-1,2-benzothiazole 1,1-dioxide for 6-bromo-2-methyl-3H-1,2-benzothiazole 1,1-dioxide and 1,3-dimethyl-5-(4,4,5,5-tetramethyl-1,3,2-dioxaborolan-2-yl)pyridin-2-one for 2-methyl-4-(4,4,5,5-tetramethyl-1,3,2-dioxaborolan-2-yl)isoquinolin-1-one. ¹H NMR (DMSO-d6, 400 MHz): δ 7.88 (s, 1H), 7.76 (s, 1H), 7.65 (s, 1H), 7.24 (s, 1H), 4.34 (s, 2H), 3.98 (d, J=6.8 Hz, 1H), 3.50 (s, 3H), 2.80 (s, 3H), 2.05 (s, 3H), 1.24 (m, 1H), 0.57 (m, 2H), 0.36 (m, 2H). LCMS: 375.1 [M+H]⁺.

Example 6

4-[5-(cyclopropylmethoxy)-2-methyl-1,1-dioxo-3H-1,2-benzothiazol-6-yl]-2-methylisoquinolin-1-one

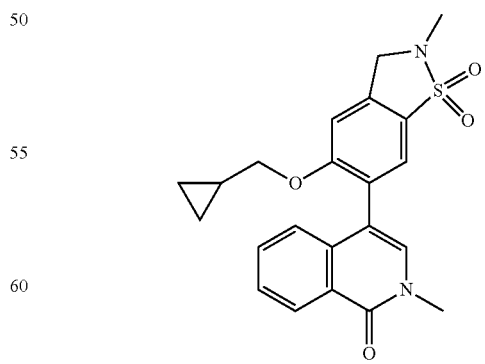

The title compound was prepared in a manner similar to Example 1, step 2, by substituting 6-bromo-5-(cyclopropylmethoxy)-2-methyl-3H-1,2-benzothiazole 1,1-dioxide for 6-bromo-2-methyl-3H-1,2-benzothiazole 1,1-dioxide. 1H NMR (DMSO-d6, 400 MHz): δ 8.29 (d, J=8.0 Hz, 1H), 7.74 (s, 1H), 7.64 (m, 1H), 7.52 (m, 2H), 7.34 (s, 1H), 7.12 (d, J=8.2 Hz, 1H), 4.42 (s, 2H), 3.95 (m, 1H), 3.89 (m, 1H), 3.56 (s, 3H), 2.82 (s, 3H), 0.94 (m, 1H), 0.35 (m, 1H), 0.26 (m, 1H), 0.06 (m, 2H). LCMS: 411.1 [M+H]$^+$.

Example 7

4-[5-(cyclopropylmethoxy)-2-ethyl-1,1-dioxo-3H-1,2-benzothiazol-6-yl]-2-methylisoquinolin-1-one Step 1: 6-bromo-5-(cyclopropylmethoxy)-2-ethyl-3H-1,2-benzothiazole 1,1-dioxide

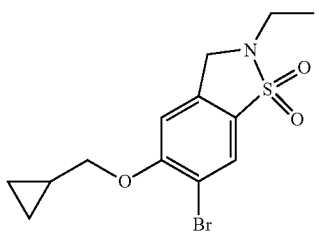 [SMILES: CCN1Cc2cc(OCC3CC3)c(Br)cc2S1(=O)=O]

The title compound was prepared in a manner similar to Example 5, step 1, by substituting ethyl iodide for methyl iodide in the synthesis of the Example 3, step 5, precursor. $^1$H NMR (CDCl$_3$, 400 MHz): δ 7.96 (s, 1H), 6.78 (s, 1H), 4.27 (s, 2H), 3.96 (s, 1H), 3.94 (s, 1H), 3.54 (q, J=7.2 Hz, 2H), 1.39-1.31 (m, 4H), 0.71-0.69 (m, 2H), 0.44-0.07 (m, 2H).

Step 2: 4-[5-(cyclopropylmethoxy)-2-ethyl-1,1-dioxo-3H-1,2-benzothiazol-6-yl]-2-methylisoquinolin-1-one

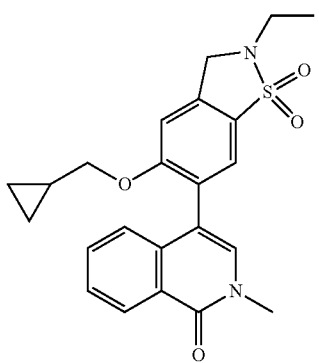 [SMILES: CCN1Cc2cc(OCC3CC3)c(-c3cn(C)c(=O)c4ccccc34)cc2S1(=O)=O]

The title compound was prepared in a manner similar to Example 4 by substituting 6-bromo-5-(cyclopropylmethoxy)-2-ethyl-3H-1,2-benzothiazole 1,1-dioxide for 6-bromo-5-methoxy-2-methyl-3H-1,2-benzothiazole 1,1-dioxide. $^1$H NMR (CDCl$_3$, 400 MHz): δ 8.51 (d, J=7.6 Hz, 1H), 7.72 (s, 1H), 7.57-7.49 (m, 2H), 7.12 (d, J=7.6 Hz, 1H), 7.06 (s, 1H), 6.90 (s, 1H), 4.40 (s, 2H), 3.87-3.81 (m, 2H), 3.67 (s, 3H), 3.40 (q, J=7.2 Hz, 2H), 1.42 (t, J=7.2 Hz, 3H), 0.98-0.95 (m, 1H), 0.44-0.35 (m, 2H), 0.90-0.70 (m, 2H). LCMS: 425.2 [M+H]$^+$.

Example 8

5-[5-(cyclopropylmethoxy)-2-ethyl-1,1-dioxo-3H-1,2-benzothiazol-6-yl]-1,3-dimethylpyridin-2-one

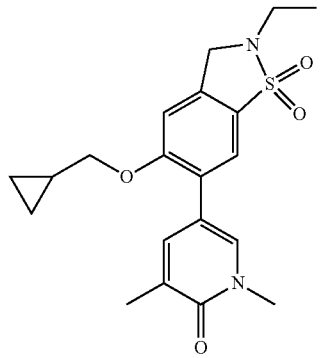 [SMILES: CCN1Cc2cc(OCC3CC3)c(-c3cc(C)c(=O)n(C)c3)cc2S1(=O)=O]

The title compound was prepared in a manner similar to Example 3 by substituting 6-bromo-5-(cyclopropylmethoxy)-2-ethyl-3H-1,2-benzothiazole 1,1-dioxide for 6-bromo-5-methoxy-2-methyl-3H-1,2-benzothiazole 1,1-dioxide in step 7. 1H NMR (CDCl3, 400 MHz): δ 7.66 (s, 1H), 7.50 (s, 2H), 6.82 (s, 1H), 4.33 (s, 2H), 3.91 (d, J=6.8 Hz, 2H), 3.62 (s, 3H), 3.37 (q, J=7.2 Hz, 2H), 2.22 (s, 3H), 1.39 (t, J=7.2 Hz, 3H), 1.28-1.25 (m, 1H), 0.70-0.65 (m, 2H), 0.37-0.34 (m, 2H). LCMS: 389.1 [M+H]$^+$.

Example 9

1,3-dimethyl-5-[2-methyl-1,1-dioxo-5-(2,2,2-trifluoroethoxy)-3H-1,2-benzothiazol-6-yl]pyridin-2-one Step 1: 6-bromo-2-methyl-5-(2,2,2-trifluoroethoxy)-3H-1,2-benzothiazole 1,1-dioxide

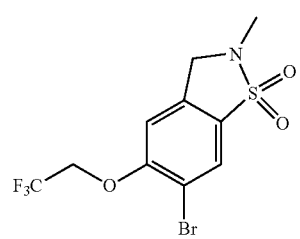 [SMILES: CN1Cc2cc(OCC(F)(F)F)c(Br)cc2S1(=O)=O]

To a solution of 6-bromo-5-fluoro-2-methyl-3H-1,2-benzothiazole 1,1-dioxide (290 mg, 1.04 mmol) and 2,2,2-trifluoroethanol (320 mg, 3.2 mmol) in DMF (10 mL) was added K$_2$CO$_3$ (717 mg, 5.2 mmol). The mixture was stirred at 60° C. for 4 hr. The mixture was cooled, poured over water (10 mL) and extracted with EtOAc (30 mL×3). The combined organic layers were washed with brine (20 mL), dried over Na$_2$SO$_4$, filtered and concentrated under reduced pressure to give the title compound that was used for the next step without further purification. $^1$H NMR (CDCl3, 400 MHz) δ 8.03 (s, 1H), 6.87 (s, 1H), 4.51-4.45 (m, 2H), 4.28 (s, 2H), 2.95 (s, 3H), 2.89 (s, 3H).

LCMS: 361.8 (M+1)$^+$.

Step 2: 1,3-dimethyl-5-[2-methyl-1,1-dioxo-5-(2,2,2-trifluoroethoxy)-3H-1,2-benzothiazol-6-yl]pyridin-2-one

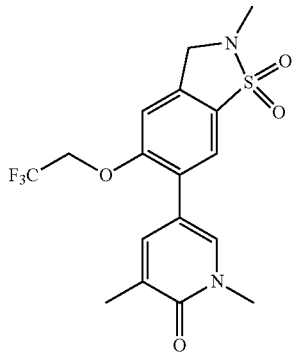 [SMILES: Cc1cc(-c2cc3c(cc2OCC(F)(F)F)CN(C)S3(=O)=O)cn(C)c1=O]

The title compound was prepared in a manner similar to Example 3 by substituting 6-bromo-2-methyl-5-(2,2,2-trifluoroethoxy)-3H-1,2-benzothiazole 1,1-dioxide for 6-bromo-5-methoxy-2-methyl-3H-1,2-benzothiazole 1,1-dioxide in step 7. $^1$H NMR (CDCl$_3$, 400 MHz): δ 7.44 (s, 1H), 7.46 (d, J=2.4 Hz, 1H), 7.42 (d, J=2.4 Hz, 1H), 6.87 (s, 1H), 4.34 (q, J=8.0 Hz, 2H), 4.35 (s, 2H), 3.62 (s, 3H), 2.97 (s, 3H), 2.21 (s, 3H). LCMS: 403.1 [M+H]$^+$.

Example 10

2-methyl-4-[2-methyl-1,1-dioxo-5-(2,2,2-trifluoroethoxy)-3H-1,2-benzothiazol-6-yl]isoquinolin-1-one

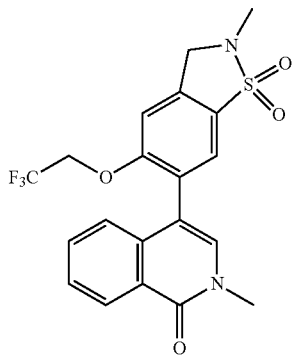 [SMILES: CN1Cc2cc(OCC(F)(F)F)c(-c3cn(C)c(=O)c4ccccc34)cc2S1(=O)=O]

The title compound was prepared in a manner similar to Example 4 by substituting 6-bromo-2-methyl-5-(2,2,2-trifluoroethoxy)-3H-1,2-benzothiazole 1,1-dioxide for 6-bromo-5-methoxy-2-methyl-3H-1,2-benzothiazole 1,1-dioxide. $^1$H NMR (CDCl$_3$, 400 MHz): δ 8.53-8.51 (m, 1H), 7.80 (s, 1H), 7.58-7.52 (m, 2H), 7.11-7.07 (m, 2H), 6.97 (s, 1H), 4.41 (s, 2H), 4.34 (q, J=8.0 Hz, 2H), 3.66 (s, 3H), 3.00 (s, 3H). LCMS: 439.1 [M+H]$^+$.

Example 11

5-[5-(2,4-difluorophenoxy)-2-methyl-1,1-dioxo-3H-1,2-benzothiazol-6-yl]-1,3-dimethylpyridin-2-one Step 1: 6-bromo-5-(2,4-difluorophenoxy)-2-methyl-3H-1,2-benzothiazole 1,1-dioxide

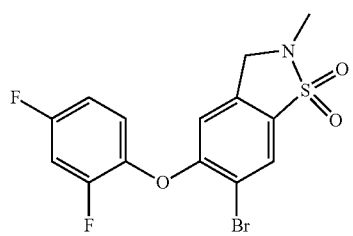 [SMILES: CN1Cc2cc(Oc3ccc(F)cc3F)c(Br)cc2S1(=O)=O]

The title compound was prepared in a manner similar to Example 9, step 1, by substituting 2,4-difluorophenol for 2,2,2-trifluoroethanol. $^1$H NMR (CDCl3, 400 MHz) δ 8.07 (s, 1H), 7.20-7.14 (m, 1H), 7.06-6.94 (m, 2H), 6.61 (s, 1H), 4.17 (s, 2H), 2.92 (s, 3H).

LCMS: 391.8 (M+1)$^+$.

Step 2: 5-[5-(2,4-difluorophenoxy)-2-methyl-1,1-dioxo-3H-1,2-benzothiazol-6-yl]-1,3-dimethylpyridin-2-one

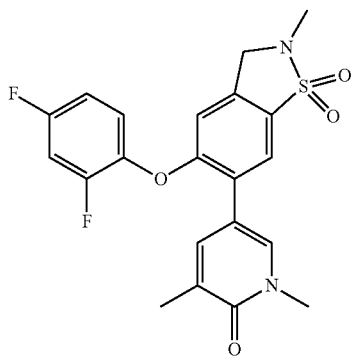

The title compound was prepared in a manner similar to Example 3 by substituting 6-bromo-5-(2,4-difluorophenoxy)-2-methyl-3H-1,2-benzothiazole 1,1-dioxide for 6-bromo-5-methoxy-2-methyl-3H-1,2-benzothiazole 1,1-dioxide in step 7. $^1$H NMR (CDCl$_3$, 400 MHz): δ 7.76 (s, 1H), 7.50 (s, 2H), 7.11-6.95 (m, 3H), 6.95 (s, 1H), 4.24 (s, 2H), 3.63 (s, 3H), 2.94 (s, 3H), 2.21 (s, 3H). LCMS: 433.1 [M+H]$^+$.

Example 12

5-[5-(2,4-difluorophenoxy)-2-methyl-1,1-dioxo-3H-1,2-benzothiazol-6-yl]-1-methylpyridin-2-one

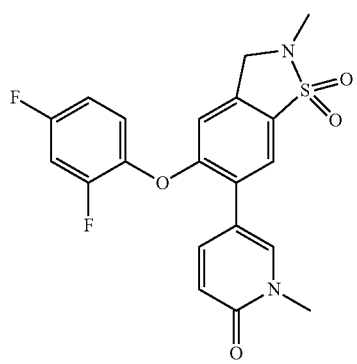

The title compound was prepared in a manner similar to Example 11 by substituting 1-methyl-5-(4,4,5,5-tetramethyl-1,3,2-dioxaborolan-2-yl)pyridin-2-one for 1,3-dimethyl-5-(4,4,5,5-tetramethyl-1,3,2-dioxaborolan-2-yl)pyridin-2-one in step 2. $^1$H NMR (CDCl$_3$, 400 MHz): δ 7.77 (s, 1H), 7.64 (dd, J$_1$=9.6 Hz, J$_2$=2.8 Hz, 1H), 7.59 (d, J=2.4 Hz, 1H), 7.12-7.10 (m, 1H), 7.08-7.05 (m, 1H), 7.03-6.96 (m, 1H), 6.66-6.64 (m, 2H), 4.24 (s, 2H), 3.63 (s, 3H), 2.94 (s, 3H). LCMS: 419.0 [M+H]$^+$.

Example 13

4-[5-(cyclopropylmethoxy)-1-methylsulfonyl-2,3-dihydroindol-6-yl]-2-methylisoquinolin-1-one Step 1: 1-(5-nitro-2,3-dihydroindol-1-yl)ethanone

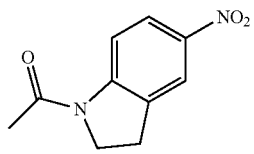

To a solution of 1-(2,3-dihydroindol-1-yl)ethanone (20 g, 124.07 mmol) in TFA (400 mL) was added a solution of KNO$_3$ (12.54 g, 124.07 mmol, 1.00 Eq) in TFA (50 mL) drop-wise at 5-10° C. during 1 hr. The mixture was stirred for 3 hr at the same temperature. The reaction mixture was poured over ice-water (500 ml) and filtered. The residue was washed with EtOH (100 ml) to provide the title compound (18 g, 70% yield) as a yellow solid. $^1$H NMR (CDCl$_3$, 400 MHz) δ 8.31 (d, J=8.8 Hz, 1H), 8.14 (m, 1H), 8.05 (s, 1H), 4.20 (t, 2H), 3.30 (t, 2H), 2.29 (s, 3H).

Step 2: 1-(5-amino-2,3-dihydroindol-1-yl)ethanone

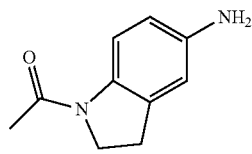

To a solution of the title compound from step 1 (18 g, 87.29 mmol) in iPrOH (300 mL) was added Pd/C (1.50 g, 87.29 mmol). The suspension was degassed by carrying out three cycles of vacuum followed by nitrogen filling. The mixture was stirred for 12 hr at 25° C. The catalyst was removed by filtration and the filtrate was concentrated under reduced pressure to provide the title compound (15 g, 97% yield) as a yellow solid which was used directly in the next step without further purification. $^1$H NMR (CDCl$_3$, 400 MHz) δ 8.01 (d, J=8.4 Hz, 1H), 6.52-6.56 (m, 2H), 4.01 (t, J=8.0 Hz, 2H), 3.12 (t, J=8.4 Hz, 2H), 3.0-3.5 (br s, 2H), 2.20 (s, 3H).

Step 3: 1-(5-hydroxy-2,3-dihydroindol-1-yl)ethanone

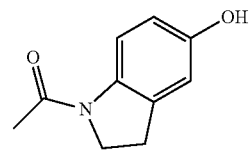

To a solution of the title compound from step 2 (13.5 g, 76.70 mmol) in H$_2$SO$_4$ (100 mL) was added slowly a solution of NaNO$_2$ (6.35 g, 92.02 mmol) in water (30 mL) at 5-10° C. After the addition was completed, the reaction contents were stirred at the same temperature for 1 hr. Then the mixture was poured over a solution of Cu$_2$O (38.39 g, 268.46 mmol) in 30% H$_2$SO$_4$ (100 mL) warmed up to 100° C. It was stirred for 1 hr at that temperature. The mixture was cooled to 25° C. and extracted with EtOAc (200 mL×3). The combined organic layers were washed with brine, filtered, dried over Na$_2$SO$_4$, and concentrated under reduced pressure. The crude product was purified by silica gel column chromatography to provide 5.3 g of crude product as a brown solid. Trituration with acetone (100 mL) afforded pure title compound (3.00 g, 22% yield). $^1$H NMR (DMSO-d6, 400 MHz) δ 9.11 (s, 1H), 7.83 (d, J=8.4 Hz, 1H), 6.63 (s, 1H), 6.50-6.52 (m, 1H), 4.02 (t, J=8.8 Hz, 2H), 3.05 (t, J=8.8 Hz, 2H), 2.09 (s, 3H). LCMS: 178.0 [M+H]$^+$.

Step 4: 1-(6-bromo-5-hydroxy-2,3-dihydroindol-1-yl)ethanone

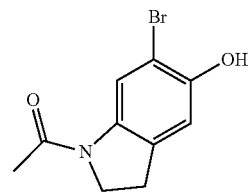

To a solution of the title compound from step 3 (3.0 g, 16.95 mmol) in AcOH (25 mL) was added a solution of NBS (3.01 g, 16.95 mmol) in AcOH (25 mL) slowly at 10° C.-20° C. The mixture was stirred at that temperature for 1 hr. It was then poured over water (50 ml) and extracted with CH$_2$Cl$_2$ (200 ml×5). The combined organic phases were washed with brine, dried over Na$_2$SO$_4$, filtered and concentrated. The residue was purified by column chromatography (PE:EA=10:1~1:1) to provide the title compound (1.10 g, 25% yield) as a solid. $^1$H NMR (DMSO-d6, 400 MHz) δ 9.90 (s, 1H), 8.14 (s, 1H), 6.83 (s, 1H), 4.05 (t, J=8.4 Hz, 2H), 3.04 (t, J=8.4 Hz, 2H), 2.11 (s, 3H). LCMS: 256.0, 258.0 [M+H]$^+$.

Step 5: 1-[6-bromo-5-(cyclopropylmethoxy)-2,3-dihydroindol-1-yl]ethanone

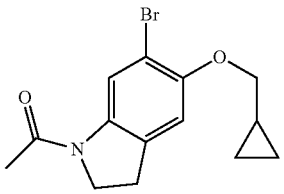 [SMILES: CC(=O)N1CCc2cc(OCC3CC3)c(Br)cc21]

To a solution of the title compound from step 4 (1.0 g, 4.0 mmol) in CH$_3$CN (20 mL) was added K$_2$CO$_3$ (830 mg, 6.0 mmol). The mixture was stirred for 30 mins. Bromomethylcyclopropane (630 mg, 4.8 mmol) was added and reaction was stirred at 70° C. for 6.5 hr. The mixture was poured over water (50 ml) and extracted with EtOAc (50 ml×3). The combined organic layers were washed with brine, dried over Na$_2$SO$_4$, filtered and concentrated under reduced pressure. The crude product was purified by column chromatography (PE:EA=10:1~3:1) to provide the title compound (900 mg, 75% yield) as a yellow solid. $^1$H NMR (CDCl$_3$, 400 MHz) δ 8.41 (s, 1H), 6.76 (s, 1H), 4.06 (t, J=8.4 Hz, 2H), 3.84 (d, J=6.8 Hz, 2H), 3.13 (t, J=8.4 Hz, 2H), 2.20 (s, 3H), 1.26-1.31 (m, 1H), 0.61-0.66 (m, 2H), 0.4 (s, 2H).
LCMS: 310.0; 312.0 [M+H]$^+$.

Step 6: 6-bromo-5-(cyclopropylmethoxy)-2,3-dihydro-1H-indole

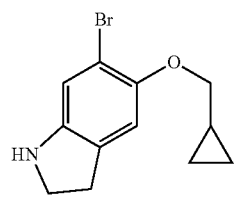 [SMILES: Brc1cc2c(cc1OCC1CC1)CCN2]

A solution of the title compound from step 5 (700 mg, 2.26 mmol) in 5 N HCl (70 mL) and MeOH (100 mL) was stirred at 70° C. The starting material was consumed after 4 hr. The pH of the reaction mixture was adjusted to 8-9 by addition of NaHCO$_3$. It was then extracted with EtOAc (100 ml×3). The combined organic layers were washed with brine, dried over Na$_2$SO$_4$, filtered and concentrated. The residue was purified by column chromatography (PE:EA=10:1~1:1) to afford the title compound (320 mg, 53% yield). $^1$H NMR (CDCl$_3$, 400 MHz) δ 7.24 (s, 1H), 6.83 (s, 1H), 3.83 (d, J=6.8 Hz, 2H), 3.72 (m, 2H), 3.10 (t, J=7.2 Hz, 2H), 1.27 (m, 1H), 0.64 (d, J=6.8 Hz, 2H), 0.39 (d, J=4.0 Hz, 2H). LCMS: 268.0; 270.0 [M+H]$^+$.

Step 7: 6-bromo-5-(cyclopropylmethoxy)-1-methylsulfonyl-2,3-dihydroindole

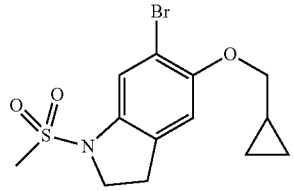 [SMILES: CS(=O)(=O)N1CCc2cc(OCC3CC3)c(Br)cc21]

To a solution of the title compound from step 6 (120 mg, 447.5 μmol) in pyridine (5 mL) was added methanesulfonyl chloride (590 mg, 5.15 mmol). The reaction mixture was stirred for 2 hr at RT. It was then poured over 1 N HCl (50 ml) and extracted with CH$_2$Cl$_2$ (50 mL×3). The combined organic layers were washed with brine, dried over Na$_2$SO$_4$, filtered and concentrated. The crude product was purified by column chromatography to provide the title compound (120 mg, 77% yield) as a solid. $^1$H NMR (CDCl$_3$, 400 MHz) δ 7.61 (s, 1H), 6.80 (s, 1H), 4.00 (t, J=8.4 Hz, 2H), 3.83 (d, J=6.8 Hz, 2H), 3.09 (t, J=8.4 Hz, 2H), 2.86 (s, 3H), 1.29-1.32 (m, 1H), 0.64-0.66 (m, 2H), 0.38-0.39 (m, 2H).

Step 8: 4-[5-(cyclopropylmethoxy)-1-methylsulfonyl-2,3-dihydroindol-6-yl]-2-methylisoquinolin-1-one

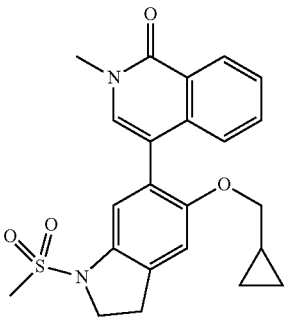 [SMILES: Cn1cc(-c2cc3c(cc2OCC2CC2)CCN3S(C)(=O)=O)c2ccccc2c1=O]

A mixture of the title compound from step 7 (50 mg, 144 umol), 2-methyl-4-(4,4,5,5-tetramethyl-1,3,2-dioxaborolan-2-yl)isoquinolin-1-one (33 mg, 159 umol), Pd(dppf)Cl$_2$ (5 mg, 7 umol), K$_3$PO$_4$ (92 mg, 433 umol) in dioxane (5 mL) and H$_2$O (0.5 mL) was degassed by performing three cycles of vacuum and N$_2$ filling. The mixture was stirred for 3 hr at 70° C. It was then cooled down to RT, filtered through Celite and concentrated under reduced pressure. The residue was purified by column chromatography (PE:EA=3:1~1:1) followed by preparative HPLC to provide the title compound (13 mg, 21% yield) as a white solid. $^1$H NMR (CDCl$_3$, 400 MHz) δ 8.52 (d, J=7.2 Hz, 1H), 7.49-7.59 (m, 2H), 7.35 (s, 1H), 7.24-7.68 (m, 1H), 7.06 (s, 1H), 6.92 (s, 1H), 4.01-4.10 (m, 2H), 3.71-3.78 (m, 2H), 3.68 (s, 3H), 3.13-3.25 (m, 2H) 2.90 (s, 3H), 0.91-0.97 (m, 1H), 0.37 (brs, 2H), 0.04 (brs, 2H). LCMS: 425.0 [M+H]$^+$.

Example 14

4-[5-(cyclopropylmethoxy)-1-ethylsulfonyl-2,3-dihydroindol-6-yl]-2-methylisoquinolin-1-one

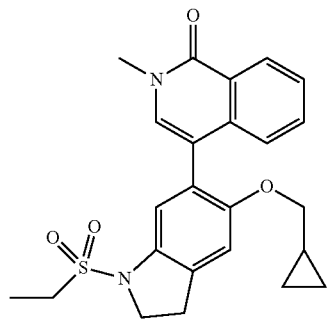 [SMILES: CCS(=O)(=O)N1CCc2cc(OCC3CC3)c(-c3cn(C)c(=O)c4ccccc34)cc21]

The title compound was prepared in a manner similar to Example 13 by substituting ethanesulfonyl chloride for methanesulfonyl chloride in step 7. $^1$H NMR (CDCl$_3$, 400 MHz) δ 8.50 (d, J=8 Hz, 1H), 7.57 (t, J=8 Hz, 1H), 7.50 (t, J=8 Hz, 1H), 7.30 (s, 1H), 7.25 (m, 1H), 7.06 (s, 1 H), 6.89 (s, 1H), 4.07-4.12 (m, 2H), 3.70-3.74 (m, 2H), 3.68 (s, 3H), 3.21 (t, J=8 Hz, 2H), 3.06-3.12 (q, J=8 Hz, 2H), 1.39 (t, J=8 Hz, 3H), 0.92 (m, 1H), 0.35 (m, 2H), 0.02 (m, 2H). LCMS: 439.1 (M+1)$^+$.

Example 15

5-[5-(cyclopropylmethoxy)-1-methylsulfonyl-2,3-dihydroindol-6-yl]-1,3-dimethylpyridin-2-one

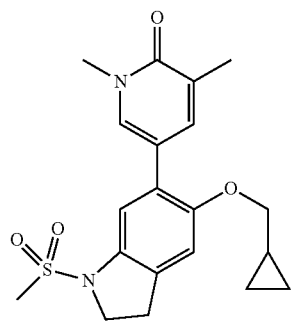 [SMILES: Cc1cc(-c2cc3c(cc2OCC2CC2)CCN3S(C)(=O)=O)cn(C)c1=O]

The title compound was prepared in a manner similar to Example 13 by substituting 1,3-dimethyl-5-(4,4,5,5-tetramethyl-1,3,2-dioxaborolan-2-yl)pyridin-2-one for 2-methyl-4-(4,4,5,5-tetramethyl-1,3,2-dioxaborolan-2-yl)isoquinolin-1-one in step 8. $^1$H NMR (CDCl$_3$, 400 MHz) δ 7.56 (s, 1H), 7.50 (d, J=2 Hz, 1H), 7.31 (s, 1H), 6.83 (s, 1H), 4.00 (t, J=8 Hz, 2H), 3.78 (d, J=6 Hz, 2H), 3.64 (s, 3H), 3.15 (t, J=8 Hz, 2H), 2.86 (s, 3H), 2.22 (s, 3H), 1.16-1.24 (m, 1H), 0.60-0.62 (m, 2H), 0.25-0.30 (m, 2H). LCMS: 389.0 (M+1)$^+$.

Example 16

5-[5-(cyclopropylmethoxy)-1-ethylsulfonyl-2,3-dihydroindol-6-yl]-1,3-dimethylpyridin-2-one

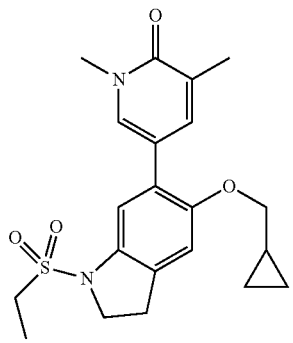 [SMILES: CCS(=O)(=O)N1CCc2cc(OCC3CC3)c(-c3cc(C)c(=O)n(C)c3)cc21]

The title compound was prepared in a manner similar to Example 14 by substituting 1,3-dimethyl-5-(4,4,5,5-tetramethyl-1,3,2-dioxaborolan-2-yl)pyridin-2-one for 2-methyl-4-(4,4,5,5-tetramethyl-1,3,2-dioxaborolan-2-yl)isoquinolin-1-one. $^1$H NMR (CDCl$_3$, 400 MHz) δ 7.54 (s, 1H), 7.49 (s, 1H), 7.28 (s, 1H), 6.82 (s, 1H), 4.07 (t, J=8 Hz, 2H), 3.77 (d, J=8 Hz, 2H), 3.63 (s, 3H), 3.15 (t, J=8 Hz, 2H), 3.04-3.10 (q, J=8 Hz, 2H), 2.21 (s, 3H), 1.39 (t, J=8 Hz, 3H), 1.14-1.20 (m, 1H), 0.58-0.63 (m, 2H), 0.28-0.31 (m, 2H). LCMS: 403.0 [M+H]$^+$.

Example 17

N-[1-benzyl-6-(2-methyl-1-oxoisoquinolin-4-yl)indol-4-yl]methanesulfonamide

Step 1: (E)-2-(4-bromo-2,6-dinitrophenyl)-N,N-dimethylethenamine

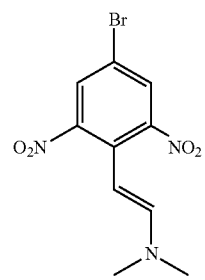 [SMILES: CN(C)/C=C/c1c([N+](=O)[O-])cc(Br)cc1[N+](=O)[O-]]

A mixture of 5-bromo-2-methyl-1,3-dinitrobenzene (5 g, 19.15 mmol) and Bredereck's reagent (10.01 g, 57.45 mmol) was heated at 110° C. for 2 hr. The mixture was cooled down to RT and concentrated to give the crude title compound (2 g) which was used directly in the next step. $^1$H NMR (CDCl$_3$, 300 MHz) δ 8.34 (s, 2H), 6.50-6.47 (d, 1H, J=10.2 Hz), 5.32~5.29 (d, 1H, J=10.2 Hz), 2.88 (s, 6H). LCMS: 316.0; 318.0 [M+H]$^+$.

Step 2: 6-bromo-1H-indol-4-amine

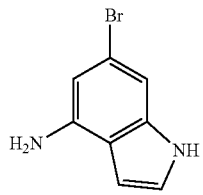

The title compound from step 1 (3 g, 9.49 mmol) was treated with TiCl$_3$ (7.32 g, 47.45 mmol) in a HCl solution (61.20 g, 167.86 mmol). The reaction mixture was stirred at 25° C. for 16 hr. It was then poured over 2 N aqueous NaOH (150 mL) and extracted with EtOAc (150 mL). The organic phase was dried, filtered and concentrated under reduced pressure. The residue was purified by column chromatography (PE to PE/EA=5/1) to give the title compound (2 g, 36%) as a gray solid. $^1$H NMR (CDCl$_3$, 400 MHz) δ 8.10 (br s, 1H), 7.09~7.08 (m, 1H), 7.02 (d, J=1.4 Hz, 1H), 6.54 (d, J=1.4 Hz, 1H), 6.44~6.43 (m, 1H), 3.98 (br s, 2H).

Step 3: 1-benzyl-6-bromoindol-4-amine

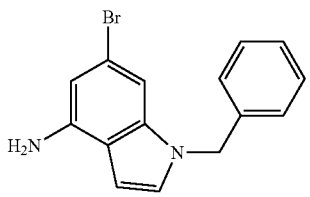 [SMILES: Nc1cc(Br)cc2c1ccn2Cc1ccccc1]

To a solution of the title compound from step 2 (50 mg, 237 μmol) in DMF (1 mL) was added NaH (6 mg, 250 μmol) at 0° C. The reaction mixture was stirred at 0° C. for 30 mins. Benzyl bromide (41 mg, 237 umol) was then added. The mixture was stirred at 25° C. for 1 hr. Water (2 mL) was added and the mixture was extracted with EtOAc (5 mL). The organic layer was dried, filtered and concentrated under reduced pressure. The residue was purified by preparative TLC to give the title compound (30 mg, 42%) as a gray solid. $^1$H NMR (CDCl$_3$, 400 MHz) δ 7.33~7.27 (m, 3H), 7.01~7.08 (d, J=6.8 Hz, 2H), 6.99~6.98 (m, 1H), 6.91 (s, 1H), 6.53 (s, 1H), 6.43~6.42 (m, 1H), 5.22 (s, 2H). LCMS: 301.0; 303.0 [M+H]$^+$.

Step 4: N-(1-benzyl-6-bromoindol-4-yl)methanesulfonamide

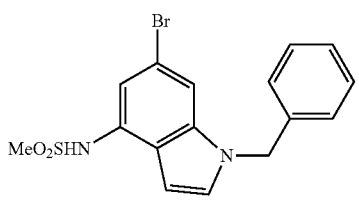

To a solution of the title compound from step 3 (30 mg, 99.6 umol) in pyridine (1 mL) at 25° C. was added MsCl (11.41 mg, 99.6 umol) in one portion. Then the reaction mixture was stirred at 25° C. for 2 hr. The mixture was concentrated under reduced pressure and the residue was purified by preparative TLC to give the title compound (30 mg, 79%) as a solid. $^1$H NMR (CDCl$_3$, 400 MHz) δ 7.37~7.32 (m, 5H), 7.14~7.11 (m, 2H), 6.63 (s, 1H), 6.52 (s, 1H), 5.28 (s, 2H), 3.07 (s, 3H). LCMS: 378.8; 381.8 [M+H]$^+$.

Step 5: N-[1-benzyl-6-(2-methyl-1-oxoisoquinolin-4-yl)indol-4-yl]methanesulfonamide

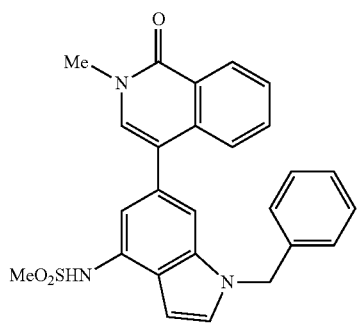

To a solution of the title compound from step 4 (50 mg, 131 umol) and 2-methyl-4-(4,4,5,5-tetramethyl-1,3,2-dioxaborolan-2-yl)isoquinolin-1-one (38 mg, 131 umol) in dioxane (20 mL) and H$_2$O (2 mL) was added Pd(dppf)Cl$_2$ (10 mg, 13.2 μmol) and Na$_2$CO$_3$ (28 mg, 263 μmol) in one portion. The mixture was submitted to two vacuum/nitrogen filling cycles and then heated at 90° C. for 3 hr. The mixture was then cooled to RT and extracted with EtOAc (30 mL), dried over Na$_2$SO$_4$, filtered and concentrated under reduced pressure. The residue was purified by silica gel column chromatography (PE:EA=5:1~1:1) followed by preparative HPLC to afford the title compound (22.5 mg, 37%) as a solid. $^1$H NMR (CDCl$_3$, 400 MHz) δ 8.52~8.53 (d, J=1.6 Hz, 1H), 7.57~7.48 (m, 3H), 7.37~7.32 (m, 3H), 7.21 (s, 1H), 7.16~7.14 (m, 2H), 7.09 (s, 1H), 6.72 (s, 1H), 6.62 (s, 1H), 5.37 (s, 2H), 3.67 (s, 3H), 3.10 (s, 3H). LCMS: 458.1 (M+1)$^+$.

Example 18

N-[1-benzyl-6-(1,5-dimethyl-6-oxopyridin-3-yl)indol-4-yl]methanesulfonamide

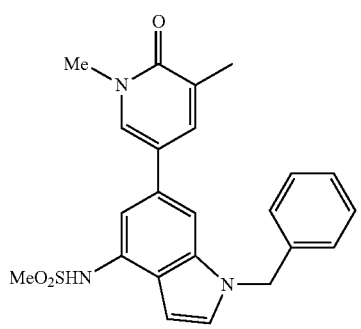

The title compound was prepared in a manner similar to Example 17 by substituting 1,3-dimethyl-5-(4,4,5,5-tetramethyl-1,3,2-dioxaborolan-2-yl)pyridin-2-one for 2-methyl-4-(4,4,5,5-tetramethyl-1,3,2-dioxaborolan-2-yl)isoquinolin-1-one in step 5. $^1$H NMR (CDCl$_3$, 400 MHz) δ 7.51 (s, 1H), 7.39 (s, 1H), 7.38~7.31 (m, 4H), 7.19~7.12 (m, 4H), 6.55 (s, 1H), 6.54 (s, 1H), 5.38 (s, 2H), 3.64 (s, 3H), 3.05 (s, 3H), 2.23 (s, 3H). LCMS: 422.0 (M+1)$^+$.

Example 19

N-[1-benzyl-6-(1,5-dimethyl-6-oxopyridin-3-yl)-2,3-dihydroindol-4-yl]methanesulfonamide Step 1: N-(1-benzyl-6-bromo-2,3-dihydroindol-4-yl)methanesulfonamide

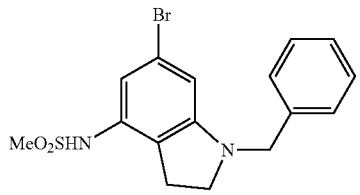

To a solution of the title compound from step 4 (200 mg, 0.53 mmol) in AcOH (5 mL) at 0° C. was added NaBH$_3$CN (166 mg, 2.64 mmol) in one portion. The mixture was then warmed to 25° C. and stirred for 10 hr. It was diluted with water (30 mL) and extracted with EtOAc (50 mL×2). The combined organic layers were washed by saturated NaHCO$_3$ (100 mL) and brine (100 mL), dried over Na$_2$SO$_4$, filtered and concentrated under reduced pressure. The residue was purified by silica gel column chromatography (PE:EA=5:1~2:1) to afford the title compound (120 mg, 59% yield) as a white solid. LCMS: 381.0; 383.0 [M+H]+.

Step 2: N-[1-benzyl-6-(1,5-dimethyl-6-oxopyridin-3-yl)-2,3-dihydroindol-4-yl]methanesulfonamide

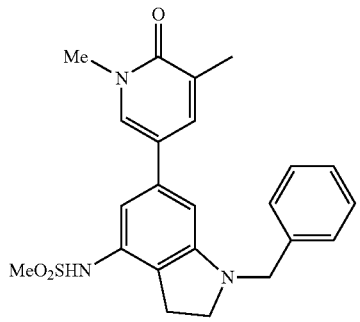

The title compound was prepared in a manner similar to Example 18 by substituting N-(1-benzyl-6-bromo-2,3-dihydroindol-4-yl)methanesulfonamide for N-(1-benzyl-6-bromoindol-4-yl)methanesulfonamide. $^1$H NMR (CDCl$_3$, 400 MHz) δ 7.42~7.26 (m, 7H), 6.78 (s, 1H), 6.34 (s, 1H), 4.33 (s, 2H), 3.60 (s, 3H), 3.45~3.43 (m, 2H), 3.07 (s, 3H), 3.01~2.97 (m, 2H), 2.22 (s, 3H).
LCMS: 424.1 (M+1)$^+$.

Example 20

N-[1-benzyl-6-(2-methyl-1-oxoisoquinolin-4-yl)-2,3-dihydroindol-4-yl]methanesulfonamide

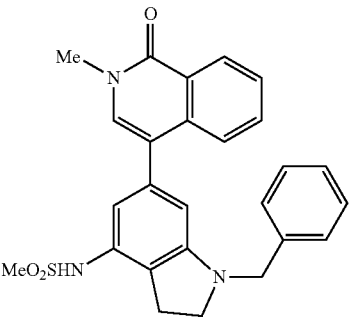

The title compound was prepared in a manner similar to Example 17 by substituting N-(1-benzyl-6-bromo-2,3-dihydroindol-4-yl)methanesulfonamide for N-(1-benzyl-6-bromoindol-4-yl)methanesulfonamide in step 5. $^1$H NMR (CDCl$_3$, 400 MHz) δ 8.51 (s, 1H), 7.58~7.50 (m, 4H), 7.33~7.27 (m, 5H), 7.05 (s, 1H), 6.75 (s, 1H), 6.39 (s, 1H), 4.30 (s, 2H), 3.64 (s, 3H), 3.51 (s, 2H), 3.09~3.05 (m, 5H). LCMS: 460.1 (M+1)$^+$.

Example 21

5-(2-ethyl-5-methylsulfonyl-1-benzofuran-7-yl)-1,3-dimethylpyridin-2-one

Step 1: 2,6-diiodo-4-methylsulfonylphenol

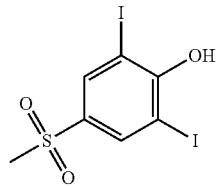

To a solution of 4-methylsulfonylphenol (2.0 g, 11.61 mmol) in an AcOH (30 mL)/H$_2$O (30 mL) mixture was added KI (4.82 g, 29 mmol), NaCl (1.7 g, 29 mmol) and NaIO$_4$ (6.21 g, 29 mmol) at RT. The reaction was stirred at 50° C. for 0.5 hr. It was then diluted with EtOAc (300 mL) and washed with H$_2$O (100 mL), Na$_2$SO$_3$ (200 mL) and brine (70 mL). The organic layer was dried over Na$_2$SO$_4$, filtered and concentrated under reduced pressure. The crude product was triturated with PE/EA=5/1 to give the title compound (4.5 g, 91%) as a white solid. $^1$H NMR (CDCl$_3$, 400 MHz) δ 8.24 (s, 2H), 6.32 (s, 1H), 3.07 (s, 3H).

Step 2:
2-ethyl-7-iodo-5-methylsulfonyl-1-benzofuran

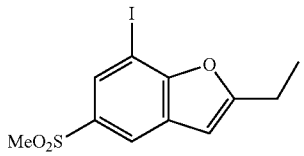 [SMILES: CCc1cc2cc(S(C)(=O)=O)cc(I)c2o1]

To a solution of the title compound from step 1 (1.00 g, 2.36 mmol) in pyridine (10 mL) was added but-1-yne (128 mg, 2.36 mmol) and Cu$_2$O (135 mg, 0.94 mmol) at 25° C. The mixture was stirred at 130° C. for 3 hr under a nitrogen atmosphere. The reaction was cooled to RT, diluted with 1N HCl (200 ml) and extracted with EtOAc (30 mL×2). The combined organic layers were washed with brine (100 mL), dried over Na$_2$SO$_4$, filtered and concentrated under reduced pressure to give a residue that was purified by column chromatography (PE:EA=10:1 to 5:1) to afford the title compound (400 mg, 48%) as a solid. $^1$H NMR (CDCl$_3$, 400 MHz) δ 8.14 (d, J=1.6 Hz, 1H), 8.06 (d, J=1.6 Hz, 1H), 6.62 (s, 1H), 3.09 (s, 3H), 2.90 (q, J=7.6 Hz, 2H), 1.38 (t, J=7.6 Hz, 3H). LCMS: 350.9 [M+H]$^+$.

Step 3: 5-(2-ethyl-5-methylsulfonyl-1-benzofuran-7-yl)-1,3-dimethylpyridin-2-one

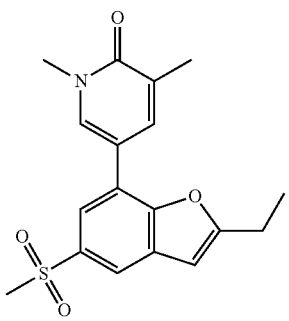 [SMILES: CCc1cc2cc(S(C)(=O)=O)cc(-c3cc(C)c(=O)n(C)c3)c2o1]

To a solution of 1,3-dimethyl-5-(4,4,5,5-tetramethyl-1,3,2-dioxaborolan-2-yl)pyridin-2-one (71 mg, 285.5 umol) and the title compound from step 2 (100 mg, 285 μmol) in dioxane (20 mL) and H$_2$O (2 mL) was added Pd(dppf)Cl$_2$ (21 mg, 28 umol) and Na$_2$CO$_3$ (61 mg, 572 μmol). The mixture was submitted to three cycles of vacuum/nitrogen filling and then heated at 90° C. for 4 hr. It was then cooled to RT and concentrated under reduced pressure. The residue was purified by silica gel column chromatography followed by preparative HPLC to afford the title compound (10 mg, 10%) as a solid. $^1$H NMR (CDCl$_3$, 400 MHz) δ 8.03 (s, 1H), 7.91 (s, 1H), 7.82 (s, 1H), 7.76 (s, 1H), 6.57 (s, 1H), 3.69 (s, 3H), 3.12 (s, 3H), 2.90 (q, J=6.8 Hz, 2H), 2.28 (s, 3H), 1.40 (t, J=6.8 Hz, 3H). LCMS: 345.9 [M+H]$^+$.

Example 22

N-[2-(1,5-dimethyl-6-oxopyridin-3-yl)-9-[(4-fluorophenyl)methyl]-8-methylpurin-6-yl]methanesulfonamide Step 1: 2,6-dichloro-9-[(4-fluorophenyl)methyl]-8-methylpurine

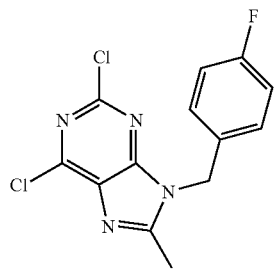 [SMILES: Cc1nc2c(Cl)nc(Cl)nc2n1Cc1ccc(F)cc1]

A mixture of 2,6-dichloro-8-methyl-9H-purine (100 mg, 0.49 mmol), K$_2$CO$_3$ (204 mg, 1.5 mmol) and 1-(bromomethyl)-4-fluorobenzene (186 mg, 0.98 mmol) in DMF (5 mL) was stirred at RT overnight. The reaction mixture was diluted with ice water (15 mL) and extracted with EtOAc (30 mL×3). The combined organic layers were washed with brine, dried over Na$_2$SO$_4$, filtered and concentrated under reduced pressure. The residue was purified by column chromate-graphy on silica gel (PE:EA=5:1) to give the title compound (90 mg, 59%) as a yellow solid. $^1$H NMR (300 MHz, CDCl$_3$): δ 7.21-7.16 (m, 2H), 7.07-7.01 (m, 2H), 5.37 (s, 2H), 2.59 (s, 3H).

Step 2: N-[2-chloro-9-[(4-fluorophenyl)methyl]-8-methylpurin-6-yl]methanesulfonamide

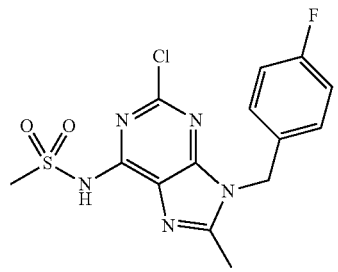 [SMILES: Cc1nc2c(NS(C)(=O)=O)nc(Cl)nc2n1Cc1ccc(F)cc1]

A mixture of the title compound from step 1 (300 mg, 0.97 mmol), MeSO$_2$NH$_2$ (93 mg, 0.97 mmol) and Cs$_2$CO$_3$ (379 mg, 1.16 mmol) in dioxane (15 mL) was stirred at 115° C. for 8 hr. The reaction mixture was cooled to RT, diluted with water (50 ml) and extracted with DCM (30 ml×3). The combined organic layers were washed with brine (30 ml×2), dried over Na$_2$SO$_4$, filtered and concentrated under reduced pressure. The residue was washed with ether (10 ml×2) to afford the title compound (200 mg, 56%) as a solid. $^1$H NMR (300 MHz, DMSO-d$_6$): δ 7.23-7.16 (m, 4H), 5.27 (s, 2H), 3.03 (s, 3H), 2.35 (s, 3H).

Step 3: N-[2-(1,5-dimethyl-6-oxopyridin-3-yl)-9-[(4-fluorophenyl)methyl]-8-methylpurin-6-yl]methanesulfonamide

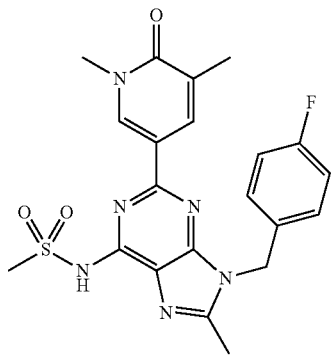 [SMILES: Cc1cc(-c2nc(NS(C)(=O)=O)c3nc(C)n(Cc4ccc(F)cc4)c3n2)cn(C)c1=O]

A mixture of the title compound from step 2 (100 mg, 0.27 mmol), 1,3-dimethyl-5-(4,4,5,5-tetramethyl-1,3,2-dioxaborolan-2-yl)pyridin-2-one (88 mg, 0.35 mmol), K$_2$CO$_3$ (75 mg, 0.54 mmol) and Pd-118 (17 mg, 0.027 mmol) in DMA (10 mL) under N$_2$ was heated to 145° C. for 3 hr. The reaction was cooled to RT and filtered. The filtrate was diluted with water, adjusted to pH 3-4 by addition a 2M HCl solution, and extracted with DCM (20 mL×3). The combined organic layers were dried over Na$_2$SO$_4$, filtered and concentrated. The residue was purified with preparative TLC (DCM:MeOH=20:1) to give the title compound (36 mg, 29%) as a solid. $^1$H NMR (300 MHz, DMSO-d$_6$): δ 8.51 (d, J=2.1 Hz, 1H), 8.20 (d, J=2.1 Hz, 1H), 7.34-7.31 (m, 2H), 7.22-7.19 (m, 2H), 5.51 (s, 2H), 3.58 (s, 3H), 3.55 (s, 3H), 2.48 (s, 3H), 2.10 (s, 3H). LCMS: 457 [M+H].

Example 23

5-(2-cyclopropyl-5-methylsulfonyl-1-benzofuran-7-yl)-1,3-dimethylpyridin-2-one

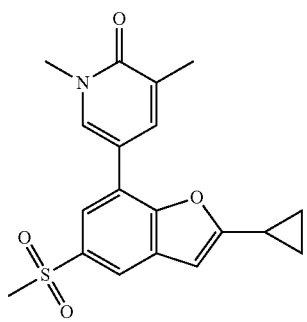 [SMILES: Cc1cc(-c2cc(S(C)(=O)=O)cc3cc(C4CC4)oc23)cn(C)c1=O]

The title compound was prepared in a manner similar to Example 21 by substituting ethynylcyclopropane for but-1-yne in step 2. $^1$H NMR (CDCl$_3$, 400 MHz) δ 7.98 (d, 1H, J=1.6 Hz), 7.87~7.86 (d, 1H, J=1.6 Hz), 7.79 (d, J=2 Hz, 1H), 7.73 (s, 1H), 6.51 (s, 1H), 3.69 (s, 3H), 3.11 (s, 3H), 2.28 (s, 3H), 2.13~2.11 (m, 1H), 1.15~1.11 (m, 2H), 1.01~0.99 (m, 2H). LCMS: 358.0 (M+H$^+$).

Example 24

4-(2-cyclopropyl-5-methylsulfonyl-1-benzofuran-7-yl)-2-methylisoquinolin-1-one

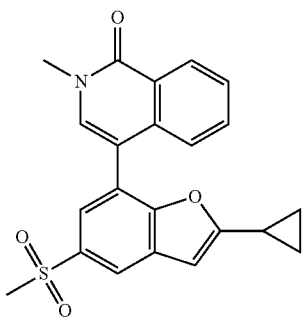 [SMILES: Cn1cc(-c2cc(S(C)(=O)=O)cc3cc(C4CC4)oc23)c2ccccc2c1=O]

The title compound was prepared in a manner similar to Example 23 by substituting 2-methyl-4-(4,4,5,5-tetramethyl-1,3,2-dioxaborolan-2-yl)isoquinolin-1-one for 1,3-dimethyl-5-(4,4,5,5-tetramethyl-1,3,2-dioxaborolan-2-yl)pyridin-2-one in the Suzuki coupling step. $^1$H NMR (MeOD, 400 MHz) δ 8.47~8.45 (dd, J=2.8 Hz, J=8.4 Hz, 1H), 8.19~8.18 (d, 1H, J=2.0 Hz), 7.83~7.82 (d, J=2 Hz, 1H), 7.68~7.65 (d, J=6.4 Hz, 1H), 7.62~7.60 (m, 2H), 7.23~7.21 (d, 1H, J=8.4 Hz), 6.73 (s, 1H), 3.71 (s, 3H), 3.20 (s, 3H), 2.07~2.03 (m, 1H), 0.98~0.95 (m, 2H), 0.79~0.77 (m, 2H). LCMS: 394.0 (M+H$^+$).

Example 25

1,3-dimethyl-5-(5-methylsulfonyl-2-phenyl-1-benzofuran-7-yl)pyridin-2-one

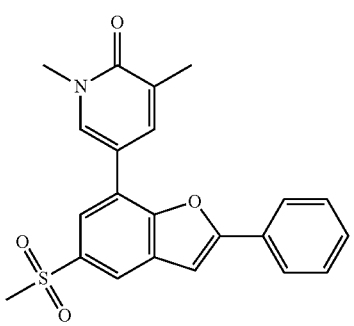 [SMILES: Cc1cc(-c2cc(S(C)(=O)=O)cc3cc(-c4ccccc4)oc23)cn(C)c1=O]

The title compound was prepared in a manner similar to Example 21 by substituting ethynylbenzene for but-1-yne in step 2. $^1$H NMR (CDCl$_3$, 400 MHz) δ 8.14 (s, 1H), 7.99 (s, 1H), 7.88-7.84 (m, 4H), 7.55-7.46 (m, 3H), 7.18 (s, 1H), 3.74 (s, 3H), 3.15 (s, 3H), 2.31 (s, 3H).

LCMS: 394.0 (M+H$^+$).

Example 26

2-methyl-4-(5-methylsulfonyl-2-phenyl-1-benzo-furan-7-yl)isoquinolin-1-one

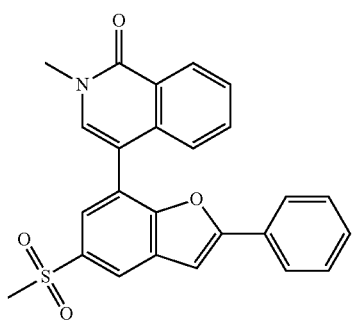 [SMILES: Cn1cc(-c2cc(S(C)(=O)=O)cc3cc(-c4ccccc4)oc23)c2ccccc2c1=O]

The title compound was prepared in a manner similar to Example 25 by substituting 2-methyl-4-(4,4,5,5-tetramethyl-1,3,2-dioxaborolan-2-yl)isoquinolin-1-one for 1,3-dimethyl-5-(4,4,5,5-tetramethyl-1,3,2-dioxaborolan-2-yl)pyridin-2-one in the Suzuki coupling step. $^1$H NMR (CDCl$_3$, 400 MHz) δ 8.60 (d, 1H, J=2.4 Hz), 8.28 (s, 1H), 7.90 (d, 1H, J=1.6 Hz), 7.68 (m, 2H), 7.60-7.58 (m, 2H), 7.43-7.36 (m, 5H), 7.21 (s, 1H), 3.73 (s, 3H), 3.18 (s, 3H). LCMS: 430.0 (M+H$^+$).

Example 27

N-[1-benzyl-6-(1,5-dimethyl-6-oxopyridin-3-yl)benzotriazol-4-yl]ethanesulfonamide

Step 1: 6-bromo-4-nitro-1H-benzotriazole

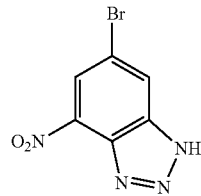 [SMILES: O=[N+]([O-])c1cc(Br)cc2[nH]nnc12]

NaNO$_2$ (937 mg, 13.6 mmol) was added to solution of 5-bromo-3-nitrobenzene-1,2-diamine (3.0 g, 12.9 mmol) in AcOH (45 mL). The mixture was stirred for 20 min at RT and for 2.5 hr at 65° C. It was then cooled to RT and treated with water (80 mL). The mixture was extracted with CH$_2$Cl$_2$ (100 mL×2). The combined organic layers were dried over Na$_2$SO$_4$, filtered and concentrated. The residue was triturated with a PE/EA (15:1, 25 mL) mixture for 10 min. It was then filtered and dried under vacuum to give the title compound (1.0 g, 32%) as a gray solid. $^1$H NMR (400 MHz, DMSO-d$_6$): δ 8.92 (s, 1H), 8.52 (s, 1H), 6.13 (s, 1H). LCMS: 243; 245 (M+H)$^+$.

Step 2: 1-benzyl-6-bromo-4-nitrobenzotriazole

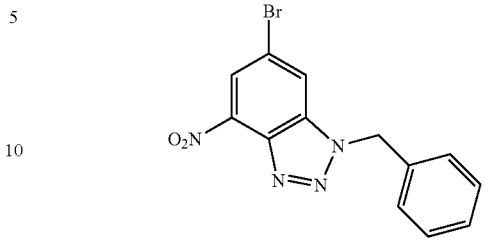

A mixture of the title compound from step 1 (500 mg, 2.07 mmol), benzyl bromide (530 mg, 3.10 mmol) and K$_2$CO$_3$ (570 g, 4.13 mmol) in DMF (8 mL) was stirred at RT overnight. The reaction was diluted with water (40 mL) and extracted with DCM (30 mL×2). The organic layers were dried over Na$_2$SO$_4$, filtered and concentrated under reduced pressure to give the title compound (110 mg, 16%) as a yellow solid. $^1$H NMR (400 MHz, CDCl$_3$) δ 8.33 (d, J=1.6 Hz, 1H), 7.84 (d, J=1.6 Hz, 1H), 7.39-7.37 (m, 3H), 7.29-7.27 (m, 2H), 5.93 (s, 2H).

LCMS: 333; 335 (M+H)$^+$.

Step 3: N-(1-benzyl-6-bromobenzotriazol-4-yl)ethanesulfonamide

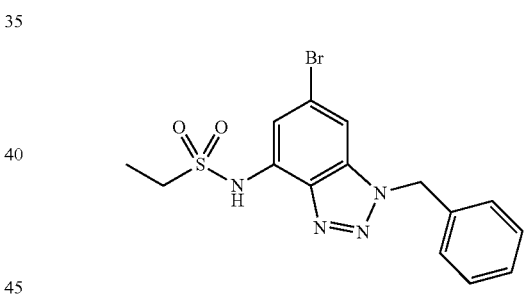

The title compound from step 2 (110 mg, 0.33 mmol) was suspended in MeOH (9 mL) and saturated NH$_4$Cl aqueous solution (3 mL) and Fe (92 mg, 1.64 mmol) were added. The resulting mixture was heated at 90° C. for 1.5 hr. It was then filtered, treated with water (30 mL) and extracted with DCM (40 mL×2). The combined organic layers were dried over Na$_2$SO$_4$, filtered and concentrated under reduced pressure. The residue was dissolved in DCM (10 mL). Et$_3$N (67 mg, 0.663 mmol) and ethanesulfonyl chloride (64 mg, 0.496 mmol) were added. The mixture was stirred at RT for 2 hr. The reaction was diluted with water (30 mL) and extracted with DCM (35 mL×2). The combined organic layers were dried over Na$_2$SO$_4$, filtered and concentrated under reduced pressure. The residue was purified with preparative TLC (DCM as elution solvent) to give the title compound (41 mg, 31% for two steps) as a white solid. $^1$H NMR (300 MHz, CDCl$_3$): δ 7.84 (s, 1H), 7.55 (d, J=1.8 Hz, 1H), 7.41-7.34 (m, 3H), 7.29-7.28 (m, 2H), 7.23 (d, J=1.8 Hz, 1H), 5.76 (s, 2H), 3.27 (q, J=7.2 Hz, 2H), 1.41 (t, J=7.2 Hz, 3H). LCMS: 395; 397 (M+H)$^+$.

Step 4: N-[1-benzyl-6-(1,5-dimethyl-6-oxopyridin-3-yl)benzotriazol-4-yl]ethanesulfonamide

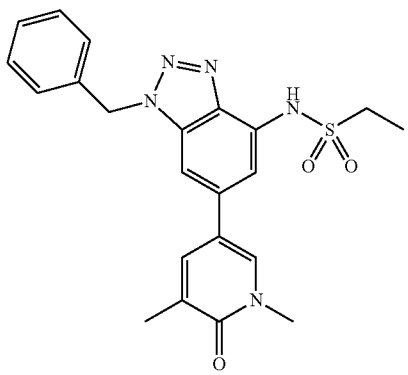 [SMILES: CCS(=O)(=O)Nc1cc(-c2cc(C)c(=O)n(C)c2)cc2c1nnn2Cc1ccccc1]

A mixture of the title compound from step 3 (41 mg, 0.104 mmol), 1,3-dimethyl-5-(4,4,5,5-tetramethyl-1,3,2-dioxaborolan-2-yl)pyridin-2-one (31 mg, 0.125 mmol), K$_2$CO$_3$ (43 mg, 0.312 mmol) and Pd(dppf)Cl$_2$ (7.6 mg, 0.010 mmol) in dioxane/H$_2$O (6 mL/2 mL) was heated to 90° C. for 2 hr. It was then cooled to RT and filtered. The filtrate was diluted with water (15 mL) and extracted with DCM (25 mL). The organic layer was dried over Na$_2$SO$_4$, filtered and concentrated under reduced pressure. The residue was purified with preparative TLC (PE/EtOAc 1:1) to give the title compound (26 mg, 57%) as a white solid. $^1$H NMR (400 MHz, CDCl$_3$) δ 7.73 (s, 1H), 7.49 (s, 1H), 7.40-7.35 (m, 5H), 7.31-7.28 (m, 2H), 7.00 (s, 1H), 5.84 (s, 2H), 3.62 (s, 3H), 3.25 (q, J=7.2 Hz, 2H), 2.22 (s, 3H), 1.43 (t, J=7.2 Hz, 3H). LCMS: 438 (M+H)$^+$.

Example 28

N-[6-(1,5-dimethyl-6-oxopyridin-3-yl)-1-[(4-fluorophenyl)methyl]benzotriazol-4-yl]ethanesulfonamide

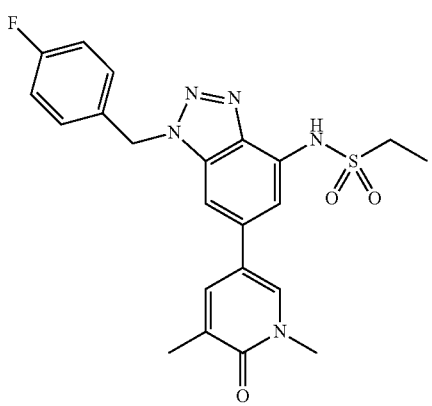 [SMILES: CCS(=O)(=O)Nc1cc(-c2cc(C)c(=O)n(C)c2)cc2c1nnn2Cc1ccc(F)cc1]

The title compound was prepared in a manner similar to Example 27 by substituting 1-(bromomethyl)-4-fluorobenzene for benzyl bromide in step 2. $^1$H NMR (300 MHz, DMSO-d$_6$) δ 10.4 (s, 1H), 8.02-8.01 (m, 1H), 7.87 (d, J=1.2 Hz, 1H), 7.75-7.74 (m, 1H), 7.48-7.43 (m, 2H), 7.39 (d, J=1.2 Hz, 1H), 7.23-7.17 (m, 2H), 5.95 (s, 2H), 3.55 (s, 3H), 3.44-3.37 (m, 2H), 2.11 (s, 3H), 1.31 (t, J=7.2 Hz, 3H). LCMS: 456 (M+H)$^+$.

Example 29

4-[6-(cyclopropylmethoxy)-1-methyl-3-methylsulfonylindazol-5-yl]-2-methylisoquinolin-1-one Step 1: methyl 5-bromo-2-fluoro-4-hydroxybenzoate

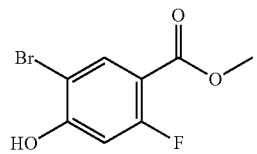

Br$_2$ (9.84 g, 61.5 mmol) in AcOH (30 mL) was added to a mixture of methyl 2-fluoro-4-hydroxybenzoate (9.50 g, 55.9 mmol) in AcOH (250 mL) at RT and then stirred at RT overnight. Concentrated, the residue was dissolved in EtOAc (150 mL), washed with H$_2$O (100 mL), brine (100 mL), dried over Na$_2$SO$_4$, filtered, concentrated and purified with column chromatography on silica gel (PE/EtOAc=50:1 to 20:1 to 10:1) to give the title compound (11.5 g, 82%) as a white solid. $^1$H NMR (300 MHz, CDCl$_3$): δ 8.11 (d, J=7.2 Hz, 1H), 6.80 (d, J=11.7 Hz, 1H), 6.13 (s, 1H), 3.90 (s, 3H). LCMS: 249, 251 (M+H$^+$).

Step 2: methyl 5-bromo-4-(cyclopropylmethoxy)-2-fluorobenzoate

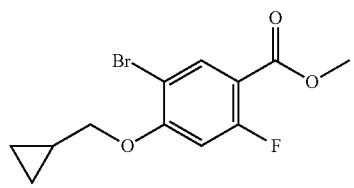 [SMILES: COC(=O)c1cc(Br)c(OCC2CC2)cc1F]

A mixture of the title compound of step 1 (10.0 g, 40.1 mmol), bromomethyl-cyclopropane (10.8 g, 80.0 mmol) and K$_2$CO$_3$ (16.6 g, 120 mmol) in DMF (150 mL) was warmed at 50° C. overnight. Cooled to RT, filtered, and the filtrate subjected to aqueous extractive work up with DCM (200 mL×2), the organic layer was dried over Na$_2$SO$_4$, filtered and concentrated to give the title compound (11.0 g, 90%) as a white solid. $^1$H NMR (300 MHz, CDCl$_3$): δ 8.13 (d, J=7.8 Hz, 1H), 6.60 (d, J=12.3 Hz, 1H), 3.91 (d, J=6.9 Hz, 2H), 3.89 (s, 3H), 1.34-1.29 (m, 1H), 0.071-0.65 (m, 2H), 0.41-0.37 (m, 2H). LCMS: 303, 305 (M+H$^+$).

Step 3: 5-bromo-6-(cyclopropylmethoxy)-1-methyl-2H-indazol-3-one

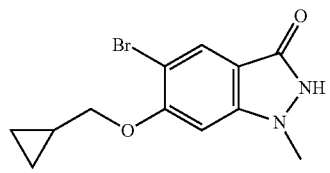 [SMILES: Cn1[nH]c(=O)c2cc(Br)c(OCC3CC3)cc21]

A mixture of the title compound of step 2 (10.5 g, 34.5 mmol) and methylhydrazine (12.0 g, 104 mmol, 40% in H₂O) in n-BuOH (100 mL) was heated to 160° C. for 10 hr. After cooling to RT, hexane (130 mL) was added. The resulting precipitate was collected, dissolved in EtOAc (100 mL), and washed with H₂O (150 mL×2). The organic layer was dried over Na₂SO₄, filtered, and concentrated to give the title compound (5.5 g, 53%) as a white solid. ¹H NMR (300 MHz, DMSO-d₆): δ 7.75 (s, 1H), 7.00 (s, 1H), 3.94 (d, J=7.2 Hz, 2H), 3.66 (s, 3H), 1.30-1.21 (m, 1H), 0.62-0.56 (m, 2H), 0.39-0.34 (m, 2H). LCMS: 297, 299 (M+H⁺).

Step 4: 5-bromo-6-(cyclopropylmethoxy)-1-methyl-3-methylsulfanylindazole

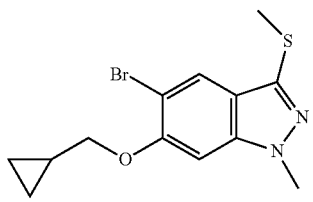 [SMILES: CSc1nn(C)c2cc(OCC3CC3)c(Br)cc12]

A mixture of the title compound of step 3 (500 mg, 1.68 mmol) and Lawesson's reagent (675 mg, 1.68 mmol) in toluene (10 mL) was heated to 130° C. for 1.5 hr. After cooling to RT and concentrating, the residue was dissolved in ACN (25 mL) and Cs₂CO₃ (3.30 g, 10.1 mmol) and iodomethane (1.43 g, 10.0 mmol) were added. The mixture was stirred at 30° C. for 18 hr, filtered and the filtrate was purified by prep-TLC (PE/EtOAc=5:1) to give the title compound (170 mg, 31%) as a white solid. ¹H NMR (300 MHz, CDCl₃): δ 7.85 (s, 1H), 6.64 (s, 1H), 3.95-3.93 (m, 5H), 2.57 (s, 3H), 1.39-1.35 (m, 1H), 0.72-0.66 (m, 2H), 0.47-0.42 (m, 2H).

Step 5: 5-bromo-6-(cyclopropylmethoxy)-1-methyl-3-methylsulfonylindazole

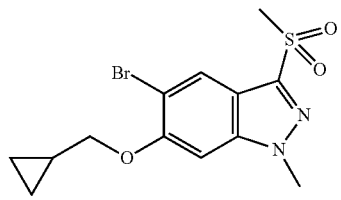 [SMILES: Cn1nc(S(C)(=O)=O)c2cc(Br)c(OCC3CC3)cc21]

A mixture of the title compound of step 4 (120 mg, 0.367 mmol) and oxone (380 mg, 0.618 mmol) in DMF (5 mL) was heated at 50° C. for 7 hr. After cooling to RT and quenching with saturated aqueous NaHSO₃ (25 mL), the mixture was neutralized with saturated aqueous NaHCO₃ (20 mL) and extracted with DCM (30 mL×2). The combined organics were dried over Na₂SO₄, filtered, and concentrated to give the title compound (120 mg, 91%) as a white solid. ¹H NMR (300 MHz, CDCl₃): δ 8.31 (s, 1H), 6.72 (s, 1H), 4.09 (s, 3H), 3.97 (d, J=6.6 Hz, 2H), 3.24 (s, 3H), 1.42-1.35 (m, 1H), 0.75-0.68 (m, 2H), 0.50-0.44 (m, 2H).). LCMS: 359, 361 (M+H⁺).

Step 6: 4-[6-(cyclopropylmethoxy)-1-methyl-3-methylsulfonylindazol-5-yl]-2-methylisoquinolin-1-one

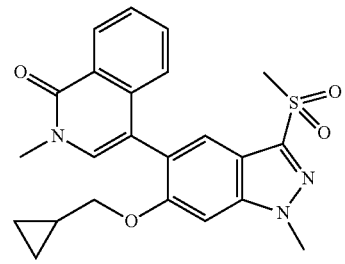 [SMILES: Cn1cc(-c2cc3c(S(C)(=O)=O)nn(C)c3cc2OCC2CC2)c2ccccc2c1=O]

A mixture of the title compound of step 5 (120 mg, 0.334 mmol), 2-methyl-4-(4,4,5,5-tetramethyl-1,3,2-dioxaborolan-2-yl)isoquinolin-1-one (115 mg, 0.404 mmol), K₂CO₃ (138 mg, 1.0 mmol) and Pd(dppf)Cl₂ (25 mg, 0.034 mmol) in dioxane (10 mL) and H₂O (3 mL) was heated to 85° C. for 1 hr and then cooled to RT. After DCM (30 mL) aqueous extractive work up, the organic layer was dried over Na₂SO₄, filtered, and concentrated. Purification by prep-TLC (PE/EtOAc=1:1) gave the title compound (21 mg, 14%) as a white solid. ¹H NMR (400 MHz, DMSO-d₆): δ 8.29 (d, J=8.0 Hz, 1H), 7.81 (s, 1H), 7.63-7.59 (m, 1H), 7.53-7.49 (m, 2H), 7.44 (s, 1H), 7.10 (d, J=8.0 Hz, 1H), 4.19 (s, 3H), 4.04-3.99 (m, 1H), 3.90-3.86 (m, 1H), 3.58 (s, 3H), 3.33 (s, 3H), 0.98-0.94 (m, 1H), 0.35-0.33 (m, 1H), 0.27-0.24 (m, 1H), 0.07-0.03 (m, 2H).

LCMS: 438 (M+H⁺).

Example 30

4-[6-(cyclopropylmethoxy)-3-ethylsulfonyl-1-methylindazol-5-yl]-2-methylisoquinolin-1-one Step 1: 5-bromo-6-(cyclopropylmethoxy)-3-ethylsulfanyl-1-methylindazole

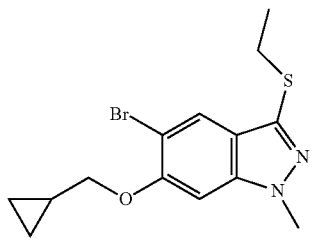 [SMILES: CCSc1nn(C)c2cc(OCC3CC3)c(Br)cc12]

A mixture of the title compound of Example 29, step 3 (500 mg, 1.68 mmol) and Lawesson's reagent (675 mg, 1.68 mmol) in toluene (10 mL) was heated at 130° C. for 1.5 hr. After cooling to RT and concentrating, the residue was dissolved in ACN (25 mL). Cs₂CO₃ (3.30 g, 10.1 mmol) and iodoethane (1.58 g, 10.1 mmol) were added. The mixture was stirred at 30° C. for 18 hr and filtered. The filtrate was concentrated and purified by prep-TLC (PE/EtOAc=5:1) to give the title compound (155 mg, 27%) as a white solid. ¹H NMR (300 MHz, CDCl₃): δ 7.88 (s, 1H), 6.66 (s, 1H), 3.97-3.94 (m, 5H), 3.00 (q, J=14.7, 7.2 Hz, 2H), 1.39-1.25 (m, 4H), 0.72-0.66 (m, 2H), 0.48-0.42 (m, 2H). LCMS: 341, 343 (M+H⁺).

Step 2: 5-bromo-6-(cyclopropylmethoxy)-3-ethyl-sulfonyl-1-methylindazole

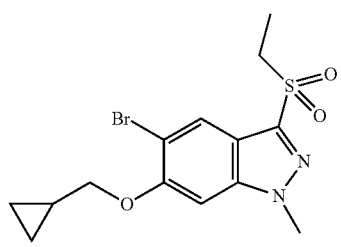 [SMILES: CCS(=O)(=O)c1nn(C)c2cc(OCC3CC3)c(Br)cc12]

A mixture of the title compound of step 1(100 mg, 0.294 mmol) and oxone (361 mg, 0.588 mmol) in DMF (5 mL) was heated at 50° C. for 7 hr. After cooling to RT and quenching with saturated aqueous NaHSO₃ (25 mL), the mixture was neutralized with saturated aqueous NaHCO₃ (20 mL) and extracted with DCM (30 mL×2). The combined organics were dried over Na₂SO₄, filtered, and concentrated to give the title compound (100 mg, 92%) as a white solid.

LCMS: 373, 375 (M+H⁺).

Step 3: 4-[6-(cyclopropylmethoxy)-3-ethylsulfonyl-1-methylindazol-5-yl]-2-methylisoquinolin-1-one

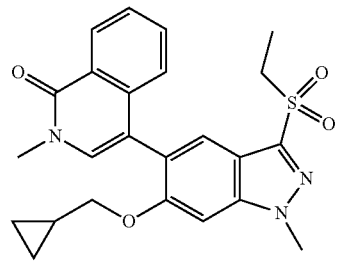 [SMILES: CCS(=O)(=O)c1nn(C)c2cc(OCC3CC3)c(-c3cn(C)c(=O)c4ccccc34)cc12]

A mixture of the title compound of step 2 (100 mg, 0.269 mmol), 2-methyl-4-(4,4,5,5-tetramethyl-1,3,2-dioxaborolan-2-yl)isoquinolin-1-one (92 mg, 0.323 mmol), K₂CO₃ (111 mg, 0.804 mmol) and Pd(dppf)Cl₂ (20 mg, 0.027 mmol) in dioxane (10 mL) and H₂O (3 mL) was heated at 85° C. for 1.5 hr and then cooled to RT. After DCM (30 mL) extractive work up, the organic layer was dried over Na₂SO₄, filtered, and concentrated. Purification by prep-TLC (PE/EtOAc 1:1) gave the title compound (35 mg, 29%) as a white solid. ¹H NMR (400 MHz, DMSO-d₆): δ 8.25 (d, J=7.6 Hz, 1H), 7.75 (s, 1H), 7.58-7.54 (m, 1H), 7.48-7.45 (m, 2H), 7.40 (s, 1H), 7.06 (d, J=8.0 Hz, 1H), 4.15 (s, 3H), 3.99-3.95 (m, 1H), 3.86-3.81 (m, 1H), 3.53 (s, 3H), 3.35 (q, J=7.2 Hz, 2H), 1.13 (t, J=7.2 Hz, 3H), 0.95-0.89 (m, 1H), 0.31-0.28 (m, 1H), 0.22-0.20 (m, 1H), 0.03-0.00 (m, 2H). LCMS: 452 (M+H⁺).

Example 31

N-[1-benzyl-6-(1,5-dimethyl-6-oxopyridin-3-yl)benzimidazol-4-yl]methanesulfonamide Step 1: 5-bromo-3-nitrobenzene-1,2-diamine

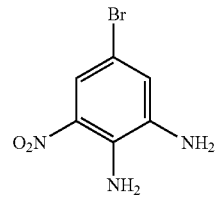 [SMILES: Nc1cc(Br)cc([N+](=O)[O-])c1N]

A mixture of 4-bromo-2,6-dinitroaniline (5.5 g, 21.2 mmol) and (NH₄)₂S (10.5 mL, 21.2 mmol) in ethanol (150 mL) was heated at 90° C. for 1 hr. TLC showed incomplete consumption of starting material. Additional (NH₄)₂S (10.5 mL, 21.2 mmol) was added, and the reaction was stirred at 90° C. for 1 hr more. The mixture was concentrated and purified on silica gel (PE/DCM=1:1) to give the title compound (2.5 g, 51%) as a red solid. LCMS: 230, 232 (M−H⁻).

Step 2: 6-bromo-4-nitro-1H-benzimidazole

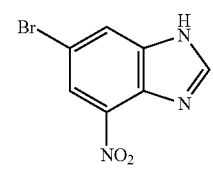

To a suspension of the title compound of step 1(500 mg, 2.2 mmol) in 4 M HCl (5 mL, 17 mmol) was added formic acid (230 mg, 4.4 mmol). The mixture was heated at 120° C. for 1.5 hr, and then cooled to RT. Water was added and neutralization with concentrated NH₄OH gave a precipitate which was collected, washed with water, and dried to give the title compound (510 mg, 97%) as a yellow solid. ¹H NMR (400 MHz, DMSO-d₆): δ 11.0 (s, 1H), 8.53 (d, J=1.6 Hz, 1H), 8.39 (d, J=1.6 Hz, 1H). LCMS: 240, 242 (M−H⁻).

Step 3: 1-benzyl-6-bromo-4-nitrobenzimidazole

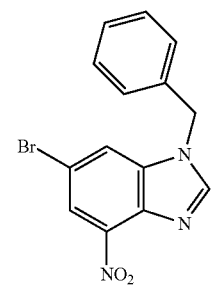 [SMILES: O=[N+]([O-])c1cc(Br)cc2c1ncn2Cc1ccccc1]

A mixture of the title compound of step 2 (400 mg, 1.57 mmol), K₂CO₃ (325 mg, 2.36 mmol) and bromomethylbenzene (322 mg, 1.88 mmol) in DMF (5 mL) was stirred at RT overnight. The mixture was partitioned between water (20 mL) and EtOAc (20 mL), extracted with EtOAc (50 mL×2) which was then washed with brine, dried over Na$_2$SO$_4$, concentrated, and purified by column chromatography on silica gel (DCM) to give the title compound (480 mg, 89%) as a yellow solid. $^1$H NMR (400 MHz, DMSO-d$_6$): δ 9.62 (br s, 1H), 8.31 (d, J=1.6 Hz, 1H), 8.11 (d, J=1.6 Hz, 1H), 7.40-7.28 (m, 3H), 7.14 (d, J=7.2 Hz, 2H), 5.62 (s, 2H).

Step 4: 1-benzyl-6-bromobenzimidazol-4-amine

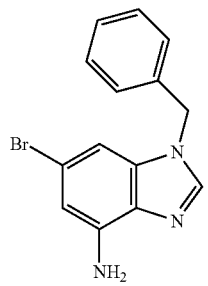

A mixture of the title compound of step 3 (320 mg, 0.97 mmol), vanadyl acetylacetonate (11 mg, 3%) and Pt/C (33 mg, 10%) in THF (10 mL) under H$_2$ was stirred at RT overnight. The insoluble components were removed by filtration, washing with THF, and the combined filtrate/washes were concentrated and purified by column chromatography on silica gel (DCM) to give the title compound (260 mg, 90%) as a yellow solid. $^1$H NMR (400 MHz, DMSO-d$_6$): δ 8.15 (s, 1H), 7.35-7.23 (m, 5H), 6.81 (d, J=2.0 Hz, 1H), 6.46 (d, J=2.4 Hz, 1H), 5.61 (br s, 2H), 5.36 (s, 2H).). LCMS: 302, 304 (M+H$^+$).

Step 5: N-(1-benzyl-6-bromobenzimidazol-4-yl)methanesulfonamide

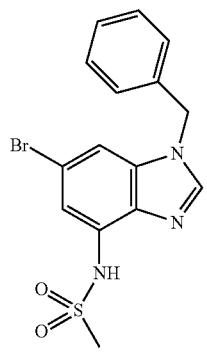 [SMILES: CS(=O)(=O)Nc1cc(Br)cc2c1ncn2Cc1ccccc1]

The title compound of step 4 (325 mg, 1.08 mmol) was dissolved in DCM (10 mL) at 0° C. and TEA (1.1 g, 10.7 mmol) was added followed by MsCl (616 mg, 5.4 mmol). The mixture was warmed to RT and stirred for 3 hr. The mixture was poured into ice-water and extracted with DCM (50 mL), dried over Na$_2$SO$_4$, filtered, and concentrated. The residue (di-sulfonylated product) (500 mg) was suspended in THF (10 mL) and 3M NaOH (2 mL) was added. The mixture was heated at 45° C. for 0.5 hr. After cooling to RT, addition of water, and EtOAc extractive work up (50 mL*2), the combined organic layers were dried over Na$_2$SO$_4$, filtered and concentrated to give the title compound (350 mg, 86%) as a yellow solid. LCMS: 380, 382 (M+H$^+$).

Step 6: N-[1-benzyl-6-(1,5-dimethyl-6-oxopyridin-3-yl)benzimidazol-4-yl]methanesulfonamide

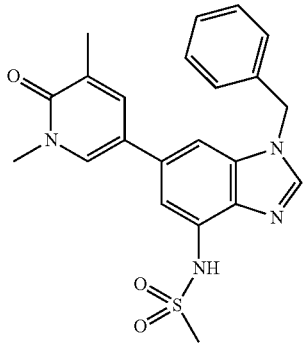 [SMILES: Cc1cc(-c2cc(NS(C)(=O)=O)c3ncn(Cc4ccccc4)c3c2)cn(C)c1=O]

A mixture of the title compound of step 5 (100 mg, 0.26 mmol), 1,3-dimethyl-5-(4,4,5,5-tetramethyl-1,3,2-dioxaborolan-2-yl)pyridin-2-one (79 mg, 0.32 mmol), K$_2$CO$_3$ (108 mg, 0.78 mmol) and Pd(dppf)Cl$_2$ (19 mg, 0.026 mmol) in dioxane/H$_2$O (9 mL/3 mL) under N$_2$ was heated at 85° C. for 2 hr. Cooled to RT and filtered, the filtrate was partitioned between water and EtOAc (50 mL), and the organic layer was dried over Na$_2$SO$_4$, filtered, and concentrated. The residue was purified by column chromatography on silica gel (PE/EtOAc=5:1 to 2:1) to give the title compound (19 mg, 17%) as a yellow solid. $^1$H NMR (400 MHz, DMSO-d$_6$): δ 9.66 (s, 1H), 8.44 (s, 1H), 7.89 (s, 1H), 7.69 (s, 1H), 7.62 (s, 1H), 7.41-7.39 (m, 1H), 7.26-7.13 (m, 5H), 5.56 (s, 2H), 3.53 (s, 3H), 3.23 (s, 3H), 2.10 (s, 3H). LCMS: 423 (M+H$^+$).

Example 32

N-[6-(1,5-dimethyl-6-oxopyridin-3-yl)-1-[(3-fluorophenyl)methyl]benzimidazol-4-yl]methanesulfonamide Step 1: 6-bromo-1-[(3-fluorophenyl)methyl]-4-nitrobenzimidazole

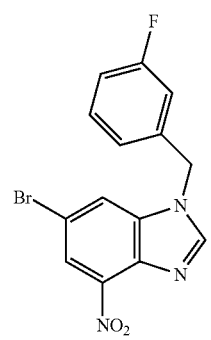 [SMILES: O=[N+]([O-])c1cc(Br)cc2c1ncn2Cc1cccc(F)c1]

A mixture of the title compound of Example 31, step 2 (1.1 g, 4.56 mmol), K$_2$CO$_3$ (944 mg, 6.84 mmol) and 3-(bromomethyl)-1-fluorobenzene (1.04 g, 5.48 mmol) in DMF (15 mL) was stirred at RT overnight. The mixture was diluted with water (50 mL) and EtOAc (30 mL), and extracted with EtOAc (50 mL*2). The combined organic layers were washed with brine, dried over Na$_2$SO$_4$, concentrated, and purified by column chromatography on silica gel (DCM) to give the title compound (1.1 g, 69%) as a red solid. LCMS: 350, 352 (M+H$^+$).

Step 2: 6-bromo-1-[(3-fluorophenyl)methyl]benzimidazol-4-amine

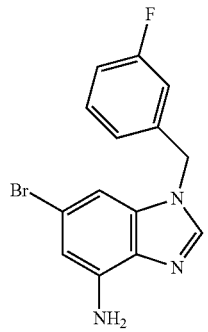

The title compound of step 1 (1.1 g, 3.14 mmol) was suspended in MeOH (18 mL) and saturated aqueous NH$_4$Cl (6 mL) and Fe (880 mg, 15.7 mmol) were added. The mixture was heated to 85° C. for 1 hr, filtered, and the filtrate partitioned between water and DCM (40 mL×2). The combined organic layers were dried over Na$_2$SO$_4$, filtered, and concentrated to give the title compound (850 mg, 85%) as a yellow solid. LCMS: 320, 322 (M+H$^+$).

Step 3: N-[6-bromo-1-[(3-fluorophenyl)methyl]benzimidazol-4-yl]methanesulfonamide

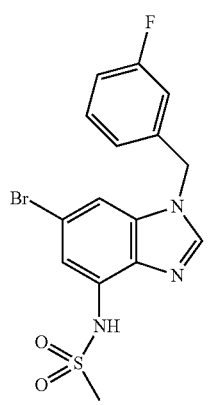 [SMILES: CS(=O)(=O)Nc1cc(Br)cc2c1ncn2Cc1cccc(F)c1]

The title compound of step 2 (400 mg, 1.25 mmol) was dissolved in DCM (10 mL) at 0° C., TEA (1.26 g, 12.5 mmol) followed by methanesulfonyl chloride (713 mg, 6.25 mmol) were added. The mixture was warmed to RT and stirred for 3 hr. The mixture was poured into ice water and extracted with DCM (50 mL), dried over Na$_2$SO$_4$, filtered, and concentrated. The residue (di-sulfonylated product) (700 mg) was suspended in THF (10 mL) and 3M NaOH (2 mL) was added. The mixture was heated at 45° C. for 0.5 hr. After cooling to RT, addition of water, and EtOAc extractive work up (50 mL×2), the combined organic layers were dried over Na$_2$SO$_4$, filtered and concentrated to give the title compound (300 mg, 60%) as a yellow solid. $^1$H NMR (400 MHz, DMSO-d$_6$): δ 9.90 (s, 1H), 8.48 (s, 1H), 7.65 (d, J=1.6 Hz, 1H), 7.43-7.37 (m, 1H), 7.24 (d, J=1.6 Hz, 1H), 7.23-7.20 (m, 1H), 7.16-7.11 (m, 2H), 5.52 (s, 2H), 3.24 (s, 3H). LCMS: 398, 400 (M+H$^+$).

Step 4: N-[6-(1,5-dimethyl-6-oxopyridin-3-yl)-1-[(3-fluorophenyl)methyl]benzimidazol-4-yl]methanesulfonamide

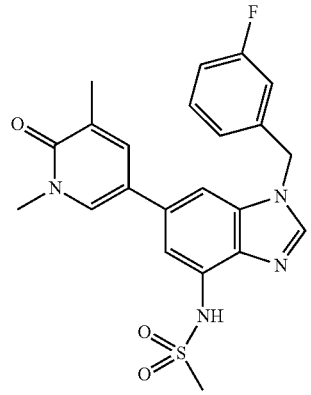 [SMILES: Cc1cc(-c2cc(NS(C)(=O)=O)c3ncn(Cc4cccc(F)c4)c3c2)cn(C)c1=O]

A mixture of the title compound of step 3 (100 mg, 0.25 mmol), 1,3-dimethyl-5-(4,4,5,5-tetramethyl-1,3,2-dioxaborolan-2-yl)pyridin-2-one (75 mg, 0.30 mmol), K$_2$CO$_3$ (104 mg, 0.75 mmol) and Pd(dppf)Cl$_2$ (19.0 mg, 0.025 mmol) in dioxane/H$_2$O (9 mL/3 mL) was heated at 85° C. for 2 hr. After filtering, the filtrate was partitioned between EtOAc (25 mL) and water. The organic layer was dried over Na$_2$SO$_4$, filtered and concentrated. Purification by prep-TLC (EtOAc) gave the title compound (19 mg, 17%) as a yellow solid. $^1$H NMR (400 MHz, DMSO-d$_6$): δ 9.65 (s, 1H), 8.43 (s, 1H), 7.88 (s, 1H), 7.68 (s, 1H), 7.62 (s, 1H), 7.42-7.37 (m, 1H), 7.25-7.10 (m, 4H), 5.55 (s, 2H), 3.53 (s, 3H), 3.23 (s, 3H), 2.10 (s, 3H). LCMS: 441 (M+H$^+$).

Example 33

N-[6-(1,5-dimethyl-6-oxopyridin-3-yl)-1-[(3-fluorophenyl)methyl]benzimidazol-4-yl]ethanesulfonamide Step 1: N-[6-bromo-1-[(3-fluorophenyl)methyl]benzimidazol-4-yl]ethanesulfonamide

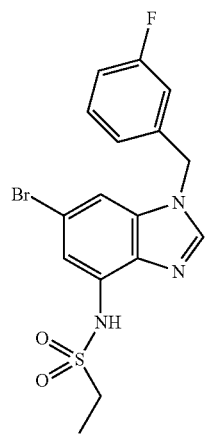 [SMILES: CCS(=O)(=O)Nc1cc(Br)cc2c1ncn2Cc1cccc(F)c1]

The title compound of Example 32, step 2 (450 mg, 1.41 mmol) was dissolved in DCM (10 mL) at 0° C. and triethylamine (1.42 g, 14.1 mmol) followed by ethanesulfonyl chloride (906 mg, 7.05 mmol) were added. The mixture was stirred at RT for 3 hr, poured into ice water, extracted with DCM (50 mL×3), dried over Na$_2$SO$_4$, filtered and concentrated. The residue (di-sulfonylated product) was suspended in THF (10 mL) and 3M NaOH solution (2.5 mL) was added. The mixture was heated at 45° C. for 0.5 hr. After cooling to RT, addition of water and EtOAc extractive work up (50 mL×2), the combined organic layers were dried over Na$_2$SO$_4$, filtered and concentrated to give the title compound (410 mg, 71%) as a yellow solid. LCMS: 412, 414 (M+H$^+$).

Step 2: N-[6-(1,5-dimethyl-6-oxopyridin-3-yl)-1-[(3-fluorophenyl)methyl]benzimidazol-4-yl]ethanesulfonamide

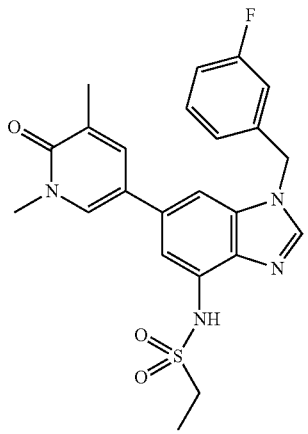 [SMILES: CCS(=O)(=O)Nc1cc(-c2cc(C)c(=O)n(C)c2)cc2c1ncn2Cc1cccc(F)c1]

A mixture of the title compound of step 1 (150 mg, 0.36 mmol), 1,3-dimethyl-5-(4,4,5,5-tetramethyl-1,3,2-dioxaborolan-2-yl)pyridin-2-one (108 mg, 0.44 mmol), K$_2$CO$_3$ (149 mg, 1.08 mmol) and Pd(dppf)Cl$_2$ (26.0 mg, 0.036 mmol) in dioxane/H$_2$O (12 mL/4 mL) was heated at 85° C. for 2 hr. After filtering, the filtrate was partitioned between EtOAc and water. After EtOAc extractive work up (25 mL*3), the organic layer was dried over Na$_2$SO$_4$, filtered, concentrated, and purified by prep-TLC (EtOAc) to give the title compound (28 mg, 17%) as a yellow solid. $^1$H NMR (400 MHz, DMSO-d$_6$): 6.9.64 (s, 1H), 8.43 (s, 1H), 7.88 (s, 1H), 7.67 (s, 1H), 7.62 (s, 1H), 7.41-7.38 (m, 1H), 7.28 (s, 1H), 7.24-7.11 (m, 3H), 5.55 (s, 2H), 3.53 (s, 3H), 3.35-3.29 (m, 2H), 2.10 (s, 3H), 1.30 (t, J=7.6 Hz, 3H). LCMS: 455 (M+H$^+$).

Example 34

N-[1-benzyl-6-(1,5-dimethyl-6-oxopyridin-3-yl)-2-methylbenzimidazol-4-yl]methanesulfonamide Step 1: 6-bromo-2-methyl-4-nitro-1H-benzimidazole

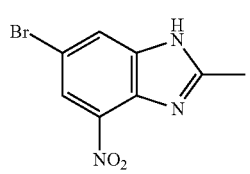

To a suspension of the title compound of Example 31, step 1 (500 mg, 2.2 mmol) in 5 M HCl (1.1 mL, 5.5 mmol) was added pentane-2,4-dione (230 mg, 4.4 mmol). The reaction mixture was heated at 120° C. for 1.5 hr. After cooling, water was added, and the mixture was neutralized with concentrated NH$_4$OH. The precipitate was collected, washed with water, and dried to give the title compound (540 mg, 97%) as a yellow solid. LCMS: 255, 257 (M+H$^+$).

Step 2: N-[1-benzyl-6-(1,5-dimethyl-6-oxopyridin-3-yl)-2-methylbenzimidazol-4-yl]methanesulfonamide

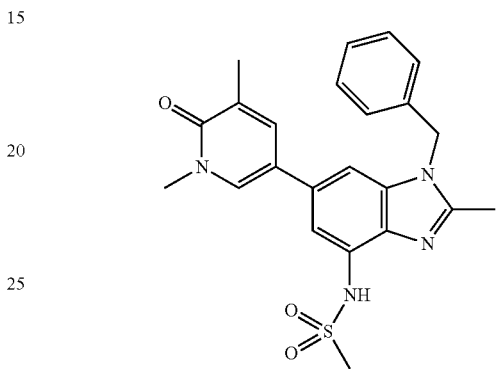

The title compound of step 1 was substituted for the title compound of Example 31, step 2 in Example 31, step 3. A four step synthesis was carried out in a similar manner as Example 31, steps 3-6 to give the title compound (25 mg, 10% for 4 steps) as a white solid. $^1$H NMR (400 MHz, DMSO-d$_6$): δ 9.59 (s, 1H), 7.88 (d, J=2.0 Hz, 1H), 7.69 (s, 1H), 7.57 (d, J=0.8 Hz, 1H), 7.36-7.26 (m, 3H), 7.23 (d, J=1.2 Hz, 1H), 7.14 (d, J=7.2 Hz, 2H), 5.53 (s, 2H), 3.52 (s, 3H), 3.21 (s, 3H), 2.5 (s, 3H), 2.08 (s, 3H). LCMS: 437 (M+H$^+$).

Example 35

N-[6-(1,5-dimethyl-6-oxopyridin-3-yl)-1-[(3-fluorophenyl)methyl]-2-methylbenzimidazol-4-yl]methanesulfonamide Step 1: 6-bromo-1-[(3-fluorophenyl)methyl]-2-methyl-4-nitrobenzimidazole

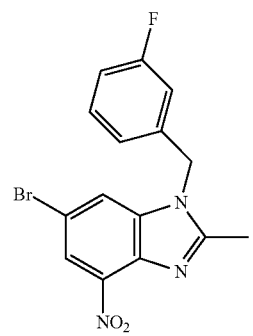 [SMILES: Cc1nc2c([N+](=O)[O-])cc(Br)cc2n1Cc1cccc(F)c1]

A mixture of the title compound of Example 34, step 1 (700 mg, 2.75 mmol), K$_2$CO$_3$ (570 mg, 4.13 mmol) and 3-(bromomethyl)-1-fluorobenzene (627 mg, 3.3 mmol) in DMF (10 mL) was stirred at RT overnight. The reaction mixture was diluted with water (50 mL) and EtOAc (30 mL) and extracted with EtOAc (50 mL×2). The combined organic layers were washed with brine, dried over Na$_2$SO$_4$, concentrated and purified by column chromatography on silica gel (DCM) to give the title compound (350 mg, 35%) as a red solid. LCMS: 364, 366 (M+H$^+$).

Step 2: N-[6-(1,5-dimethyl-6-oxopyridin-3-yl)-1-[(3-fluorophenyl)methyl]-2-methylbenzimidazol-4-yl]methanesulfonamide

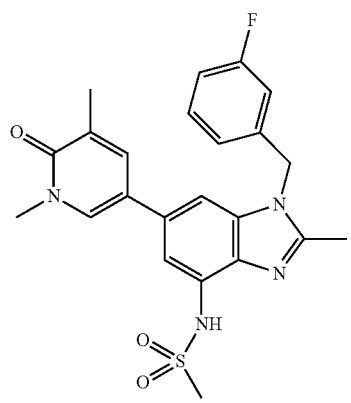 [SMILES: Cc1cc(-c2cc(NS(C)(=O)=O)c3nc(C)n(Cc4cccc(F)c4)c3c2)cn(C)c1=O]

The title compound of step 1 was substituted for the title compound of Example 32, step 1 in Example 32, step 2. A three step synthesis was carried out in a similar manner as Example 32, steps 2-4 to give the title compound (19 mg, 10% for 3 steps) as a yellow solid. $^1$H NMR (400 MHz, DMSO-d$_6$): δ. 9.59 (s, 1H), 7.88 (d, J=2.0 Hz, 1H), 7.69 (s, 1H), 7.57 (s, 1H), 7.41-7.36 (m, 1H), 7.24 (s, 1H), 7.15-7.10 (m, 1H), 7.00 (d, J=10.0 Hz, 1H), 5.55 (s, 2H), 3.52 (s, 3H), 3.22 (s, 3H), 2.50 (s, 3H), 2.08 (s, 3H). LCMS: 455 (M+H$^+$).

Example 36

N-[6-(1,5-dimethyl-6-oxopyridin-3-yl)-1-[(3-fluorophenyl)methyl]-2-methylbenzimidazol-4-yl]ethanesulfonamide

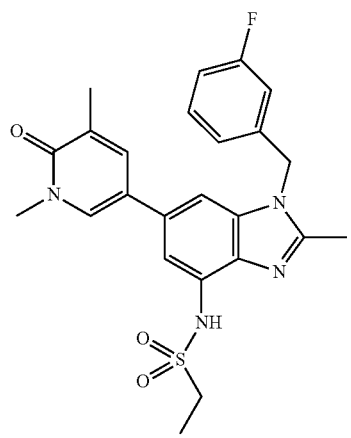 [SMILES: CCS(=O)(=O)Nc1cc(-c2cc(C)c(=O)n(C)c2)cc2c1nc(C)n2Cc1cccc(F)c1]

The title compound (26 mg) was prepared in a similar manner to Example 35 except that ethanesulfonyl chloride was substituted for methanesulfonyl chloride. $^1$H NMR (400 MHz, DMSO-d$_6$): 6.9.57 (s, 1H), 7.87 (d, J=2.4 Hz, 1H), 7.68 (s, 1H), 7.56 (d, J=1.2 Hz, 1H), 7.41-7.36 (m, 1H), 7.25 (d, J=0.8 Hz, 1H), 7.15-7.10 (m, 1H), 6.98 (d, J=5.6 Hz, 1H), 6.91 (d, J=7.6 Hz, 1H), 5.54 (s, 2H), 3.52 (s, 3H), 3.31-3.27 (m, 2H), 2.50 (s, 3H), 2.00 (s, 3H), 1.30 (t, J=7.2 Hz, 3H). LCMS: 469 (M+H$^+$).

Example 37

N-[6-(1,5-dimethyl-6-oxopyridin-3-yl)-1-[(4-fluorophenyl)methyl]-2-methylbenzimidazol-4-yl]methanesulfonamide Step 1: 6-bromo-1-[(4-fluorophenyl)methyl]-2-methyl-4-nitrobenzimidazole

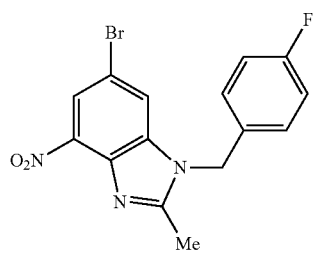 [SMILES: Cc1nc2c([N+](=O)[O-])cc(Br)cc2n1Cc1ccc(F)cc1]

The title compound was prepared in a manner similar to Example 31, step 3, by substituting 6-bromo-2-methyl-4-nitro-1H-benzimidazole for 6-bromo-4-nitro-1H-benzimidazole and 1-(bromomethyl)-4-fluorobenzene for bromomethylbenzene. LCMS: 364; 366 (M+H$^+$).

Step 2: N-[6-(1,5-dimethyl-6-oxopyridin-3-yl)-1-[(4-fluorophenyl)methyl]-2-methylbenzimidazol-4-yl]methanesulfonamide

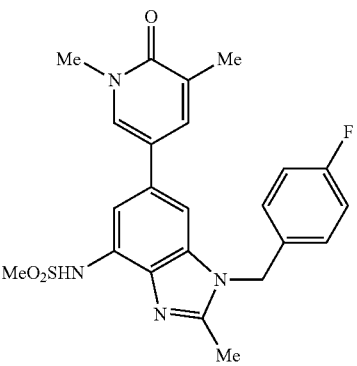

The title compound was prepared in a manner similar to Example 32, steps 2 through 4, by substituting 6-bromo-1-[(4-fluorophenyl)methyl]-2-methyl-4-nitrobenzimidazole for 6-bromo-1-[(3-fluorophenyl)methyl]-4-nitrobenzimidazole in step 2. $^1$H NMR (300 MHz, DMSO-d$_6$) δ 9.59 (s, 1H), 7.89 (d, J=2.4 Hz, 1H), 7.70-7.69 (m, 1H), 7.59 (d, J=1.5 Hz, 1H), 7.23-7.14 (m, 5H), 5.51 (s, 2H), 3.53 (s, 3H), 3.22 (s, 3H), 2.50 (s, 3H), 2.09 (s, 3H). LCMS: 455 (M+H$^+$).

Example 38

N-[1-[(4-fluorophenyl)methyl]-6-(5-methoxy-1-methyl-6-oxopyridin-3-yl)-2-methylbenzimidazol-4-yl]methanesulfonamide

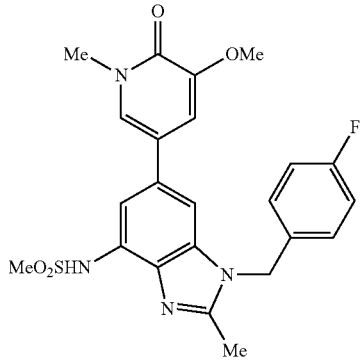

The title compound was prepared in a manner similar to Example 37 by substituting 3-methoxy-1-methyl-5-(4,4,5,5-tetramethyl-1,3,2-dioxaborolan-2-yl)pyridin-2-one for 1,3-dimethyl-5-(4,4,5,5-tetramethyl-1,3,2-dioxaborolan-2-yl)pyridin-2-one in the Suzuki coupling step. $^1$H NMR (400 MHz, CDCl3): δ 7.48 (s, 1H), 7.10-7.03 (m, 5H), 6.99 (s, 1H), 6.81 (s, 1H), 5.34 (s, 2H), 3.87 (s, 3H), 3.63 (s, 3H), 3.08 (s, 3H), 2.59 (s, 3H). LCMS: 471 (M+H$^+$).

Example 39

N-[1-(cyclopropylmethyl)-6-(1,5-dimethyl-6-oxopyridin-3-yl)-2-methylbenzimidazol-4-yl]methanesulfonamide Step 1: 6-bromo-1-(cyclopropylmethyl)-2-methyl-4-nitrobenzimidazole

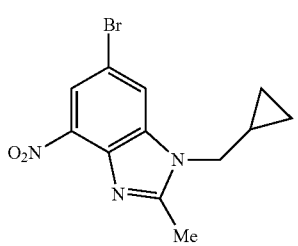 [SMILES: Cc1nc2c([N+](=O)[O-])cc(Br)cc2n1CC1CC1]

The title compound was prepared in a manner similar to Example 31, step 3, by substituting 6-bromo-2-methyl-4-nitro-1H-benzimidazole for 6-bromo-4-nitro-1H-benzimidazole and bromomethylcyclopropane for bromomethylbenzene. $^1$H NMR (300 MHz, CDCl$_3$): δ 8.21 (s, 1H), 7.75 (s, 1H), 4.05 (d, J=6.9 Hz, 2H), 2.73 (s, 3H), 1.25-1.19 (m, 1H), 0.71-0.65 (m, 2H), 0.43-0.37 (m, 2H).

Step 2: N-[1-(cyclopropylmethyl)-6-(1,5-dimethyl-6-oxopyridin-3-yl)-2-methylbenzimidazol-4-yl]methanesulfonamide

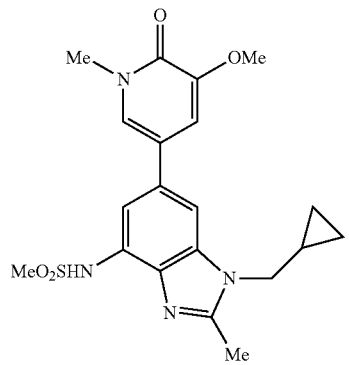

The title compound was prepared in a manner similar to Example 32, steps 2 through 4, by substituting 6-bromo-1-(cyclopropylmethyl)-2-methyl-4-nitrobenzimidazole for 6-bromo-1-[(3-fluorophenyl)methyl]-4-nitrobenzimidazole in step 2. $^1$H NMR (400 MHz, CDCl$_3$): δ 7.52 (s, 1H), 7.46 (s, 1H), 7.42 (s 1H), 7.11 (s, 1H), 4.05 (d, J=6.4 Hz, 2H), 3.65 (s, 3H), 3.07 (s, 3H), 2.66 (s, 3H), 2.25 (s, 3H), 1.27-1.24 (m, 1H), 0.68-0.0.66 (m, 2H), 0.44-0.42 (m, 2H). LCMS: 401 (M+H$^+$).

Example 40

N-[1-butyl-6-(1,5-dimethyl-6-oxopyridin-3-yl) benzimidazol-4-yl]ethanesulfonamide Step 1: 6-bromo-1-butyl-4-nitrobenzimidazole

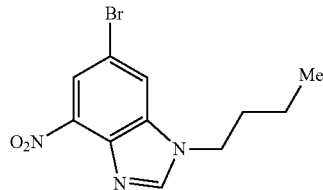 [SMILES: CCCCn1cnc2c([N+](=O)[O-])cc(Br)cc21]

The title compound was prepared in a manner similar to Example 31, step 3, by substituting 1-bromobutane for bromomethylbenzene. $^1$H NMR (300 MHz, DMSO-d$_6$) δ 8.60 (s, 1H), 8.49 (d, J=1.6 Hz, 1H), 8.16 (d, J=1.6 Hz, 1H), 4.35 (t, J=7.2 Hz, 2H), 1.83-1.73 (m, 2H), 1.32-1.20 (m, 2H), 0.90 (t, J=7.2 Hz, 3H).

Step 2: N-[1-butyl-6-(1,5-dimethyl-6-oxopyridin-3-yl) benzimidazol-4-yl]ethanesulfonamide

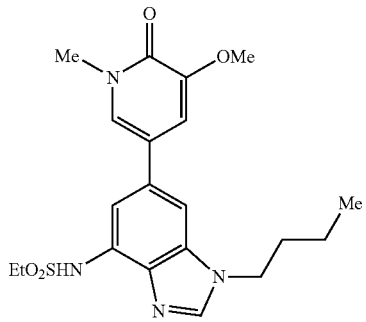

The title compound was prepared in a manner similar to Example 32, steps 2 through 4, by substituting 6-bromo-1-butyl-4-nitrobenzimidazole for 6-bromo-1-[(3-fluorophenyl)methyl]-4-nitrobenzimidazole in step 2 and ethanesulfonyl chloride for methanesulfonyl chloride in step 3. $^1$H NMR (300 MHz, DMSO-$d_6$): δ 9.60 (s, 1H), 8.27 (s, 1H), 7.94 (d, J=2.1 Hz, 1H), 7.75 (s, 1H), 7.60 (s, 1H), 7.27 (s, 1H), 4.25-4.30 (m, 2H), 3.55 (s, 3H), 3.34-3.27 (m, 2H), 2.12 (s, 3H), 1.79-1.84 (m, 2H), 1.18-1.33 (m, 5H), 0.89-0.94 (m, 3H).

LCMS: 403 (M+H)$^+$.

Example 41

N-[1-[(2,4-difluorophenyl)methyl]-6-(1,5-dimethyl-6-oxopyridin-3-yl)benzimidazol-4-yl]ethanesulfonamide Step 1: 6-bromo-1-[(2,4-difluorophenyl)methyl]-4-nitrobenzimidazole

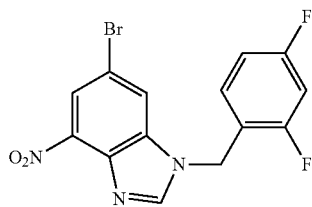 [SMILES: O=[N+]([O-])c1cc(Br)cc2c1ncn2Cc1ccc(F)cc1F]

The title compound was prepared in a manner similar to Example 31, step 3, by substituting 1-(bromomethyl)-2,4-difluorobenzene for bromomethylbenzene.

LCMS: 368; 370 (M+H$^+$).

Step 2: N-[1-[(2,4-difluorophenyl)methyl]-6-(1,5-dimethyl-6-oxopyridin-3-yl)benzimidazol-4-yl]ethanesulfonamide

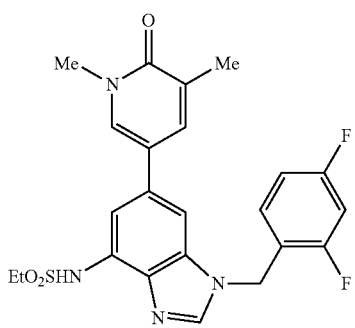

The title compound was prepared in a manner similar to Example 32, steps 2-4, by substituting 6-bromo-1-[(2,4-difluorophenyl)methyl]-4-nitrobenzimidazole for 6-bromo-1-[(3-fluorophenyl)methyl]-4-nitrobenzimidazole in step 2 and ethanesulfonyl chloride for methanesulfonyl chloride in step 3. $^1$H NMR (400 MHz, CDCl$_3$) δ 8.07 (m, 2H), 7.40-7.49 (m, 4H), 7.13 (s, 1H), 6.90-6.92 (m, 2H), 5.44 (s, 2H), 3.64 (s, 3H), 3.19 (q, J=7.2 Hz, 2H), 2.24 (s, 3H), 1.38 (t, J=7.2 Hz, 3H). LCMS: 473 (M+H)$^+$.

Example 42

N-[1-benzyl-6-(1,5-dimethyl-6-oxopyridin-3-yl)indazol-4-yl]ethanesulfonamide

Step 1: 1-benzyl-6-bromo-4-nitroindazole

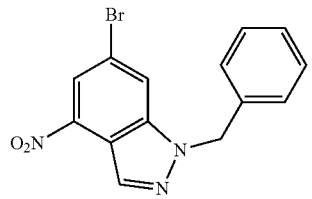 [SMILES: O=[N+]([O-])c1cc(Br)cc2c1cnn2Cc1ccccc1]

To a mixture of 6-bromo-4-nitro-1H-indazole (500 mg, 2 mmol) in DMF (10 mL) was added NaH (50 mg, 2 mmol) in one portion at 0° C. under N$_2$. The mixture was stirred at 0° C. for 10 min and then BnBr (354 mg, 2 mmol) was added. The mixture was stirred at 25° C. for 12 hr. After this time, it was diluted with water and extracted with EtOAc (30 ml). The combined organic layers were concentrated under reduced pressure. The residue was purified by silica gel column chromatography (PE:EA=25:1) to afford the title compound (150 mg, 22% yield) as solid. $^1$H NMR (CDCl$_3$, 400 MHz) δ 8.65 (d, J=0.8 Hz, 1H), 8.27 (m, 1H), 7.87 (s, 1H), 7.21-7.42 (m, 5H), 5.66 (s, 2H). LCMS: 332.0 (M+H)$^+$.

Step 2: 5-(1-benzyl-4 nitroindazol-6-yl)-1,3-dimethylpyridin-2-one

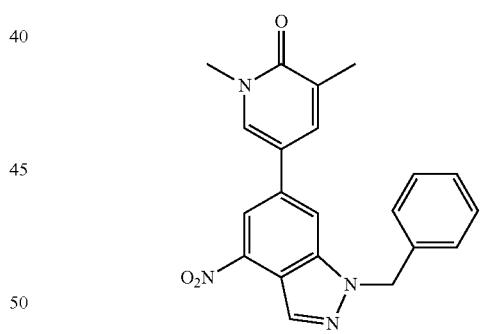

To a mixture of the title compound from step 1 (100 mg, 301 umol) and 1,3-dimethyl-5-(4,4,5,5-tetramethyl-1,3,2-dioxaborolan-2-yl)pyridin-2-one (90 mg, 361 umol) in 1,4-dioxane (5 mL) and H$_2$O (0.5 mL) at 25° C. was added K$_3$PO$_4$ (127 mg, 602 umol) and Pd(dppf)Cl$_2$ (11 mg, 15 umol) in one portion under N$_2$. The mixture was stirred at 90° C. for 12 hr. After cooling to RT, the reaction contents were concentrated under reduced pressure. The residue was purified by silica gel column chromatography (PE:EA=3:1~1:1) followed by preparative HPLC to afford the title compound (50 mg, 44% yield) as a yellow solid. $^1$H NMR (CDCl$_3$, 400 MHz) δ 8.67 (s, 1H), 8.20 (s, 1H), 7.60 (s, 1H), 7.47 (m, 2H), 7.21-7.35 (m, 5H), 5.73 (s, 2H), 3.67 (s, 3H), 2.26 (s, 3H).

Step 3: 5-(4-amino-1-benzylindazol-6-yl)-1,3-dimethylpyridin-2-one

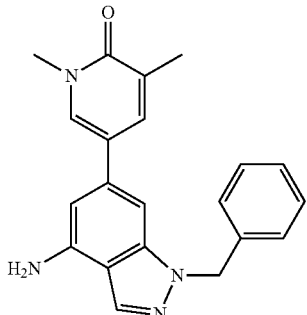

To a mixture of the title compound from step 2 (50 mg, 134 µmol) in EtOH (2 mL) and H₂O (1 mL) at RT was added NH₄Cl (36 mg, 667 µmol) and Fe (37 mg, 667 µmol) in one portion under N₂. The mixture was stirred at 90° C. for 1 hr. It was then cooled to RT, filtered and concentrated under reduced pressure. The residue was diluted with water and extracted by EtOAc (20 mL). The combined organic layers were dried over Na₂SO₄, filtered and concentrated under reduced pressure to afford the title compound as a yellow solid that was used directly in the next step without further purification. LCMS: 345.1 (M+H)⁺.

Step 4: N-[1-benzyl-6-(1,5-dimethyl-6-oxopyridin-3-yl)indazol-4-yl]ethanesulfonamide

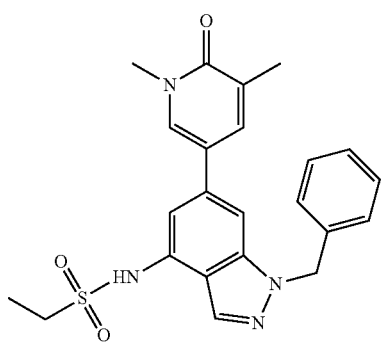 [SMILES: CCS(=O)(=O)Nc1cc(-c2cc(C)c(=O)n(C)c2)cc2c1cnn2Cc1ccccc1]

A mixture of the title compound from step 3 (100 mg, 290 µmol) and ethanesulfonyl chloride (74 mg, 580 µmol) in pyridine (2 mL) was stirred at 25° C. for 4 hr. The reaction mixture was quenched with MeOH and purified by preparative HPLC to afford the title compound (18.8 mg, 16% yield). ¹H NMR (CDCl₃, 400 MHz) δ 8.16 (s, 1H), 7.51 (s, 1H), 7.43 (s, 1H), 7.29-7.34 (m, 4H), 7.22-7.24 (m, 2H), 7.17 (m, 1H), 7.12 (s, 1H), 5.63 (s, 2H), 3.67 (s, 3H), 3.22 (q, J=7.2 Hz, 2H), 2.25 (s, 3H), 1.41 (t, J=7.2 Hz, 3H). LCMS: 437.0 (M+H)⁺.

Example 43

N-[6-(1,5-dimethyl-6-oxopyridin-3-yl)-1-[(4-fluorophenyl) methyl]indazol-4-yl]ethanesulfonamide

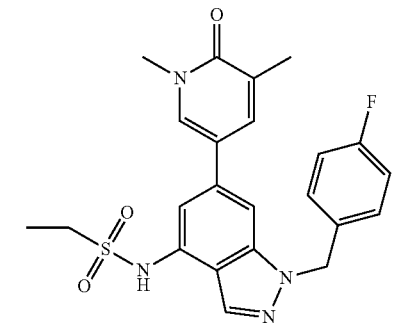 [SMILES: CCS(=O)(=O)Nc1cc(-c2cc(C)c(=O)n(C)c2)cc2c1cnn2Cc1ccc(F)cc1]

The title compound was prepared in a manner similar to Example 42 by substituting 1-(bromomethyl)-4-fluorobenzene for bromomethylbenzene in step 1. ¹H NMR (CDCl₃, 400 MHz) δ 8.14 (s, 1H), 7.48 (s, 1H), 7.41 (d, J=2.4 Hz, 1H), 7.29 (s, 1H), 7.21 (m, 2H), 7.19 (s, 1H), 7.09 (m, 2H), 5.58 (s, 2H), 3.65 (s, 3H), 3.22 (q, J=7.2 Hz, 2H), 2.25 (s, 3H), 1.41 (t, J=7.2 Hz, 3H). LCMS: 455.0 (M+H)⁺.

Examples 44 and 45

N-[6-(1,5-dimethyl-6-oxopyridin-3-yl)-2-methyl-1-[(1S)-(1-phenylethyl)]benzimidazol-4-yl]methanesulfonamide and N-[6-(1,5-dimethyl-6-oxopyridin-3-yl)-2-methyl-1-[(1R)-(1-phenylethyl)]benzimidazol-4-yl]methanesulfonamide Step 1: 6-bromo-2-methyl-4-nitro-1-(1-phenylethyl)benzimidazole

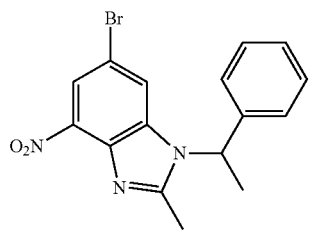 [SMILES: Cc1nc2c([N+](=O)[O-])cc(Br)cc2n1C(C)c1ccccc1]

The title compounds was prepared in a manner similar to Example 31, step 3, by substituting 6-bromo-2-methyl-4-nitro-1H-benzimidazole for 6-bromo-4-nitro-1H-benzimidazole and 1-bromoethylbenzene for bromomethylbenzene. ¹H NMR (400 MHz, DMSO-d₆): δ 8.06 (s, 1H), 7.83 (s, 1H), 7.46-7.25 (m, 5H), 6.12 (q, J=6.8 Hz, 1H), 3.30 (s, 3H), 2.60 (s, 3H), 1.93 (d, J=6.8 Hz, 3H). LCMS: 360; 362 (M+H)⁺.

Step 2: N-[6-(1,5-dimethyl-6-oxopyridin-3-yl)-2-methyl-1-(1-phenylethyl)benzimidazol-4-yl]methanesulfonamide

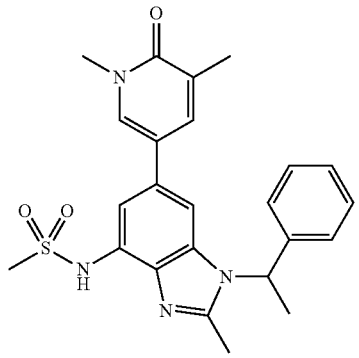 [SMILES: Cc1cc(-c2cc(NS(C)(=O)=O)c3nc(C)n(C(C)c4ccccc4)c3c2)cn(C)c1=O]

The title compound was prepared in a manner similar to Example 32, steps 2 through 4, by substituting 6-bromo-2-methyl-4-nitro-1-(1-phenylethyl)benzimidazole for 6-bromo-1-[(3-fluorophenyl)methyl]-4-nitrobenzimidazole in step 2. $^1$H NMR (400 MHz, DMSO-$d_6$): δ 9.50 (br, 1H), 7.77 (s, 1H), 7.52 (s, 1H), 7.40-7.25 (m, 5H), 7.19 (s, 1H), 7.17 (s, 1H), 6.02 (q, J=6.8 Hz, 1H), 3.50 (s, 3H), 3.30 (s, 3H), 3.20 (s, 3H), 2.07 (s, 3H), 1.97 (d, J=6.8 Hz, 3H).

Step 3: N-[6-(1,5-dimethyl-6-oxopyridin-3-yl)-2-methyl-1-[(1S)-(1-phenylethyl)]benzimidazol-4-yl]methanesulfonamide and N-[6-(1,5-dimethyl-6-oxopyridin-3-yl)-2-methyl-1-[(1R)-(1-phenylethyl)]benzimidazol-4-yl]methanesulfonamide

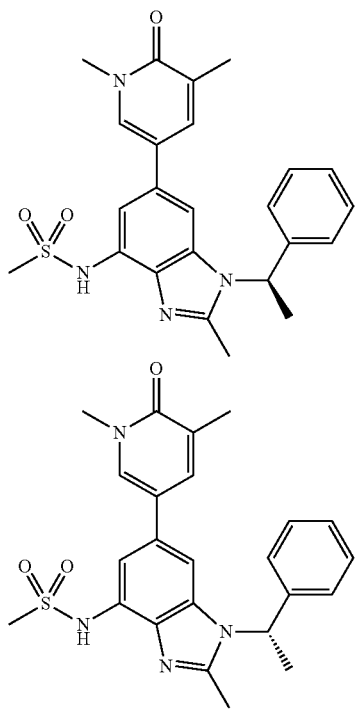

The title compound from Step 2 was submitted to chiral phase HPLC separation (Chiralcelpak IB, 250 mm*4.6 mm 5 um; MeOH:EtOH=50:50; Flow: 1.0 ml/min) to afford its two enantioemers: Example 44 (Rt=5.454 min) and Example 45 (Rt=7.487 min). The absolute configuration has been assigned randomly.

Example 46

N-[6-(1,5-dimethyl-6-oxopyridin-3-yl)-1-[(2R)-1-methoxypropan-2-yl]-2-methylbenzimidazol-4-yl]methanesulfonamide

Step 1: 5-bromo-3-fluoro-N-[(2R)-1-methoxypropan-2-yl]-2-nitroaniline

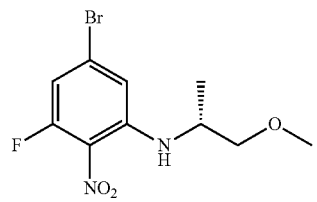

To a solution of (2R)-1-methoxypropan-2-amine (638 mg, 5.1 mmol) in DMF (15 mL) was added t-BuOK (1.08 g, 9.7 mmol). The mixture was stirred for 30 min. 5-bromo-1,3-difluoro-2-nitrobenzene (1.1 g, 4.6 mmol) was added and the reaction mixture was heated to 30° C. for 2 hr. It was then diluted with water (40 mL) and DCM (40 mL). The mixture was acidified to pH <6 by addition of AcOH. The organic layer was separated and the aqueous one was extracted with EtOAc (50 mL×2). The combined organic layers were washed with brine, dried over $Na_2SO_4$, filtered and concentrated. The residue was purified by silica gel column chromatography (PE:EA=30:1 to 20:1) to give the title compound (600 mg, 43%) as a brown solid. LCMS: 307; 309 (M+H)$^+$.

Step 2: N-[5-bromo-3-[[(2R)-1-methoxypropan-2-yl]amino]-2-nitrophenyl]methanesulfonamide

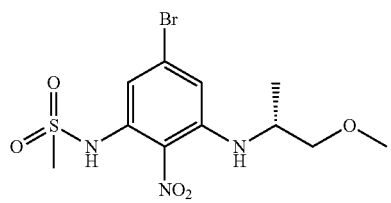 [SMILES: COC[C@@H](C)Nc1cc(Br)cc(NS(C)(=O)=O)c1[N+](=O)[O-]]

To a solution of methanesulfonamide (280 mg, 2.95 mmol) in DMF (10 mL) was added t-BuOK (307 mg, 2.74 mmol). The mixture was stirred for 30 min. 5-bromo-3-fluoro-N-[(2R)-1-methoxypropan-2-yl]-2-nitroaniline (600 mg, 1.96 mmol) was added and the reaction was heated to 30° C. for 3 hr. The mixture was diluted with water (40 mL) followed by dropwise addition of AcOH to pH <6 and extraction with EtOAc (50 mL×2). The combined organic layers were washed with brine, dried over $Na_2SO_4$, filtered and concentrated. The residue was purified by silica gel column chromatography (PE:EA=20:1) to give the title compound (400 mg, 54%) as a brown solid. $^1$H NMR (300 MHz, DMSO-d6): δ 9.82 (s, 1H), 7.07 (d, J=1.5 Hz, 1H), 6.86 (d, J=1.5 Hz, 1H), 6.80 (d, J=8.1 Hz, 1H), 4.00-3.88 (m, 1H), 3.40 (d, J=4.8 Hz, 2H), 3.29 (s, 3H), 3.12 (s, 3H), 1.14 (d, J=6.6 Hz, 3H). LCMS: 382; 384 (M+H)+.

Step 3: N-[2-amino-5-bromo-3-[[(2R)-1-methoxy-propan-2-yl]amino]phenyl]methane sulfonamide

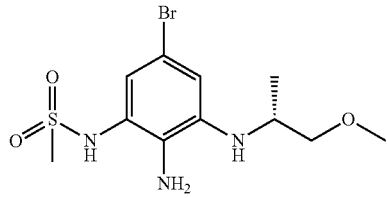 [SMILES: COC[C@@H](C)Nc1cc(Br)cc(NS(C)(=O)=O)c1N]

The title compound was prepared in a manner similar to Example 32, step 2, by substituting the title compound from step 2 for 6-bromo-1-[(3-fluorophenyl)methyl]-4-nitrobenzimidazole. ¹H NMR (300 MHz, CDCl3): δ 6.83 (s, 1H), 6.81 (s, 1H), 3.65-3.57 (m, 1H), 3.44 (d, J=3.3 Hz, 2H), 3.39 (s, 3H), 3.05 (s, 3H), 1.24 (d, J=4.8 Hz, 3H).
LCMS: 352; 354 (M+H)+.

Step 4: N-[6-bromo-1-[(2R)-1-methoxypropan-2-yl]-2-methylbenzimidazol-4-yl]methanesulfonamide

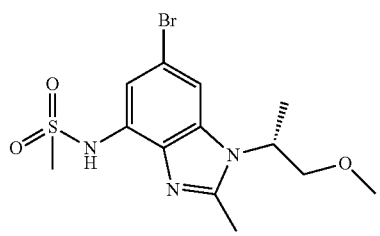 [SMILES: COC[C@@H](C)n1c(C)nc2c(NS(C)(=O)=O)cc(Br)cc21]

To a suspension of the title compound from step 3 (80 mg, 0.23 mmol) in EtOH (5 mL) was added 5 M HCl (3 mL). The reaction mixture was heated to reflux followed by addition of pentane-2,4-dione (0.17 mL, 0.46 mmol) in one portion. After 1 hr, the mixture was cooled to RT and neutralized with concentrated ammonium hydroxide. The mixture was extracted with DCM (50 mL×2). The combined organic layers were washed with brine, dried over Na2SO4, filtered and concentrated to give the title compound (74 mg, 87%) as a yellow solid. LCMS: 376; 378 (M+H)+.

Step 5: N-[6-(1,5-dimethyl-6-oxopyridin-3-yl)-1-[(2R)-1-methoxypropan-2-yl]-2-methylbenzimidazol-4-yl]methanesulfonamide

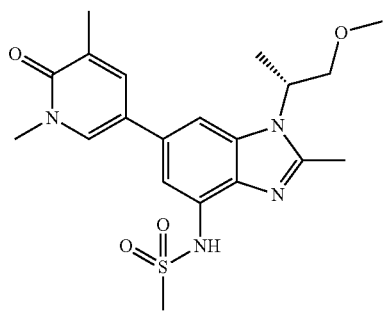 [SMILES: COC[C@@H](C)n1c(C)nc2c(NS(C)(=O)=O)cc(-c3cc(C)c(=O)n(C)c3)cc21]

The title compound was prepared in a manner similar to Example 31, step 6, by substituting the title compound from step 4 for N-(1-benzyl-6-bromobenzimidazol-4-yl)methanesulfonamide. ¹H NMR (300 MHz, DMSO-d6): δ 9.47 (br, 1H), 7.91 (s, 1H), 7.72 (s, 1H), 7.53 (s, 1H), 7.19 (s, 1H), 4.86-4.72 (m, 1H), 3.99-3.82 (m, 1H), 3.72-3.64 (m, 1H), 3.55 (s, 3H), 3.20 (s, 6H), 2.57 (s, 3H), 2.11 (s, 3H), 1.58 (d, J=7.2 Hz). LCMS: 419 (M+H)+.

Example 47

N-[2-cyclopropyl-7-(1,5-dimethyl-6-oxopyridin-3-yl)-1,3-benzoxazol-5-yl]ethanesulfonamide Step 1: N-(3-chloro-2-hydroxy-5-nitrophenyl)cyclopropanecarboxamide

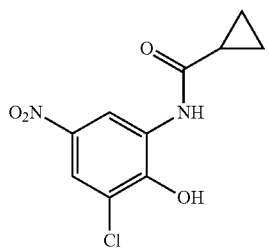 [SMILES: O=C(Nc1cc([N+](=O)[O-])cc(Cl)c1O)C1CC1]

A solution of 2-amino-6-chloro-4-nitrophenol (1.88 g, 10 mmol) in a mixture of pyridine (80 mL) and DCM (20 mL) stirred at 0° C. under an atmosphere of nitrogen was treated with cyclopropanecarbonyl chloride (904 uL, 10 mmol) by dropwise over 10 min. The mixture was allowed to gradually warm to rt. After stirring for 12 hr, the mixture was treated with water (20 mL) and then concentrated to near dryness in vacuo. The resulting mixture was treated with additional water (80 mL) and was stirred vigorously for 10 min. The resulting suspension was filtered; the filter cake was washed with water (50 ml) and hexanes (50 ml) and dried in vacuo to afford the title compound (2.38 g, 99%) as a tan solid.

Step 2: 7-chloro-2-cyclopropyl-5-nitro-1,3-benzoxazole

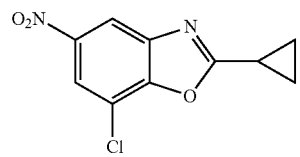 [SMILES: O=[N+]([O-])c1cc(Cl)c2oc(C3CC3)nc2c1]

A mixture of N-(3-chloro-2-hydroxy-5-nitrophenyl)cyclopropanecarboxamide (2.38 g, 9.3 mmol) and pyridinium p-toluenesulfonate (466 mg, 1.9 mmol) suspended in xylenes (62 mL) was heated to 150° C. in a sealed tube for 12 hr. The crude reaction mixture was filtered through a short plug of celite; the celite plug was washed with MeOH (~10 mL). The resulting filtrate was concentrated in vacuo. The resulting residue was diluted with EtOAc (50 ml) and washed with saturated bicarbonate solution (aq), dried over anhydrous magnesium sulfate, filtered, and concentrated in vacuo. The resulting residue was purified by silica gel column chromatography using a gradient of MeOH (0 to 10%) in DCM to afford the title compound (711 mg, 98%) as a brown solid. LCMS (M+H)+=239.

Step 3: 5-(2-cyclopropyl-5-nitro-1,3-benzoxazol-7-yl)-1,3-dimethylpyridin-2-one

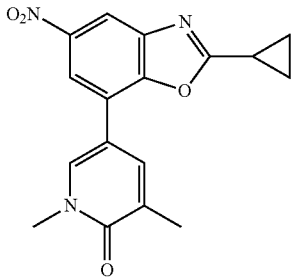 [SMILES: Cc1cc(-c2cc([N+](=O)[O-])cc3nc(C4CC4)oc23)cn(C)c1=O]

A mixture of 7-chloro-2-cyclopropyl-5-nitro-1,3-benzoxazole (91 mg, 0.38 mmol), 1,3-dimethyl-5-(4,4,5,5-tetramethyl-1,3,2-dioxaborolan-2-yl)pyridin-2-one (108 mg, 0.44 mmol), $K_3PO_4$ (247 mg, 1.1 mmol), $Pd_2(dba)_3$ (17 mg, 5%) and S-Phos (16 mg, 10%) in dioxane (2.4 mL) and $H_2O$ (120 uL) was bubbled with nitrogen for 5 min. The sealed vial was stirred at 80° C. for 180 min. After the reaction mixture was filtered through a short plug of celite, the celite plug was washed with EtOAc (35 mL). The filtrate was washed with water and brine; the organic layer was dried over sodium sulfate, filtered and concentrated in vacuo to afford a tan residue. The resulting residue was purified by silica gel column chromatography using a gradient of EtOAc (0 to 100%) in DCM to afford the title compound (71 mg, 57%) as a tan solid. LCMS (M+H)+=326.

Step 4: 5-(5-amino-2-cyclopropyl-1,3-benzoxazol-7-yl)-1,3-dimethylpyridin-2-one

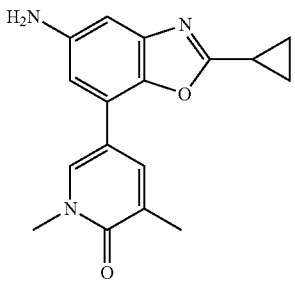

A solution of 5-(2-cyclopropyl-5-nitro-1,3-benzoxazol-7-yl)-1,3-dimethylpyridin-2-one (71 mg, 0.22 mmol) in a mixture of THF (770 uL), MeOH (770 uL), and water (260 uL) was treated with Iron (62 mg, 1.1 mmol) and $NH_4Cl$ (30 mg, 0.55 mmol). The mixture was heated to 90° C. for 3 hr. After cooling to rt, the mixture was filtered through a short bed of celite; the filtrate was partitioned between water and EtOAc (40 mL×2). The combined organic layers were dried over $Na_2SO_4$, filtered, and concentrated to give the title compound (55 mg, 85%) as a yellow solid.

LCMS (M+H)+=296.

Step 5: N-[2-cyclopropyl-7-(1,5-dimethyl-6-oxopyridin-3-yl)-1,3-benzoxazol-5-yl]ethanesulfonamide

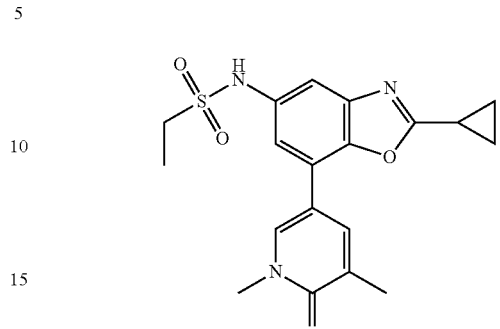

Ethylsulfonyl chloride (18 uL, 0.19 mmol) was added to a solution of 5-(5-amino-2-cyclopropyl-1,3-benzoxazol-7-yl)-1,3-dimethylpyridin-2-one (55 mg, 0.19 mmol) and pyridine (61 uL, 0.57 mmol) in DCM (1 mL) stirred at 0° C. under nitrogen. The mixture was allowed to warm to rt. After stirring for 12 hr, the mixture was treated with 1N HCl (2 mL) and extracted with DCM (3×15 mL); the combined organic extracts were washed with saturated bicarbonate solution (aq), dried over sodium sulfate, filtered and concentrated in vacuo. The resulting residue was purified by prep-HPLC to afford the title compound (36 mg, 56%) as a tan solid. $^1$H NMR (400 MHz, DMSO-d6) δ ppm 1.13-1.24 (m, 7H) 2.07-2.15 (m, 3H) 2.26-2.36 (m, 1H) 3.03-3.14 (m, 2H) 3.53-3.59 (m, 3H) 7.23-7.28 (m, 1H) 7.32-7.36 (m, 1H) 7.68-7.76 (m, 1H) 8.09 (m, 1H) 9.67-9.85 (bs, 1H). LCMS (M+H)+=388.

Example 48

N-[2-cyclopropyl-7-(2-methyl-1-oxoisoquinolin-4-yl)-1,3-benzoxazol-5-yl]ethanesulfonamide Step 1: 4-(2-cyclopropyl-5-nitro-1,3-benzoxazol-7-yl)-2-methylisoquinolin-1-one

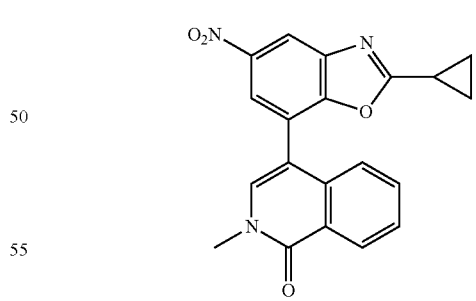

A mixture of 7-chloro-2-cyclopropyl-5-nitro-1,3-benzoxazole (70 mg, 0.31 mmol), 2-methyl-4-(4,4,5,5-tetramethyl-1,3,2-dioxaborolan-2-yl)isoquinolin-1-one (100 mg, 0.35 mmol), $K_3PO_4$ (202 mg, 0.93 mmol), $Pd_2(dba)_3$ (14 mg, 5%) and S-Phos (13 mg, 10%) in dioxane (2.0 mL) and $H_2O$ (100 uL) was bubbled with nitrogen for 5 min. The sealed vial was stirred at 85° C. for 12 hr. After the reaction mixture was filtered through a short plug of celite, the celite plug was washed with EtOAc (25 mL). The filtrate was washed with water and brine; the organic layer was dried over sodium sulfate, filtered and concentrated in vacuo to afford a tan residue. The resulting residue was purified by silica gel column chromatography using a gradient of EtOAc (0 to 100%) in DCM to afford the title compound (73 mg, 65%) as a tan solid. LCMS (M+H)+=362.

Step 2: 4-(5-amino-2-cyclopropyl-1,3-benzoxazol-7-yl)-2-methylisoquinolin-1-one

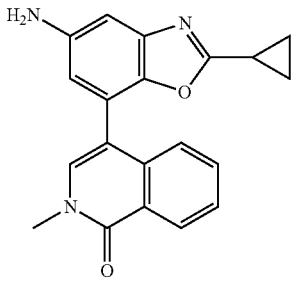 [SMILES: Cn1cc(-c2cc([N+](=O)[O-])cc3nc(C4CC4)oc23)c2ccccc2c1=O]

A solution of 4-(2-cyclopropyl-5-nitro-1,3-benzoxazol-7-yl)-2-methylisoquinolin-1-one (73 mg, 0.20 mmol) in a mixture of THF (700 uL), MeOH (700 uL), and water (266 uL) was treated with Iron (57 mg, 1.0 mmol) and NH4Cl (22 mg, 0.4 mmol). The mixture was heated to 90° C. for 4 hr. After cooling to rt, the mixture was filtered through a short bed of celite; the filtrate was partitioned between water and EtOAc (40 mL×2). The combined organic layers were dried over Na2SO4, filtered, and concentrated to give the title compound (58 mg, 85%) as a yellow solid. LCMS (M+H)+=332.

Step 3: N-[2-cyclopropyl-7-(2-methyl-1-oxoisoquinolin-4-yl)-1,3-benzoxazol-5-yl]ethanesulfonamide

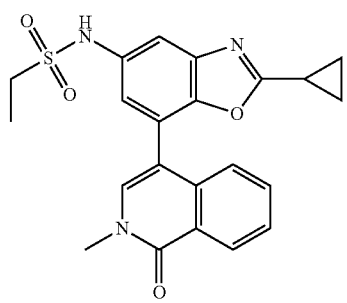 [SMILES: CCS(=O)(=O)Nc1cc(-c2cn(C)c(=O)c3ccccc23)c2oc(C3CC3)nc2c1]

Ethylsulfonyl chloride (170 uL, 1.8 mmol) was added to a solution of 4-(5-amino-2-cyclopropyl-1,3-benzoxazol-7-yl)-2-methylisoquinolin-1-one (440 mg, 1.8 mmol) and pyridine (725 uL) in DCM (4.5 mL) stirred at 0° C. under nitrogen. The mixture was allowed to warm to rt and stir for 12 h: the mixture was treated with 1N HCl (5 mL) and extracted with DCM (3×50 mL); the combined organic extracts were washed with saturated bicarbonate solution (aq), dried over sodium sulfate, filtered and concentrated in vacuo. The resulting residue was purified by prep-HPLC to afford the title compound (34 mg, 71%) as a tan solid. 1H NMR (400 MHz, DMSO-d6) δ ppm 0.99-1.07 (m, 2H) 1.07-1.17 (m, 2H) 1.18-1.27 (m, 3H) 2.15-2.27 (m, 1H) 3.08-3.20 (m, 2H) 3.56-3.65 (m, 3H) 7.15-7.25 (m, 1H) 7.26-7.36 (m, 1H) 7.47-7.53 (m, 1H) 7.53-7.62 (m, 1H) 7.65-7.77 (m, 2H) 8.31-8.41 (m, 1H) 9.83-9.94 (bs, 1H). LCMS (M+H)+=424.

Example 49

4-[7-(cyclopropylmethoxy)-4-ethylsulfonyl-2,3-dihydro-1,4-benzoxazin-6-yl]-2-methylisoquinolin-1-one Step 1: 6-bromo-7-hydroxy-4H-1,4-benzoxazin-3-one

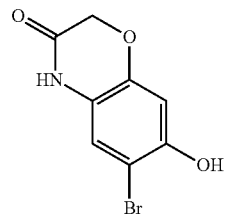 [SMILES: O=C1COc2cc(O)c(Br)cc2N1]

A solution of 7-hydroxy-4H-1,4-benzoxazin-3-one (165 mg, 1 mmol) in acetic acid (5.6 mL) stirred in the dark at 10° C. was treated with a solution of Br2 (168 mg, 1.05 mmol) in acetic acid (1 mL) dropwise over 15 min. The reaction mixture was allowed to warm gradually to rt. After 90 min, the mixture was treated with 10% sodium thiosulfate (aq) (3 mL). After the mixture was concentrated in vacuo, the resulting residue was treated with water, sonicated for 3 min and filtered. The filter cake was washed with Et2O and dried in vacuo to afford the title compound (243 mg, 99%) as a white solid. LCMS (M+H)+=246.

Step 2: 6-bromo-7-(cyclopropylmethoxy)-4H-1,4-benzoxazin-3-one

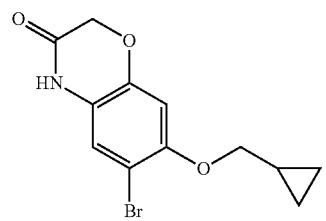 [SMILES: O=C1COc2cc(OCC3CC3)c(Br)cc2N1]

A solution of 6-bromo-7-hydroxy-4H-1,4-benzoxazin-3-one (243 mg, 0.99 mmol) in DMF (4 mL) stirred at 0° C. was treated K2CO3 (152 mg, 1.09 mmol). After 15 min the reaction mixture was treated with bromomethylcyclopropane (165 uL, 1.09 mmol). The reaction mixture was allowed to warm gradually to rt. After stirring for 12 hr, the mixture was treated with water and extracted with EtOAc (3×50 mL). The combined organic layers were washed with brine, dried over MgSO4, filtered and concentrated in vacuo to afford the title compound (232 mg, 78%) as a tan solid. LCMS (M+H)+=299.

Step 3: 6-bromo-7-(cyclopropylmethoxy)-3,4-dihydro-2H-1,4-benzoxazine

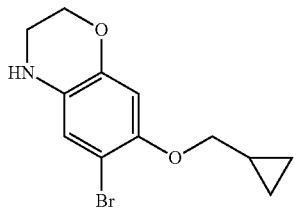 [SMILES: Brc1cc2c(cc1OCC1CC1)OCCN2]

A solution of borane in THF (1.0 M, 1.2 mL, 1.2 mmol) was added to an ice-cold solution of 6-bromo-7-(cyclopropylmethoxy)-4H-1,4-benzoxazin-3-one (230 mg, 0.77 mmol) in THF (5 mL). The ice bath was removed and the reaction was allowed to warm to rt. After 30 min, the flask was fitted with a reflux condenser and was heated to 70° C. under nitrogen. After 2 hr, the mixture was cooled to 0° C. and quenched with 1 N NaOH (2 mL). After the mixture was stirred for 15 min, it was diluted with water (5 mL) and evaporated to remove THF. The aqueous residue was extracted with EtOAc and washed with water (5 mL) and 0.5 N NaOH (5 mL). The organic layer was washed with brine, dried over MgSO$_4$, filtered and concentrated in vacuo. The resulting residue was purified by silica gel column chromatography using a gradient of EtOAc (10 to 90%) in DCM to afford the title compound (219 mg, 78%) as a white solid. LCMS (M+H)$^+$=285.

Step 4: 6-bromo-7-(cyclopropylmethoxy)-4-ethylsulfonyl-2,3-dihydro-1,4-benzoxazine

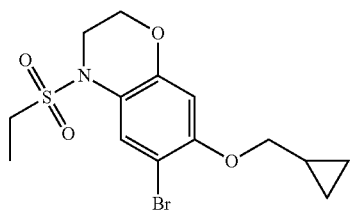 [SMILES: CCS(=O)(=O)N1CCOc2cc(OCC3CC3)c(Br)cc21]

Ethylsulfonyl chloride (94 uL, 0.96 mmol) was added to a solution of 6-bromo-7-(cyclopropylmethoxy)-3,4-dihydro-2H-1,4-benzoxazine (219 mg, 0.77 mmol) and pyridine (310 μL) in DCM (4 mL) stirred at 0° C. under nitrogen. After the mixture was allowed to warm to RT and stirred for 12 hr, it was treated with 1N HCl (10 mL) and extracted with DCM (3×10 mL); the combined organic extracts were washed with saturated bicarbonate solution (aq), dried over sodium sulfate, filtered and concentrated in vacuo. The resulting residue was purified by silica gel column chromatography using a gradient of EtOAc (10 to 50%) in DCM to afford the title compound (277 mg, 96%) as a white solid. LCMS (M+H)$^+$=377.

Step 5: 4-[7-(cyclopropylmethoxy)-4-ethylsulfonyl-2,3-dihydro-1,4-benzoxazin-6-yl]-2-methylisoquinolin-1-one

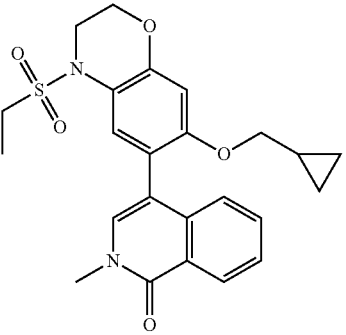 [SMILES: CCS(=O)(=O)N1CCOc2cc(OCC3CC3)c(-c3cn(C)c(=O)c4ccccc34)cc21]

A mixture of 6-bromo-7-(cyclopropylmethoxy)-4-ethylsulfonyl-2,3-dihydro-1,4-benzoxazine (100 mg, 0.27 mmol), 2-methyl-4-(4,4,5,5-tetramethyl-1,3,2-dioxaborolan-2-yl)isoquinolin-1-one (76 mg, 0.27 mmol), K$_3$PO$_4$ (145 mg, 0.66 mmol), Pd(dppf)Cl$_2$ (19 mg, 10%) in dioxane/H$_2$O (1.6 mL/177 μL) was bubbled with nitrogen for 5 min. The sealed vial was stirred at 77° C. for 4 hr. The reaction mixture was filtered through a short plug of celite; the celite plug was washed with EtOAc (15 mL). The filtrate was washed with water and brine; the organic layer was dried over sodium sulfate, filtered and concentrated in vacuo to afford a tan residue. The resulting residue was purified by prep-HPLC to afford the title compound (58 mg, 48%) as a tan solid. $^1$H NMR (400 MHz, DMSO-d$_6$) δ ppm 0.02-0.11 (m, 4H) 0.18-0.39 (m, 2H) 0.80-0.95 (m, 1H) 1.14-1.29 (m, 3H) 3.51-3.61 (m, 3H) 3.64-3.96 (m, 4H) 4.25-4.37 (m, 2H) 6.60-6.75 (m, 1H) 7.14-7.25 (m, 1H) 7.34-7.43 (m, 2H) 7.43-7.56 (m, 1H) 7.56-7.70 (m, 1H) 8.21-8.32 (m, 1H). LCMS (M+H)$^+$=455.

Example 50

5-[7-(cyclopropylmethoxy)-4-ethylsulfonyl-2,3-dihydro-1,4-benzoxazin-6-yl]-1,3-dimethylpyridin-2-one

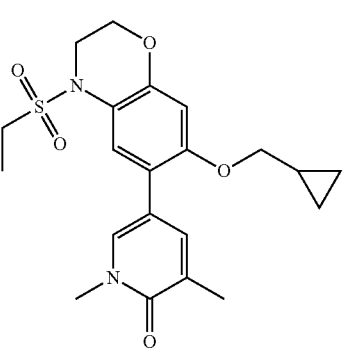 [SMILES: CCS(=O)(=O)N1CCOc2cc(OCC3CC3)c(-c3cc(C)c(=O)n(C)c3)cc21]

The title compound (44 mg, 43%) was prepared as a tan solid in a similar manner to step 5 of Example 49 except that 1,3-dimethyl-5-(4,4,5,5-tetramethyl-1,3,2-dioxaborolan-2-yl)pyridin-2-one was substituted for 2-methyl-4-(4,4,5,5-tetramethyl-1,3,2-dioxaborolan-2-yl)isoquinolin-1-one. $^1$H NMR (400 MHz, DMSO-d$_6$) δ ppm 0.25-0.35 (m, 2H) 0.47-0.57 (m, 2H) 1.09-1.27 (m, 4H) 2.00-2.07 (m, 3H) 3.27-3.39 (m, 2H) 3.44-3.52 (m, 3H) 3.72-3.87 (m, 4H) 4.21-4.32 (m, 2H) 6.55-6.63 (m, 1H) 7.32-7.39 (m, 1H) 7.43-7.49 (m, 1H) 7.59-7.67 (m, 1H). LCMS (M+H)$^+$=419.

Example 51

N-[2-cyclopropyl-7-(1,5-dimethyl-6-oxopyridin-3-yl)-1,3-benzoxazol-5-yl]propane-2-sulfonamide

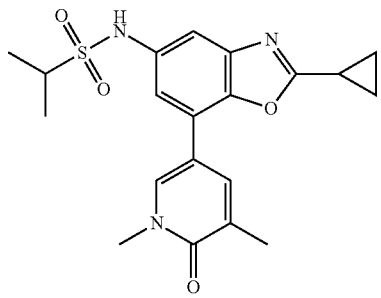 [SMILES: Cc1cc(-c2cc(NS(=O)(=O)C(C)C)cc3nc(C4CC4)oc23)cn(C)c1=O]

The title compound (53 mg) was prepared as a tan solid in a similar manner to step 5 of Example 47 except that propane-2-sulfonyl chloride was substituted for ethylsulfonyl chloride.

LCMS (M+H)$^+$=402.

Example 52

N-[2-cyclopentyl-7-(1,5-dimethyl-6-oxopyridin-3-yl)-1,3-benzoxazol-5-yl]ethanesulfonamide

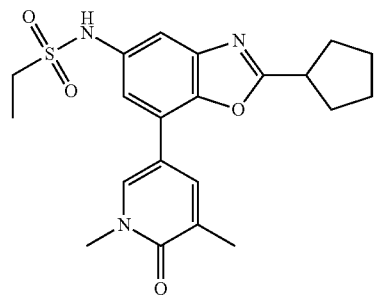 [SMILES: CCS(=O)(=O)Nc1cc(-c2cc(C)c(=O)n(C)c2)c2oc(C3CCCC3)nc2c1]

The title compound (16 mg) was prepared as a tan solid in a similar manner to Example 47 except that cyclopentanecarbonyl chloride was substituted for cyclopropane-carbonyl chloride in step 1. $^1$H NMR (400 MHz, DMSO-d$_6$) δ ppm 1.17-1.24 (m, 3H) 1.61-1.82 (m, 4H) 1.90-2.02 (m, 2H) 2.04-2.16 (m, 5H) 3.05-3.13 (m, 2H) 3.40-3.50 (m, 1H) 3.55-3.59 (m, 3H) 7.27-7.32 (m, 1H) 7.39-7.43 (m, 1H) 7.72-7.76 (m, 1H) 8.07-8.12 (m, 1H) 9.61-9.93 (m, 1H). LCMS (M+H)$^+$=416.

Example 53

N-[2-cyclopentyl-7-(2-methyl-1-oxoisoquinolin-4-yl)-1,3-benzoxazol-5-yl]ethanesulfonamide

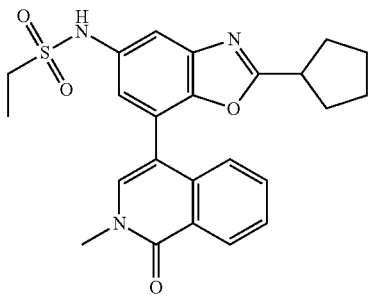 [SMILES: CCS(=O)(=O)Nc1cc(-c2cn(C)c(=O)c3ccccc23)c2oc(C3CCCC3)nc2c1]

The title compound (42 mg) was prepared as a tan solid in a similar manner to Example 47 except that cyclopentanecarbonyl chloride was substituted for cyclopropane-carbonyl chloride in step 1 and 2-methyl-4-(4,4,5,5-tetramethyl-1,3,2-dioxaborolan-2-yl)isoquinolin-1-one was substituted for 1,3-dimethyl-5-(4,4,5,5-tetramethyl-1,3,2-dioxaborolan-2-yl)pyridin-2-one in step 3. $^1$H NMR (400 MHz, DMSO-d$_6$) δ ppm 1.18-1.29 (m, 3H) 1.54-1.74 (m, 4H) 1.79-1.93 (m, 2H) 1.94-2.06 (m, 2H) 3.08-3.19 (m, 2H) 3.59 (s, 3H) 7.21-7.27 (m, 1H) 7.28-7.34 (m, 1H) 7.55-7.62 (m, 2H) 7.64-7.71 (m, 1H) 7.73 (s, 1H) 8.31-8.39 (m, 1H) 9.86-9.94 (bs, 1H). LCMS (M+H)$^+$=452.

Example 54

N-[2-cyclopropyl-7-(1,5-dimethyl-6-oxopyridin-3-yl)-3-methylbenzimidazol-5-yl]ethanesulfonamide Step 1: 4-bromo-2-cyclopropyl-1-methyl-6-nitrobenzimidazole

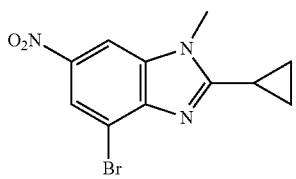 [SMILES: Cn1c(C2CC2)nc2c(Br)cc([N+](=O)[O-])cc21]

A mixture of 4-bromo-2-cyclopropyl-6-nitro-1H-benzimidazole (732 mg, 2.6 mmol) and K$_2$CO$_3$ (1.07 g, 7.8 mmol) stirred at rt in DMF (8.6 mL) under nitrogen was treated with MeI (517 mg, 3.6 mmol). The resulting suspension was heated to 60° C. for 30 min before being stirred at RT for 13 hr. The reaction mixture was treated water and was extracted with EtOAc. The combined organic layers were washed with water, brine, dried over Na$_2$SO$_4$, filtered, and concentrated in vacuo. The residue was purified by silica gel column chromatography using a gradient of EtOAc (10 to 100%) in DCM to afford the title compound (320 mg, 85%) as a red solid.

LCMS (M+H)$^+$297.

Step 2:
7-bromo-2-cyclopropyl-3-methylbenzimidazol-5-amine

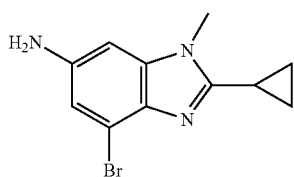

4-bromo-2-cyclopropyl-1-methyl-6-nitrobenzimidazole (317 mg, 1.07 mmol) was dissolved in a mixture of THF (3 mL), MeOH (3 mL), and water (1.1 mL) and was treated with Iron (181 mg, 5.4 mmol) and NH$_4$Cl (144 mg, 2.7 mmol). The mixture was heated to 90° C. for 4 hr. After cooling to rt, the mixture was filtered through a short bed of celite; the filtrate was partitioned between water and EtOAc (20 mL×2). The combined organic layers were dried over Na$_2$SO$_4$, filtered, and concentrated to give the title compound (260 mg, 91%) as a tan solid.
LCMS (M+H)$^+$266.

Step 3: N-(7-bromo-2-cyclopropyl-3-methylbenzimidazol-5-yl)ethanesulfonamide

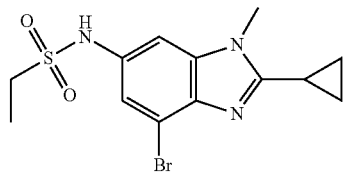 [SMILES: CCS(=O)(=O)Nc1cc(Br)c2nc(C3CC3)n(C)c2c1]

Ethylsulfonyl chloride (111 μL, 1.2 mmol) was added to a solution of 7-bromo-2-cyclopropyl-3-methylbenzimidazol-5-amine (260 mg, 0.98 mmol) and pyridine (500 uL) in DCM (5 mL) stirred at 0° C. under nitrogen. After the mixture was allowed to warm to rt and stir for 12 hr, it was treated with 1N HCl (15 mL) and extracted with DCM (3×15 mL); the combined organic extracts were washed with saturated bicarbonate solution (aq), dried over Na$_2$SO$_4$, filtered and concentrated in vacuo. The resulting residue was purified by silica gel column chromatography using a gradient of EtOAc (0 to 70%) in DCM to afford the title compound (279 mg, 80%) as an off-white solid. LCMS (M+H)$^+$=359.

Step 4: N-[2-cyclopropyl-7-(1,5-dimethyl-6-oxopyridin-3-yl)-3-methylbenzimidazol-5-yl]ethanesulfonamide

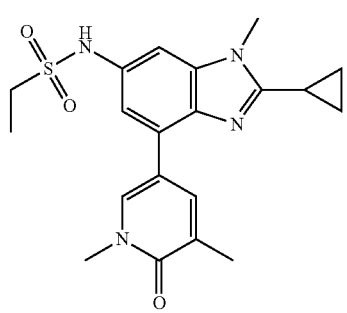 [SMILES: CCS(=O)(=O)Nc1cc(-c2cc(C)c(=O)n(C)c2)c2nc(C3CC3)n(C)c2c1]

A mixture of N-(7-bromo-2-cyclopropyl-3-methylbenzimidazol-5-yl)ethanesulfonamide (60 mg, 0.17 mmol), 1,3-dimethyl-5-(4,4,5,5-tetramethyl-1,3,2-dioxaborolan-2-yl)pyridin-2-one (41 mg, 0.17 mmol), K$_3$PO$_4$ (91 mg, 0.42 mmol), Pd(dppf)Cl$_2$ (12 mg, 10%) in dioxane/H$_2$O (1 mL/120 μL) was bubbled with nitrogen for 5 min. The sealed vial was stirred at 70° C. for 12 hr. The reaction mixture was filtered through a short plug of celite; the celite plug was washed with EtOAc (15 mL). The filtrate was washed with water and brine; the organic layer was dried over Na$_2$SO$_4$, filtered and concentrated in vacuo to afford a tan residue. The resulting residue was purified by prep-HPLC to afford the title compound (30 mg, 44%) as a white solid. LCMS (M+H)$^+$=401.

Example 55

N-[2-cyclopropyl-3-methyl-7-(2-methyl-1-oxoisoquinolin-4-yl)benzimidazol-5-yl]ethanesulfonamide

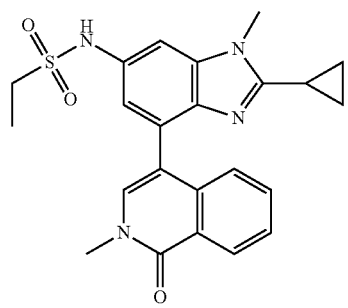 [SMILES: CCS(=O)(=O)Nc1cc(-c2cn(C)c(=O)c3ccccc23)c2nc(C3CC3)n(C)c2c1]

The title compound (42 mg, 59%) was prepared as a white solid in a similar manner to step 4 of Example 54 except that 2-methyl-4-(4,4,5,5-tetramethyl-1,3,2-dioxaborolan-2-yl)isoquinolin-1-one was substituted for 1,3-dimethyl-5-(4,4,5,5-tetramethyl-1,3,2-dioxaborolan-2-yl)pyridin-2-one. $^1$H NMR (400 MHz, DMSO-d$_6$) δ ppm 0.76-0.88 (m, 2H) 0.92-1.03 (m, 2H) 1.18-1.27 (m, 3H) 2.12-2.26 (m, 1H) 3.05-3.16 (m, 3H) 3.58 (s, 3H) 3.84 (s, 3H) 6.99-7.06 (m, 1H) 7.24-7.30 (m, 1H) 7.33-7.37 (m, 1H) 7.52 (s, 3H) 8.29-8.35 (m, 1H) 9.64-9.75 (m, 1H). LCMS (M+H)$^+$=437.

Example 56

5-[2-cyclopropyl-5-(methylsulfonylmethyl)-1,3-benzoxazol-7-yl]-1,3-dimethylpyridin-2-one Step 1: methyl 3-bromo-5-(cyclopropanecarbonylamino)-4-hydroxybenzoate

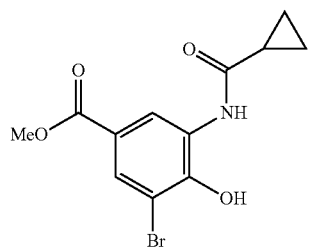 [SMILES: COC(=O)c1cc(Br)c(O)c(NC(=O)C2CC2)c1]

The title compound (690 mg, 92%) was prepared as a light yellow solid in a similar manner to step 1 of Example 47 except that methyl 3-amino-5-bromo-4-hydroxybenzoate was substituted for 2-amino-6-chloro-4-nitrophenol. LCMS (M+H)⁺=315.

Step 2: methyl 7-bromo-2-cyclopropyl-1,3-benzoxazole-5-carboxylate

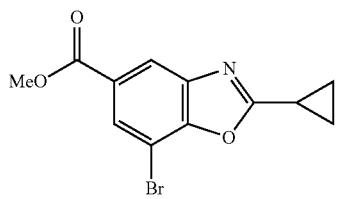 [SMILES: COC(=O)c1cc(Br)c2oc(C3CC3)nc2c1]

The title compound (410 mg, 63%) was prepared as a white solid in a similar manner to step 2 of Example 47 except that methyl 3-bromo-5-(cyclopropanecarbonylamino)-4-hydroxybenzoate was substituted for N-(3-chloro-2-hydroxy-5-nitrophenyl)cyclopropanecarboxamide. LCMS (M+H)⁺=297.

Step 3: (7-bromo-2-cyclopropyl-1,3-benzoxazol-5-yl)methanol

A solution of DIBAL in hexanes (1.0 M, 3.4 mL, 3.4 mmol) was added dropwise over 7 min to an ice-cold solution of methyl 7-bromo-2-cyclopropyl-1,3-benzoxazole-5-carboxylate (404 mg, 1.36 mmol) in THF (6.8 mL). After 15 min, the ice bath was removed and the reaction was allowed to warm to rt. After 12 hr, the reaction was cooled to 0° C. and was treated with a saturated aqueous solution of potassium sodium tartrate (8 mL). After the mixture was stirred vigorously for 30 min, it was diluted with water (5 mL) and evaporated to remove THF. The aqueous residue was extracted with EtOAc. The combined organic layers were washed with brine, dried over MgSO₄, filtered and concentrated in vacuo. The resulting residue was purified by silica gel column chromatography using a gradient of EtOAc (0 to 100%) in hexanes to afford the title compound (250 mg, 68%) as a tan solid. LCMS (M+H)⁺=269.

Step 4: 7-bromo-5-(bromomethyl)-2-cyclopropyl-1,3-benzoxazole

A 0.15 M solution of (7-bromo-2-cyclopropyl-1,3-benzoxazol-5-yl)methanol (248 mg, 0.93 mmol) in DCM stirred at 0° C. under an atmosphere of nitrogen was treated with PBr₃ (87 µL, 0.93 mmol). The ice bath was removed and the reaction mixture was allowed to stir at rt for 3 hr. The reaction mixture was cooled to 0° C., treated with water and extracted with EtOAc. The combined organic layers were washed with water, brine, dried over Na₂SO₄, filtered, and concentrated in vacuo. The residue was purified by silica gel chromatography using a gradient of EtOAc (10 to 100%) in hexanes to afford the title compound (142 mg, 46%) as a tan solid. LCMS (M+H)⁺=332.

Step 5: 7-bromo-2-cyclopropyl-5-(methylsulfonylmethyl)-1,3-benzoxazole

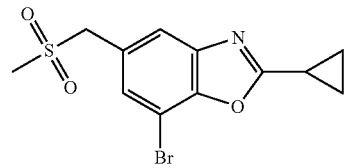 [SMILES: CS(=O)(=O)Cc1cc(Br)c2oc(C3CC3)nc2c1]

A 0.4 M solution of 7-bromo-5-(bromomethyl)-2-cyclopropyl-1,3-benzoxazole (32 mg, 0.1 mmol) in DMF (20 mL) stirred at rt under an atmosphere of nitrogen was treated with sodium methanesulfinate (85%, 40 mg, 0.4 mmol). After the mixture was heated to 50° C. for 3 hr, it was stirred at RT for 48 hr. The mixture was treated with water (3 mL), sonicated for 2 min and filtered; the filter cake was washed with water (5 ml) and hexanes (5 ml) and dried in vacuo to afford the title compound (30 mg, 99%) as a white solid. LCMS (M+H)⁺=331.

Step 6: 5-[2-cyclopropyl-5-(methylsulfonylmethyl)-1,3-benzoxazol-7-yl]-1,3-dimethylpyridin-2-one

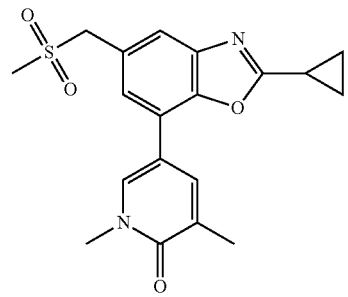 [SMILES: Cc1cc(-c2cc(CS(C)(=O)=O)cc3nc(C4CC4)oc23)cn(C)c1=O]

A mixture of 7-bromo-2-cyclopropyl-5-(methylsulfonylmethyl)-1,3-benzoxazole (30 mg, 0.1 mmol), 1,3-dimethyl-5-(4,4,5,5-tetramethyl-1,3,2-dioxaborolan-2-yl)pyridin-2-one (22 mg, 0.1 mmol), K₃PO₄ (50 mg, 0.25 mmol), Pd(dppf)Cl₂ (7 mg, 10%) in dioxane/H₂O (600 L/50 uL) was bubbled with nitrogen for 7 min. The sealed vial was stirred at 70° C. for 12 hr. The reaction mixture was filtered through a short plug of celite; the celite plug was washed with EtOAc (15 mL). The filtrate was washed with water and brine; the organic layer was dried over sodium sulfate, filtered and concentrated in vacuo to afford a tan residue. The resulting residue was purified by silica gel column chromatography using a gradient of MeOH (0 to 5%) in DCM to afford the title compound (26 mg, 72%) as an off-white solid. $^1$H NMR (400 MHz, DMSO-d$_6$) δ ppm 0.78-0.94 (m, 4H) 2.12 (s, 3H) 2.29-2.41 (m, 1H) 2.91 (s, 3H) 3.57 (s, 3H) 4.52-4.63 (m, 2H) 7.51-7.58 (m, 2H) 7.80-7.85 (m, 1H) 8.13-8.18 (m, 1H). LCMS (M+H)$^+$=373.

Example 57

N-[2-cyclopentyl-7-(5-methoxy-1-methyl-6-oxopyridin-3-yl)-1,3-benzoxazol-5-yl]ethanesulfonamide

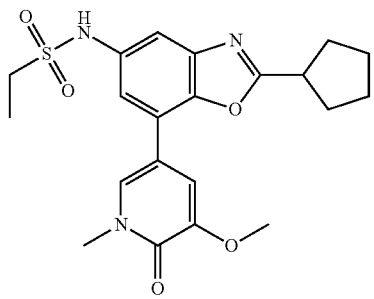 [SMILES: CCS(=O)(=O)Nc1cc(-c2cc(OC)c(=O)n(C)c2)c2oc(C3CCCC3)nc2c1]

The title compound (42 mg) was prepared as a pink solid in a similar manner to Example 47 except that cyclopentanecarbonyl chloride was substituted for cyclopropane-carbonyl chloride in step 1 and 3-methoxy-1-methyl-5-(4,4,5,5-tetramethyl-1,3,2-dioxaborolan-2-yl)pyridin-2-one was substituted for 1,3-dimethyl-5-(4,4,5,5-tetramethyl-1,3,2-dioxaborolan-2-yl)pyridin-2-one in step 3. $^1$H NMR (400 MHz, DMSO-d$_6$) δ ppm 1.17-1.28 (m, 3H) 1.60-1.83 (m, 4H) 1.91-2.03 (m, 2H) 2.05-2.18 (m, 2H) 3.04-3.15 (m, 2H) 3.40-3.51 (m, 1H) 3.57 (s, 3H) 3.80 (s, 3H) 7.18-7.27 (m, 1H) 7.30-7.37 (m, 1H) 7.41-7.46 (m, 1H) 7.77-7.84 (m, 1H) 9.71-9.85 (bs, 1H). LCMS (M+H)$^+$=432.

Example 58

5-[6-(cyclopropylmethoxy)-1-methyl-3-methylsulfonylindazol-5-yl]-1,3-dimethylpyridin-2-one

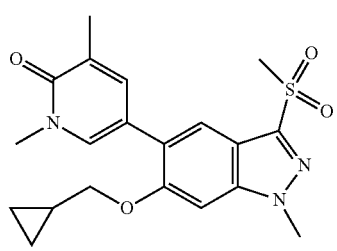 [SMILES: Cc1cc(-c2cc3c(S(C)(=O)=O)nn(C)c3cc2OCC2CC2)cn(C)c1=O]

A mixture of the title compound of Example 29, step 5 (40 mg, 0.11 mmol), 1,3-dimethyl-5-(4,4,5,5-tetramethyl-1,3,2-dioxaborolan-2-yl)pyridin-2-one (33 mg, 0.13 mmol), K$_2$CO$_3$ (46 mg, 0.33 mmol) and Pd(dppf)Cl$_2$ (8 mg, 0.01 mmol) in dioxane (6 mL) and H$_2$O (2 mL) was heated at 85° C. for 1 hr, cooled, diluted with H$_2$O (20 mL), and extracted with DCM (35 mL×2). The combined organic layers were dried over Na$_2$SO$_4$, filtered, concentrated, and the residue was purified using prep-TLC (PE/EtOAc 1:1) to give the title compound (21 mg, 46%) as a white solid. $^1$H NMR (400 MHz, DMSO-d$_6$): δ 7.76 (s, 1H), 7.74 (s, 1H), 7.55 (s, 1H), 7.36 (s, 1H), 4.12 (s, 3H), 4.02 (d, J=7.2 Hz, 2H), 3.51 (s, 3H), 3.33 (s, 3H), 2.06 (s, 3H), 1.29-1.24 (m, 1H), 0.61-0.56 (m, 2H), 0.39-0.35 (m, 2H). LCMS: 402 (M+H$^+$).

Example 59

5-[6-(cyclopropylmethoxy)-1-methyl-3-methylsulfonylindazol-5-yl]-3-methoxy-1-methylpyridin-2-one

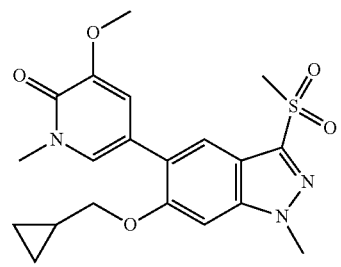 [SMILES: COc1cc(-c2cc3c(S(C)(=O)=O)nn(C)c3cc2OCC2CC2)cn(C)c1=O]

A mixture of the title compound of Example 29, step 5 (48 mg, 0.13 mmol), 3-methoxy-1-methyl-5-(4,4,5,5-tetramethyl-1,3,2-dioxaborolan-2-yl)pyridin-2-one (42 mg, 0.16 mmol), K$_2$CO$_3$ (56 mg, 0.41 mmol) and Pd(dppf)Cl$_2$ (10 mg, 0.01 mmol) in dioxane (6 mL) and H$_2$O (2 mL) was heated at 85° C. for 2 hr, cooled to RT, diluted with H$_2$O (30 mL), and extracted with DCM (30 mL×2). The combined organic layers were dried over Na$_2$SO$_4$, filtered, concentrated, and the residue was purified using prep-TLC (EtOAc) to give the title compound (26 mg, 46%) as a white solid. $^1$H NMR (400 MHz, CDCl$_3$): δ 7.99 (s, 1H), 7.18 (s, 1H), 7.02 (s, 1H), 6.80 (s, 1H), 4.17 (s, 3H), 3.98 (d, J=6.4 Hz, 2H), 3.91 (s, 3H), 3.70 (s, 3H), 3.32 (s, 3H), 1.37-1.31 (m, 1H), 0.73-0.71 (m, 2H), 0.43-0.42 (m, 2H). LCMS: 418 (M+H$^+$).

Example 60

N-[6-(1,5-dimethyl-6-oxopyridin-3-yl)-1-[(4-fluorophenyl)methyl]-2-methylimidazo[4,5-c]pyridin-4-yl]methanesulfonamide Step 1: 4,6-dichloro-1-[(4-fluorophenyl)methyl]-2-methylimidazo[4,5-c]pyridine

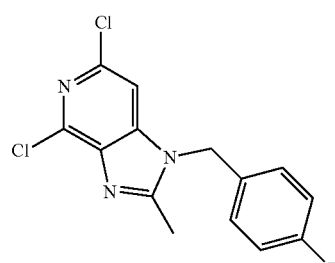

A mixture of 4,6-dichloro-2-methyl-1H-imidazo[4,5-c]pyridine (400 mg, 1.99 mmol), K$_2$CO$_3$ (414 mg, 3.0 mmol) and 4-fluorobenzyl bromide (454 mg, 2.39 mmol) in DMF (5 mL) was stirred at RT overnight. The mixture was partitioned between water (50 mL) and DCM (30 mL) and extracted with DCM (50 mL*2). The combined organic layers were washed with brine, dried over Na$_2$SO$_4$, filtered, concentrated, and purified using silica gel chromatography (PE:EA=5:1) to give the title compound (400 mg, 65%) as a brown solid. $^1$H NMR (300 MHz, DMSO-d$_6$): δ7.90 (s, 1H), 7.29-7.12 (m, 4H), 5.53 (s, 2H), 2.55 (s, 3H). LCMS: 310, 312 (M+H$^+$).

Step 2: N-[6-chloro-1-[(4-fluorophenyl)methyl]-2-methylimidazo[4,5-c]pyridin-4-yl]methanesulfonamide

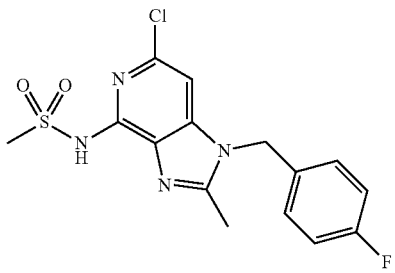 [SMILES: Cc1nc2c(NS(C)(=O)=O)nc(Cl)cc2n1Cc1ccc(F)cc1]

The title compound of step 1 (1.0 g, 3.2 mmol), methanesulfonamide (461 mg, 4.9 mmol) (AcO)$_2$Pd (72 mg, 0.32 mmol), Xantphos (203 mg, 0.35 mmol) and Cs$_2$CO$_3$ (1.36 g, 4.16 mmol) in DMF (8 mL) were microwaved at 120° C. under N$_2$ for 10 hr. The mixture was partitioned between water (50 mL) and DCM (30 mL) and extracted with DCM (50 mL×2). The combined organic layers were washed with brine, dried over Na$_2$SO$_4$, filtered, concentrated, and purified using silica gel chromatography (PE:EA=5:1) to give the title compound (318 mg, 27%) as a white solid. $^1$H NMR (300 MHz, DMSO-d$_6$): δ 11.10 (br, 1H), 7.52 (s, 1H), 7.26-7.17 (m, 4H), 5.49 (s, 2H), 3.46 (s, 3H), 2.52 (s, 3H). LCMS: 369 (M+H$^+$).

Step 3: N-[6-(1,5-dimethyl-6-oxopyridin-3-yl)-1-[(4-fluorophenyl)methyl]-2-methylimidazo[4,5-c]pyridin-4-yl]methanesulfonamide

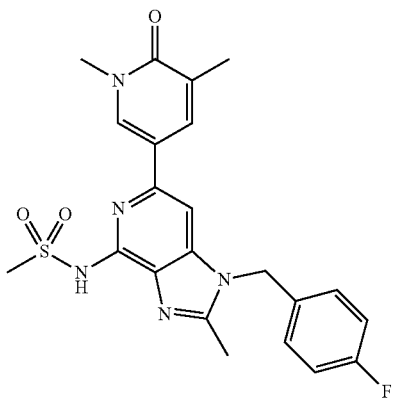 [SMILES: Cc1cc(-c2cc3c(nc(C)n3Cc3ccc(F)cc3)c(NS(C)(=O)=O)n2)cn(C)c1=O]

The title compound of step 2 (200 mg, 0.54 mmol), 1,3-dimethyl-5-(4,4,5,5-tetramethyl-1,3,2-dioxaborolan-2-yl)pyridin-2-one (161 mg, 0.65 mmol), KOAc (159 mg, 1.62 mmol) and dichloro[1,1'-bis(di-tert-butylphosphino)ferrocene]palladiumII (35 mg, 0.054 mmol) in DMF/H$_2$O (5 mL/1.0 mL) under N$_2$ were heated at 100° C. overnight, cooled, filtered, and the filtrate diluted with H$_2$O and extracted with EtOAc (50 mL). The organic layer was dried over Na$_2$SO$_4$, filtered, concentrated, and purified using prep-TLC (DCM:MeOH=15:1) followed by prep-HPLC to give the title compound (57 mg, 23%) as a white solid. $^1$H NMR (300 MHz, DMSO-d$_6$): δ 10.70 (br, 1H), 8.23 (s, 1H), 8.06 (s, 1H), 7.84 (s, 1H), 7.26-7.12 (m, 4H), 5.51 (s, 2H), 3.54 (s, 3H), 3.51 (s, 3H), 2.48 (s, 3H), 2.10 (s, 3H). LCMS: 456 (M+H$^+$).

Example 61

N-[1-benzyl-6-(1,5-dimethyl-6-oxopyridin-3-yl)-2-methylimidazo[4,5-c]pyridine-4-yl]methanesulfonamide

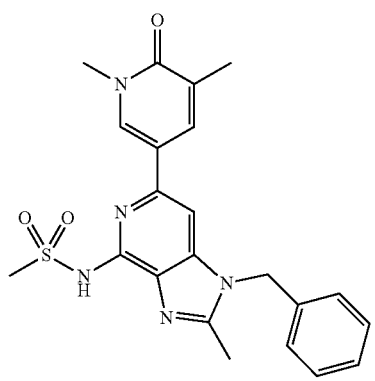 [SMILES: Cc1cc(-c2cc3c(nc(C)n3Cc3ccccc3)c(NS(C)(=O)=O)n2)cn(C)c1=O]

A three step synthesis was carried out in a similar manner as Example 60 except that benzyl bromide was substituted for 4-fluorobenzyl bromide in step 1. After purification, the title compound (52 mgs) was obtained as a white solid in 2% overall yield for the three steps. $^1$H NMR (400 MHz, DMSO-d$_6$): δ 10.70 (br, 1H), 8.23 (s, 1H), 8.05 (s, 1H), 7.82 (s, 1H), 7.36-7.12 (m, 5H), 5.53 (s, 2H), 3.53 (s, 3H), 3.52 (s, 3H), 2.48 (s, 3H), 2.10 (s, 3H). LCMS: 438 (M+H$^+$).

Example 62

N-[1-[(2,4-difluorophenyl)methyl]-6-(1,5-dimethyl-6-oxopyridin-3-yl)-2-methylimidazo[4,5-c]pyridin-4-yl]methanesulfonamide

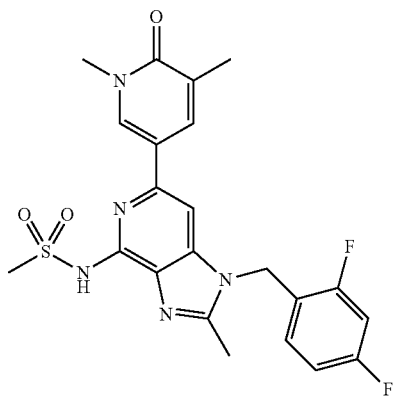 [SMILES: Cc1cc(-c2cc3c(nc(C)n3Cc3ccc(F)cc3F)c(NS(C)(=O)=O)n2)cn(C)c1=O]

A three step synthesis was carried out in a similar manner as Example 60 except that 2,4-difluorobenzyl bromide was substituted for 4-fluorobenzyl bromide in step 1. After purification, the title compound (37 mgs) was obtained as a white solid in 1% overall yield for the three steps. ¹H NMR (300 MHz, DMSO-d₆): δ 10.66 (br, 1H), 8.20 (s, 1H), 8.02 (s, 1H), 7.78 (s, 1H), 7.39-6.92 (m, 3H), 5.56 (s, 2H), 3.54 (s, 3H), 3.51 (s, 3H), 2.50 (s, 3H), 2.10 (s, 3H). LCMS: 474 (M+H⁺).

Example 63

5-[2-cyclopropyl-5-(methylsulfonylmethyl)-1,3-benzoxazol-7-yl]-3-methoxy-1-methylpyridin-2-one

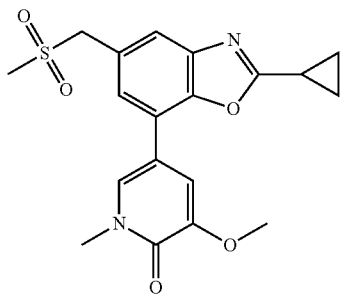 [SMILES: COc1cc(-c2cc(CS(C)(=O)=O)cc3nc(C4CC4)oc23)cn(C)c1=O]

The title compound (21 mg) was prepared as a white solid in a similar manner to Example 56 except that 3-methoxy-1-methyl-5-(4,4,5,5-tetramethyl-1,3,2-dioxaborolan-2-yl)pyridin-2-one was substituted for 1,3-dimethyl-5-(4,4,5,5-tetramethyl-1,3,2-dioxaborolan-2-yl)pyridin-2-one in step 6. ¹H NMR (400 MHz, DMSO-d₆) δ ppm 1.16-1.28 (m, 4H) 2.30-2.42 (m, 1H) 2.86-2.99 (s, 3H) 3.53-3.64 (s, 3H) 3.82 (s, 3H) 4.46-4.67 (s, 2H) 7.24-7.32 (m, 1H) 7.52-7.61 (m, 2H) 7.84-7.90 (m, 1H). LCMS (M+H)⁺=389.

Example 64

N-[6-(1,5-dimethyl-6-oxopyridin-3-yl)-3-fluoro-1-[(4-fluorophenyl)methyl]indazol-4-yl]methanesulfonamide Step 1: 6-bromo-3-fluoro-4-nitro-1H-indazole

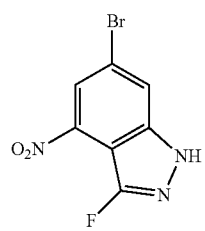 [SMILES: O=[N+]([O-])c1cc(Br)cc2[nH]nc(F)c12]

To a mixture of 6-bromo-4-nitro-1H-indazole (3 g, 6.2 mmol) in ACN (30 mL) and CH₃COOH (6 mL) was added Selectfluor (8.76 g, 12.4 mmol) in one portion at 25° C. under N₂. The mixture was stirred at 100° C. for 2 days. It was concentrated under reduced pressure, diluted with DCM (50 mL) and filtered. The filtrate was concentrated under reduced pressure and purified by silica gel column chromatography (PE:EA=20:1) and preparative HPLC to the title compound (1.2 g, 37%). ¹H NMR (CDCl₃, 400 MHz) δ 8.22 (s, 1H), 7.94 (s, 1H).

Step 2: 6-bromo-3-fluoro-1-[(4-fluorophenyl)methyl]-4-nitroindazole

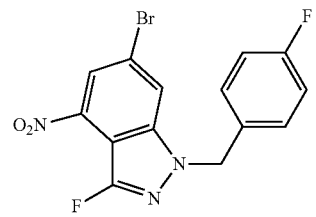 [SMILES: O=[N+]([O-])c1cc(Br)cc2c1c(F)nn2Cc1ccc(F)cc1]

To the title compound from step 1 (200 mg, 770 μmol) in THF (3 mL) was added NaH (40 mg, 1000 μmol) at 0° C. under a N₂ atmosphere. The mixture was stirred at that temperature for 10 min before addition of 1-(bromomethyl)-4-fluoro-benzene (190 mg, 1000 μmol). The reaction mixture was stirred at 25° C. for 12 hr. It was then concentrated under reduced pressure and purified by silica gel column chromatography (PE:EA=20:1) to give the title compound (220 mg, 78%). ¹H NMR (CDCl₃, 400 MHz) δ 8.16 (d, J=1.2 Hz, 1H), 7.79 (s, 1H), 7.24 (m, 2H), 7.06 (m, 2H), 5.43 (s, 2H).

Step 3: 5-[3-fluoro-1-[(4-fluorophenyl)methyl]-4-nitroindazol-6-yl]-1,3-dimethylpyridin-2-one

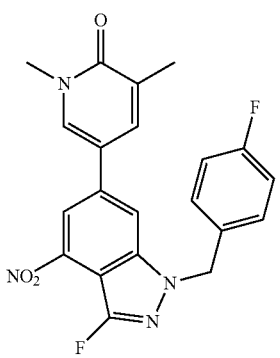 [SMILES: Cc1cc(-c2cc([N+](=O)[O-])c3c(F)nn(Cc4ccc(F)cc4)c3c2)cn(C)c1=O]

To a mixture of the title compound from step 2 (110 mg, 300 μmol) and 1,3-dimethyl-5-(4,4,5,5-tetramethyl-1,3,2-dioxaborolan-2-yl)pyridin-2-one (97 mg, 390 umol) in 1,4-dioxane (5 mL) and H₂O (0.5 mL) was added K₃PO₄ (127 mg, 600 μmol) and Pd(dppf)Cl₂ (11 mg, 15 μmol) in one portion under N₂. The mixture was stirred at 90° C. for 12 hr. After cooling to RT, it was concentrated under reduced pressure. The residue was purified by silica gel column chromatography (PE:EA=20:1) to afford the title compound (110 mg, 90% yield) as a yellow solid.

LCMS: 411 (M+H)⁺.

Step 4: 5-[4-amino-3-fluoro-1-[(4-fluorophenyl)methyl]indazol-6-yl]-1,3-dimethylpyridin-2-one

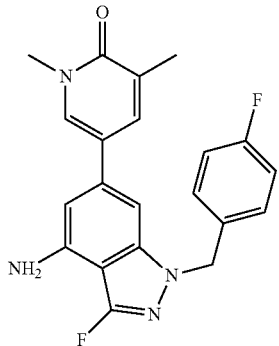

To the title compound from step 3 (110 mg, 268 umol) in EtOH (6 mL) and H₂O (3 mL) was added NH₄Cl (72 mg, 1.34 mmol) and Fe (75 mg, 1.34 mmol) in one portion under N₂. The reaction was stirred at 100° C. for 1 hr. The mixture was filtered, basified and extracted with DCM (30 mL). The organic layer was concentrated under reduced pressure to afford the title compound that was used directly in next step without further purification. LCMS: 381.1 (M+H⁺).

Step 5: N-[6-(1,5-dimethyl-6-oxopyridin-3-yl)-3-fluoro-1-[(4-fluorophenyl)methyl]indazol-4-yl]methanesulfonamide

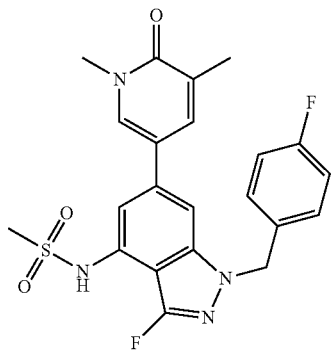 [SMILES: Cc1cc(-c2cc(NS(C)(=O)=O)c3c(F)nn(Cc4ccc(F)cc4)c3c2)cn(C)c1=O]

The title compound was prepared in a manner similar to Example 17, step 4, by substituting 5-[4-amino-3-fluoro-1-[(4-fluorophenyl)methyl]indazol-6-yl]-1,3-dimethylpyridin-2-one for 1-benzyl-6-bromoindol-4-amine. ¹H NMR (CDCl₃, 400 MHz) δ 7.46 (s, 1H), 7.43 (s, 1H), 7.31 (s, 1H), 7.23-7.24 (m, 2H), 7.01-7.06 (m, 3H), 6.89 (s, 1H), 5.39 (s, 2H), 3.65 (s, 3H), 3.15 (s, 3H), 2.25 (s, 3H). LCMS: 459.0 (M+H⁺).

Example 65

N-[3-fluoro-1-[(4-fluorophenyl)methyl]-6-(5-methoxy-1-methyl-6-oxopyridin-3-yl)indazol-4-yl]methanesulfonamide

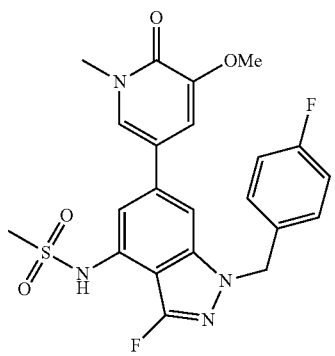 [SMILES: COc1cc(-c2cc(NS(C)(=O)=O)c3c(F)nn(Cc4ccc(F)cc4)c3c2)cn(C)c1=O]

The title compound was prepared in a manner similar to Example 64 by substituting 3-methoxy-1-methyl-5-(4,4,5,5-tetramethyl-1,3,2-dioxaborolan-2-yl)pyridin-2-one for 1,3-dimethyl-5-(4,4,5,5-tetramethyl-1,3,2-dioxaborolan-2-yl)pyridin-2-one in step 3. ¹H NMR (CDCl₃, 400 MHz) δ 7.34 (s, 1H), 7.25-7.27 (m, 2H), 7.17 (d, J=2.4 Hz, 1H), 7.06-7.08 (m, 2H), 7.00 (s, 1H), 6.81 (m, 1H), 6.80 (s, 1H), 5.42 (s, 2H), 3.92 (s, 3H), 3.69 (s, 3H), 3.16 (s, 3H). LCMS: 475.1 (M+H⁺).

Example 66

N-[1-(cyclopropylmethyl)-6-(1,5-dimethyl-6-oxopyridin-3-yl)-3-fluoroindazol-4-yl]methanesulfonamide

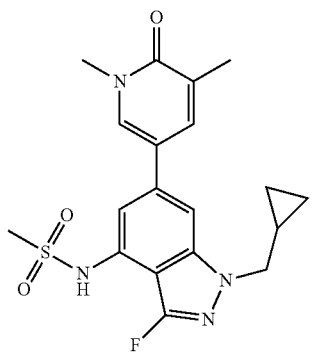 [SMILES: Cc1cc(-c2cc(NS(C)(=O)=O)c3c(F)nn(CC4CC4)c3c2)cn(C)c1=O]

The title compound was prepared in a manner similar to Example 64 by substituting bromomethylcyclopropane for 1-(bromomethyl)-4-fluoro-benzene in step 2. ¹H NMR (CDCl₃, 400 MHz) δ 7.52 (s, 1H), 7.47 (s, 1H), 7.30 (s, 1H), 7.08 (s, 1H), 6.87 (s, 1H), 4.12 (d, J=7.2 Hz, 2H), 3.67 (s, 3H), 3.14 (s, 3H), 2.27 (s, 3H), 1.31 (m, 1H), 0.63 (m, 2H), 0.43 (m, 2H). LCMS: 405.0 (M+H⁺).

Example 67

5-(3-benzyl-2-methyl-7-methylsulfonylbenzimidazol-5-yl)-1,3-dimethylpyridin-2-one Step 1: N-benzyl-5-bromo-3-fluoro-2-nitroaniline

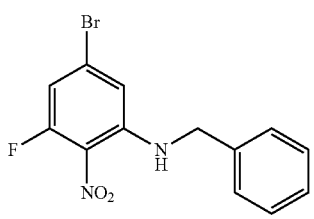 [SMILES: O=[N+]([O-])c1c(F)cc(Br)cc1NCc1ccccc1]

A mixture of 5-bromo-1,3-difluoro-2-nitrobenzene (3.00 g, 12.6 mmol), K₂CO₃ (8.7 g, 63 mmol) and benzyl amine (1.35 g, 12.6 mmol) in THF (150 mL) was stirred at RT for 3 hr. The reaction mixture was diluted with water (300 mL) and DCM (100 mL). The aqueous phase was separated and extracted with DCM (100 mL×2). The combined organic layers were washed with brine, dried over Na₂SO₄, filtered and concentrated under reduced pressure. The residue was purified by column chromatography on silica gel (PE: DCM=5:1) to give the title compound (3.5 g, 85%) as a yellow solid. ¹H NMR (300 MHz, CDCl₃): δ 7.62 (s, 1H), 7.40-7.26 (m, 5H), 6.77 (t, J=1.8 Hz, 1H), 6.64 (m, 1H), 4.45 (d, J=5.4 Hz, 2H). LCMS: 325; 327 (M+H)+.

Step 2:
N-benzyl-5-bromo-3-methylsulfanyl-2-nitroaniline

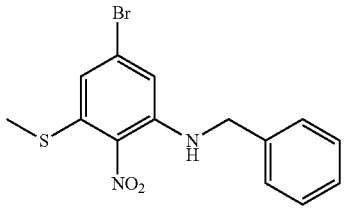 [SMILES: CSc1cc(Br)cc(NCc2ccccc2)c1[N+](=O)[O-]]

To a solution of the title compound from step 1 (750 mg, 2.3 mmol) in THF (20 mL) was added sodium methanethiolate (240 mg, 3.5 mmol). The reaction mixture was stirred at rt overnight. The mixture was poured over ice water (30 ml) and extracted with DCM (30 mL×2). The combined organic layers were washed with brine, dried over Na₂SO₄, filtered and concentrated. The residue was purified by column chromatography on silica gel (PE:DCM=5:1) to give the title compound (300 mg, 37%) as a solid. LCMS: 353; 355 (M+H)⁺.

Step 3:
N-benzyl-5-bromo-3-methylsulfonyl-2-nitroaniline

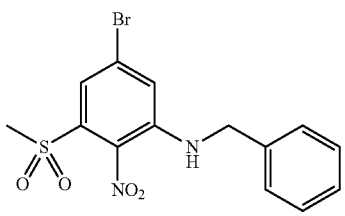 [SMILES: CS(=O)(=O)c1cc(Br)cc(NCc2ccccc2)c1[N+](=O)[O-]]

To a solution of the title compound form step 2 (750 mg, 2.1 mmol) in DCM (70 mL) was added 3-chloroperoxybenzoic acid (1.65 mg, 9.6 mmol). The reaction mixture was stirred at RT overnight. The mixture was poured over ice water (30 ml) and extracted with DCM (30 mL×2). The combined organic layers were washed with brine and saturated NaHCO₃ solution (100 ml), dried over Na₂SO₄, filtered and concentrated under reduced pressure. The residue was purified by column chromatography on silica gel (PE: EA=30:1) to give the title compound (820 mg, 85%). ¹H NMR (300 MHz, CDCl₃): δ 7.56 (s, 1H), 7.40-7.23 (m, 6H), 6.51 (s, 1H), 4.45 (d, J=4.2 Hz, 2H), 3.44 (s, 3H). LCMS: 402; 404 (M+NH₄)⁺.

Step 4: 1-benzyl-6-bromo-2-methyl-4-methylsulfonylbenzimidazole

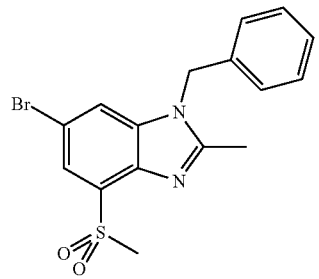 [SMILES: Cc1nc2c(S(C)(=O)=O)cc(Br)cc2n1Cc1ccccc1]

The title compound from step 3 (350 mg, 0.9 mmol) was suspended in MeOH (30 mL) and saturated NH₄Cl aqueous solution (10 mL). Iron (300 mg, 5.4 mmol) was added and the mixture was heated to 80° C. for 1 hr. The reaction mixture was then filtered. The filtrate was diluted with H₂O and extracted with EtOAc (30 mL×2). The combined organic layers were dried over Na₂SO₄, filtered and concentrated under reduced pressure. The residue was dissolved in 5M HCl (2 mL, 10 mmol) followed by 2,4-pentanedione (753 mg, 7.5 mmol) addition. The reaction mixture was heated to 75° C. for 1 hr. After cooling to RT and neutralization with a NaHCO₃ solution, it was extracted with EtOAc (30 mL×3). The combined organic layers were washed with brine, dried over Na₂SO₄, filtered and concentrated under reduced pressure to give the title compound (260 mg, 76%) as a solid. ¹H NMR (300 MHz, CDCl₃): δ 8.01 (s, 1H), 7.62 (s, 1H), 7.34-7.26 (m, 3H), 7.07-7.00 (m, 2H), 5.33 (s, 2H), 3.47 (s, 3H), 2.64 (s, 3H).
LCMS: 379; 381 (M+H)⁺

Step 5: 5-(3-benzyl-2-methyl-7-methylsulfonylbenzimidazol-5-yl)-1,3-dimethylpyridin-2-one

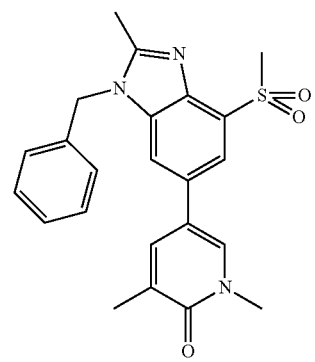 [SMILES: Cc1cc(-c2cc(S(C)(=O)=O)c3nc(C)n(Cc4ccccc4)c3c2)cn(C)c1=O]

The title compound form step 4 (100 mg, 0.26 mmol), 1,3-dimethyl-5-(4,4,5,5-tetramethyl-1,3,2-dioxaborolan-2-yl)pyridin-2-one (90 mg, 0.36 mmol), K₂CO₃ (108 mg, 0.78 mmol) and Pd(dppf)Cl₂ (40 mg, 0.054 mmol) in a DMF/H₂O mixture (10 mL/1 mL) under N₂ was heated to 100° C. for 3 hr. After cooling to RT, addition of water, and EtOAc extractive work up (50 mL×3), the combined organic layers were dried over Na₂SO₄, filtered and concentrated under reduced pressure. The residue was chromatographed on silica gel (EtOAc/MeOH, 15:1) to give the title compound (55 mg, 50%). ¹H NMR (300 MHz, CDCl₃): δ 7.92 (s, 1H), 7.46-7.41 (m, 3H), 7.36-7.26 (m, 3H), 7.08-7.05 (m, 2H), 5.41 (s, 2H), 3.62 (s, 3H), 3.51 (s, 3H), 2.65 (s, 3H), 2.22 (s, 3H).
LCMS: 422 (M+H)⁺.

Example 68

5-(3-benzyl-7-ethylsulfonyl-2-methylbenzimidazol-5-yl)-3-methoxy-1-methylpyridin-2-one

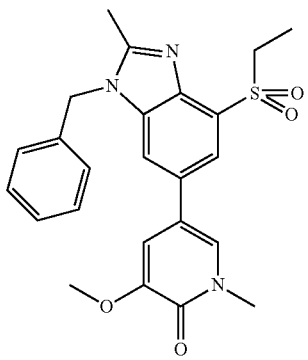 [SMILES: CCS(=O)(=O)c1cc(-c2cc(OC)c(=O)n(C)c2)cc2c1nc(C)n2Cc1ccccc1]

The title compound was prepared in a manner similar to Example 67 by substituting sodium ethanethiolate for sodium methanethiolate in step 2 and 3-methoxy-1-methyl-5-(4,4,5,5-tetramethyl-1,3,2-dioxaborolan-2-yl)pyridin-2-one for 1,3-dimethyl-5-(4,4,5,5-tetramethyl-1,3,2-dioxaborolan-2-yl)pyridin-2-one in step 5. ¹H NMR (300 MHz, CDCl₃): δ 7.92 (s, 1H), 7.42-7.26 (m, 4H), 7.13-7.08 (m, 3H), 6.81 (d, J=1.8 Hz, 1H), 5.42 (s, 2H), 3.88 (s, 3H), 3.75 (q, J=7.5 Hz, 2H), 3.64 (s, 3H), 2.65 (s, 3H), 1.32 (t, J=7.2 Hz, 3H). LCMS: 452 (M+H)⁺.

Example 69

5-[3-(cyclopropylmethyl)-7-ethylsulfonyl-2-methyl-benzimidazol-5-yl]-1,3-dimethylpyridin-2-one

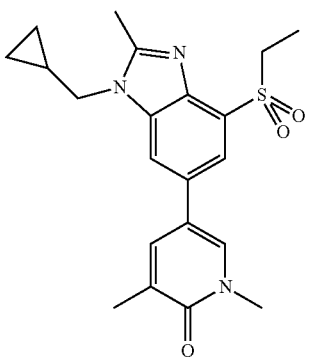 [SMILES: CCS(=O)(=O)c1cc(-c2cc(C)c(=O)n(C)c2)cc2c1nc(C)n2CC1CC1]

The title compound was prepared in a manner similar to Example 67 by substituting cyclopropylmethanamine for benzyl amine in step 1 and sodium ethanethiolate for sodium methanethiolate in step 2. ¹H NMR (400 MHz, DMSO-d₆): δ 8.14 (s, 1H), 8.07 (s, 1H), 7.83 (s, 1H), 7.78 (s, 1H), 4.23 (d, J=7.2 Hz, 2H), 3.73-3.68 (m, 2H), 3.56 (s, 3H), 2.70 (s, 3H), 2.13 (s, 3H), 1.35-1.32 (m, 1H), 1.09 (t, J=7.2 Hz, 3H), 0.55-0.45 (m, 4H). LCMS: 400 (M+H)+.

Example 70

5-[3-(cyclopropylmethyl)-7-ethylsulfonyl-2-methyl-benzimidazol-5-yl]-3-methoxy-1-methylpyridin-2-one

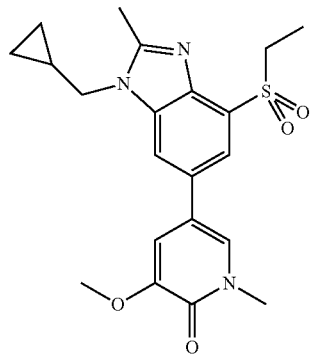 [SMILES: CCS(=O)(=O)c1cc(-c2cc(OC)c(=O)n(C)c2)cc2c1nc(C)n2CC1CC1]

The title compound was prepared in a manner similar to Example 67 by substituting cyclopropylmethanamine for benzyl amine in step 1, sodium ethanethiolate for sodium methanethiolate in step 2 and 3-methoxy-1-methyl-5-(4,4,5,5-tetramethyl-1,3,2-dioxaborolan-2-yl)pyridin-2-one for 1,3-dimethyl-5-(4,4,5,5-tetramethyl-1,3,2-dioxaborolan-2-yl)pyridin-2-one in step 5. ¹H NMR (400 MHz, DMSO-d₆): δ 8.14 (s, 1H), 7.79 (s, 1H), 7.76 (d, J=1.6 Hz, 1H), 7.21 (s, 1H), 4.25 (d, J=6.8 Hz, 2H), 3.85 (s, 3H), 3.74-3.68 (m, 2H), 3.56 (s, 3H), 2.67 (s, 3H), 1.34-1.32 (m, 1H), 1.11 (t, J=7.2 Hz, 3H), 0.54-0.46 (m, 4H). LCMS: 416 (M+H)⁺.

Example 71

5-[3-(cyclopropylmethyl)-2-methyl-7-methylsulfonyl benzimidazol-5-yl]-1,3-dimethylpyridin-2-one

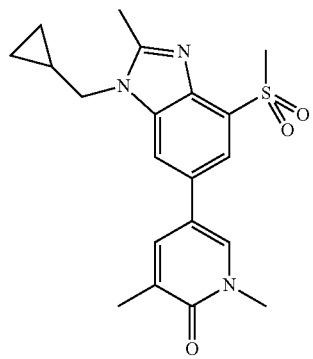 [SMILES: Cc1cc(-c2cc(S(C)(=O)=O)c3nc(C)n(CC4CC4)c3c2)cn(C)c1=O]

The title compound was prepared in a manner similar to Example 67 by substituting cyclopropylmethanamine for benzyl amine in step 1. ¹H NMR (400 MHz, DMSO-d₆): δ 8.13 (s, 1H), 8.07 (s, 1H), 7.82 (s, 1H), 7.79 (s, 1H), 4.24 (d, J=7.2 Hz, 2H), 3.56 (s, 3H), 3.52 (s, 3H), 2.68 (s, 3H), 2.13 (s, 3H), 1.34-1.31 (m, 1H), 0.53-0.48 (m, 4H). LCMS: 386 (M+H)⁺.

Example 72

N-[1-(cyclopropylmethyl)-6-(1,5-dimethyl-6-oxopyridin-3-yl)-2-ethoxybenzimidazol-4-yl]methanesulfonamide Step 1: 5-bromo-N-(cyclopropylmethyl)-3-fluoro-2-nitroaniline

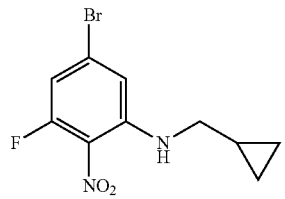

5-bromo-1,3-difluoro-2-nitrobenzene was converted to the title compound in a manner similar to Example 67, step 1 except that cyclopropylmethylamine was substituted for benzylamine.

Step 2: N-[5-bromo-3-(cyclopropylmethylamino)-2-nitrophenyl]methanesulfonamide

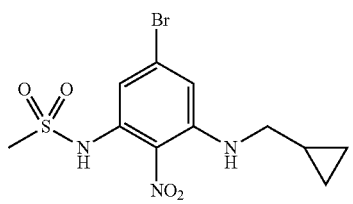 [SMILES: CS(=O)(=O)Nc1cc(Br)cc(NCC2CC2)c1[N+](=O)[O-]]

To methanesulfonamide (1.32 g, 13.9 mmol) in DMF (40 ml) was added t-BuOK (1.09 g, 9.7 mmol) at RT. After stirring for 30 min, the title compound from step 1 (2.0 g, 6.9 mmol) was added. The mixture was stirred overnight, poured into ice water (50 ml), adjusted to pH 6-7 with acetic acid, and extracted with EA (50 mL×2). The combined organic layers were washed with brine, dried over $Na_2SO_4$, and concentrated to give a red residue which was then triturated with ether (30 ml). The yellow solid that remained was dried to give the title compound (1.1 g, 44%). $^1$H NMR (300 MHz, DMSO-$d_6$): δ 9.81 (s, 1H), 7.07-7.04 (m, 1H), 6.96 (d, J=1.8 Hz, 1H), 6.84 (d, J=1.8 Hz, 1H), 3.14-3.04 (m, 5H), 1.10-1.04 (m, 1H), 0.50-0.44 (m, 2H), 0.27-0.21 (m, 2H). LCMS: 364, 366 (M+H$^+$).

Step 3: N-[2-amino-5-bromo-3-(cyclopropylmethylamino)phenyl]methanesulfonamide

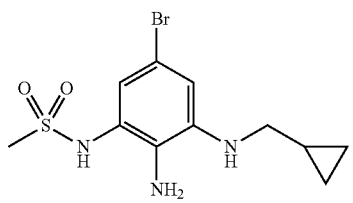

To the title compound from step 2 (850 mg, 2.34 mmol) in MeOH (30 mL) was added saturated aqueous $NH_4Cl$ (10 mL) and Fe (655 mg, 11.7 mmol). The mixture was heated at 80° C. for 1 hr and then filtered. The solids removed by filtration were washed with EA, and water was added to the combined filtrate and washings. EA extraction (40 mL×2) was carried out, and the combined organic layers were dried over $Na_2SO_4$, filtered, and concentrated to give the title compound (690 mg, 88%) as a yellow solid. LCMS: 334, 336 (M+H$^+$).

Step 4: N-[6-bromo-1-(cyclopropylmethyl)-2-ethoxy-benzimidazol-4-yl]methanesulfonamide

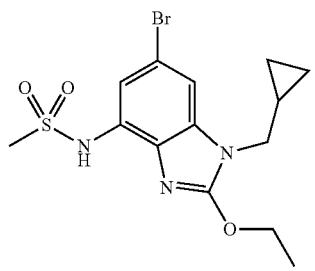 [SMILES: CCOc1nc2c(NS(C)(=O)=O)cc(Br)cc2n1CC1CC1]

To the title compound of step 3 (150 mg, 0.45 mmol) in AcOH (4 mL) was added tetraethylorthocarbonate (259 mg, 1.35 mmol). The mixture was heated at 60° C. for 0.5 hr, cooled, diluted with water, neutralized with saturated aqueous $NaHCO_3$, and extracted with EA (30 mL×2). The combined organic layers were washed with brine, dried over $Na_2SO_4$, concentrated, and purified using silica gel chromatography (PE:EA=2:1) to give the title compound (75 mg, 43%) as a white solid. $^1$H NMR (300 MHz, DMSO-$d_6$): δ 9.55 (s, 1H), 7.56 (d, J=2.1 Hz, 1H), 7.12 (d, J=2.1 Hz, 1H), 4.57 (q, J=7.2 Hz, 2H), 3.90 (d, J=5.1 Hz, 2H), 3.25 (s, 3H), 1.28-1.17 (m, 1H), 1.09 (t, J=6.9 Hz, 3H), 0.52-0.36 (m, 4H). LCMS: 388, 390 (M+H$^+$).

Step 5: N-[1-(cyclopropylmethyl)-6-(1,5-dimethyl-6-oxopyridin-3-yl)-2-ethoxybenzimidazol-4-yl]methanesulfonamide

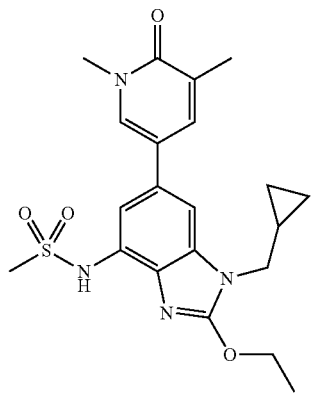 [SMILES: CCOc1nc2c(NS(C)(=O)=O)cc(-c3cc(C)c(=O)n(C)c3)cc2n1CC1CC1]

The title compound of step 4 (75 mg, 0.19 mmol), 1,3-dimethyl-5-(4,4,5,5-tetra-methyl-1,3,2-dioxaborolan-2-yl)pyridin-2-one (58 mg, 0.23 mmol), $K_2CO_3$ (79 mg, 0.57 mmol) and Pd(dppf)Cl$_2$ (15 mg, 0.019 mmol) in dioxane/

H₂O (9 mL/3 mL) under N₂ were heated at 85° C. for 3 hr. The mixture was cooled and filtered, and the filtrate was diluted with water and extracted with EtOAc (30 mL×3). The combined organic layers were dried over Na₂SO₄, filtered, and concentrated to give a residue which was triturated with EA/ether (3 ml/20 ml). The white solid that remained was dried to give the title compound (48 mg, 58%). ¹H NMR (400 MHz, DMSO-d₆): δ 9.36 (s, 1H), 7.91 (s, 1H), 7.72 (s, 1H), 7.49 (s, 1H), 7.13 (s, 1H), 4.57 (q, J=6.4 Hz, 2H), 3.92 (d, J=6.4 Hz, 2H), 3.54 (s, 3H), 3.26 (s, 3H), 2.10 (s, 3H), 1.43 (t, J=6.8 Hz, 3H), 1.31-1.28 (m, 1H), 0.51-0.42 (m, 4H). LCMS: 431 (M+H⁺).

Example 73

N-[1-(cyclopropylmethyl)-6-(1,5-dimethyl-6-oxopyridin-3-yl)-2-methoxybenzimidazol-4-yl]methanesulfonamide Step 1: N-[6-bromo-1-(cyclopropylmethyl)-2-methoxybenzimidazol-4-yl]methanesulfonamide

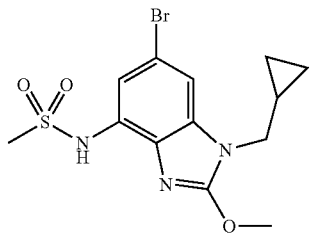 [SMILES: COc1nc2c(NS(C)(=O)=O)cc(Br)cc2n1CC1CC1]

To the title compound of Example 72, step 3 (200 mg, 0.60 mmol) in AcOH (5 mL) was added tetramethylorthocarbonate (245 mg, 1.8 mmol). The mixture was heated at 60° C. for 0.5 hr, cooled, diluted with water, neutralized with saturated aqueous NaHCO₃, and extracted with EA (40 mL×2). The combined organic layers were washed with brine, dried over Na₂SO₄, filtered, concentrated and purified using silica gel chromatography (PE:EA=2:1) to give the title compound (130 mg, 58%) as a white solid. LCMS: 374, 376 (M+H⁺).

Step 2: N-[1-(cyclopropylmethyl)-6-(1,5-dimethyl-6-oxopyridin-3-yl)-2-methoxybenzimidazol-4-yl]methanesulfonamide

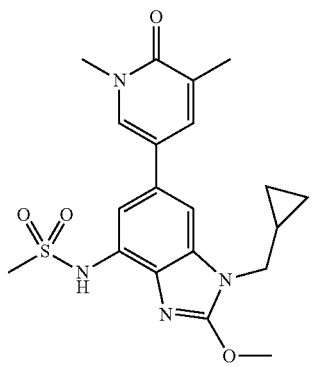 [SMILES: COc1nc2c(NS(C)(=O)=O)cc(-c3cc(C)c(=O)n(C)c3)cc2n1CC1CC1]

The title compound of step 1 (130 mg, 0.35 mmol), 1,3-dimethyl-5-(4,4,5,5-tetramethyl-1,3,2-dioxaborolan-2-yl)pyridin-2-one (104 mg, 0.41 mmol), K₂CO₃ (145 mg, 1.05 mmol) and Pd(dppf)Cl₂ (26 mg, 0.035 mmol) in dioxane/H₂O (12 mL/4 mL) under N₂ were heated at 85° C. for 3 hr. The mixture was cooled and filtered, and the filtrate was diluted with water and extracted with EtOAc (50 mL×3). The combined organic layers were dried over Na₂SO₄, filtered, and concentrated to give a residue which was triturated with EA (5 ml). The white solid that remained was dried to give the title compound (69 mg, 48%). ¹H NMR (400 MHz, DMSO-d₆): δ 9.38 (s, 1H), 7.91 (s, 1H), 7.73 (s, 1H), 7.49 (s, 1H), 7.14 (s, 1H), 4.15 (s, 3H), 3.92 (d, J=7.2 Hz, 2H), 3.54 (s, 3H), 3.26 (s, 3H), 2.10 (s, 3H), 1.30-1.29 (m, 1H), 0.50-0.41 (m, 4H). LCMS: 417 (M+H⁺).

Example 74

N-[1-(cyclopropylmethyl)-6-(1,5-dimethyl-6-oxopyridin-3-yl)-2-ethylbenzimidazol-4-yl]methanesulfonamide Step 1: N-[6-bromo-1-(cyclopropylmethyl)-2-ethylbenzimidazol-4-yl]methanesulfonamide

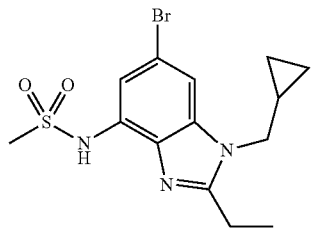 [SMILES: CCc1nc2c(NS(C)(=O)=O)cc(Br)cc2n1CC1CC1]

To the title compound of Example 72, step 3 (150 mg, 0.45 mmol) in AcOH (5 mL) was added triethylorthopropionate (238 mg, 1.35 mmol). The mixture was heated at 60° C. for 0.5 hr, cooled, diluted with water, neutralized with saturated aqueous NaHCO₃, and extracted with EA (20 mL×2). The combined organic layers were washed with brine, dried over Na₂SO₄, filtered, concentrated and purified using silica gel chromatography (PE:EA=2:1) to give the title compound (80 mg, 48%) as a white solid. ¹H NMR (300 MHz, DMSO-d₆): δ 7.65 (d, J=1.2 Hz, 1H), 7.15 (d, J=1.2 Hz, 1H), 4.10 (d, J=6.6 Hz, 2H), 2.95-2.88 (q, J=7.5 Hz, 2H), 2.65 (s, 3H), 1.36 (t, J=7.5 Hz, 3H), 1.23-1.18 (m, 1H), 0.51-0.39 (m, 4H). LCMS: 372, 374 (M+H⁺).

Step 2: N-[1-(cyclopropylmethyl)-6-(1,5-dimethyl-6-oxopyridin-3-yl)-2-ethylbenzimidazol-4-yl]methanesulfonamide

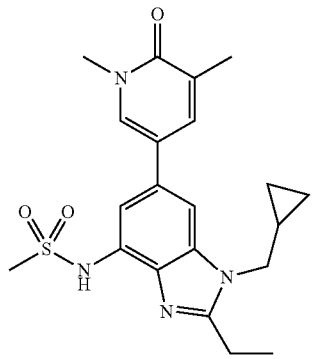 [SMILES: CCc1nc2c(NS(C)(=O)=O)cc(-c3cc(C)c(=O)n(C)c3)cc2n1CC1CC1]

The title compound of step 1 (80 mg, 0.22 mmol), 1,3-dimethyl-5-(4,4,5,5-tetramethyl-1,3,2-dioxaborolan-2-yl)pyridin-2-one (64 mg, 0.26 mmol), K2CO3 (89 mg, 0.65 mmol) and Pd(dppf)Cl₂ (16 mg, 0.022 mmol) in dioxane/

H₂O (9 mL/3 mL) under N₂ were heated at 85° C. for 3 hr. The mixture was cooled and filtered, and the filtrate was diluted with water and extracted with EtOAc (50 mL×3). The combined organic layers were dried over Na₂SO₄, filtered, and concentrated to give a residue which was purified by prep-TLC (DCM:MeOH:20:1) to give the title compound (23 mg, 25%) as a yellow solid. ¹H NMR (400 MHz, DMSO-d₆): δ 9.36 (s, 1H), 7.91 (s, 1H), 7.72 (s, 1H), 7.49 (s, 1H), 7.13 (s, 1H), 4.57 (q, J=6.4 Hz, 2H), 3.92 (d, J=6.4 Hz, 2H), 3.54 (s, 3H), 3.26 (s, 3H), 2.10 (s, 3H), 1.43 (t, J=6.8 Hz, 3H), 1.31-1.28 (m, 1H), 0.51-0.42 (m, 4H) LCMS: 415 (M+H⁺).

Example 75

5-(1-ethyl-4-methylsulfonylindol-2-yl)-1,3-dimethylpyridin-2-one

Step 1: 4-methylsulfanyl-1H-indole

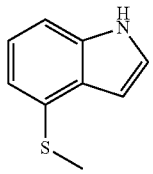

To a solution of 4-bromo-1H-indole (8.0 g, 41 mmol) in dry THF (100 mL) was added sodium hydride (50%, 3.6 g, 90 mmol) at 0° C. Twenty minutes later, the reaction mixture was cooled to −78° C. and t-BuLi (1.3 M in THF, 63 mL) was added dropwise under nitrogen. After thirty min, a solution of dimethyl disulfide (7.7 g, 82 mmol) in THF (10 mL) was added drop wise at −78° C. Thirty min later, the reaction was poured over ice water (100 mL) and extracted with ethyl acetate (3×100 mL). The combined organic layers were washed with brine, dried over sodium sulfate, filtered and concentrated under reduced pressure. The residue was purified by silica gel flash chromatography (EtOAc/petroleum ether, 0-10%) to give the title product (3.7 g, 56%). ¹H NMR (CDCl₃, 300 MHz): δ 8.25 (brs, 1H), 7.26-7.24 (m, 2H), 7.19 (t, J=7.8 Hz, 1H), 7.02 (d, J=7.5 Hz, 1H), 6.69 (m, 1H), 2.59 (s, 3H). LCMS: 164 (M+H⁺).

Step 2: 1-(benzenesulfonyl)-4-methylsulfanylindole

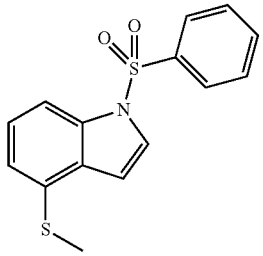 [SMILES: CSc1cccc2c1ccn2S(=O)(=O)c1ccccc1]

To a solution of the title compound from step 1 (3.6 g, 22 mmol) in dry DMF (100 mL) cooled with an ice bath was added NaH (60%, 1.3 g, 33 mmol). The mixture was stirred for thirty min. Benzenesulfonyl chloride (5.8 g, 33 mmol) was added drop wise at 0° C. and the reaction was stirred for 2 hr. After this time, the mixture was poured over ice water and filtered to give the title compound as a yellow solid (4.6 g, 70%). ¹H NMR (CDCl₃, 300 MHz): δ 8.05 (d, J=8.1 Hz, 1H), 7.87 (m, 2H), 7.81 (d, J=8.1 Hz, 1H), 7.58 (d, J=3.9 Hz, 1H), 7.43 (m, 2H), 7.26 (t, J=3.9 Hz, 1H), 7.08 (d, J=8.4 Hz, 1H), 6.78 (d, J=3.6 Hz, 1H), 2.51 (s, 3H). LCMS: 304 (M+H)⁺.

Step 3:
1-(benzenesulfonyl)-2-bromo-4-methylsulfanylindole

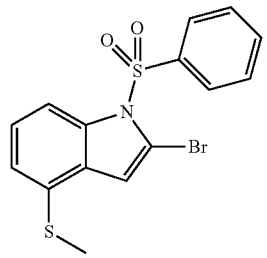 [SMILES: CSc1cccc2c1cc(Br)n2S(=O)(=O)c1ccccc1]

To a solution of the title compounds from step 2 (1.6 g, 5.2 mmol) in dry THF (20 mL) was added LDA (2.0 M in THF, 3.9 mL, 7.8 mmol) under nitrogen at −78° C. The reaction was stirred for 30 min. A solution of 1,2-dibromo-1,1,2,2-tetrachloroethane (2.6 g, 7.9 mmol) in dry THF (10 mL) was added drop wise at the same temperature over 20 min and the reaction was stirred for 1 hr. The mixture was slowly poured over aqueous NH₄Cl (50 mL) cooled with an ice bath. It was extracted with ethyl acetate (3×30 mL). The combined organic layers were washed with brine, dried over sodium sulfate, filtered and concentrated under reduced pressure. The residue was purified by column chromatography on silica gel (petroleum ether/ethyl acetate, 5:1) to give the title product as a white solid (1.3 g, 65%). ¹H NMR (CDCl₃, 400 MHz): δ 8.09 (d, J=8.8 Hz, 1H), 7.89 (m, 2H), 7.56 (m, 1H), 7.44 (m, 2H), 7.28 (m, 1H), 7.11 (d, J=7.6 Hz, 1H), 6.87 (s, 1H), 2.50 (s, 3H). LCMS: 382; 384 (M+H)⁺.

Step 4:
1-(benzenesulfonyl)-2-bromo-4-methylsulfonylindole

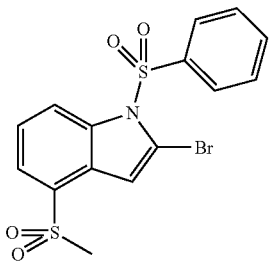 [SMILES: CS(=O)(=O)c1cccc2c1cc(Br)n2S(=O)(=O)c1ccccc1]

A solution of the title compound from step 3 (1.3 g, 4.3 mmol) and 3-chloroperoxybenzoic acid (85%, 2.2 g, 11 mmol) in dichloromethane (30 mL) was stirred at RT for 1 hr followed by addition of saturated aqueous NaHSO₃ (30 mL). The organic layer was separated and washed with saturated sodium hydrogen carbonate, dried over sodium sulfate, filtered and concentrated under reduced pressure to give the title compound as a white solid (1.17 g, 66%). ¹H NMR (CDCl₃, 300 MHz): δ 8.60 (d, J=8.4 Hz, 1H), 7.94-

7.86 (m, 3H), 7.64 (t, J=7.2 Hz, 1H), 7.52-7.47 (m, 3H), 7.31 (s, 1H), 3.06 (s, 3H). LCMS: 431; 433 (M+NH$_4$)$^+$.

Step 5: 2-bromo-4-methylsulfonyl-1H-indole

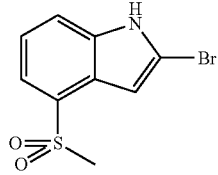

To a solution of title compound from step 4 (1.17 g, 2.8 mmol) in THF (30 mL) was added sodium hydroxide (124 mg, 3.1 mmol). The mixture was refluxed for 1 hr. The solvent was removed under reduced pressure and the residue was dissolved in ethyl acetate (30 mL). The organic layer was washed with saturated sodium hydrogen carbonate, dried over sodium sulfate, filtered and concentrated under reduced pressure to give the title compound as solid (550 mg, 71%). $^1$H NMR (CDCl$_3$, 300 MHz): δ 7.75 (d, J=7.5 Hz, 1H), 7.58 (d, J=8.1 Hz, 1H), 7.29 (t, J=7.8 Hz, 1H), 7.04 (s, 1H), 3.11 (s, 3H). LCMS: 274; 276 (M+H)$^+$.

Step 6: 2-bromo-1-ethyl-4-methylsulfonylindole

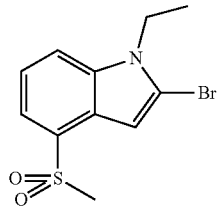 [SMILES: CCn1c(Br)cc2c(S(C)(=O)=O)cccc21]

A mixture of the title compound from step 5 (200 mg, 0.7 mmol), iodoethane (125 mg, 0.8 mmol) and potassium carbonate (300 mg, 2.17 mmol) in DMF (5 mL) was stirred at RT for 2 hr. Water (50 mL) and ethyl acetate (50 mL) were added. The organic layer was separated and washed with brine, dried over sodium sulfate, filtered and concentrated under reduced pressure. The residue was purified by preparative TLC (petroleum ether/ethyl acetate, 3:1) to give the title compound (147 mg, 67%). $^1$H NMR (CDCl$_3$, 300 MHz): δ 7.68 (d, J=7.6 Hz, 1H), 7.46 (d, J=8.0 Hz, 1H), 7.25 (t, J=8.0 Hz, 1H), 7.00 (s, 1H), 4.26 (q, J=7.2 Hz, 2H), 3.04 (s, 3H), 1.317 (t, J=7.2 Hz, 3H). LCMS: 302; 304 (M+H)$^+$.

Step 7: 5-(1-ethyl-4-methylsulfonylindol-2-yl)-1,3-dimethylpyridin-2-one

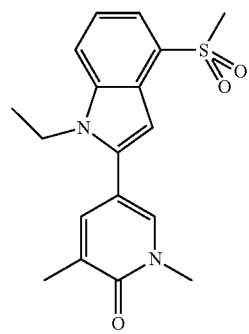 [SMILES: CCn1c(-c2cc(C)c(=O)n(C)c2)cc2c(S(C)(=O)=O)cccc21]

The title compound was prepared in a manner similar to Example 1, step 2, by substituting 1,3-dimethyl-5-(4,4,5,5-tetramethyl-1,3,2-dioxaborolan-2-yl)pyridin-2-one for 2-methyl-4-(4,4,5,5-tetramethyl-1,3,2-dioxaborolan-2-yl) isoquinolin-1-one and 2-bromo-1-ethyl-4-methylsulfonylindole for 6-bromo-2-methyl-3H-1,2-benzothiazole 1,1-dioxide. $^1$H NMR (DMSO-d6, 400 MHz): δ 7.94 (m, 2H), 7.61 (d, J=7.4 Hz, 1H), 7.58 (s, 1H), 7.37 (m, 1H), 6.81 (s, 1H), 4.30 (q, J=6.8 Hz, 2H), 3.54 (s, 3H), 3.20 (s, 3H), 2.10 (s, 3H), 1.23 (t, J=6.8 Hz, 3H). LCMS: 345.05 (M+H)$^+$.

Example 76

5-[1-(cyclopropylmethyl)-4-methylsulfonylindol-2-yl]-1,3-dimethylpyridin-2-one

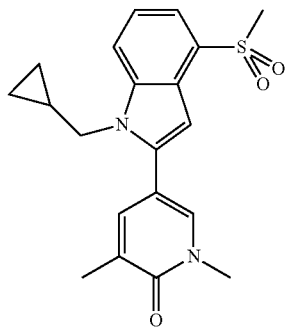 [SMILES: Cc1cc(-c2cc3c(S(C)(=O)=O)cccc3n2CC2CC2)cn(C)c1=O]

The title compound was prepared in a manner similar to Example 75 by substituting bromomethylcyclopropane for iodoethane in step 6. $^1$H NMR (DMSO-d6, 400 MHz): δ 8.0 (d, J=7.8 Hz, 1H), 7.96 (s, 1H), 7.61 (m, 2H), 7.36 (m, 1H), 6.82 (s, 1H), 4.21 (d, J=6.2 Hz, 2H), 3.54 (s, 3H), 3.22 (s, 3H), 2.10 (s, 3H), 0.99 (m, 1H), 0.37 (m, 2H), 0.21 (m, 2H). LCMS: 371.05 (M+H)$^+$.

Example 77

5-[1-(2-cyclopropylethyl)-4-methylsulfonylindol-2-yl]-1,3-dimethylpyridin-2-one

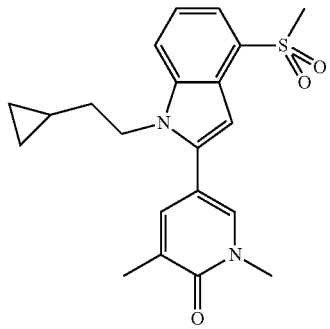 [SMILES: Cc1cc(-c2cc3c(S(C)(=O)=O)cccc3n2CCC2CC2)cn(C)c1=O]

The title compound was prepared in a manner similar to Example 75 by substituting 2-iodoethylcyclopropane for iodoethane in step 6. $^1$H NMR (DMSO-d6, 400 MHz): δ 7.95 (m, 2H), 7.60 (m, 2H), 7.36 (m, 1H), 6.81 (s, 1H), 4.35 (m, 2H), 3.54 (s, 3H), 3.20 (s, 3H), 2.10 (s, 3H), 1.51 (m, 2H), 0.44 (m, 1H), 0.26 (m, 2H), −0.12 (m, 2H). LCMS: 385.1 (M+H)$^+$.

Example 78

4-[1-(cyclopropylmethyl)-4-methylsulfonylindol-2-yl]-2-methylisoquinolin-1-one

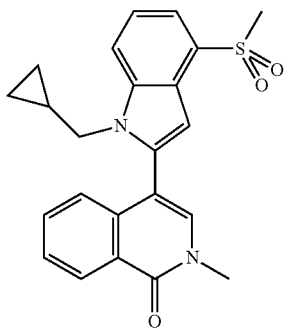 [SMILES: Cn1cc(-c2cc3c(S(C)(=O)=O)cccc3n2CC2CC2)c2ccccc2c1=O]

The title compound was prepared in a manner similar to Example 76 by substituting 2-methyl-4-(4,4,5,5-tetramethyl-1,3,2-dioxaborolan-2-yl)isoquinolin-1-one for 1,3-dimethyl-5-(4,4,5,5-tetramethyl-1,3,2-dioxaborolan-2-yl)pyridin-2-one. $^1$H NMR (DMSO-d6, 400 MHz) 8.34 (d, J=7.9 Hz, 1H), 8.06 (d, J=8.3 Hz, 1H), 7.83 (s, 1H), 7.68 (m, 2H), 7.57 (m, 1H), 7.43 (t, J=8.1 Hz, 1H), 7.21 (d, J=8.0 Hz, 1H), 6.92 (s, 1H), 4.21 (m, 1H), 3.78 (m, 1H), 3.61 (s, 3H), 3.24 (s, 3H), 0.95 (m, 1H), 0.29 (m, 2H), 0.10 (m, 2H). LCMS: 407.05 (M+H)$^+$.

Example 79

N-[2-cyclopropyl-7-(2-methyl-1-oxoisoquinolin-4-yl)-1-benzofuran-5-yl]methanesulfonamide

Step 1: 2-cyclopropyl-7-iodo-5-nitro-1-benzofuran

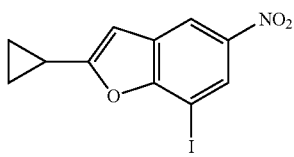 [SMILES: O=[N+]([O-])c1cc(I)c2oc(C3CC3)cc2c1]

A solution of 2,6-diiodo-4-nitrophenol (10 g, 25.6 mmol), ethynylcyclopropane (1.9 g, 28.8 mmol) and Cu$_2$O (1.9 mg, 13.2 mmol) in 100 mL of dry pyridine was refluxed for 2 hr. The reaction mixture was poured into 1 L of water and stirred for 10 min. The resulting mixture was filtered. The cake was purified by column chromatography on silica gel eluting with EtOAc/PE (0-20%) to give the title compound (6.6 g, 78% yield) as a yellow solid. $^1$H NMR (CDCl$_3$, 400 MHz): δ 8.47 (d, J=2.4 Hz, 1H), 8.32 (d, J=2.4 Hz, 1H), 6.58 (s, 1H), 2.13-2.07 (m, 1H), 1.14-1.04 (m, 4H).

Step 2: 4-(2-cyclopropyl-5-nitro-1-benzofuran-7-yl)-2-methylisoquinolin-1-one

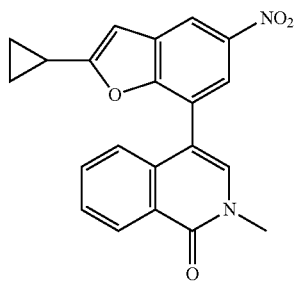 [SMILES: Cn1cc(-c2cc([N+](=O)[O-])cc3cc(C4CC4)oc23)c2ccccc2c1=O]

To a mixture of 2-cyclopropyl-7-iodo-5-nitro-1-benzofuran (200 mg, 0.61 mmol), 2-methyl-4-(4,4,5,5-tetramethyl-1,3,2-dioxaborolan-2-yl)isoquinolin-1-one (101 mg, 0.67 mmol) and Na$_2$CO$_3$ (120 mg, 1.22 mmol) in DMF/H$_2$O (12 mL/3 mL) under N$_2$ was added Pd(dppf)Cl$_2$ (23 mg). The reaction mixture was heated to 100° C. for 1 hr. Water (30 mL) and ethyl acetate (30 mL) were added. The organic layer was separated, washed with brine, dried over sodium sulfate, filtered and concentrated under reduced pressure. The residue was purified by column chromatography on silica gel (petroleum ether/ethyl acetate, 4:1) to afford the title compound (127 mg, 58% yield).
LCMS: 378 (M+18)$^+$.

Step 3: 4-(5-amino-2-cyclopropyl-1-benzofuran-7-yl)-2-methylisoquinolin-1-one

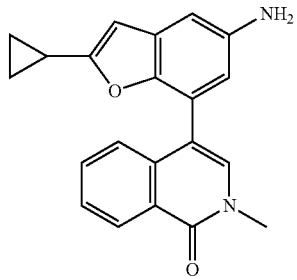 [SMILES: Cn1cc(-c2cc(N)cc3cc(C4CC4)oc23)c2ccccc2c1=O]

The title compound was prepared in a manner similar to Example 32, step 2, by substituting 4-(2-cyclopropyl-5-nitro-1-benzofuran-7-yl)-2-methylisoquinolin-1-one for 6-bromo-1-[(3-fluorophenyl)methyl]-4-nitrobenzimidazole. LCMS: 331 (M+18)$^+$.

Step 4: N-[2-cyclopropyl-7-(2-methyl-1-oxoisoquinolin-4-yl)-1-benzofuran-5-yl]methane sulfonamide

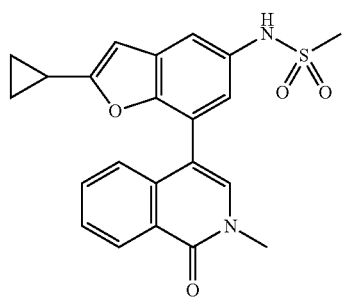 [SMILES: Cn1cc(-c2cc(NS(C)(=O)=O)cc3cc(C4CC4)oc23)c2ccccc2c1=O]

To a solution of the title compound from step 3 (100 mg, 0.30 mmol) and pyridine (64 mg, 0.90 mmol) in dichloromethane (10 mL) was added methanesulfonyl chloride (34 mg, 0.30 mmol) at rt. The reaction was stirred for 1.5 hr. It was diluted with dichloromethane (30 mL) and washed with 1 N HCl (10 mL), water and brine. The organic phase was dried over sodium sulfate, filtered and concentrated under reduced pressure. The residue was purified by preparative TLC (EtOAc) to give the title compound (12.6 mg, 10%). $^1$H NMR (CDCl$_3$, 400 MHz): δ 8.47 (d, J=7.6 Hz, 1H), 7.52-7.43 (m, 2H), 7.35 (d, J=1.6 Hz, 1H), 7.23 (d, J=8.0 Hz, 1H), 7.14 (s, 1H), 7.00 (d, J=2.0 Hz, 1H), 6.43 (s, 1H), 6.32 (s, 1H), 3.61 (s, 3H), 2.96 (s, 3H), 1.81-1.85 (m, 1H), 0.89-0.79 (m, 2H), 0.74-0.71 (m, 2H). LCMS: 409 (M+1)$^+$.

Example 80

N-[2-cyclopropyl-7-(1,5-dimethyl-6-oxopyridin-3-yl)-1-benzofuran-5-yl]methane sulfonamide

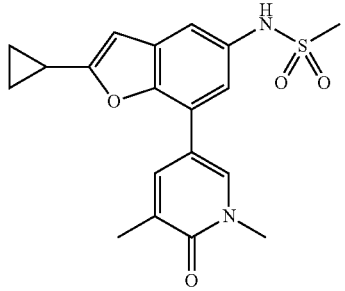 [SMILES: Cc1cc(-c2cc(NS(C)(=O)=O)cc3cc(C4CC4)oc23)cn(C)c1=O]

The title compound was prepared in a manner similar to Example 79 by substituting 1,3-dimethyl-5-(4,4,5,5-tetramethyl-1,3,2-dioxaborolan-2-yl)pyridin-2-one for 2-methyl-4-(4,4,5,5-tetramethyl-1,3,2-dioxaborolan-2-yl)isoquinolin-1-one in step 2. $^1$H NMR (CDCl$_3$, 300 MHz): δ 8.08 (d, J=2.1 Hz, 1H), 7.90 (s, 1H), 7.34 (d, J=2.1 Hz, 1H), 7.20 (d, J=1.8 Hz, 1H), 6.50 (s, 1H), 3.70 (s, 3H), 2.95 (s, 3H), 2.24 (s, 3H), 2.17-2.11 (m, 1H), 1.11-0.94 (m, 4H).
LCMS: 373 (M+1)$^+$.

Example 81

N-[9-(cyclopropylmethyl)-2-(1,5-dimethyl-6-oxopyridin-3-yl)-8-methylpurin-6-yl]methanesulfonamide

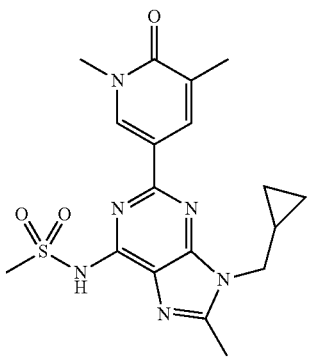 [SMILES: Cc1cc(-c2nc(NS(C)(=O)=O)c3nc(C)n(CC4CC4)c3n2)cn(C)c1=O]

The title compound was prepared in a manner similar to Example 22 by substituting bromomethylcyclopropane for 1-(bromomethyl)-4-fluoro-benzene in step 1. $^1$H NMR (400 MHz, DMSO-d$_6$): δ 8.46 (s, 1H), 8.19 (s, 1H), 4.13 (d, J=6.8 Hz, 2H), 3.58 (s, 3H), 3.55 (s, 3H), 2.63 (s, 3H), 2.11 (s, 3H), 1.34-1.31 (m, 1H), 0.52-0.50 (m, 4H). LCMS: 403 [M+H].

Example 82

N-[2-cyclopropyl-7-(2-methyl-1-oxoisoquinolin-4-yl)-1-benzofuran-5-yl]ethanesulfonamide

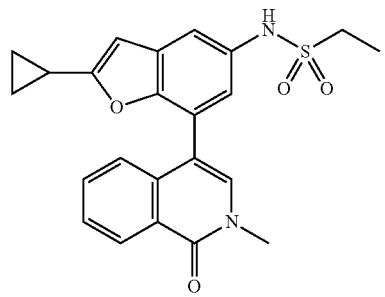 [SMILES: CCS(=O)(=O)Nc1cc(-c2cn(C)c(=O)c3ccccc23)c2oc(C3CC3)cc2c1]

The title compound was prepared in a manner similar to Example 79 by substituting ethanesulfonyl chloride for methanesulfonyl chloride. $^1$H NMR (CDCl$_3$, 300 MHz): δ 8.57 (d, J=7.8 Hz, 1H), 7.61-7.51 (m, 2H), 7.43 (s, 1H), 7.34 (d, J=7.8 Hz, 1H), 7.23 (s, 1H), 7.07 (s, 1H), 6.44 (brs, 1H), 6.41 (s, 1H), 3.70 (s, 3H), 3.19 (q, J=7.5 Hz, 2H), 2.01-1.92 (m, 1H), 1.43 (t, J=7.5 Hz, 3H), 0.95-0.91 (m, 2H), 0.81-0.78 (m, 2H). LCMS: 423 (M+1)$^+$.

Example 83

N-[7-(1,5-dimethyl-6-oxopyridin-3-yl)-2-phenyl-1-benzofuran-5-yl]methane-sulfonamide Step 1: 7-iodo-5-nitro-2-phenyl-1-benzofuran

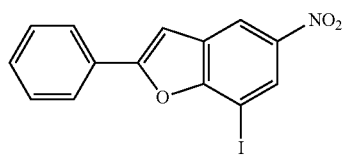 [SMILES: O=[N+]([O-])c1cc(I)c2oc(-c3ccccc3)cc2c1]

To a solution of 2,6-diiodo-4-nitrophenol (1.0 g, 2.6 mmol) and ethynylbenzene (265 mg, 2.6 mmol) in pyridine (15 mL) was added Cu$_2$O (186 mg, 1.3 mmol). The mixture was refluxed under N$_2$ overnight. The solvent was removed under reduced pressure and the residue was partitioned between water (20 mL) and ethyl acetate (30 mL). The organic layer was separated and washed with brine, dried over sodium sulfate, filtered and concentrated under vacuum. The residue was purified by column chromatography on silica gel (EtOAc/PE, 0-20%) to give the title compound (0.6 g, 63%) as a yellow solid. $^1$H NMR (CDCl$_3$, 400 MHz): δ 8.60 (d, J=2.4 Hz, 1H), 8.49 (d, J=2.4 Hz, 1H), 7.97 (d, J=8.0 Hz, 2H), 7.78 (s, 1H), 7.60-7.51 (m, 3H).

Step 2: 7-iodo-2-phenyl-1-benzofuran-5-amine

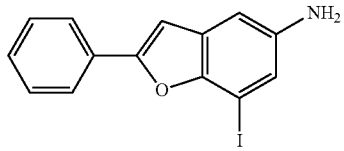 [SMILES: Nc1cc(I)c2oc(-c3ccccc3)cc2c1]

To a mixture of the title compound from step 1 (400 mg, 1.1 mmol) and Fe (184 mg, 3.3 mmol) in methanol (5 mL) was added saturated aqueous NH$_4$Cl (176 mg, 3.3 mmol) and water (2 mL). The reaction was refluxed for 30 min. Solvents were removed under reduced pressure. The residue was partitioned between water (10 mL) and ethyl acetate (10 mL) followed by filtration. The organic phase was separated, dried over sodium sulfate, filtered and concentrated under reduced pressure to give the title compound (154 mg, 42%) as a solid that was used in the next step without further purification. LCMS: 336 (M+1)$^+$.

Step 3: N-(7-iodo-2-phenyl-1-benzofuran-5-yl)methanesulfonamide

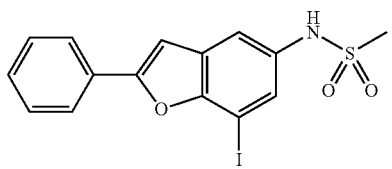 [SMILES: CS(=O)(=O)Nc1cc(I)c2oc(-c3ccccc3)cc2c1]

The title compound was prepared in a manner similar to Example 79, step 4, by substituting 7-iodo-2-phenyl-1-benzofuran-5-amine for 4-(5-amino-2-cyclopropyl-1-benzofuran-7-yl)-2-methylisoquinolin-1-one. $^1$H NMR (CDCl$_3$, 400 MHz): δ 7.88 (d, J=7.2 Hz, 2H), 7.52-7.41 (m, 5H), 7.09 (s, 1H), 6.52 (brs, 1H), 3.02 (s, 3H).

Step 4: N-[7-(1,5-dimethyl-6-oxopyridin-3-yl)-2-phenyl-1-benzofuran-5-yl]methanesulfonamide

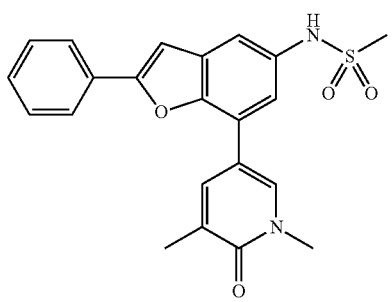 [SMILES: Cc1cc(-c2cc(NS(C)(=O)=O)cc3cc(-c4ccccc4)oc23)cn(C)c1=O]

To a mixture of the title compound from step 3 (30 mg, 0.09 mmol), 1,3-dimethyl-5-(4,4,5,5-tetramethyl-1,3,2-dioxaborolan-2-yl)pyridin-2-one (27 mg, 0.11 mmol) and KOAc (27 mg, 0.28 mmol) in DMF (3 mL) was added dichloro[1,1'-bis(di-tert-butylphos-phino)ferrocene]palladiumII (3 mg) under N$_2$. The reaction was heated at 100° C. for 3 hr. Water (30 mL) was added and the resulting mixture was filtered. The cake was purified by preparative TLC (ethyl acetate/petroleum ether=2:1) to give the title compound (15 mg, 41%). $^1$H NMR (CD$_3$OD, 400 MHz): δ 8.25 (d, J=1.2 Hz, 1H), 8.02 (s, 1H), 7.94-7.92 (m, 2H), 7.54-7.51 (m, 3H), 7.45-7.43 (d, J=7.2 Hz, 1H), 7.33-7.32 (d, J=2.4 Hz, 1H), 7.29 (s, 1H), 3.77 (s, 3H), 3.01 (s, 3H), 2.29 (s, 3H). LCMS: 409 (M+1)$^+$.

Example 84

N-[7-(2-methyl-1-oxoisoquinolin-4-yl)-2-phenyl-1-benzofuran-5-yl]methane sulfonamide

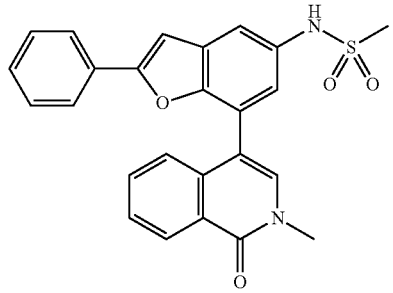 [SMILES: Cn1cc(-c2cc(NS(C)(=O)=O)cc3cc(-c4ccccc4)oc23)c2ccccc2c1=O]

The title compound was prepared in a manner similar to Example 83 by substituting 2-methyl-4-(4,4,5,5-tetramethyl-1,3,2-dioxaborolan-2-yl)isoquinolin-1-one for 1,3-dimethyl-5-(4,4,5,5-tetramethyl-1,3,2-dioxaborolan-2-yl)pyridin-2-one in step 4. $^1$H NMR (CD$_3$OD, 400 MHz): δ 8.51 (d, J=7.2 Hz, 1H), 7.71-7.61 (m, 6H), 7.47 (d, J=8.0 Hz, 1H), 7.39-7.34 (m, 3H), 7.31 (s, 1H), 7.28 (d, J=2.4 Hz, 1H), 3.76 (s, 3H), 3.05 (s, 3H). LCMS: 445 (M+1)$^+$.

Example 85

8-[2-(cyclopropylmethoxy)-5-methylsulfonylphenyl]-6-methyl-2,3-dihydro-1H-indolizin-5-one

Step 1: methyl 6-methyl-5-oxo-2,3-dihydro-1H-indolizine-8-carboxylate

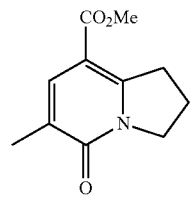

To methyl 5-oxo-6-((trifluoromethyl) sulfonyloxy)-1,2,3-trihydroindolizine-8-carboxylate (170 mg, 0.50 mmol), prepared as described previously (Padwa et al., 64 J. Org. Chem. 8648 (1999)), Pd(dppf)Cl$_2$ (7 mg, 0.01 mmol), and Na$_2$CO$_3$ (105 mg, 1 mmol) in THF (2 mL) was added methylboronic acid (45 mg, 0.75 mmol) at RT under N$_2$. The mixture was stirred at 80° C. for 12 hr, cooled, concentrated, and purified using silica gel chromatography (PE:EA=10:1 to 5:1) to give the title compound (90 mg, 87% yield) as a yellow solid. $^1$H NMR (CDCl$_3$, 400 MHz) δ 7.77 (s, 1H), 4.18 (t, J=7.6 Hz, 2H), 3.85 (s, 3H), 3.52 (d, J=7.6 Hz, 2H), 2.24 (d, J=7.6 Hz, 2H), 2.15 (s, 3H). LCMS: 208 (M+H$^+$).

Step 2: 6-methyl-2,3-dihydro-1H-indolizin-5-one

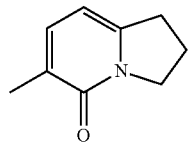

The title compound of step 1 (60 mg, 0.29 mmol) in aqueous 48% HBr (4 mL) was stirred at 170° C. for 24 hr. The mixture was cooled and the volatile components removed under vacuum to give the title compound (40 mg) as a yellow solid which was carried on without purification. LCMS: 150 (M+H$^+$).

Step 3: 8-bromo-6-methyl-2,3-dihydro-1H-indolizin-5-one

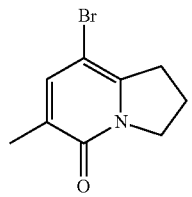

To the title compound of step 2 (combined with material from earlier preparations) (220 mg, 1.47 mmol) in MeCN (5 mL) was added NBS (262 mg, 1.47 mmol) at RT under N$_2$. The mixture was stirred at RT for 3 hr, concentrated, diluted with water, and extracted with DCM (20 mL×2). The combined organic layers were washed with brine (10 mL), dried over Na$_2$SO$_4$, filtered, and concentrated to dryness to afford the title compound (300 mg, 89% yield) as gray solid which was carried without purification. $^1$H NMR (DMSO, 400 MHz) δ 7.36 (s, 1H), 3.96 (t, J=8.0 Hz, 2H), 2.97 (t, J=7.6 Hz, 2H), 2.44 (s, 3H), 2.06 (m, 2H).

Step 4: 8-[2-(cyclopropylmethoxy)-5-methylsulfonylphenyl]-6-methyl-2,3-dihydro-1H-indolizin-5-one

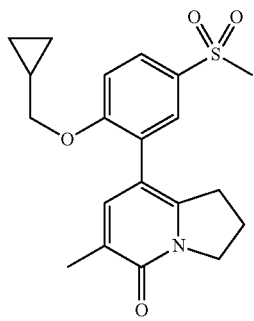 [SMILES: Cc1cc(-c2cc(S(C)(=O)=O)ccc2OCC2CC2)c2n(c1=O)CCC2]

To the title compound of step 3 (50 mg, 0.22 mmol) and 2-[2-(cyclopropylmethoxy)-5-methylsulfonylphenyl]-4,4,5,5-tetramethyl-1,3,2-dioxaborolane (78 mg, 0.22 mmol) in dioxane (4 mL) and H$_2$O (0.4 mL) was added Pd(dppf)Cl$_2$ (8 mg, 0.01 mmol) and K$_3$PO$_4$ (103 mg, 0.49 mmol) at RT under N$_2$. The mixture was stirred at 90° C. for 12 hr, cooled, concentrated, and purified using silica gel chromatography (PE:EA=1:1~0:1) followed by preparative HPLC to give the title compound (15 mg, 37% yield) as a white solid. $^1$H NMR (CDCl$_3$, 400 MHz) δ 7.89 (q, J=6.4 Hz, 1H), 7.75 (t, J=2.4 Hz, 1H), 7.34 (s, 1H), 7.04 (d, J=8.8 Hz, 1H), 4.30 (t, J=7.2 Hz, 2H), 3.91 (d, J=6.8 Hz, 2H), 3.07 (s, 3H), 3.03 (t, J=7.6 Hz, 2H), 2.17-2.22 (m, 5H), 1.20-1.26 (m, 1H), 0.63-0.68 (m, 2H), 0.33 (d, J=4.8 Hz, 2H). LCMS: 374 (M+H$^+$).

Example 86

N-[4-(2,4-difluorophenoxy)-3-(6-methyl-5-oxo-2,3-dihydro-1H-indolizin-8-yl)phenyl]methanesulfonamide

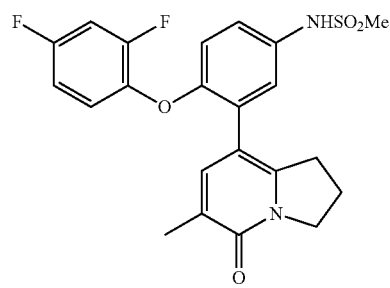

To the title compound of Example 85, step 3 (40 mg, 0.18 mmol) and N-[4-(2,4-difluorophenoxy)-3-(4,4,5,5-tetramethyl-1,3,2-dioxaborolan-2-yl)phenyl]methanesulfonamide (111 mg, 0.26 mmol) in 1,4-dioxane (3 mL) and H$_2$O (0.3 mL) was added K$_3$PO$_4$ (74 mg, 0.35 mmol) and Pd(dppf)Cl$_2$ (6 mg, 0.01 mmol) at RT under N$_2$. The mixture was stirred at 90° C. for 12 hr, cooled, concentrated, and purified by silica gel chromatography (PE:EA=1:1~0:1) followed by preparative HPLC to give the title compound (27.26 mg, 38% yield) as a white solid. $^1$H NMR (CDCl$_3$, 400 MHz) δ 7.39 (s, 1H), 7.20 (d, J=2.4 Hz, 1H), 7.15 (dd, J$_1$=2.8 Hz, J$_2$=8.8 Hz, 1H), 6.91-6.98 (m, 2H), 6.75-6.87 (m, 2H), 4.31 (t, J=7.2 Hz, 2H), 3.12 (t, J=8 Hz, 2H), 3.05 (s, 3H), 2.23 (t, J=7.2 Hz, 2H), 2.19 (s, 3H). LCMS: 447 (M+H$^+$).

Example 87

8-[2-(cyclopropylmethoxy)-5-methylsulfonylphenyl]-2,2,6-trimethyl-1,3-dihydroindolizin-5-one

Step 1: 1-[2-(benzenesulfonyl)acetyl]-4,4-dimethylpyrrolidin-2-one

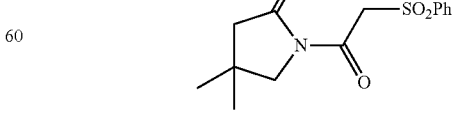

To phenylsulfonylacetic acid (9.50 g, 47.45 mmol) in toluene (80 mL) was added (COCl)$_2$ (6.02 g, 47.45 mmol) containing DMF (0.3 g, 4.75 mmol) at 20° C. under N$_2$. The mixture was stirred at 20° C. for 1 hr and then concentrated under vacuum to remove excess (COCl)$_2$. Toluene (80 ml) was added to the residue/crude acid chloride, and this solution was added to 4,4-dimethylpyrrolidin-2-one (4.30 g, 37.96 mmol) in toluene (80 ml). The mixture was refluxed for 8 hr, cooled, concentrated, diluted with water and extracted with EA (100 mL×3). The combined organic layers were washed with brine (80 mL), dried over Na$_2$SO$_4$, filtered, concentrated, and purified using silica gel chromatography (PE:EA=5:1~1:1) to give the title compound (11 g, 78% yield) as a white solid. $^1$H NMR (CDCl$_3$, 400 MHz) δ 7.97 (d, J=7.2 Hz, 2H), 7.68 (t, J=8.0 Hz, 1H), 7.58 (t, J=8.0 Hz, 2H), 4.97 (s, 2H), 3.54 (s, 2H), 2.41 (s, 2H), 1.17 (s, 6H).

Step 2: 1-[2-(benzenesulfonyl)-2-diazoacetyl]-4,4-dimethylpyrrolidin-2-one

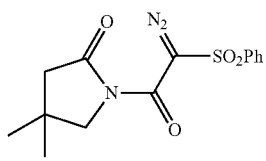

The title compound of step 1 (10 g, 33.86 mmol) and Et$_3$N (8.76 g, 86.57 mmol) in CH$_3$CN (100 mL) were stirred at 0° C. under N$_2$. After 30 min, p-acetamidophenylsulfonyl azide (10 g, 41.63 mmol) was added. The mixture was warmed to RT and stirred for 12 hr, then concentrated, diluted with water, and extracted with DCM (120 ml×3). The combined organic layers were dried with Na$_2$SO$_4$, filtered, concentrated, and purified using silica gel chromatography (PE:EA=5:1~3:1) to give the title compound (9 g, 82% yield) as a yellow solid. $^1$H NMR (CDCl$_3$, 400 MHz) δ 8.08 (d, J=7.6 Hz, 2H), 7.66 (t, J=7.2 Hz, 1H), 7.57 (t, J=7.6 Hz, 2H), 3.48 (s, 2H), 2.38 (s, 2H), 1.15 (s, 6H).

Step 3: methyl 6-hydroxy-2,2-dimethyl-5-oxo-1,3-dihydroindolizine-8-carboxylate

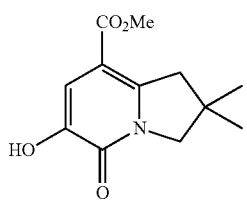 [SMILES: COC(=O)c1cc(O)c(=O)n2c1CC(C)(C)C2]

To the title compound of step 2 (5.00 g, 15.56 mmol) and methyl acrylate (6.70 g, 77.80 mmol) in toluene (100 mL) was added Rh$_2$(OAc)$_4$ (69 mg, 155.6 umol) at RT under N$_2$. The mixture was refluxed for 3 hr, cooled, concentrated, diluted with water, and extracted with EA (100 mL×3). The combined organic layers were washed with brine (50 mL×2), dried over Na$_2$SO$_4$, filtered, concentrated, and purified using silica gel chromatography (PE:EA=3:1~1:1) to give the title compound (1.50 g, 41% yield) as a yellow solid.

Step 4: methyl 2,2-dimethyl-5-oxo-6-(trifluoromethylsulfonyloxy)-1,3-dihydroindolizine-8-carboxylate

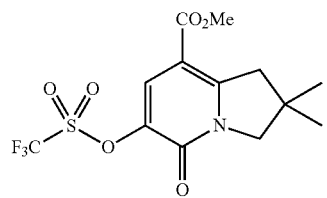 [SMILES: COC(=O)c1cc(OS(=O)(=O)C(F)(F)F)c(=O)n2c1CC(C)(C)C2]

To the title compound of step 3 (1.50 g, 6.32 mmol) in DCM (30 mL) was added N-phenylbis(trifluoromethanesulfonamide) (4.52 g, 12.64 mmol) and Et$_3$N (1.28 g, 12.64 mmol) at RT under N$_2$. The mixture was stirred at RT for 3 hr, diluted with water, and extracted with DCM (50 ml×2). The combined organic layers were concentrated and purified using silica gel chromatography (PE:EA=10:1~5:1) to give the title compound (1 g, 42% yield) as a yellow solid. $^1$H NMR (CDCl$_3$, 400 MHz) δ 7.92 (s, 1H), 3.98 (s, 2H), 3.88 (s, 3H), 3.37 (s, 2H), 1.26 (s, 6H). LCMS: 370 (M+H$^+$).

Step 5: methyl 2,26-trimethyl-5-oxo-1,3-dihydroindolizine-8-carboxylate

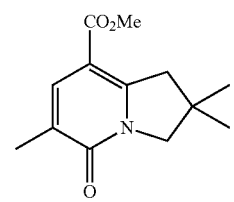

To the title compound of step 4 (170 mg, 0.46 mmol) in THF (5 mL) and H$_2$O (0.5 mL) was added methylboronic acid (90 mg, 1.5 mmol), Na$_2$CO$_3$ (106 mg, 1 mmol), and Pd(dppf)Cl$_2$ (8 mg, 0.01 mmol) at RT under N$_2$. The mixture was stirred at 80° C. for 12 hr, cooled, concentrated, and purified using silica gel chromatography (PE:EA=10:1) to give the title compound (40 mg, 37% yield) as yellow solid. $^1$H NMR (CDCl$_3$, 400 MHz) δ 7.75 (s, 1H), 3.90 (s, 2H), 3.85 (s, 3H), 3.29 (s, 2H), 2.15 (s, 3H), 1.23 (s, 6H). LCMS: 236 (M+H$^+$).

Step 6: 2,2,6-trimethyl-1,3-dihydroindolizin-5-one

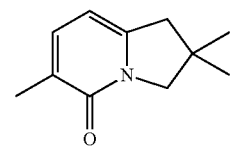

The title compound of step 5 (250 mg, 1.21 mmol) in aqueous 48% HBr (5 mL) was stirred at 170° C. for 24 hr. The mixture was cooled and the volatile components removed under vacuum at 45° C. to give the title compound (160 mg) as a yellow solid which was carried on without purification. LCMS: 178 (M+H$^+$).

Step 7: 8-bromo-2,2,6-trimethyl-1,3-dihydroindolizin-5-one

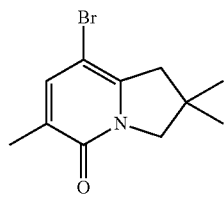

To the title compound from step 6 (30 mg, 0.17 mmol) in MeCN (2 mL) was added NBS (30 mg, 0.17 mmol) at RT under $N_2$. The mixture was stirred at RT for 1 hr, diluted with water and extracted with EA (20 mL×2). The combined organic layers were dried over $Na_2SO_4$, filtered, and concentrated to give the title compound (30 mg, 77% yield) as yellow solid which was carried on without purification. LCMS: 256, 258 (M+H$^+$).

Step 8: 8-[2-(cyclopropylmethoxy)-5-methylsulfonylphenyl]-2,2,6-trimethyl-1,3-dihydroindolizin-5-one

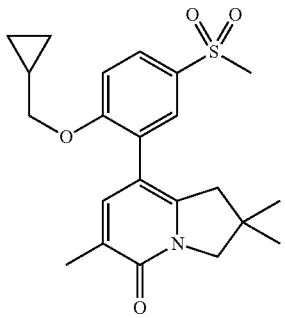 [SMILES: Cc1cc(-c2cc(S(C)(=O)=O)ccc2OCC2CC2)c2n(c1=O)CC(C)(C)C2]

To the title compound of step 7 (35 mg, 0.14 mmol) and 2-[2-(cyclopropylmethoxy)-5-methylsulfonylphenyl]-4,4,5,5-tetramethyl-1,3,2-dioxaborolane (48 mg, 0.14 mmol) in 1,4-dioxane (3 mL) and $H_2O$ (0.3 mL) was added $K_3PO_4$ (58 mg, 0.27 mmol), and Pd(dppf)Cl$_2$ (5 mg, 0.01 mmol) at RT under $N_2$. The mixture was stirred at 90° C. for 12 hr, cooled, concentrated, and purified using silica gel chromatography (PE:EA=1:1~0:1) followed by preparative HPLC to give the title compound (20 mg, 36% yield) as a white solid. $^1$H NMR (CDCl$_3$, 400 MHz) δ 7.87 (q, J=6.4 Hz, 1H), 7.73 (d, J=2.4 Hz, 1H), 7.29 (s, 1H), 7.03 (d, J=8.4 Hz, 1H), 4.00 (s, 2H), 3.91 (d, J=7.2 Hz, 2H), 3.08 (s, 3H), 2.79 (s, 2H), 2.20 (s, 3H), 1.24 (m, 1H), 1.20 (s, 6H), 0.64 (m, 2H), 0.31 (q, J=5.6 Hz, 2H). LCMS: 402 (M+H$^+$).

Example 88

N-[4-(2,4-difluorophenoxy)-3-(2,2,6-trimethyl-5-oxo-1,3-dihydroindolizin-8-yl)phenyl]methanesulfonamide

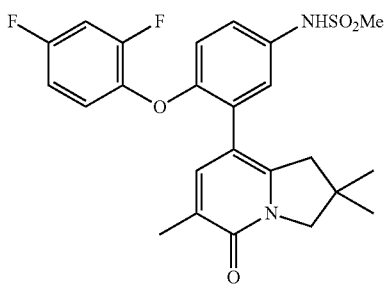

To the title compound of Example 87, step 7 (50 mg, 0.20 mmol) and N-[4-(2,4-difluorophenoxy)-3-(4,4,5,5-tetramethyl-1,3,2-dioxaborolan-2-yl)phenyl]methanesulfonamide (125 mg, 0.29 mmol) in 1,4-dioxane (5 mL) and $H_2O$ (0.5 mL) was added $K_3PO_4$ (82 mg, 0.39 mmol) and Pd(dppf)Cl$_2$ (7 mg, 0.01 mmol) at RT under $N_2$. The mixture was stirred at 90° C. for 12 hr, and then cooled, concentrated, and purified using silica gel chromatography (PE:EA=1:1) followed by preparative HPLC to give the title compound (10 mg, 11% yield) as a brown solid. $^1$H NMR (CDCl$_3$, 400 MHz) δ 7.29 (s, 1H), 7.13-7.16 (m, 2H), 6.90 (q, J=6.8 Hz, 2H), 6.82 (d, J=8.4 Hz, 2H), 6.48 (s, 1H), 3.96 (s, 2H), 3.05 (s, 3H), 2.85 (s, 2H), 2.17 (s, 3H), 1.17 (s, 6H). LCMS: 475 (M+H$^+$).

Example 89

8-[2-(cyclopropylmethoxy)-5-methylsulfonylphenyl]-1,1-difluoro-6-methyl-2,3-dihydroindolizin-5-one

Step 1: tert-butyl 1-hydroxy-6-methyl-5-oxo-3H-indolizine-2-carboxylate

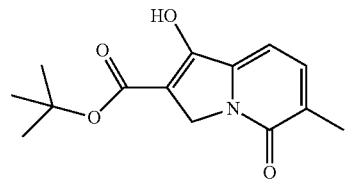 [SMILES: Cc1ccc2n(c1=O)CC(C(=O)OC(C)(C)C)=C2O]

Using modifications of procedures described previously (Henegar & Baughman, 40 J. Heterocyclic Chem. 601 (2003)), methyl 5-methyl-6-oxo-1H-pyridine-2-carboxylate (1.0 g, 6.0 mmol), Cs$_2$CO$_3$ (3.9 g, 12 mmol) and t-butyl acrylate (7.7 g, 60 mmol) in DMSO (50 mL) were heated at 65° C. for 3 hr. The mixture was cooled to 0° C. and 0.5 M HCl (60 mL) was added such that the internal temperature remained <15° C. The resulting solid was collected and washed with PE and then dissolved in DCM. After washing with brine, the organic layer was separated, dried, filtered, and concentrated to dryness under vacuum to give the title compound (1.4 g, 88%) as a white solid which was carried on without purification. $^1$H NMR (300 MHz, CDCl$_3$): δ7.38 (d, =7.2 Hz, 1H), 6.57 (d, J=7.2 Hz, 1H), 4.63 (s, 2H), 2.24 (s, 3H), 1.56 (s, 9H). LCMS: 264 (M+H$^+$).

Step 2: 6-methyl-2,3-dihydroindolizine-1,5-dione

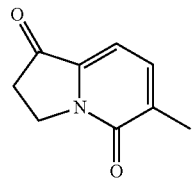

The title compound of step 1 (250 mg, 0.95 mmol) and TFA (0.45 mL) in toluene (18 mL) were heated at 75° C. for 24 hr. After cooling, the volatile components were removed under vacuum. Toluene (20 mL) was added, and again the volatile components were removed under vacuum. Purification using silica gel chromatography (PE/EA 1:1) gave the title compound (130 mg, 84%) as a brown solid. ¹H NMR (400 MHz, CDCl₃): δ 7.42 (d, J=6.8 Hz, 1H), 6.83 (d, J=6.8 Hz, 1H), 4.31 (t, J=6.8 Hz, 2H), 2.90 (t, J=6.8 Hz, 2H), 2.27 (s, 3H). LCMS: 164 (M+H⁺).

Step 3:
1,1-difluoro-6-methyl-2,3-dihydroindolizin-5-one

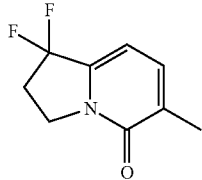

To the title compound of step 2 (150 mg, 0.92 mmol) in DCM (10 mL) was added DAST (1.09 mL, 9.2 mmol). The mixture was stirred at RT for 24 hr and then poured onto ice and saturated aqueous NaHCO₃ (30 mL). DCM extractive work up (40 mL×2) gave a residue which was purified using preparative TLC (PE:EA 3:1) to give the title compound (68.0 mg, 40%) as a brown oil. ¹H NMR (400 MHz, CDCl₃): δ 7.34 (d, J=6.8 Hz, 1H), 6.49-6.43 (m, 1H), 4.21 (t, J=6.8 Hz, 2H), 2.76-2.64 (m, 2H), 2.20 (s, 3H). LCMS: 186 (M+H⁺).

Step 4: 8-bromo-1,1-difluoro-6-methyl-2,3-dihydroindolizin-5-one

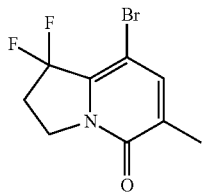

A solution of 1M bromine in AcOH (0.38 mL) was added slowly to the title compound of step 3 (68 mg, 0.37 mmol) in AcOH (3 mL). The mixture was stirred at RT for 1.5 hr and then poured into water. DCM extractive work up (40 mL×2) gave a residue which was purified using preparative TLC (PE/EA 1:1) to give the title compound (70.0 mg, 72%) as a brown oil. ¹H NMR (300 MHz, CDCl₃): δ 7.40 (s, 1H), 4.23-4.16 (m, 2H), 2.86-2.69 (m, 2H), 2.23-2.19 (m, 3H).

Step 5: 8-[2-(cyclopropylmethoxy)-5-methylsulfonylphenyl]-1,1-difluoro-6-methyl-2,3-dihydroindolizin-5-one

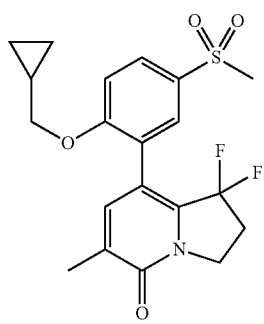 [SMILES: Cc1cc(-c2cc(S(C)(=O)=O)ccc2OCC2CC2)c2n(c1=O)CCC2(F)F]

The title compound of step 4 (40 mg, 0.152 mmol), 2-[2-(cyclopropylmethoxy)-5-methylsulfonylphenyl]-4,4,5,5-tetramethyl-1,3,2-dioxaborolane (64 mg, 0.18 mmol), K₂CO₃ (63 mg, 0.46 mmol) and Pd(dppf)Cl₂ (11.1 mg, 0.015 mmol) in DMF/H₂O (2 mL/0.5 mL) were N₂ purged and microwaved at 120° C. for 2 hr. Filtration and DCM extractive work up of the filtrate gave a residue that was purified using preparative HPLC to give the title compound (17 mg, 27%) as a white solid. ¹H NMR (400 MHz, CDCl₃): δ 7.92 (dd, J=8.4 Hz, 2.4 Hz, 1H), 7.85 (d, J=2.0 Hz, 1H), 7.34 (s, 1H), 7.03 (d, J=9.2 Hz, 1H), 4.32-4.21 (m, 2H), 3.92 (d, J=6.8 Hz, 2H), 3.04 (s, 3H), 2.75-2.62 (m, 2H), 2.24 (s, 3H), 1.20-1.17 (m, 1H), 0.62-0.57 (m, 2H), 0.33-0.27 (m, 2H). LCMS: 410 (M+H⁺).

Example 90

(±)-8-[2-(cyclopropylmethoxy)-5-methylsulfonylphenyl]-1-fluoro-6-methyl-2,3-dihydro-1H-indolizin-5-one Step 1: (±)-1-hydroxy-6-methyl-2,3-dihydro-1H-indolizin-5-one

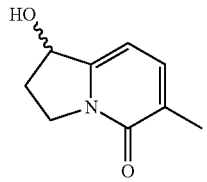

The title compound of Example 89, step 2 (150 mg, 0.92 mmol) was added to a stirred suspension of NaBH₄ (175 mg, 4.6 mmol) in MeOH (15 mL) at RT. The mixture generated heat and gave a clear solution. Within a few minutes, water and DCM were added. DCM extractive work up (10 mL×6) gave the racemic title compound (120 mg, 79%) as a colorless oil which was carried on without purification. LCMS: 166 (M+H⁺).

Step 2: (±)-1-fluoro-6-methyl-2,3-dihydro-1H-indolizin-5-one

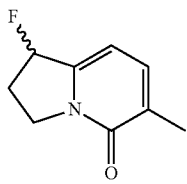

To the title compound of step 1 (120 mg, 0.73 mmol) in DCM (10 mL) was added DAST (1.0 mL, 7.3 mmol). The mixture was stirred at RT overnight and then poured onto ice and saturated aqueous NaHCO₃ (30 mL). DCM extractive work up (40 mL×2) gave a residue that was purified using preparative TLC (PE/EA 3:1) to give the racemic title compound (100 mg, 82%) as a brown oil. ¹H NMR (400 MHz, CDCl₃): δ 7.28-7.30 (m, 1H), 6.38 (dd, J=6.8, 4.4 Hz, 1H), 5.81 (ddd, J=55.6, 5.2, 2.8 Hz, 1H), 4.34-4.17 (m, 2H), 2.54-2.39 (m, 2H), 2.18 (d, J=3.6 Hz, 3H).

Step 3: (±)-8-bromo-1-fluoro-6-methyl-2,3-dihydro-1H-indolizin-5-one

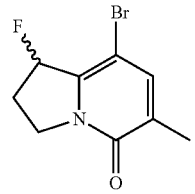

A solution of 1M bromine in AcOH (0.62 mL) was added slowly to the title compound of step 2 (100 mg, 0.60 mmol) in AcOH (3 mL). The mixture was stirred at RT for 1.5 hr and then poured into water. DCM extractive work up (40 mL×2) gave a residue that was purified using preparative TLC (PE/EA 1:1) to give the racemic title compound (100 mg, 68%) as a brown oil. $^1$H NMR (400 MHz, CDCl$_3$): δ 7.36 (s, 1H), 6.05-5.84 (m, 1H), 4.51-4.18 (m, 2H), 2.64-2.32 (m, 2H), 2.19 (d, J=3.6 Hz, 3H). LCMS: 246, 248 (M+H$^+$).

Step 4: (±)-8-[2-(cyclopropylmethoxy)-5-methylsulfonylphenyl]-1-fluoro-6-methyl-2,3-dihydro-1H-indolizin-5-one

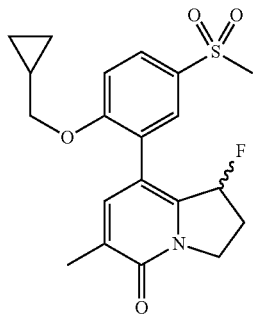 [SMILES: Cc1cc(-c2cc(S(C)(=O)=O)ccc2OCC2CC2)c2n(c1=O)CCC2F]

The title compound of step 3 (50 mg, 0.20 mmol), 2-[2-(cyclopropylmethoxy)-5-methylsulfonylphenyl]-4,4,5,5-tetramethyl-1,3,2-dioxaborolane (86 mg, 0.25 mmol), K$_2$CO$_3$ (85 mg, 0.61 mmol) and Pd(dppf)Cl$_2$ (15 mg, 0.02 mmol) in DMF/H$_2$O (2 mL/0.5 mL) were N$_2$ purged and microwaved at 120° C. for 2 hr. Filtration and DCM extractive work up of the filtrate gave a residue that was purified using preparative HPLC to give the racemic title compound (26 mg, 33%) as a white solid. $^1$H NMR (400 MHz, CDCl$_3$): δ 7.95-7.85 (m, 2H), 7.37 (s, 1H), 7.04 (d, J=8.4 Hz, 1H), 5.71 (dd, J=58.4 Hz, 5.2 Hz, 1H), 4.42-4.21 (m, 2H), 3.92 (d, J=6.8 Hz, 2H), 3.06 (s, 3H), 2.55-2.32 (m, 2H), 2.23 (d, J=2.8 Hz, 3H), 1.25-1.15 (m, 1H), 0.65-0.57 (m, 2H), 0.33-0.29 (m, 2H). LCMS: 392 (M+H$^+$).

Example 91

5-[1-(2-cyclopropylethyl)-4-methylsulfonylindol-2-yl]-3-methoxy-1-methylpyridin-2-one

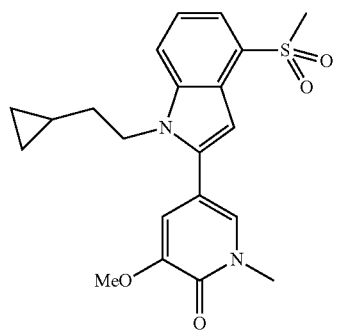 [SMILES: COc1cc(-c2cc3c(S(C)(=O)=O)cccc3n2CCC2CC2)cn(C)c1=O]

The title compound was prepared in a manner similar to Example 75 by substituting 2-iodoethylcyclopropane for iodoethane in step 6 and 3-methoxy-1-methyl-5-(4,4,5,5-tetramethyl-1,3,2-dioxaborolan-2-yl)pyridin-2-one for 1,3-dimethyl-5-(4,4,5,5-tetramethyl-1,3,2-dioxaborolan-2-yl)pyridin-2-one in step 7. $^1$H NMR (DMSO-d6, 400 MHz): δ 7.96 (d, J=8.1 Hz, 1H), 7.65 (s, 1H), 7.61 (d, J=6.9 Hz, 1H), 7.37 (m, 1H), 7.02 (s, 1H), 6.84 (s, 1H), 4.37 (m, 2H), 3.78 (s, 3H), 3.54 (s, 3H), 3.21 (s, 3H), 1.52 (m, 2H), 0.45 (m, 1H), 0.25 (m, 2H), −0.13 (m, 2H). LCMS: 401.1 (M+H)$^+$.

Example 92

N-[1-(cyclopropylmethyl)-6-(1,5-dimethyl-6-oxopyridin-3-yl)-2-(trifluoromethyl)benzimidazol-4-yl]methanesulfonamide

Step 1: N-[6-bromo-1-(cyclopropylmethyl)-2-(trifluoromethyl) benzimidazol-4-yl]methanesulfonamide

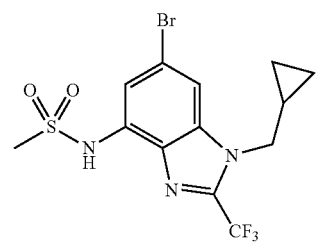 [SMILES: CS(=O)(=O)Nc1cc(Br)cc2c1nc(C(F)(F)F)n2CC1CC1]

Trifluoroacetic anhydride (160 mg, 0.75 mmol) in toluene (2 mL) was added dropwise to the title compound of Example 72, step 3 (250 mg, 0.75 mmol) in toluene (12 mL) at ice bath temperature. After warming to RT and stirring for 2 hr, the mixture was heated to 90° C. for 2 hr, cooled to RT, neutralized with aqueous saturated NaHCO$_3$ at ice bath temperature, and extracted with EtOAc (40 mL×2). The combined extracts were washed with brine, dried over Na$_2$SO$_4$, concentrated, and purified using silica gel chromatography (PE/EtOAc=10:1) to give the title compound (150 mg, 49%) as a white solid. $^1$H NMR (400 MHz, DMSO-d$_6$):

δ 10.22 (s, 1H), 7.97 (s, 1H), 7.40 (s, 1H), 4.32 (d, J=7.2 Hz, 2H), 3.28 (s, 3H), 1.27-1.24 (m, 1H), 0.56-0.45 (m, 4H). LCMS: 412, 414 (M+H+).

Step 2: N-[1-(cyclopropylmethyl)-6-(1,5-dimethyl-6-oxopyridin-3-yl)-2-(trifluoromethyl)benzimidazol-4-yl]methanesulfonamide

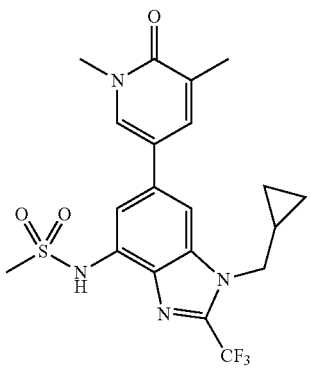 [SMILES: Cc1cc(-c2cc(NS(C)(=O)=O)c3nc(C(F)(F)F)n(CC4CC4)c3c2)cn(C)c1=O]

The title compound of step 1 (130 mg, 0.32 mmol), 1,3-dimethyl-5-(4,4,5,5-tetramethyl-1,3,2-dioxaborolan-2-yl)pyridin-2-one (94 mg, 0.38 mmol), K$_2$CO$_3$ (133 mg, 0.96 mmol) and Pd(dppf)Cl$_2$ (24 mg, 0.032 mmol) in dioxane/H$_2$O (12 mL/4 mL) under N$_2$ were heated at 85° C. for 3 hr. After cooling to RT, the mixture was filtered, rinsing with EtOAC. The combined filtrate/rinse was diluted with water. After extraction with EtOAc (50 mL×3), the combined extracts were dried over Na$_2$SO$_4$, filtered, concentrated, and the residue was purified by prep-TLC (EtOAc) to give the title compound (74 mg, 51%) as a white solid. $^1$H NMR (400 MHz, DMSO-d$_6$): δ 9.99 (s, 1H), 8.02 (s, 1H), 7.81 (s, 1H), 7.79 (s, 1H), 7.41 (s, 1H), 4.36 (d, J=6.8 Hz, 2H), 3.56 (s, 3H), 3.28 (s, 3H), 2.12 (s, 3H), 1.31-1.28 (m, 1H), 0.56-0.52 (m, 4H).
LCMS: 455 (M+H+).

Example 93

N-[1-(cyclopropylmethyl)-6-(5-methoxy-1-methyl-6-oxopyridin-3-yl)-2-(trifluoromethyl)benzimidazol-4-yl]methanesulfonamide

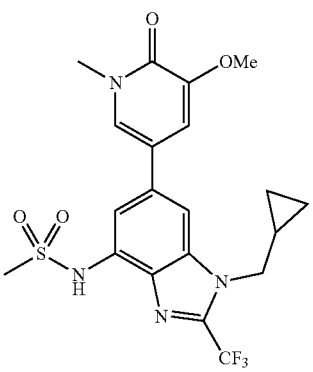 [SMILES: COc1cc(-c2cc(NS(C)(=O)=O)c3nc(C(F)(F)F)n(CC4CC4)c3c2)cn(C)c1=O]

The title compound of Example 92, step 1 (100 mg, 0.24 mmol), 3-methoxy 1-methyl-5-(4,4,5,5-tetramethyl-1,3,2-dioxaborolan-2-yl)pyridin-2-one (78 mg, 0.29 mmol), K$_2$CO$_3$ (100 mg, 0.72 mmol) and Pd(dppf)Cl$_2$ (18 mg, 0.024 mmol) in dioxane/H$_2$O (9 mL/3 mL) under N$_2$ were heated at 85° C. for 3 hr. After cooling to RT, the mixture was filtered, rinsing with EtOAC. The combined filtrate/rinse was diluted with water. After extraction with EtOAc (50 mL×3), the combined extracts were dried over Na$_2$SO$_4$, filtered, concentrated, and the residue was washed with ether (20 mL) to give the title compound (59 mg, 52%) as a white solid. $^1$H NMR (400 MHz, DMSO-d$_6$): δ 9.99 (s, 1H), 7.82 (s, 1H), 7.73 (d, J=2.4 Hz, 1H), 7.43 (s, 1H), 7.17 (d, J=2.0 Hz, 1H), 4.37 (d, J=6.8 Hz, 2H), 3.84 (s, 3H), 3.56 (s, 3H), 3.28 (s, 3H), 1.36-1.34 (m, 1H), 0.59-0.51 (m, 4H). LCMS: 471 (M+H+).

Example 94

N-[1-butyl-6-(1,5-dimethyl-6-oxopyridin-3-yl)-2-methylbenzimidazol-4-yl]methanesulfonamide hydrochloride Step 1: 5-bromo-N-butyl-3-fluoro-2-nitroaniline

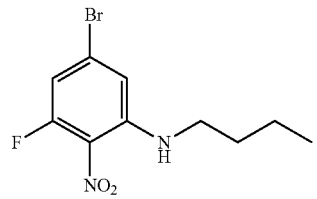 [SMILES: CCCCNc1cc(Br)cc(F)c1[N+](=O)[O-]]

5-bromo-1,3-difluoro-2-nitrobenzene (2.50 g, 10.5 mmol), K$_2$CO$_3$ (4.40 g, 31.5 mmol) and n-butylamine (768 mg, 10.5 mmol) in THF (70 mL) were stirred at RT overnight. Water (100 mL) was added, and the mixture was extracted with DCM (50 mL×2). The combined extracts were washed with brine, dried over Na$_2$SO$_4$, concentrated, and the residue was purified by silica gel chromatography (PE/EtOAc=100:1) to give the title compound (1.5 g, 50%) as a yellow solid. LCMS: 291, 293 (M+H+).

Step 2: N-[5-bromo-3-(butylamino)-2-nitrophenyl]methanesulfonamide

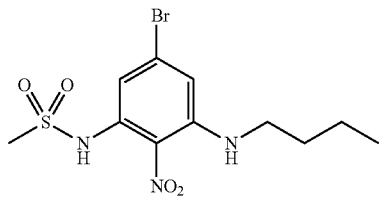 [SMILES: CCCCNc1cc(Br)cc(NS(C)(=O)=O)c1[N+](=O)[O-]]

To MeSO$_2$NH$_2$ (563 mg, 5.93 mmol) in DMF (25 mL) was added t-BuOK (466 mg, 4.16 mmol) at RT. The mixture was stirred for 30 min, and the title compound of step 1 (860 mg, 2.97 mmol) was then added and stirring continued overnight. The mixture was poured into ice water (50 mL), and the pH was adjusted to 6-7 with HOAc. The resulting mixture was extracted with EtOAc (30 mL×2). The combined extracts were washed with brine, dried over Na$_2$SO$_4$, and concentrated to give a residue which was washed with ether (20 mL) to give the title compound (450 mg, 41%) as a red solid. ¹H NMR (400 MHz, CDCl₃): δ 10.33 (s, 1H), 8.37 (s, 1H), 7.13 (d, J=1.6 Hz, 1H), 6.72 (d, J=2.0 Hz, 1H), 3.29-3.24 (m, 2H), 3.14 (s, 3H), 1.76-1.69 (m, 2H), 1.53-1.45 (m, 2H), 0.99 (t, J=7.6 Hz, 3H). LCMS: 366, 368 (M+H⁺).

Step 3: N-[2-amino-5-bromo-3-(butylamino)phenyl]methanesulfonamide

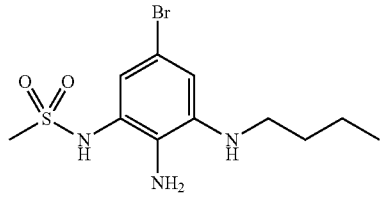

The title compound of step 2 (450 mg, 1.23 mmol) was suspended in MeOH (30 mL). Saturated aqueous NH₄Cl (10 mL) and Fe (345 mg, 6.16 mmol) were added, and the mixture was heated at 85° C. for 1 hr and then filtered. The insoluble components were rinsed with methanol (30 mL), and the combined filtrate/rinse was diluted with water and extracted with EtOAc (40 mL×2). The combined extracts were dried over Na₂SO₄, filtered, and concentrated to give the the title compound (400 mg, 97%) as a white solid. LCMS: 336, 338 (M+H⁺).

Step 4: N-(6-bromo-1-butyl-2-methylbenzimidazol-4-yl)methanesulfonamide

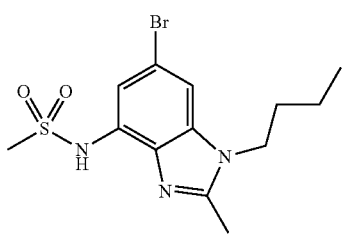 [SMILES: CCCCn1c(C)nc2c(NS(C)(=O)=O)cc(Br)cc21]

To the title compound of step 3 (300 mg, 0.9 mmol) in 4 M HCl (0.5 mL, 2.0 mmol) was added 2,4-pentanedione (448 mg, 4.5 mmol). The mixture was heated at 75° C. for 1 hr and then cooled to RT, diluted with water, neutralized with aqueous, saturated NaHCO₃, and extracted with EtOAc (30 mL×2). The combined extracts were washed with brine, dried over Na₂SO₄, filtered, concentrated, and purified by silica gel chromatography (PE:EtOAc=1:1) to give the title compound (230 mg, 72%) as a white solid. ¹H NMR (300 MHz, DMSO-d₆): δ 7.60 (d, J=1.8 Hz, 1H), 7.18 (d, J=1.8 Hz, 1H), 4.16 (t, J=7.5 Hz, 2H), 3.20 (s, 3H), 2.54 (s, 3H), 1.63-1.68 (m, 2H), 1.34-1.26 (m, 2H), 0.90 (t, J=7.2 Hz, 3H). LCMS: 360, 362 (M+H⁺).

Step 5: N-[1-butyl-6-(1,5-dimethyl-6-oxopyridin-3-yl)-2-methylbenzimidazol-4-yl]methanesulfonamide

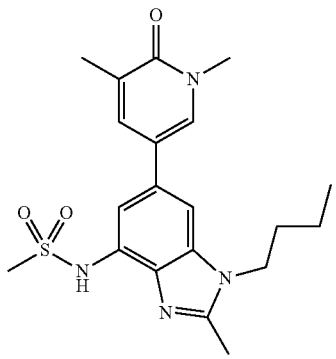 [SMILES: CCCCn1c(C)nc2c(NS(C)(=O)=O)cc(-c3cc(C)c(=O)n(C)c3)cc21]

The title compound of step 4 (100 mg, 0.28 mmol), 1,3-dimethyl-5-(4,4,5,5-tetramethyl-1,3,2-dioxaborolan-2-yl)pyridin-2-one (83 mg, 0.33 mmol), K₂CO₃ (115 mg, 0.84 mmol) and Pd(dppf)Cl₂ (21 mg, 0.028 mmol) in dioxane/H₂O (9 mL/3 mL) under N₂ were heated at 85° C. for 3 hr. After cooling to RT, the mixture was filtered, diluted with water (20 mL), and extracted with EtOAc (30 mL×3). The combined extracts were dried over Na₂SO₄, filtered, concentrated, and the residue was purified by prep-TLC (DCM:MeOH=20:1) to give the title compound (45 mg, 40%) as a white solid. ¹H NMR (400 MHz, DMSO-d₆): δ 9.53 (s, 1H), 7.91 (d, J=2.8 Hz, 1H), 7.73 (s, 1H), 7.49 (d, J=0.8 Hz, 1H), 7.19 (d, J=1.2 Hz, 1H), 4.23-4.19 (m, 2H), 3.54 (s, 3H), 3.19 (s, 3H), 2.57 (s, 3H), 2.11 (s, 3H), 1.74-1.69 (m, 2H), 1.36-1.30 (m, 2H), 0.91 (t, J=7.2 Hz, 3H). LCMS: 403 (M+H⁺).

Step 6: N-[1-butyl-6-(1,5-dimethyl-6-oxopyridin-3-yl)-2-methylbenzimidazol-4-yl]methanesulfonamide hydrochloride

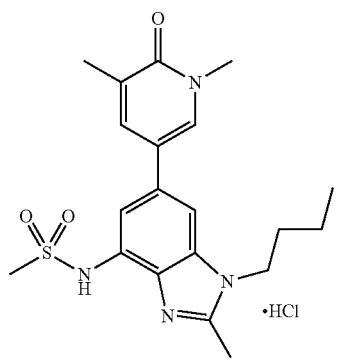 [SMILES: CCCCn1c(C)nc2c(NS(C)(=O)=O)cc(-c3cc(C)c(=O)n(C)c3)cc21 ; Cl]

The title compound of step 5 (45 mg, 0.11 mmol) in DCM (3 mL) was converted to the hydrochloride by adding 2M HCl in methanol (0.55 mL, 11 mmol) at ice bath temperature. After stirring 5 min, the mixture was concentrated under reduced pressure. DCM (3 mL) was added and evaporated twice. The resulting residue was dried under vacuum to give the title compound (39 mg, 80%) as a white solid. ¹H NMR (400 MHz, DMSO-d₆): δ 10.09 (s, 1H), 8.09 (d, J=2.4 Hz, 1H), 7.99 (s, 1H), 7.81 (d, J=2.4 Hz, 1H), 7.58

(s, 1H), 4.44-4.41 (m, 2H), 3.57 (s, 3H), 3.16 (s, 3H), 2.86 (s, 3H), 2.13 (s, 3H), 1.83-1.79 (m, 2H), 1.43-1.37 (m, 2H), 0.93 (t, J=7.2 Hz, 3H).
LCMS: 403 (M+H$^+$).

Example 95

N-[1-butyl-6-(5-methoxy-1-methyl-6-oxopyridin-3-yl)-2-methylbenzimidazol-4-yl]methanesulfonamide hydrochloride Step 1: N-[1-butyl-6-(5-methoxy-1-methyl-6-oxopyridin-3-yl)-2-methyl-benzimidazol-4-yl]methanesulfonamide

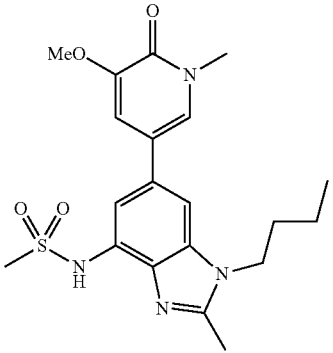 [SMILES: CCCCn1c(C)nc2c(NS(C)(=O)=O)cc(-c3cc(OC)c(=O)n(C)c3)cc21]

The title compound of Example 94, step 4 (100 mg, 0.28 mmol), 3-methoxy-1-methyl-5-(4,4,5,5-tetramethyl-1,3,2-dioxaborolan-2-yl)pyridin-2-one (89 mg, 0.33 mmol), K$_2$CO$_3$ (116 mg, 0.84 mmol) and Pd(dppf)Cl$_2$ (21 mg, 0.028 mmol) in dioxane/H$_2$O (9 mL/3 mL) under N$_2$ were heated at 85° C. for 3 hr. After cooling to RT, the mixture was filtered, diluted with water (20 mL), and extracted with EtOAc (50 mL×3). The combined extracts were dried over Na$_2$SO$_4$, filtered, and concentrated. The residue was washed with EtOAc (5 mL) and then dried under vacuum to give the title compound (90 mg, 78%) as a white solid. $^1$H NMR (300 MHz, DMSO-d$_6$): δ 9.60 (s, 1H), 7.63 (s, 1H), 7.51 (s, 1H), 7.21 (s, 1H), 7.12 (s, 1H), 4.25-4.20 (m, 2H), 3.82 (s, 3H), 3.54 (s, 3H), 3.21 (s, 3H), 2.57 (s, 3H), 1.75-1.70 (m, 2H), 1.34-1.29 (m, 2H), 0.91 (t, J=7.2 Hz, 3H). LCMS: 419 (M+H$^+$).

Step 2: N-[1-butyl-6-(5-methoxy-1-methyl-6-oxopyridin-3-yl)-2-methylbenzimidazol-4-yl]methanesulfonamide hydrochloride

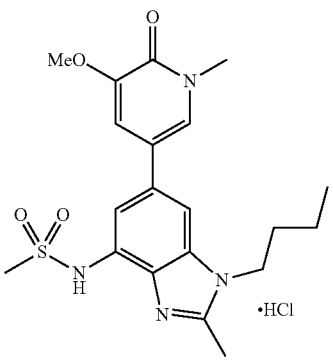 [SMILES: CCCCn1c(C)nc2c(NS(C)(=O)=O)cc(-c3cc(OC)c(=O)n(C)c3)cc21 ; Cl]

The title compound of step 1(90 mg, 0.22 mmol) in DCM (3 mL) was converted to the hydrochloride by adding 2M HCl in methanol (1.1 mL, 22 mmol) at ice bath temperature. After stirring 5 min, the mixture was concentrated under reduced pressure. DCM (3 mL) was added and evaporated twice. The resulting residue was dried under vacuum to give the title compound (88 mg, 90%) as a white solid. $^1$H NMR (300 MHz, DMSO-d$_6$): δ 10.02 (s, 1H), 7.98 (s, 1H), 7.78 (d, J=2.1 Hz, 1H), 7.57 (s, 1H), 7.19 (d, J=2.1 Hz, 1H), 4.45-4.41 (m, 2H), 3.84 (s, 3H), 3.56 (s, 3H), 3.16 (s, 3H), 2.85 (s, 3H), 1.83-1.77 (m, 2H), 1.39-1.34 (m, 2H), 0.93 (t, J=7.2 Hz, 3H).
LCMS: 419 (M+H$^+$).

Example 96

5-[3-(cyclopropylmethyl)-2-methyl-7-(methylsulfonylmethyl) benzimidazol-5-yl]-1,3-dimethylpyridin-2-one Step 1: 4-bromo-2-(methylsulfanylmethyl)-6-nitroaniline

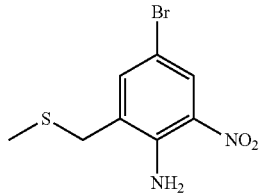

To a solution of 4-bromo-2-nitroaniline (5.0 g, 23 mmol) and dimethyl sulfide (8.4 mL, 115 mmol) in DCM (150 mL) was added NCS (15.4 g, 115 mmol). The resulting mixture was stirred for 30 min at RT. Triethylamine (16 ml, 115 mmol) was added and the mixture was heated to reflux for 15 hr. The reaction was cooled to RT, diluted with 10% NaOH aqueous solution (30 mL) and extracted with DCM (50 mL×3). The combined organic layers were washed with brine (30 mL), dried over Na$_2$SO$_4$, filtered and concentrated under reduced pressure. The residue was purified by column chromatography on silica gel (PE:EtOAc=20:1 to 10:1) to give the title compound (1.5 g, 24%) as a yellow solid. $^1$H NMR (300 MHz, CDCl$_3$) δ 8.28 (d, J=2.4 Hz, 1H), 7.38 (d, J=2.1 Hz, 1H), 6.68-6.66 (br, 2H), 3.73 (s, 2H), 2.04 (s, 3H).

Step 2: 5-bromo-3-(methylsulfanylmethyl)benzene-1,2-diamine

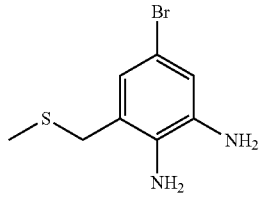

The title compound was prepared in a manner similar to Example 32, step 2, by substituting the title compound from step 1 for 6-bromo-1-[(3-fluorophenyl)methyl]-4-nitrobenzimidazole. ¹H NMR (300 MHz, CDCl₃): δ 6.81 (d, J=2.4 Hz, 1H), 6.73 (d, J=2.1 Hz, 1H), 3.62 (s, 2H), 2.00 (s, 3H).

Step 3: 6-bromo-2-methyl-4-(methylsulfanylmethyl)-1H-benzimidazole

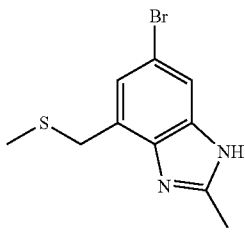

A mixture of the title compound from step 2 (300 mg, 1.2 mmol) and pentane-2,4-dione (0.25 mL, 2.4 mmol) in ethanol (5 mL) and HCl (5 M, 0.6 mL, 3 mmol) was heated at 80° C. for 1 hr. It was then was cooled to RT, neutralized with saturated NaHCO₃ solution (50 mL) and extracted with EtOAc (30 mL×2). The combined organic layers were washed with brine (30 mL), dried over Na₂SO₄, filtered and concentrated under reduced pressure to give the title compound (310 mg, 94%) as a white solid. ¹H NMR (300 MHz, CDCl₃): δ 7.62 (s, 1H), 7.20 (s, 1H), 3.95 (s, 2H), 2.63 (s, 3H), 1.99 (s, 3H).

Step 4: 6-bromo-1-(cyclopropylmethyl)-2-methyl-4-(methylsulfanylmethyl)benzimidazole

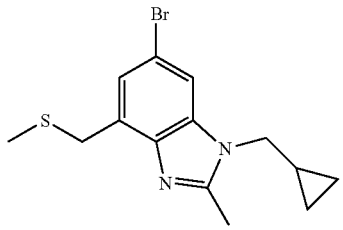 [SMILES: CSCc1cc(Br)cc2c1nc(C)n2CC1CC1]

The title compound was prepared in a manner similar to Example 31, step 3, by substituting the title compound from step 3 for 6-bromo-4-nitro-1H-benzimidazole and bromomethylcyclopropane for bromomethylbenzene. ¹H NMR (400 MHz, CDCl₃): δ 7.36 (s, 1H), 7.29 (s, 1H), 4.06 (s, 2H), 3.95 (d, J=6.8 Hz, 2H), 2.62 (s, 3H), 2.09 (s, 3H), 1.20-1.18 (m, 1H), 0.65-0.60 (m, 2H), 0.40-0.36 (m, 2H).

Step 5: 6-bromo-1-(cyclopropylmethyl)-2-methyl-4-(methylsulfonylmethyl)benzimidazole

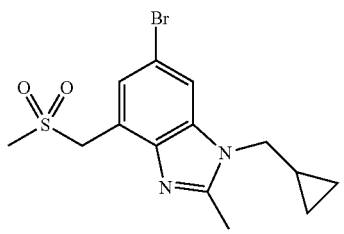 [SMILES: Cc1nc2c(CS(C)(=O)=O)cc(Br)cc2n1CC1CC1]

A mixture of the title compound from step 4 (150 mg, 0.46 mmol) and oxone (569 mg, 0.93 mmol) in DMF (8 ml) was stirred for 4 hr at RT. It was then poured over water (20 mL) and extracted with DCM (20 mL×3). The combined organic layers were washed with brine (30 mL), dried over Na₂SO₄, filtered and concentrated under reduced pressure to afford the title compound (145 mg, 88%) as a solid that was used in the next step without further purification. ¹H NMR (300 MHz, CDCl₃): δ 7.49 (m, 2H), 4.67 (s, 2H), 3.97 (d, J=6.6 Hz, 2H), 2.83 (s, 3H), 2.61 (s, 3H), 1.22-1.18 (m, 1H), 0.69-0.62 (m, 2H), 0.42-0.38 (m, 2H). LCMS: 357; 359 (M+H)⁺.

Step 6: 5-[3-(cyclopropylmethyl)-2-methyl-7-(methylsulfonylmethyl) benzimidazol-5-yl]-1,3-dimethyl-pyridin-2-one

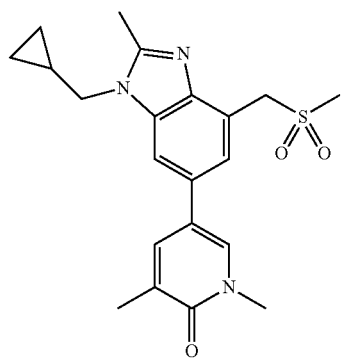 [SMILES: Cc1cc(-c2cc(CS(C)(=O)=O)c3nc(C)n(CC4CC4)c3c2)cn(C)c1=O]

The title compound was prepared in a manner similar to Example 31, step 6, by substituting the title compound from step 5 for N-(1-benzyl-6-bromobenzimidazol-4-yl)methanesulfonamide. ¹H NMR (300 MHz, CDCl₃): δ 7.53 (s, 1H), 7.42 (m, 2H), 7.32 (s, 1H), 4.76 (s, 2H), 4.05 (d, J=6.9 Hz, 2H), 3.64 (s, 3H), 2.85 (s, 3H), 2.65 (s, 3H), 2.24 (s, 3H), 1.25-1.20 (m, 1H), 0.68-0.65 (m, 2H), 0.44-0.41 (m, 2H). LCMS: 400 (M+H)⁺.

Example 97

5-[3-(cyclopropylmethyl)-2-ethoxy-7-(methylsulfonylmethyl)benzimidazol-5-yl]-1,3-dimethylpyridin-2-one Step 1:
6-bromo-2-ethoxy-4-methyl-1H-benzimidazole

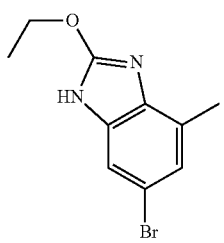

The title compound was prepared in a manner similar to Example 72, step 4, by substituting 5-bromo-3-methylbenzene-1,2-diamine for N-[2-amino-5-bromo-3-(cyclopropylmethylamino)phenyl]methanesulfonamide.

Step 2: 6-bromo-1-(cyclopropylmethyl)-2-ethoxy-4-methylbenzimidazole

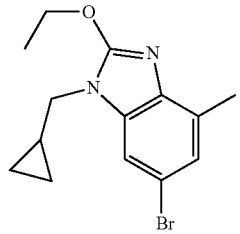 [SMILES: CCOc1nc2c(C)cc(Br)cc2n1CC1CC1]

The title compound was prepared in a manner similar to Example 31, step 3, by substituting the title compound from step 1 for 6-bromo-4-nitro-1H-benzimidazole and bromomethylcyclopropane for bromomethylbenzene. $^1$H NMR (400 MHz, CDCl$_3$): δ 7.16 (s, 1H), 7.09 (s, 1H), 4.61 (q, J=7.2 Hz, 2H), 3.78 (d, J=6.8 Hz, 2H), 2.52 (s, 3H), 1.46 (t, J=7.2 Hz, 3H), 1.21-1.18 (m, 1H), 0.56-0.51 (m, 2H), 0.38-0.34 (m, 2H).

Step 3: 6-bromo-4-(bromomethyl)-1-(cyclopropylmethyl)-2-ethoxybenzimidazole

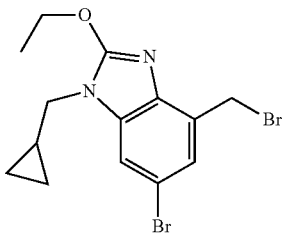 [SMILES: CCOc1nc2c(CBr)cc(Br)cc2n1CC1CC1]

To a solution of the title compound from step 2 (200 mg, 0.65 mmol) and NBS (116 mg, 0.65 mmol) in dry benzene (4 mL) was added BPO (15.7 mg, 0.06 mmol). The mixture was heated to reflux for 3 hr under N$_2$. Cooled to RT, it was partitioned between water (10 mL) and EtOAc (30 mL×3). The combined organic layers were washed with brine (35 mL), dried over Na$_2$SO$_4$, filtered and concentrated under reduced pressure. The residue was purified by column chromatography on silica gel (PE/EtOAc=30:1) to give the title compound (90 mg, 35%). $^1$H NMR (300 MHz, CDCl$_3$): δ 7.34-7.25 (m, 2H), 4.82 (s, 2H), 4.63 (q, J=6.6 Hz, 2H), 3.78 (d, J=6.9 Hz, 2H), 1.47 (t, J=6.9 Hz, 3H), 1.21-1.17 (m, 1H), 0.57-0.55 (m, 2H), 0.38-0.36 (m, 2H).

Step 4: 6-bromo-1-(cyclopropylmethyl)-2-ethoxy-4-(methylsulfonylmethyl)benzimidazole

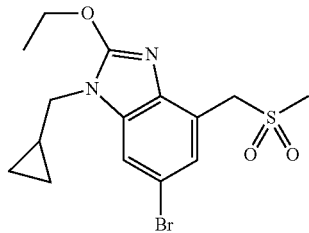 [SMILES: CCOc1nc2c(CS(C)(=O)=O)cc(Br)cc2n1CC1CC1]

A mixture of the title compound from step 3 (175 mg, 0.45 mmol) and NaSO$_2$Me (138 mg, 1.4 mmol) in DMF (10 mL) was heated at 65° C. for 2 hr. The reaction mixture was cooled to RT and partitioned between water (10 mL) and DCM (20 mL×2). The combined organic layers were washed with brine (30 mL), dried over Na$_2$SO$_4$, filtered and concentrated under reduced pressure. The residue was suspended in PE/EtOAc (10 mL, 10:1) and filtered. The cake was dried to give the title compound (170 mg, 97%) as a solid. $^1$H NMR (300 MHz, CDCl$_3$) δ 7.40 (d, J=1.8 Hz, 1H), 7.33 (d, J=1.8 Hz, 1H), 4.61-4.54 (m, 4H), 3.78 (d, J=7.2 Hz, 2H), 2.80 (s, 3H), 1.47 (t, J=7.2 Hz, 3H), 1.22-1.17 (m, 1H), 0.60-0.55 (m, 2H), 0.40-0.36 (m, 2H).
LCMS: 387; 389 (M+H)$^+$.

Step 5: 5-[3-(cyclopropylmethyl)-2-ethoxy-7-(methylsulfonylmethyl) benzimidazol-5-yl]-1,3-dimethylpyridin-2-one

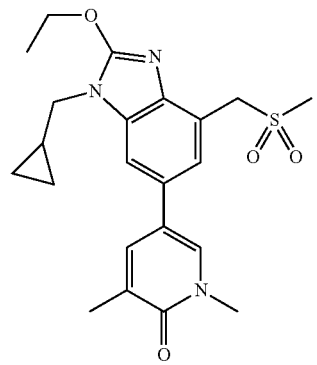 [SMILES: CCOc1nc2c(CS(C)(=O)=O)cc(-c3cc(C)c(=O)n(C)c3)cc2n1CC1CC1]

The title compound was prepared in a manner similar to Example 31, step 6, by substituting 6-bromo-1-(cyclopropylmethyl)-2-ethoxy-4-(methylsulfonylmethyl) benzimidazole for N-(1-benzyl-6-bromobenzimidazol-4-yl)methanesulfonamide. $^1$H NMR (400 MHz, DMSO-d$_6$): δ 7.93 (s, 1H), 7.78 (s, 1H), 7.66 (s, 1H), 7.35 (s, 1H), 4.65 (s, 2H), 4.58 (q, J=7.2 Hz, 2H), 3.93 (d, J=7.2 Hz, 2H), 3.54 (s, 3H), 2.96 (s, 3H), 2.10 (s, 3H), 1.41 (t, J=7.2 Hz, 3H), 1.29-1.26 (m, 1H), 0.51-0.49 (m, 2H), 0.42-0.40 (m, 2H). LCMS: 430 (M+H)$^+$.

Example 98

5-[3-(cyclopropylmethyl)-2-ethoxy-7-(methylsulfonylmethyl)benzimidazol-5-yl]-3-methoxy-1-methylpyridin-2-one

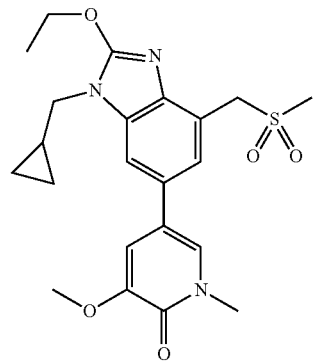 [SMILES: CCOc1nc2c(CS(C)(=O)=O)cc(-c3cc(OC)c(=O)n(C)c3)cc2n1CC1CC1]

The title compound was prepared in a manner similar to Example 97 by substituting 3-methoxy-1-methyl-5-(4,4,5,5-tetramethyl-1,3,2-dioxaborolan-2-yl)pyridin-2-one for 1,3-dimethyl-5-(4,4,5,5-tetramethyl-1,3,2-dioxaborolan-2-yl)pyridin-2-one in step 5. ¹H NMR (300 MHz, CDCl₃) δ 7.33 (s, 1H), 7.19 (s, 1H), 7.12 (s, 1H), 6.90 (s, 1H), 4.67 (s, 2H), 4.64-4.59 (m, 2H), 3.91-3.87 (m, 5H), 3.65 (s, 3H), 2.83 (s, 3H) 1.49-1.46 (m, 3H), 1.25-1.24 (m, 1H), 0.60-0.57 (m, 2H), 0.43-0.41 (m, 2H). LCMS: 446 (M+H)⁺.

Example 99

5-[3-(cyclopropylmethyl)-2-methoxy-7-(methylsulfonylmethyl)benzimidazol-5-yl]-1,3-dimethylpyridin-2-one Step 1: 6-bromo-2-methoxy-4-(methylsulfanylmethyl)-1H-benzimidazole

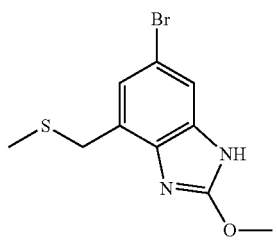

The title compound was prepared in a manner similar to Example 73, step 1, by substituting the title compound from Example 96, step 2, for N-[2-amino-5-bromo-3-(cyclopropylmethylamino)phenyl]methanesulfonamide. LCMS: 287; 289 (M+H)⁺.

Step 2: 6-bromo-1-(cyclopropylmethyl)-2-methoxy-4-(methylsulfanylmethyl)benzimidazole

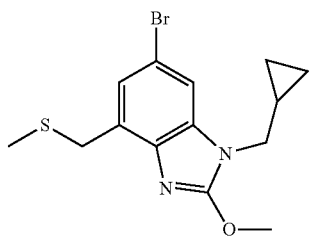 [SMILES: COc1nc2c(CSC)cc(Br)cc2n1CC1CC1]

The title compound was prepared in a manner similar to Example 31, step 3, by substituting the title compound from step 1 for 6-bromo-4-nitro-1H-benzimidazole and bromomethylcyclopropane for bromomethylbenzene. ¹H NMR (400 MHz, CDCl₃) δ 7.23-7.21 (m, 2H), 4.17 (s, 3H), 3.99 (s, 2H), 3.78 (d, J=6.8 Hz, 2H), 2.10 (s, 3H), 1.22-1.17 (m, 1H), 0.57-0.52 (m, 2H), 0.38-0.33 (m, 2H). LCMS: 341; 343 (M+H)⁺.

Step 3: 6-bromo-1-(cyclopropylmethyl)-2-methoxy-4-(methylsulfonylmethyl)benzimidazole

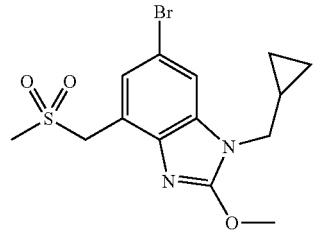 [SMILES: COc1nc2c(CS(C)(=O)=O)cc(Br)cc2n1CC1CC1]

The title compound was prepared in a manner similar to Example 96, step 5, by substituting the title compound from step 2 for 6-bromo-1-(cyclopropylmethyl)-2-methyl-4-(methylsulfanylmethyl)benzimidazole. LCMS: 373; 375 (M+H)⁺.

Step 4: 5-[3-(cyclopropylmethyl)-2-methoxy-7-(methylsulfonylmethyl) benzimidazol-5-yl]-1,3-dimethylpyridin-2-one

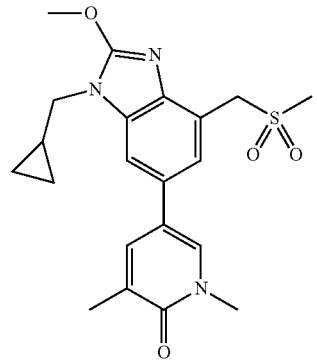 [SMILES: COc1nc2c(CS(C)(=O)=O)cc(-c3cc(C)c(=O)n(C)c3)cc2n1CC1CC1]

The title compound was prepared in a manner similar to Example 31, step 6, by substituting the title compound from step 3 for N-(1-benzyl-6-bromobenzimidazol-4-yl)methanesulfonamide. ¹H NMR (300 MHz, CD₃OD): δ 7.85-7.82 (m, 2H), 7.54 (s, 1H), 7.39 (s, 1H), 4.77 (s, 2H), 4.22 (s, 3H), 3.96 (q, J=6.9 Hz, 2H), 3.66 (s, 3H), 2.90 (s, 3H), 2.21 (s, 3H), 1.32-1.26 (m, 1H), 0.56-0.54 (m, 2H), 0.44-0.42 (m, 2H). LCMS: 416 (M+H)⁺.

Example 100

5-[2-cyclopropyl-5-(ethylsulfonylmethyl)-1,3-benzoxazol-7-yl]-3-methoxy-1-methylpyridin-2-one

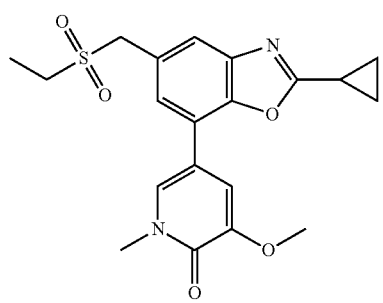 [SMILES: CCS(=O)(=O)Cc1cc(-c2cc(OC)c(=O)n(C)c2)c2oc(C3CC3)nc2c1]

The title compound (44 mg) was prepared as an off-white solid in a similar manner to Example 56 except that sodium ethanesulfinate was substituted for sodium methanesulfinate in step 5 and 3-methoxy-1-methyl-5-(4,4,5,5-tetramethyl-1,3,2-dioxaborolan-2-yl)pyridin-2-one was substituted for 1,3-dimethyl-5-(4,4,5,5-tetramethyl-1,3,2-dioxaborolan-2-yl)pyridin-2-one in step 6. ¹H NMR (400 MHz, DMSO-d₆) δ ppm 1.20-1.24 (m, 7H) 2.33-2.36 (m, 1H) 3.02-3.07 (m, 2H) 3.57 (s, 3H) 3.82 (s, 3H) 4.54-4.58 (s, 2H) 7.27-7.29 (m, 1H) 7.55-7.57 (m, 2H) 7.85-7.86 (m, 1H). LCMS (M+H)⁺ =403.

Example 101

N-[3-(cyclopropylmethyl)-5-(1,5-dimethyl-6-oxopyridin-3-yl)-2-oxo-1,3-benzoxazol-7-yl]methane sulfonamide Step 1: 5-bromo-3-(cyclopropylmethyl)-7-nitro-1,3-benzoxazol-2-one

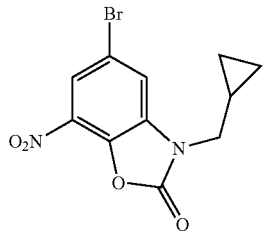 [SMILES: O=c1oc2c([N+](=O)[O-])cc(Br)cc2n1CC1CC1]

A mixture of 5-bromo-7-nitro-3H-1,3-benzoxazol-2-one (700 mg, 2.69 mmol), K₂CO₃ (1.1 g, 8.07 mmol) and bromomethylcyclopropane (727 mg, 5.38 mmol) in DMF (30 mL) was stirred at 80° C. for 4 hr. The reaction was cooled to RT, diluted with ice water (50 mL) and extracted with EtOAc (30 mL×3). The combined organic layers were washed with brine, dried over Na₂SO₄, filtered and concentrated. The residue was purified by column chromatography on silica gel (PE:EtOAc=20:1) to give the title compound (480 mg, 57%) as a yellow solid. ¹H NMR (300 MHz, CDCl₃): δ 8.03 (d, J=1.8 Hz, 1H), 7.43 (d, J=1.5 Hz, 1H), 3.75 (d, J=7.5 Hz, 2H), 1.26-1.19 (m, 1H), 0.70-0.64 (m, 2H), 0.50-0.45 (m, 2H).

Step 2: 7-amino-5-bromo-3-(cyclopropylmethyl)-1,3-benzoxazol-2-one

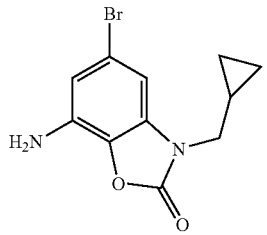

A mixture of the title compound from step 1 (550 mg, 1.76 mmol) and Fe (493 mg, 8.81 mmol) in a methanol/saturated NH₄Cl aqueous solution (30 mL/10 mL) was stirred at 85° C. for 1 hr. The reaction mixture was filtered and the cake was washed with methanol (10 mL×2). The filtrate was diluted with water (50 mL) and extracted with EtOAc (30 mL×3). The combined organic layers were washed with brine (30 mL×3), dried over Na₂SO₄, filtered and concentrated. The residue was washed with ether (10 mL×2) to give the title compound (450 mg, 91%) as a yellow solid. LCMS: 300, 302 (M+NH₄)⁺.

Step 3: N-[5-bromo-3-(cyclopropylmethyl)-2-oxo-1,3-benz-oxazol-7-yl]methanesulfonamide

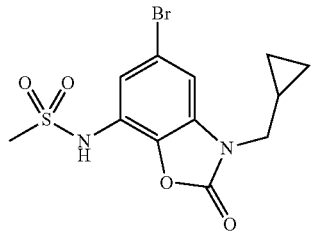 [SMILES: CS(=O)(=O)Nc1cc(Br)cc2c1oc(=O)n2CC1CC1]

To a solution of the title compound from step 2 (250 mg, 0.89 mmol) in DCM (10 mL) at 0° C. was added TEA (895 mg, 8.86 mmol) and MsCl (505 mg, 4.43 mmol). The reaction was allowed to warm to RT and stirred for 2 hr. It was then poured over ice-water and extracted with DCM (20 mL×3). The combined organic layers were dried over Na₂SO₄, filtered and concentrated. The residue was dissolved in THF (5 mL) and TBAF (2 mL, 1M in THF) was added. The reaction was stirred at RT for 1 hr. Water (30 mL) was added and the resulting precipitate was filtered. The solids were washed with water (10 mL×2) and ether (5 mL), and dried under reduced pressure to give the title compound (200 mg, 69%) as a solid. ¹H NMR (300 MHz, CDCl₃): δ 7.45 (d, J=1.5 Hz, 1H), 7.02 (d, J=1.5 Hz, 1H), 6.66 (s, 1H), 3.68 (d, J=7.5 Hz, 2H), 3.15 (s, 3H), 1.22-1.20 (m, 1H), 0.68-0.63 (m, 2H), 0.48-0.43 (m, 2H).

Step 4: N-[3-(cyclopropylmethyl)-5-(1,5-dimethyl-6-oxopyridin-3-yl)-2-oxo-1,3-benzoxazol-7-yl]methane sulfonamide

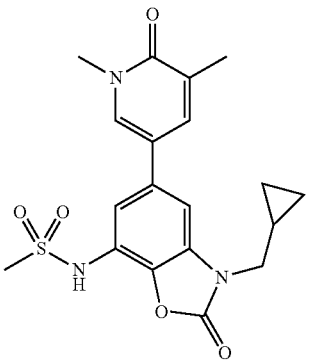 [SMILES: Cc1cc(-c2cc(NS(C)(=O)=O)c3oc(=O)n(CC4CC4)c3c2)cn(C)c1=O]

A mixture of the title compound from step 3 (100 mg, 0.28 mmol), 1,3-dimethyl-5-(4,4,5,5-tetramethyl-1,3,2-dioxaborolan-2-yl)pyridin-2-one (83 mg, 0.33 mmol), K₂CO₃ (116 mg, 0.84 mmol) and Pd(dppf)Cl₂ (21 mg, 0.028 mmol) in dioxane/H₂O (9 mL/3 mL) under N₂ was heated to 85° C. for 3 hr. The reaction mixture was cooled to RT and filtered. The filtrate was diluted with water and extracted with EtOAc (30 mL×3). The combined organic layers were dried over Na₂SO₄, filtered and concentrated. The residue was purified by preparative TLC (EtOAc) to give the title compound (42 mg, 38%) as a solid. ¹H NMR (300 MHz, DMSO-d₆): δ 9.94 (s, 1H), 8.97 (s, 1H), 7.71 (s, 1H), 7.46 (s, 1H), 7.17 (s, 1H), 3.75 (d, J=6.9 Hz, 2H), 3.53 (s, 3H), 3.14 (s, 3H), 2.10 (s, 3H), 1.34-1.31 (m, 1H), 0.54-0.45 (m, 4H). LCMS: 404 (M+H).

Example 102

N-[5-(1,5-dimethyl-6-oxopyridin-3-yl)-3-[(4-fluorophenyl)methyl]-2-oxo-1,3-benzoxazol-7-yl]methane sulfonamide

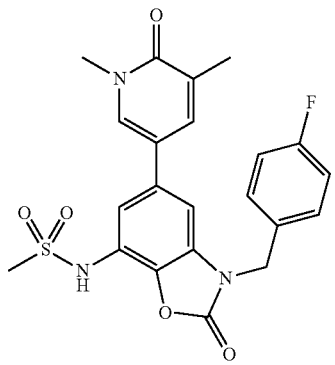 [SMILES: Cc1cc(-c2cc(NS(C)(=O)=O)c3oc(=O)n(Cc4ccc(F)cc4)c3c2)cn(C)c1=O]

The title compound was prepared in a manner similar to Example 101 by substituting 1-(bromomethyl)-4-fluorobenzene for bromomethylcyclopropane in step 1. ¹H NMR (300 MHz, DMSO-d₆): δ 9.95 (s, 1H), 7.91 (d, J=1.8 Hz, 1H), 7.66 (s, 1H), 7.52-7.43 (m, 3H), 7.24-7.17 (m, 3H), 5.07 (s, 2H), 3.52 (s, 3H), 3.13 (s, 3H), 2.09 (s, 3H). LCMS: 458 [M+H]⁺.

Example 103

N-[1-(cyclopropylmethyl)-6-(1,5-dimethyl-6-oxopyridin-3-yl)-2-methoxybenzimidazol-4-yl]ethanesulfonamide

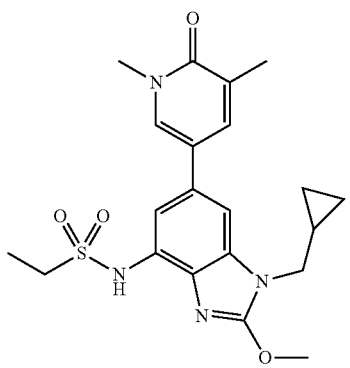 [SMILES: CCS(=O)(=O)Nc1cc(-c2cc(C)c(=O)n(C)c2)cc2c1nc(OC)n2CC1CC1]

The title compound was prepared in a manner similar to Example 72 by substituting ethanesulfonamide for methanesulfonamide in step 2 and tetraethylorthocarbonate for tetramethylorthocarbonate in step 4. ¹H NMR (300 MHz, DMSO-d₆) δ 9.35 (s, 1H), 7.90 (s, 1H), 7.72 (s, 1H), 7.49 (s, 1H), 7.15 (s, 1H), 4.14 (s, 3H), 3.92 (m, 2H), 3.52 (s, 3H), 3.30 (m, 2H), 2.10 (s, 3H), 1.37 (dd, J=7.2 Hz, 3H), 1.27 (m, 1H), 0.48 (m, 2H), 0.40 (m, 2H). LCMS: 431.2 (M+H)+.

Example 104

N-[1-benzyl-6-(1,5-dimethyl-6-oxopyridin-3-yl)-3-fluoroindazol-4-yl]methanesulfonamide

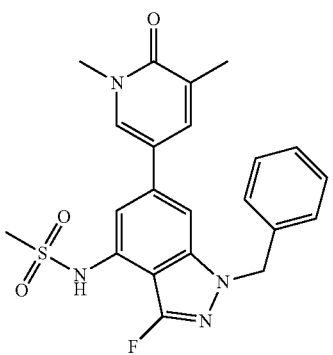 [SMILES: Cc1cc(-c2cc(NS(C)(=O)=O)c3c(F)nn(Cc4ccccc4)c3c2)cn(C)c1=O]

The title compound was prepared in a manner similar to Example 64 by substituting benzyl bromide for 1-(bromomethyl)-4-fluoro-benzene in step 2. ¹H NMR (300 MHz, DMSO-d₆) δ 9.74 (s, 1H), 8.10 (s, 1H), 7.88 (s, 1H), 7.80 (s, 1H), 7.30 (m, 5H), 7.20 (s, 1H), 5.55 (s, 2H), 3.55 (s, 3H), 3.10 (s, 3H), 2.11 (s, 3H). LCMS: 441.1 (M+H)⁺.

Example 105

N-[6-(1,5-dimethyl-6-oxopyridin-3-yl)-3-fluoro-1-[(4-fluorophenyl)methyl]indazol-4-yl]ethanesulfonamide

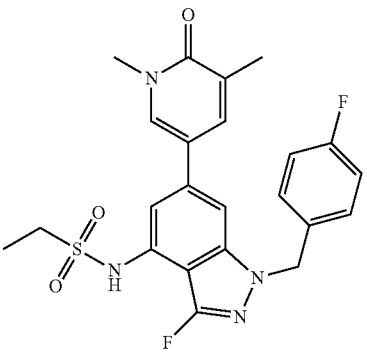 [SMILES: CCS(=O)(=O)Nc1cc(-c2cc(C)c(=O)n(C)c2)cc2c1c(F)nn2Cc1ccc(F)cc1]

The title compound was prepared in a manner similar to Example 64 by substituting ethanesulfonyl chloride for methanesulfonyl chloride in step 5. ¹H NMR (300 MHz, CDCl3-d₆) δ 7.44 (s, 1H), 7.41 (s, 1H), 7.32 (s, 1H), 7.21 (m, 1H), 7.0 (m, 3H), 6.82 (s, 1H), 5.38 (s, 2H), 3.64 (s, 3H), 3.24 (q, J=7.4 Hz, 2H), 2.24 (s, 3H), 1.42 (q, J=7.4 Hz, 3H). LCMS: 473.1 (M+H)⁺.

Example 106

N-[1-benzyl-6-(1,5-dimethyl-6-oxopyridin-3-yl)-3-fluoroindazol-4-yl]ethanesulfonamide

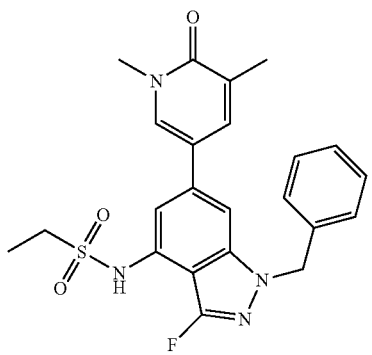 [SMILES: CCS(=O)(=O)Nc1cc(-c2cc(C)c(=O)n(C)c2)cc2c1c(F)nn2Cc1ccccc1]

The title compound was prepared in a manner similar to Example 64 by substituting benzyl bromide for 1-(bromomethyl)-4-fluoro-benzene in step 2 and ethanesulfonyl chloride for methanesulfonyl chloride in step 5. $^1$H NMR (400 MHz, DMSO-$d_6$) δ 9.79 (s, 1H), 8.04 (d, J=1.6 Hz, 1H), 7.86 (s, 1H), 7.79 (s, 1H), 7.31 (m, 5H), 7.18 (s, 1H), 5.54 (s, 2H), 2.05 (q, J=7.4 Hz, 2H), 2.11 (s, 3H), 1.27 (t, J=7.4 Hz, 3H). LCMS: 455.1 (M+H)$^+$.

II. Biological Evaluation

Example 1: In Vitro Enzyme Inhibition Assay

Determination of the IC$_{50}$ for the heterocyclic derivative BRD4 inhibitors disclosed herein was performed as follows. His-tagged BRD4 was cloned, expressed and purified to homogeneity. Filipakopoulos et al., 468 Nature 1067 (2010). BRD4 binding and inhibition was assessed by monitoring the interaction of biotinylated H4-tetraacetyl peptide (AnaSpec, H4K5/8/12/16 (Ac), biotin—labeled) with the target using the AlphaScreen technology (Life Technologies). In a 384-well ProxiPlate BRD4 (BD1) (2 nM final) was combined with peptide (15 nM final) in 50 mM HEPES (pH 7.3), 10 mM NaCl, 0.25 mM TCEP, 0.1% (w/v) BSA, and 0.005% (w/v) Brij-35 either in the presence of DMSO (final 0.4% DMSO) or compound dilution series in DMSO. After 20 min incubation at RT, Alpha streptavidin donor beads and Nickel Chelate acceptor beads were added to a final concentration of 5 μg/mL. After 2 hr of equilibration, plates were read on an Envision instrument and the IC$_{50}$ was calculated using a four parameter non-linear curve fit.

The ability of the compounds disclosed herein to inhibit BRD4 activity was quantified and the respective IC$_{50}$ value was determined. The IC$_{50}$ values of various compounds disclosed herein is provided in Table 3.

Example 2: In Vitro Cell-Based Assay

A colorimetric cellular proliferation assay (Cell-MTS assay) was performed to assess the ability of the heterocyclic derivative BRD4 inhibitors disclosed herein to effect the proliferation of established cancer cell lines.

Assay Principle:

The Cell-MTS assay is a 7-day plate-based colorimetric assay which quantifies the amount of newly generated NADH in the presence or absence of test compound. The NADH level is used for the quantification of cancer cell proliferation.

Assay Method:

Established cancer cell lines with a variety of driving mutations were obtained from American Type Culture Collection (ATCC) and routinely passaged according to ATCC protocols. For routine assay, these cells were seeded at densities which enabled ~90% confluence after 7 days of culture. Raji, human Burkitts lymphoma cells, (cMYC) were seeded at 15,000 cells per 96-well. HL-60, human proleukemia cells, (NRAS, p16, p53, c-Myc amplified) were seeded at 5,000 cells per 96-well. NCI-H460, human non-small cell lung cancer cells, (KRAS, PIK3CA, STLK11, p16) were seeded at 3,000 cells per 96-well. 24 hr after plating, cells received an 11 point dilution of test compound with final concentration ranges from 100 □M to 2.0 nM. Cells were incubated in the presence of compound for 168 hr at 37° C., and 5% CO2. At the end of this incubation period, 80 □L of media is removed and 20 □L of CellTiter 96® AQueous Non-Radioactive Cell Proliferation Assay solution (Promega) was added. The cells were incubated until the OD490 was >0.6. IC50 values were calculated using the IDBS XLfit software package and include background subtracted OD490 values and normalization to DMSO controls. Cellular proliferation IC50 values were uploaded and archived using the Chem Biography Platform. Table 3 provides the results of the in vitro enzyme inhibition assay experiments and the in vitro cell-based assay experiments performed with the compounds disclosed herein:

TABLE 3

| Ex. No | Coumpound Name | BRD4 IC$_{50}$* | Raji IC$_{50}$ | HL-60 IC$_{50}$ | H460 IC$_{50}$ |
|---|---|---|---|---|---|
| 1 | 2-methyl-4-(2-methyl-1,1-dioxo-3H-1,2-benzothiazol-6-yl)isoquinolin-1-one | B | B | B | B |
| 2 | 4-(1,1-dioxo-2,3-dihydro-1,2-benzothiazol-6-yl)-2-methylisoquinolin-1-one | B | C | B | C |
| 3 | 5-(5-methoxy-2-methyl-1,1-dioxo-3H-1,2-benzothiazol-6-yl)-1,3-dimethylpyridin-2-one | A | C | B | C |
| 4 | 4-(5-methoxy-2-methyl-1,1-dioxo-3H-1,2-benzothiazol-6-yl)-2-methylisoquinolin-1-one | A | B | A | B |
| 5 | 5-[5-(cyclopropylmethoxy)-2-methyl-1,1-dioxo-3H-1,2-benzothiazol-6-yl]-1,3-dimethylpyridin-2-one | A | B | A | C |
| 6 | 4-[5-(cyclopropylmethoxy)-2-methyl-1,1-dioxo-3H-1,2-benzothiazol-6-yl]-2-methylisoquinolin-1-one | A | B | A | B |
| 7 | 4-[5-(cyclopropylmethoxy)-2-ethyl-1,1-dioxo-3H-1,2-benzothiazol-6-yl]-2-methylisoquinolin-1-one | A | A | A | B |
| 8 | 5-[5-(cyclopropylmethoxy)-2-ethyl-1,1-dioxo-3H-1,2-benzothiazol-6-yl]-1,3-dimethylpyridin-2-one | A | B | A | B |

TABLE 3-continued

| Ex. No | Compound Name | BRD4 IC$_{50}$* | Raji IC$_{50}$ | HL-60 IC$_{50}$ | H460 IC$_{50}$ |
|---|---|---|---|---|---|
| 9 | 1,3-dimethyl-5-[2-methyl-1,1-dioxo-5-(2,2,2-trifluoroethoxy)-3H-1,2-benzothiazol-6-yl]pyridine-2-one | A | B | A | C |
| 10 | 2-methyl-4-[2-methyl-1,1-dioxo-5-(2,2,2-trifluoroethoxy)-3H-1,2-benzothiazol-6-yl]isoquinolin-1-one | A | B | A | B |
| 11 | 5-[5-(2,4-difluorophenoxy)-2-methyl-1,1-dioxo-3H-1,2-benzothiazol-6-yl]-1,3-dimethylpyridin-2-one | A | A | A | C |
| 12 | 5-[5-(2,4-difluorophenoxy)-2-methyl-1,1-dioxo-3H-1,2-benzothiazol-6-yl]-1-methylpyridin-2-one | A | — | — | — |
| 13 | 4-[5-(cyclopropylmethoxy)-1-methylsulfonyl-2,3-dihydroindol-6-yl]-2-methylisoquinolin-1-one | A | A | A | B |
| 14 | 4-[5-(cyclopropylmethoxy)-1-ethylsulfonyl-2,3-dihydroindol-6-yl]-2-methylisoquinolin-1-one | A | A | A | B |
| 15 | 5-[5-(cyclopropylmethoxy)-1-methylsulfonyl-2,3-dihydroindol-6-yl]-1,3-dimethylpyridin-2-one | A | A | A | C |
| 16 | 5-[5-(cyclopropylmethoxy)-1-ethylsulfonyl-2,3-dihydroindol-6-yl]-1,3-dimethylpyridin-2-one | A | A | A | C |
| 17 | N-[1-benzyl-6-(2-methyl-1-oxoisoquinolin-4-yl)indol-4-yl]methanesulfonamide | A | A | A | B |
| 18 | N-[1-benzyl-6-(1,5-dimethyl-6-oxopyridin-3-yl)indol-4-yl]methanesulfonamide | A | A | A | B |
| 19 | N-[1-benzyl-6-(1,5-dimethyl-6-oxopyridin-3-yl)-2,3-dihydroindol-4-yl]methanesulfonamide | A | A | A | B |
| 20 | N-[1-benzyl-6-(2-methyl-1-oxoisoquinolin-4-yl)-2,3-dihydroindol-4-yl]methanesulfonamide | A | A | A | B |
| 21 | 5-(2-ethyl-5-methylsulfonyl-1-benzofuran-7-yl)-1,3-dimethylpyridin-2-one | A | — | — | — |
| 22 | N-[2-(1,5-dimethyl-6-oxopyridin-3-yl)-9-[(4-fluorophenyl)methyl]-8-methylpurin-6-yl]methanesulfonamide | A | — | — | — |
| 23 | 5-(2-cyclopropyl-5-methylsulfonyl-1-benzofuran-7-yl)-1,3-dimethylpyridin-2-one | A | B | A | C |
| 24 | 4-(2-cyclopropyl-5-methylsulfonyl-1-benzofuran-7-yl)-2-methylisoquinolin-1-one | A | A | A | B |
| 25 | 1,3-dimethyl-5-(5-methylsulfonyl-2-phenyl-1-benzofuran-7-yl)pyridin-2-one | A | — | — | — |
| 26 | 2-methyl-4-(5-methylsulfonyl-2-phenyl-1-benzofuran-7-yl)isoquinolin-1-one | A | A | A | B |
| 27 | N-[1-benzyl-6-(1,5-dimethyl-6-oxopyridin-3-yl)benzotriazol-4-yl]ethanesulfonamide | A | A | A | B |
| 28 | N-[6-(1,5-dimethyl-6-oxopyridin-3-yl)-1-[(4-fluorophenyl)methyl]benzotriazol-4-yl]ethanesulfonamide | A | A | A | B |
| 29 | 4-[6-(cyclopropylmethoxy)-1-methyl-3-methylsulfonylindazol-5-yl]-2-methylisoquinolin-1-one | A | A | A | B |
| 30 | 4-[6-(cyclopropylmethoxy)-3-ethylsulfonyl-1-methylindazol-5-yl]-2-methylisoquinolin-1-one | A | A | A | B |
| 31 | N-[1-benzyl-6-(1,5-dimethyl-6-oxopyridin-3-yl)benzimidazol-4-yl]methanesulfonamide | A | A | A | B |
| 32 | N-[6-(1,5-dimethyl-6-oxopyridin-3-yl)-1-[(3-fluorophenyl)methyl]benzimidazol-4-yl]methanesulfonamide | A | A | A | B |
| 33 | N-[6-(1,5-dimethyl-6-oxopyridin-3-yl)-1-[(3-fluorophenyl)methyl]benzimidazol-4-yl]ethanesulfonamide | A | A | A | B |
| 34 | N-[1-benzyl-6-(1,5-dimethyl-6-oxopyridin-3-yl)-2-methylbenzimidazol-4-yl]methanesulfonamide | A | A | A | C |
| 35 | N-[6-(1,5-dimethyl-6-oxopyridin-3-yl)-1-[(3-fluorophenyl)methyl]-2-methylbenzimidazol-4-yl]methanesulfonamide | A | A | A | B |
| 36 | N-[6-(1,5-dimethyl-6-oxopyridin-3-yl)-1-[(3-fluorophenyl)methyl]-2-methylbenzimidazol-4-yl]ethanesulfonamide | A | A | A | A |
| 37 | N-[6-(1,5-dimethyl-6-oxopyridin-3-yl)-1-[(4-fluorophenyl)methyl]-2-methylbenzimidazol-4-yl]methanesulfonamide | A | A | A | B |
| 38 | N-[1-[(4-fluorophenyl)methyl]-6-(5-methoxy-1-methyl-6-oxopyridin-3-yl)-2-methylbenzimidazol-4-yl]methanesulfonamide | A | A | A | C |
| 39 | N-[1-(cyclopropylmethyl)-6-(1,5-dimethyl-6-oxopyridin-3-yl)-2-methylbenzimidazol-4-yl]methanesulfonamide | A | A | A | C |
| 40 | N-[1-butyl-6-(1,5-dimethyl-6-oxopyridin-3-yl)benzimidazol-4-yl]ethanesulfonamide | A | A | A | C |

TABLE 3-continued

| Ex. No | Compound Name | BRD4 IC$_{50}$* | Raji IC$_{50}$ | HL-60 IC$_{50}$ | H460 IC$_{50}$ |
|---|---|---|---|---|---|
| 41 | N-[1-[(2,4-difluorophenyl)methyl]-6-(1,5-dimethyl-6-oxopyridin-3-yl)benzimidazol-4-yl]ethanesulfonamide | A | A | A | B |
| 42 | N-[1-benzyl-6-(1,5-dimethyl-6-oxopyridin-3-yl)indazol-4-yl]ethanesulfonamide | A | A | A | B |
| 43 | N-[6-(1,5-dimethyl-6-oxopyridin-3-yl)-1-[(4-fluorophenyl)methyl]indazol-4-yl]ethanesulfonamide | A | A | A | A |
| 44 | N-[6-(1,5-dimethyl-6-oxopyridin-3-yl)-2-methyl-1-(1-phenylethyl)benzimidazol-4-yl]methanesulfonamide | A | A | A | B |
| 45 | N-[6-(1,5-dimethyl-6-oxopyridin-3-yl)-2-methyl-1-(1-phenylethyl)benzimidazol-4-yl]methanesulfonamide | A | A | A | B |
| 46 | N-[6-(1,5-dimethyl-6-oxopyridin-3-yl)-1-[(2R)-1-methoxypropan-2-yl]-2-methylbenzimidazol-4-yl]methanesulfonamide | A | A | A | C |
| 47 | N-[2-cyclopropyl-7-(1,5-dimethyl-6-oxopyridin-3-yl)-1,3-benzoxazol-5-yl]ethanesulfonamide | A | A | A | C |
| 48 | N-[2-cyclopropyl-7-(2-methyl-1-oxoisoquinolin-4-yl)-1,3-benzoxazol-5-yl]ethanesulfonamide | A | A | A | A |
| 49 | 4-[7-(cyclopropylmethoxy)-4-ethylsulfonyl-2,3-dihydro-1,4-benzoxazin-6-yl]-2-methylisoquinolin-1-one | A | A | A | B |
| 50 | 5-[7-(cyclopropylmethoxy)-4-ethylsulfonyl-2,3-dihydro-1,4-benzoxazin-6-yl]-1,3-dimethylpyridin-2-one | A | A | A | C |
| 51 | N-[2-cyclopropyl-7-(1,5-dimethyl-6-oxopyridin-3-yl)-1,3-benzoxazol-5-yl]propane-2-sulfonamide | A | B | A | C |
| 52 | N-[2-cyclopentyl-7-(1,5-dimethyl-6-oxopyridin-3-yl)-1,3-benzoxazol-5-yl]ethanesulfonamide | A | A | A | C |
| 53 | N-[2-cyclopentyl-7-(2-methyl-1-oxoisoquinolin-4-yl)-1,3-benzoxazol-5-yl]ethanesulfonamide | A | A | A | C |
| 54 | N-[2-cyclopropyl-7-(1,5-dimethyl-6-oxopyridin-3-yl)-3-methylbenzimidazol-5-yl]ethanesulfonamide | A | — | — | — |
| 55 | N-[2-cyclopropyl-3-methyl-7-(2-methyl-1-oxoisoquinolin-4-yl)benzimidazol-5-yl]ethanesulfonamide | A | — | — | — |
| 56 | 5-[2-cyclopropyl-5-(methylsulfonylmethyl)-1,3-benzoxazol-7-yl]-1,3-dimethylpyridin-2-one | A | B | A | C |
| 57 | N-[2-cyclopentyl-7-(5-methoxy-1-methyl-6-oxopyridin-3-yl)-1,3-benzoxazol-5-yl]ethanesulfonamide | A | A | A | C |
| 58 | 5-[6-(cyclopropylmethoxy)-1-methyl-3-methylsulfonylindazol-5-yl]-1,3-dimethylpyridin-2-one | A | A | A | C |
| 59 | 5-[6-(cyclopropylmethoxy)-1-methyl-3-methylsulfonylindazol-5-yl]-3-methoxy-1-methylpyridin-2-one | A | A | A | C |
| 60 | N-[6-(1,5-dimethyl-6-oxopyridin-3-yl)-1-[(4-fluorophenyl)methyl]-2-methylimidazo[4,5-c]pyridin-4-yl]methanesulfonamide | A | A | A | C |
| 61 | N-[1-benzyl-6-(1,5-dimethyl-6-oxopyridin-3-yl)-2-methylimidazo[4,5-c]pyridin-4-yl]methanesulfonamide | A | A | A | C |
| 62 | N-[1-[(2,4-difluorophenyl)methyl]-6-(1,5-dimethyl-6-oxopyridin-3-yl)-2-methylimidazo[4,5-c]pyridin-4-yl]methanesulfonamide | A | A | A | C |
| 63 | 5-[2-cyclopropyl-5-(methylsulfonylmethyl)-1,3-benzoxazol-7-yl]-3-methoxy-1-methylpyridin-2-one | A | — | — | — |
| 64 | N-[6-(1,5-dimethyl-6-oxopyridin-3-yl)-3-fluoro-1-[(4-fluorophenyl)methyl]indazol-4-yl]methanesulfonamide | A | A | A | C |
| 65 | N-[3-fluoro-1-[(4-fluorophenyl)methyl]-6-(5-methoxy-1-methyl-6-oxopyridin-3-yl)indazol-4-yl]methanesulfonamide | A | A | A | C |
| 66 | N-[1-(cyclopropylmethyl)-6-(1,5-dimethyl-6-oxopyridin-3-yl)-3-fluoroindazol-4-yl]methanesulfonamide | A | A | A | C |
| 67 | 5-(3-benzyl-2-methyl-7-methylsulfonylbenzimidazol-5-yl)-1,3-dimethylpyridin-2-one | A | A | A | C |
| 68 | 5-(3-benzyl-7-ethylsulfonyl-2-methylbenzimidazol-5-yl)-3-methoxy-1-methylpyridin-2-one | A | B | B | C |
| 69 | 5-[3-(cyclopropylmethyl)-7-ethylsulfonyl-2-methylbenzimidazol-5-yl]-1,3-dimethylpyridin-2-one | A | — | — | — |
| 70 | 5-[3-(cyclopropylmethyl)-7-ethylsulfonyl-2-methylbenzimidazol-5-yl]-3-methoxy-1-methylpyridin-2-one | A | — | — | — |
| 71 | 5-[3-(cyclopropylmethyl)-2-methyl-7-methylsulfonylbenzimidazol-5-yl]-1,3-dimethylpyridin-2-one | A | C | B | C |

TABLE 3-continued

| Ex. No | Compound Name | BRD4 IC$_{50}$* | Raji IC$_{50}$ | HL-60 IC$_{50}$ | H460 IC$_{50}$ |
|---|---|---|---|---|---|
| 72 | N-[1-(cyclopropylmethyl)-6-(1,5-dimethyl-6-oxopyridin-3-yl)-2-ethoxybenzimidazol-4-yl]methanesulfonamide | A | A | A | B |
| 73 | N-[1-(cyclopropylmethyl)-6-(1,5-dimethyl-6-oxopyridin-3-yl)-2-methoxybenzimidazol-4-yl]methanesulfonamide | A | A | A | B |
| 74 | N-[1-(cyclopropylmethyl)-6-(1,5-dimethyl-6-oxopyridin-3-yl)-2-ethylbenzimidazol-4-yl]methanesulfonamide | A | — | — | — |
| 75 | 5-(1-ethyl-4-methylsulfonylindol-2-yl)-1,3-dimethylpyridin-2-one | A | — | — | — |
| 76 | 5-[1-(cyclopropylmethyl)-4-methylsulfonylindol-2-yl]-1,3-dimethylpyridin-2-one | A | — | — | — |
| 77 | 5-[1-(2-cyclopropylethyl)-4-methylsulfonylindol-2-yl]-1,3-dimethylpyridin-2-one | A | — | — | — |
| 78 | 4-[1-(cyclopropylmethyl)-4-methylsulfonylindol-2-yl]-2-methylisoquinolin-1-one | A | — | — | — |
| 79 | N-[2-cyclopropyl-7-(2-methyl-1-oxoisoquinolin-4-yl)-1-benzofuran-5-yl]methanesulfonamide | A | A | A | A |
| 80 | N-[2-cyclopropyl-7-(1,5-dimethyl-6-oxopyridin-3-yl)-1-benzofuran-5-yl]methanesulfonamide | A | A | A | B |
| 81 | N-[9-(cyclopropylmethyl)-2-(1,5-dimethyl-6-oxopyridin-3-yl)-8-methylpurin-6-yl]methanesulfonamide | A | — | — | — |
| 82 | N-[2-cyclopropyl-7-(2-methyl-1-oxoisoquinolin-4-yl)-1-benzofuran-5-yl]ethanesulfonamide | A | A | A | A |
| 83 | N-[7-(1,5-dimethyl-6-oxopyridin-3-yl)-2-phenyl-1-benzofuran-5-yl]methanesulfonamide | A | B | B | B |
| 84 | N-[7-(2-methyl-1-oxoisoquinolin-4-yl)-2-phenyl-1-benzofuran-5-yl]methanesulfonamide | A | A | A | A |
| 85 | 8-[2-(cyclopropylmethoxy)-5-methylsulfonylphenyl]-6-methyl-2,3-dihydro-1H-indolizin-5-one | A | B | A | C |
| 86 | N-[4-(2,4-difluorophenoxy)-3-(6-methyl-5-oxo-2,3-dihydro-1H-indolizin-8-yl)phenyl]methanesulfonamide | A | A | A | C |
| 87 | 8-[2-(cyclopropylmethoxy)-5-methylsulfonylphenyl]-2,2,6-trimethyl-1,3-dihydroindolizin-5-one | A | A | A | C |
| 88 | N-[4-(2,4-difluorophenoxy)-3-(2,2,6-trimethyl-5-oxo-1,3-dihydroindolizin-8-yl)phenyl]methanesulfonamide | A | A | A | C |
| 89 | 8-[2-(cyclopropylmethoxy)-5-methylsulfonylphenyl]-1,1-difluoro-6-methyl-2,3-dihydroindolizin-5-one | B | — | — | — |
| 90 | 8-[2-(cyclopropylmethoxy)-5-methylsulfonylphenyl]-1-fluoro-6-methyl-2,3-dihydro-1H-indolizin-5-one | A | — | — | — |
| 91 | 5-[1-(2-cyclopropylethyl)-4-methylsulfonylindol-2-yl]-3-methoxy-1-methylpyridin-2-one | A | A | A | C |
| 92 | N-[1-(cyclopropylmethyl)-6-(1,5-dimethyl-6-oxopyridin-3-yl)-2-(trifluoromethyl)benzimidazol-4-yl]methanesulfonamide | A | A | A | B |
| 93 | N-[1-(cyclopropylmethyl)-6-(5-methoxy-1-methyl-6-oxopyridin-3-yl)-2-(trifluoromethyl)benzimidazol-4-yl]methanesulfonamide | A | A | A | C |
| 94 | N-[1-butyl-6-(1,5-dimethyl-6-oxopyridin-3-yl)-2-methylbenzimidazol-4-yl]methanesulfonamide | A | A | A | C |
| 95 | N-[1-butyl-6-(5-methoxy-1-methyl-6-oxopyridin-3-yl)-2-methylbenzimidazol-4-yl]methanesulfonamide | A | A | A | C |
| 96 | 5-[3-(cyclopropylmethyl)-2-methyl-7-(methylsulfonylmethyl)benzimidazol-5-yl]-1,3-dimethylpyridin-2-one | A | A | A | C |
| 97 | 5-[3-(cyclopropylmethyl)-2-ethoxy-7-(methylsulfonylmethyl)benzimidazol-5-yl]-1,3-dimethylpyridin-2-one | A | A | A | C |
| 98 | 5-[3-(cyclopropylmethyl)-2-ethoxy-7-(methylsulfonylmethyl)benzimidazol-5-yl]-3-methoxy-1-methylpyridin-2-one | A | A | A | C |
| 99 | 5-[3-(cyclopropylmethyl)-2-methoxy-7-(methylsulfonylmethyl)benzimidazol-5-yl]-1,3-dimethylpyridin-2-one | A | A | A | C |
| 100 | 5-[2-cyclopropyl-5-(ethylsulfonylmethyl)-1,3-benzoxazol-7-yl]-3-methoxy-1-methylpyridin-2-one | A | A | A | C |
| 101 | N-[3-(cyclopropylmethyl)-5-(1,5-dimethyl-6-oxopyridin-3-yl)-2-oxo-1,3-benzoxazol-7-yl]methanesulfonamide | A | B | B | C |
| 102 | N-[5-(1,5-dimethyl-6-oxopyridin-3-yl)-3-[(4-fluorophenyl)methyl]-2-oxo-1,3-benzoxazol-7-yl]methanesulfonamide | A | A | A | C |

TABLE 3-continued

| Ex. No | Coumpound Name | BRD4 IC$_{50}$* | Raji IC$_{50}$ | HL-60 IC$_{50}$ | H460 IC$_{50}$ |
|---|---|---|---|---|---|
| 103 | N-[1-(cyclopropylmethyl)-6-(1,5-dimethyl-6-oxopyridin-3-yl)-2-methoxybenzimidazol-4-yl]ethanesulfonamide | A | — | — | — |
| 104 | N-[1-benzyl-6-(1,5-dimethyl-6-oxopyridin-3-yl)-3-fluoroindazol-4-yl]methanesulfonamide | A | — | — | — |
| 105 | N-[6-(1,5-dimethyl-6-oxopyridin-3-yl)-3-fluoro-1-[(4-fluorophenyl)methyl]indazol-4-yl]ethanesulfonamide | A | — | — | — |
| 106 | N-[1-benzyl-6-(1,5-dimethyl-6-oxopyridin-3-yl)-3-fluoroindazol-4-yl]ethanesulfonamide | A | — | — | — |
|  | 4-(2-ethyl-5-methylsulfonyl-1-benzofuran-7-yl)-2-methylisoquinolin-1-one | A | A | A | B |
|  | N-[2-cyclopropyl-7-(1,5-dimethyl-6-oxopyridin-3-yl)-1-benzofuran-5-yl]ethanesulfonamide | A | A | A | B |

*All IC$_{50}$ data were calculated μM. IC$_{50}$ data are designated within the following ranges: A: ≤0.5 μM; B: >0.5 μM to ≤5.0 μM; C: >5.0 μM

Example 3: In Vivo Xenograph Study—Antitumor Efficacy in Xenograft Models of NUT Midline Carcinoma (NMC)

Xenograft models of NMC in mice are used in this study. Matched cohorts of mice with established tumors are randomized to treatment with a test compound or vehicle, administered by daily intraperitoneal injection. Before randomization and after four days of therapy, mice are evaluated by 18F-fluorodeoxyglucose (FDG)-PET imaging. Tumor-volume measurements are also made, as are measures of toxicity or weight loss. Tumors are obtained and sectioned and immunohistochemically examined for the BRD4-NUT oncoprotein, cell spreading, keratin expression, nuclear Ki67, and TUNEL staining. Paired samples from treated and untreated mice are prepared and analyzed using standardized protocols and commercially available software (i.e., ImageScopt; Aperio Technologies).

Example 4: In Vivo Xenograph Study—Antitumor Efficacy in Xenograft Models of MCF-7 Breast Cancer Time release pellets containing 0.72 mg 17-β Estradiol are subcutaneously implanted into nu/nu mice. MCF-7 cells are grown in RPMI containing 10% FBS at 37° C. in 5% CO$_2$. Cells are spun down and re-suspended in 50% RPMI (serum free) and 50% Matrigel at 1×10$^7$ cells/mL. MCF-7 cells are subcutaneously injected (100 μL/animal) on the right flank 2-3 days post pellet implantation and tumor volume (length×width 2/2) is monitored biweekly. When tumors reach an average volume of ~200 mm$^3$ animals are randomized and treatment is started. Animals are treated with a test compound or vehicle daily for four weeks. Tumor volume and body weight are monitored biweekly throughout the study. At the conclusion of the treatment period, plasma and tumor samples are taken for pharmacokinetic and pharmacodynamic analyses, respectively.

III. Preparation of Pharmaceutical Dosage Forms

Example 1: Oral Tablet

A tablet is prepared by mixing 48% by weight of a compound of Formula I, or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:

1. A compound of Formula III, or a pharmaceutically acceptable salt thereof,

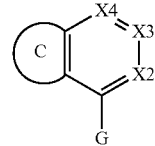

Formula III wherein,
Ring C is an optionally substituted 5- or 6-membered heteroaryl ring containing at least one O, S or N atom;
X2 is N or CR$^{12}$, wherein R$^{12}$ is hydrogen, halogen, alkyl, or alkoxy;
X3 is N or CR$^{13}$, wherein R$^{13}$ is —Y—Z, in which
Y is a bond, —CH$_2$—, or —CH(C$_1$-C$_4$ alkyl)-;
Z is —SO$_2$R$^b$, —N(R$^a$)SO$_2$R$^b$, —SO$_2$N(R$^a$)$_2$, —N(R$^a$)SO$_2$N(R$^a$)$_2$, —CON(R$^a$)$_2$, —N(R$^a$)CO$_2$R$^a$, —N(R$^a$)CON(R$^a$)$_2$, —N(R$^a$)COR$^a$, —OC(O)N(R$^a$)$_2$, —OSO$_2$N(R$^a$)$_2$, or —N(R$^a$)SO$_3$R$^b$; wherein
each R$^a$ is independently hydrogen, alkyl, cycloalkyl, cycloalkylalkyl, aryl, aralkyl, heterocyclyl, heterocyclylalkyl, heteroaryl, or heteroarylalkyl;
R$^b$ is alkyl, cycloalkyl, cycloalkylalkyl, aryl, aralkyl, heterocyclyl, heterocyclylalkyl, heteroaryl, or heteroarylalkyl;
X4 is N or C—R$^{14}$, wherein R$^{14}$ is hydrogen, halogen, —CN, alkyl, cycloalkyl, or alkoxy; and
G is described by:

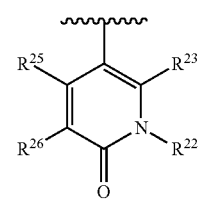

wherein,

R²² is alkyl;

R²³ is hydrogen, halogen, or alkyl; or, optionally, when R²³ is alkyl, then R²² and R²³ join to form an optionally substituted ring;

R²⁵ is hydrogen, halogen, alkyl, alkoxy, or alkenyl;

R²⁶ is hydrogen, halogen, alkyl, alkoxy, aminoalkyl, or alkenyl; or, optionally, when R²³ is hydrogen, R²⁵ is not hydrogen, and R²⁶ is not hydrogen or halogen, then R²⁵ and R²⁶ join to form an optionally substituted cycloalkyl, heterocyclyl, or $C_6$-aryl ring;

provided that the compound of Formula III is neither 4-(2-ethyl-5-(methylsulfonyl)benzofuran-7-yl)-2-methyl-isoquinolin-1(2H)-one, nor 4-(2-cyclopropyl-5-(methylsulfonyl)benzofuran-7-yl)-2-methylisoquinolin-1(2H)-one.

2. The compound of claim 1, or a pharmaceutically acceptable salt thereof, wherein G is:

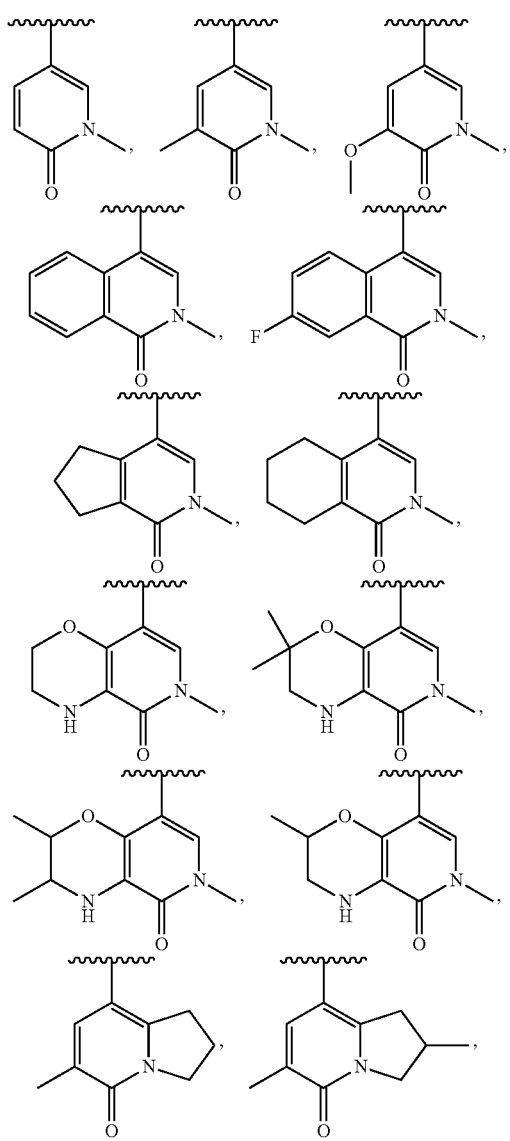

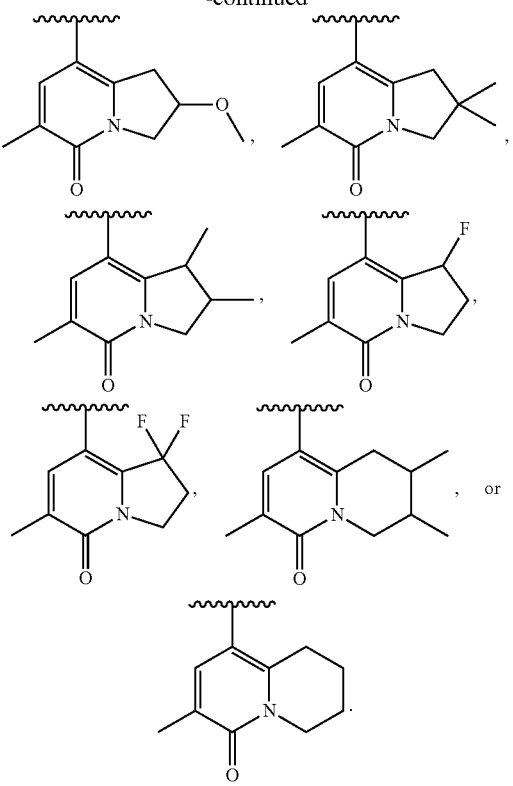

3. The compound of claim 1, or a pharmaceutically acceptable salt thereof, wherein G is:

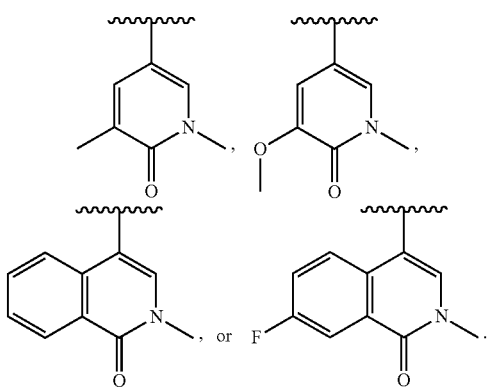

4. The compound of claim 1, or a pharmaceutically acceptable salt thereof, wherein G is:

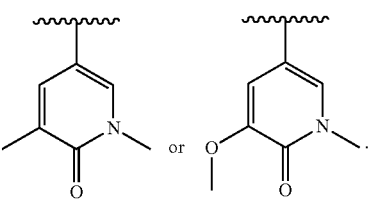

5. The compound of claim 1, or a pharmaceutically acceptable salt thereof, wherein G is:

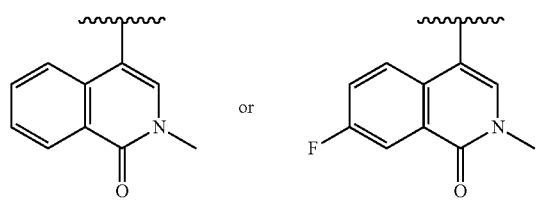

6. The compound of claim 1, or a pharmaceutically acceptable salt thereof, wherein X2 is N.

7. The compound of claim 1, or a pharmaceutically acceptable salt thereof, wherein X3 is N.

8. The compound of claim 1, or a pharmaceutically acceptable salt thereof, wherein X4 is N.

9. The compound of claim 1, or a pharmaceutically acceptable salt thereof, wherein X2 is C—$R^{12}$.

10. The compound of claim 1, or a pharmaceutically acceptable salt thereof, wherein X3 is C—$R^{13}$.

11. The compound of claim 1, or a pharmaceutically acceptable salt thereof, wherein X4 is C—$R^{14}$.

12. The compound of claim 1, or a pharmaceutically acceptable salt thereof, wherein ring C is an optionally substituted 5- or 6-membered heterocyclyl ring containing at least one S or N atom.

13. The compound of claim 1, or a pharmaceutically acceptable salt thereof, wherein ring C is an optionally substituted 5- or 6-membered heteroaryl ring that contains at least one S atom.

14. The compound of claim 1, or a pharmaceutically acceptable salt thereof, wherein ring C is an optionally substituted 5- or 6-membered heteroaryl ring that contains at least one N atom.

15. The compound of claim 12, or a pharmaceutically acceptable salt thereof, wherein the optionally substituted 5- or 6-membered heterocyclyl ring contains at least one S atom.

16. The compound of claim 12, or a pharmaceutically acceptable salt thereof, wherein the optionally substituted 5- or 6-membered heterocyclyl ring contains at least one N atom.

17. The compound of claim 1, or a pharmaceutically acceptable salt thereof, wherein X2 is C—$R^{12}$, X3 is C—$R^{13}$, and X4 is C—$R^{14}$.

18. The compound of claim 17, or a pharmaceutically acceptable salt thereof, wherein ring C is selected to provide one of the following:

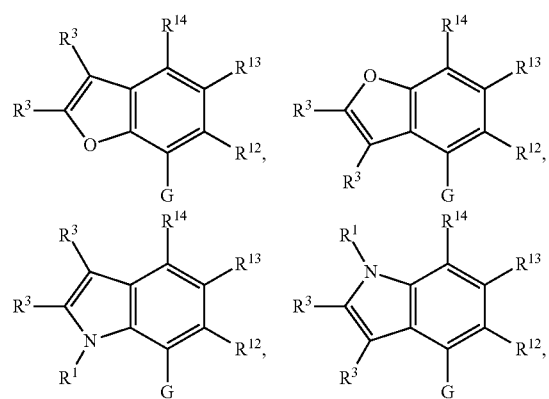

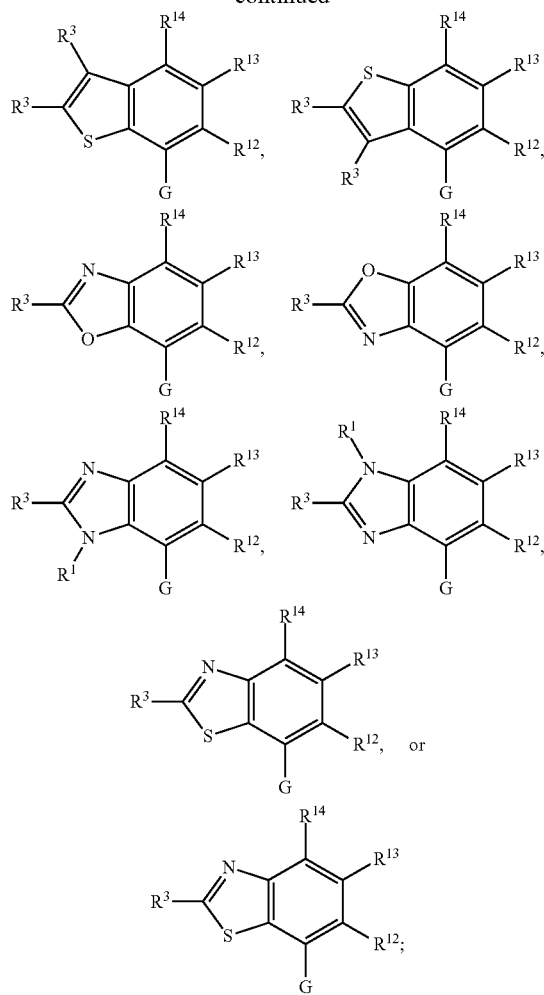

and wherein:

$R^1$ is hydrogen, alkyl, cycloalkyl, cycloalkylalkyl, aryl, aralkyl, heterocyclyl, heterocyclylalkyl, heteroaryl, or heteroarylalkyl; and $R^3$ is hydrogen, halogen, alkyl, alkylsulfonyl, alkylsulfinyl, alkoxy, alkoxyalkyl, cycloalkyl, cycloalkylalkyl, aryl, aralkyl, heterocyclyl, heterocyclylalkyl, heteroaryl, or heteroarylalkyl.

19. The compound of claim 18, or a pharmaceutically acceptable salt thereof, wherein ring C is selected to provide one of the following:

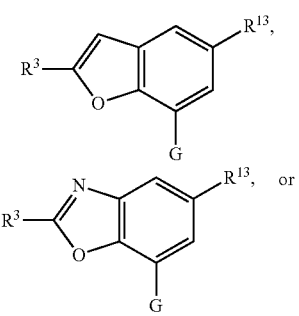

-continued

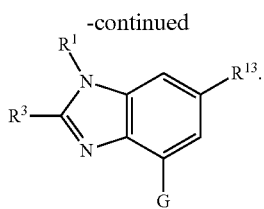

20. The compound of claim 18, or a pharmaceutically acceptable salt thereof, wherein:
   $R^{13}$ is —Y—Z, in which Y is s a bond or —$CH_2$—, Z is —$SO_2R^b$, —$N(R^a)SO_2R^b$ or —$SO_2N(R^a)_2$, each $R^a$ is independently hydrogen, alkyl, cycloalkyl, cycloalkylalkyl, aryl, aralkyl, heterocyclyl, heterocyclylalkyl, heteroaryl, or heteroarylalkyl, and $R^b$ is alkyl, cycloalkyl, cycloalkylalkyl, aryl, aralkyl, heterocyclyl, heterocyclylalkyl, heteroaryl, or heteroarylalkyl;
   $R^1$ is hydrogen, alkyl, cycloalkyl, cycloalkylalkyl, aryl, aralkyl, heterocyclyl, heterocyclylalkyl, heteroaryl, or heteroarylalkyl; and
   $R^3$ is hydrogen, halogen, alkyl, alkylsulfonyl, alkylsulfinyl, alkoxy, alkoxyalkyl, cycloalkyl, cycloalkylalkyl, aryl, aralkyl, heterocyclyl, heterocyclylalkyl, heteroaryl, or heteroarylalkyl.

21. The compound of any one of claim 18 or 19-20, or a pharmaceutically acceptable salt thereof, wherein:
   $R^{13}$ is —Y—Z, in which Y is a bond or —$CH_2$—, Z is —$SO_2R^b$ or —$N(R^a)SO_2R^b$, in which each $R^a$ is independently hydrogen or alkyl, and $R^b$ is alkyl;
   $R^1$ is alkyl; and
   $R^3$ is alkyl, cycloalkyl, or aryl.

22. A pharmaceutical composition comprising the compound of claim 1.

23. An oral dosage form comprising the pharmaceutical composition of claim 22.

24. A medicament comprising the pharmaceutical composition of claim 22 for use in the therapeutic treatment of cancer or other neoplastic disease.

* * * * *